(12) United States Patent
Pratilas et al.

(10) Patent No.: US 7,812,143 B2
(45) Date of Patent: Oct. 12, 2010

(54) BIOMARKERS FOR CANCER TREATMENT

(75) Inventors: Christine Pratilas, New York, NY (US); Neal Rosen, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 368 days.

(21) Appl. No.: 11/732,362

(22) Filed: Apr. 2, 2007

(65) Prior Publication Data

US 2008/0131885 A1 Jun. 5, 2008

Related U.S. Application Data

(60) Provisional application No. 60/788,014, filed on Mar. 31, 2006.

(51) Int. Cl.
*C07H 21/04* (2006.01)

(52) U.S. Cl. .................. 536/23.1; 530/350; 422/61; 435/6

(58) Field of Classification Search .................. None
See application file for complete search history.

(56) References Cited

OTHER PUBLICATIONS

Davies, et al. "Mutations of the BRAF gene in human cancer" Nature. 2002. vol. 417, pp. 949-954.
Solit et al., "BRAF mutation predicts sensitivity to MEK inhibition" Nature. 2006. vol. 439, pp. 358-362.
Tsavachidou et al., "SPRY2 Is an Inhibitor of the Ras/Extracellular Signal-Regulated Kinase Pathway in Melanocytes and Melanoma Cells with Wild-Type *BRAF* but Not with the V599E Mutant" Cancer Research. 2004, vol. 64, pp. 5556-5559.
Bloethner et al., "Effect of common B-RAF and N-RAS mutations on global gene expression in melanoma cell lines" Carcinogenesis. 2005. vol. 26, pp. 1224-1232.

*Primary Examiner*—Misook Yu
(74) *Attorney, Agent, or Firm*—Edwards Angell Palmer & Dodge LLP; Peter C. Lauro, Esq.; Melissa Hunter-Ensor, Esq.

(57) ABSTRACT

The present invention provides identification of a thirty-five gene set that predicts the anticancer activity of inhibitors of the RAF/MEK/MAPK pathway, methods of qualifying cancer status in a subject, methods of identifying an anti-tumor response in a subject, methods of monitoring the efficacy of a therapeutic drug in a subject, and methods of identifying an agent useful in the treatment of a cancer based on expression of the thirty-five gene set.

9 Claims, 51 Drawing Sheets

FIG. 1

IER3

MCHSRSCHPTMTILQAPTPAPSTIPGPRRGSGPEIFTFDPLPEPAAAPAGRPSASRGHRKRSRRVLYPRVVRRQLPV
EEPNPAKRLLFLLLTIVFCQILMAEEGVPAPLPPEDAPNAASLAPTPVSAVLEPFNLTSEPSDYALDLSTFLQQHPA
AF (SEQ ID NO:1)

```
   1 ctcacttggc cttacactcc gctcggctca ccatgtgtca ctctcgcagc tgccacccga
  61 ccatgaccat cctgcaggcc ccgaccccgg cccctccac catcccggga ccccggcggg
 121 gctccggtcc tgagatcttc accttcgacc ctctcccgga gccgcagcg gcccctgccg
 181 ggcgcccag cgcctctcgc gggcaccgaa agcgcagccg cagggttctc taccctcgag
 241 tggtccggcg ccagctgcca gtcgaggaac cgaacccagc caaaaggctt ctctttctgc
 301 tgctcaccat cgtcttctgc cagatcctga tggctgaaga gggtgtgccg gcgccctgc
 361 ctccagagga cgcccctaac gccgcatccc tggcgcccac ccctgtgtcc gccgtcctcg
 421 agcccttaa tctgacttcg gagccctcgg actacgctct ggacctcagc actttcctcc
 481 agcaacaccc ggccgccttc taactgtgac tccccgcact ccccaaaaag aatccgaaaa
 541 accacaaaga aacaccaggc gtacctggtg cgcgagagcg tatcccaac tgggacttcc
 601 gaggcaactt gaactcagaa cactacagcg gagacgccac ccggtgcttg aggcgggacc
 661 gaggcgcaca gagaccgagg cgcatagaga ccgaggcaca gcccagctgg ggctaggccc
 721 ggtgggaagg agagcgtcgt taatttattt cttattgctc ctaattaata tttatatgta
 781 tttatgtacg tcctcctagg tgatggagat gtgtacgtaa tatttatttt aacttatgca
 841 agggtgtgag atgttccccc tgctgtaaat gcaggtctct tggtatttat tgagctttgt
 901 gggactggtg gaagcaggac acctggaact gcggcaaagt aggagaagaa atggggagga
 961 ctcgggtggg ggaggacgtc ccggctggga tgaagtctgg tggtgggtcg taagtttagg
1021 aggtgactgc atcctccagc atctcaactc cgtctgtcta ctgtgtgaga cttcggcgga
1081 ccattaggaa tgagatccgt gagatccttc catcttcttg aagtcgcctt tagggtggct
1141 gcgaggtaga gggttggggg ttggtgggct gtcacggagc gactgtcgag atcgcctagt
1201 atgttctgtg aacacaaata aaattgattt actgtctgca aaaaaaaaa aaaa (SEQ ID
NO:2)
```

EGR1

MAAAKAEMQLMSPLQISDPFGSFPHSPTMDNYPKLEEMMLLSNGAPQFLGAAGAPEGSGSNSSSSSSGGGGGGGGS
NSSSSSSTFNPQADTGEQPYEHLTAESFPDISLNNNEKVLVETSYPSQTTRLPPITYTGRFSLEPAPNSGNTLWPEPL
FSLVSGLVSMTNPPASSSSAPSPAASSASASQSPPLSCAVPSNDSSPIYSAAPTFPTPNTDIFPEPQSQAFPGSAGT
ALQYPPPAYPAAKGGFQVPMIPDYLFPQQQGDLGLGTPDQKPFQGLESRTQQPSLTPLSTIKAFATQSGSQDLKALN
TSYQSQLIKPSRMRKYPNRPSKTPPHERPYACPVESCDRRFSRSDELTRHIRIHTGQKPFQCRICMRNFSRSDHLTT
HIRTHTGEKPFACDICGRKFARSDERKRHTKIHLRQKDKKADKSVVASSATSSLSSYPSPVATSYPSPVTTSYPSPA
TTSYPSPVPTSFSSPGSSTYPSPVHSGFPSPSVATTYSSVPPAFPAQVSSFPSSAVTNSFSASTGLSDMTATFSPRT
IEIC (SEQ ID NO:3)

```
  1 gcgcagaact tggggagccg ccgccgccat ccgccgccgc agccagcttc cgccgccgca
 61 ggaccggccc ctgccccagc ctccgcagcc gcggcgcgtc cacgcccgcc cgcgcccagg
121 gcgagtcggg gtcgccgcct gcacgcttct cagtgttccc cgcgcccgc atgtaacccg
181 gccaggcccc cgcaactgtg tccctgcag ctccagcccc gggctgcacc ccccgcccc
241 gacaccagct ctccagcctg ctcgtccagg atggccgcgg ccaaggccga gatgcagctg
301 atgtccccgc tgcagatctc tgacccgttc ggatcctttc ctcactcgcc caccatggac
361 aactacccta agctggagga gatgatgctg ctgagcaacg gggctcccca gttcctcggc
421 gccgccgggg ccccagaggg cagcggcagc aacagcagca gcagcagcag cgggggcggt
```

FIG 1. (cont'd)

```
 481 ggaggcggcg ggggcggcag caacagcagc agcagcagca gcaccttcaa ccctcaggcg
 541 gacacgggcg agcagccta cgagcacctg accgcagagt cttttcctga catctctctg
 601 aacaacgaga aggtgctggt ggagaccagt taccccagcc aaaccactcg actgcccccc
 661 atcacctata ctggccgctt ttccctggag cctgcaccca acagtggcaa caccttgtgg
 721 cccgagcccc tcttcagctt ggtcagtggc ctagtgagca tgaccaaccc accggcctcc
 781 tcgtcctcag caccatctcc agcggcctcc tccgcctccg cctcccagag cccacccctg
 841 agctgcgcag tgccatccaa cgacagcagt cccatttact cagcggcacc caccttcccc
 901 acgccgaaca ctgacatttt ccctgagcca caaagccagg ccttcccggg ctcggcaggg
 961 acagcgctcc agtacccgcc tcctgcctac cctgccgcca agggtggctt ccaggttccc
1021 atgatccccg actacctgtt tccacagcag caggggatc tgggcctggg caccccagac
1081 cagaagccct tccagggcct ggagagccgc acccagcagc cttcgctaac ccctctgtct
1141 actattaagg cctttgccac tcagtcgggc tccaggacc tgaaggccct caataccagc
1201 taccagtccc agctcatcaa acccagccgc atgcgcaagt accccaaccg gcccagcaag
1261 acgcccccc acgaacgccc ttacgcttgc ccagtggagt cctgtgatcg ccgcttctcc
1321 cgctccgacg agctcacccg ccacatccgc atccacacag gccagaagcc cttccagtgc
1381 cgcatctgca tgcgcaactt cagccgcagc gaccacctca cacccacat ccgcacccac
1441 acaggcgaaa agcccttcgc ctgcgacatc tgtggaagaa agtttgccag gagcgatgaa
1501 cgcaagaggc ataccaagat ccacttgcgg cagaaggaca agaaagcaga caaaagtgtt
1561 gtggcctctt cggccaccctc ctctctctct tcctacccgt ccccggttgc tacctcttac
1621 ccgtccccgg ttactacctc ttatccatcc ccggccacca cctcatccc atcccctgtg
1681 cccacctcct tctcctctcc cggctcctcg acctacccat ccctgtgca cagtggcttc
1741 ccctccccgt cggtggccac cacgtactcc tctgttcccc ctgctttccc ggcccaggtc
1801 agcagcttcc cttcctcagc tgtcaccaac tccttcagcg cctccacagg gctttcggac
1861 atgacagcaa ccttttctcc caggacaatt gaaatttgct aaagggaaag gggaaagaaa
1921 gggaaaaggg agaaaagaa acacaagaga cttaaaggac aggaggagga gatgccata
1981 ggagaggagg gttcctctta ggtcagatgg aggttctcag agccaagtcc tccctctcta
2041 ctggagtgga aggtctattg gccaacaatc ctttctgccc acttcccctt ccccaattac
2101 tattcccttt gacttcagct gcctgaaaca gccatgtcca agttcttcac ctctatccaa
2161 agaacttgat ttgcatggat tttggataaa tcatttcagt atcatctcca tcatatgcct
2221 gaccccttgc tcccttcaat gctagaaaat cgagttggca aaatggggtt tgggcccctc
2281 agagccctgc cctgcaccct tgtacagtgt ctgtgccatg gatttcgttt ttcttggggt
2341 actcttgatg tgaagataat ttgcatattc tattgtatta tttggagtta ggtcctcact
2401 tggggaaaa aaaaaaaga aaagccaagc aaaccaatgg tgatcctcta ttttgtgatg
2461 atgctgtgac aataagtttg aaccttttt tttgaaacag cagtcccagt attctcagag
2521 catgtgtcag agtgttgttc cgttaacctt tttgtaaata ctgcttgacc gtactctcac
2581 atgtggcaaa atatggtttg gtttttcttt tttttttttt ttgaaagtgt tttttcttcg
2641 tccttttggt ttaaaagtt tcacgtcttg gtgcttttg tgtgatgcgc cttgctgatg
2701 gcttgacatg tgcaattgtg agggacatgc tcacctctag ccttaagggg ggcagggagt
2761 gatgatttgg gggaggcttt gggagcaaaa taggaagag ggctgagctg agcttcggtt
2821 ctccagaatg taagaaaaca aaatctaaaa caaaatctga actctcaaaa gtctatttt
2881 ttaactgaaa atgtaaattt ataaatatat tcaggagttg gaatgttgta gttacctact
2941 gagtaggcgg cgattttgt atgttatgaa catgcagttc attatttgt ggttctattt
3001 tactttgtac ttgtgtttgc ttaaacaaag tgactgtttg gcttataaac acattgaatg
3061 cgctttattg cccatgggat atgtggtgta tatccttcca aaaaattaaa acgaaaataa
3121 agtagctgcg attggg (SEQ ID NO:4)
```

FIG 1. (cont'd)

IER2

MEVQKEAQRIMTLSVWKMYHSRMQRGGLRLHRSLQLSLVMRSARELYLSAKVEALEPEVSLPAALPSDPRLHPPREA
ESTAETATPDGEHPFPEPMDTQEAPTAEETSACCAPRPAKVSRKRRSSSLSDGGDAGLVPSKKARLEEKEEEEGASS
EVADRLQPPPAQAEGAFPNLARVLQRRFSGLLNCSPAAPPTAPPACEAKPACRPADSMLNVLVRAVVAF (SEQ ID NO:5)

```
   1 ggtccgagtt cggaatttcg gttcaaggcc cagttcctcg gattgttcct gcgcaacttc
  61 agtttccctt ccaggcacgg gcaatgagtg tttggccgcg acgagttgga aagcccggat
 121 gcgtccttcg gttgggcggg gtgtctcagt gacgtcactg ggggtataaa agggcctggg
 181 tggcgggcgc ctgggcagag cgtcctagca gtgtcactgc gtgggttggt ttgtgtagag
 241 aggcgtgagc gagcccgttg tccggagtgc acctgctgcc tgttctgtcc ctcccgggag
 301 cccccgccgc tgtcgccgtc gagtcgccat ggaagtgcag aaagaggcac agcgcatcat
 361 gaccctgtcg gtgtggaaga tgtatcactc ccgcatgcag cgcggtggcc tgcggctgca
 421 ccggagtctg cagctgtcgc tggtcatgcg cagcgcccgg gagctctacc tctcggccaa
 481 ggtggaggcc ctcgagcccg aggtgtcgtt gccggccgcc ctcccctctg accctcgcct
 541 gcacccgccc cgagaagccg agtccacggc cgagacagcg acccccgacg gtgagcaccc
 601 gtttccggag ccaatggaca cgcaggaggc gccgacagcc gaggagacct ccgcctgctg
 661 tgccccgcgc cccgccaaag tcagccgcaa acgacgcagc agcagcctga gcgacggcgg
 721 ggacgctgga ctggtcccga gcaagaaagc ccgtctggaa gaaaaggaag aagaggaggg
 781 agcgtcatcc gaagtcgccg atcgcctgca gccccctccg gcgcaagcgg agggcgcctt
 841 tcccaacctg gcccgcgtcc tgcagaggcg cttctccggc ctcctgaact gcagccccgc
 901 ggcccctccg acggcgccgc ccgcgtgcga ggcaaagccc gcttgccgcc cggcggacag
 961 catgctcaac gtgctcgtgc gggccgtggt ggccttctga ggacccccgag cggcgctgcc
1021 ggagcccaga gcgcgcgtcg aaccgtcggc ccgagggcgc agacctgagg cgaggccacc
1081 cccctccatc ctgggggaag cgcccgcgaa aaccgtggag agaagccgcc gcccgggctg
1141 ctgagaggcc cggagaggga ctctgtcccc ggggagccat cgccttcagt gtgcagggac
1201 ggcaccgagg agtctgagcc gggggcgcgg gcgccttccg cagagacctg cgcccacagg
1261 tgctgtctta gtggactggg acgtgaacct ttcgctctcc ttctggactg ggagaaggga
1321 ggcttgggtg ttgtgttttt tgttttgttt gtttgtttgt ttttaaagat ctcctcaggg
1381 tcggacttca ttttgtactg tgggctgtgc tggcccttc aaggttttc aagagttggt
1441 tttcgctttc caacctcgga gaattccagg cactcccctt cccctccgc tgacatactt
1501 gtataagcgg tcatcgttgc gtcatggggc aggcgtgggg agcttcctgt cgccttgcgt
1561 gggtgtgggg cctgggagga ggtcctgggg cgtgcacccg ccctgggcag tggggaggag
1621 agtggcctga gttacttcac ccccgcgtgc tgctggttaa tgtcccgcgt ctctgcacct
1681 tcgggtggga gcggggactg atctactttc acattctcaa gttttctca tctgcattag
1741 aggtgcccag taggttccca ggttccagcg tgcccctccc tcagacacac ggacacaatc
1801 agccgagaag ttcctggtct gaatcacgag aatgtggagg ggtgggggt gtcagtggaa
1861 aggcataagg ctgagctgag accagttgct ggtgaaactg gccaatctg ggggagggaa
1921 catccttgcc agggagtttc tgagggtctg cttgtttac ctttcgtgcg gtggattctt
1981 tttaactccg tctacctggc gttttgttag aaatgtcaga taggaaaata aaaaccattt
2041 gagtaaaaaa aaaaaaaaaa aaaaaaaaaa aaaaaaaaaa aaaaaaaa (SEQ ID NO:6)
```

MYC

MDFFRVVENQQPPATMPLNVSFTNRNYDLDYDSVQPYFYCDEEENFYQQQQQSELQPPAPSEDIWKKFELLPTPPLS
PSRRSGLCSPSYVAVTPFSLRGDNDGGGGSFSTADQLEMVTELLGGDMVNQSFICDPDDETFIKNIIIQDCMWSGFS
AAAKLVSEKLASYQAARKDSGSPNPARGHSVCSTSSLYLQDLSAAASECIDPSVVFPYPLNDSSSPKSCASQDSSAF
SPSSDSLLSSTESSPQGSPEPLVLHEETPPTTSSDSEEEQEDEEEIDVVSVEKRQAPGKRSESGSPSAGGHSKPPHS

FIG 1. (cont'd)

PLVLKRCHVSTHQHNYAAPPSTRKDYPAAKRVKLDSVRVLRQISNNRKCTSPRSSDTEENVKRRTHNVLERQRRNEL
KRSFFALRDQIPELENNEKAPKVVILKKATAYILSVQAEEQKLISEEDLLRKRREQLKHKLEQLRNSCA (SEQ ID
NO:7)

```
   1 acccccgagc tgtgctgctc gcggccgcca ccgccgggcc ccggccgtcc ctggctcccc
  61 tcctgcctcg agaagggcag ggcttctcag aggcttggcg ggaaaaagaa cggagggagg
 121 gatcgcgctg agtataaaag ccggttttcg gggctttatc taactcgctg tagtaattcc
 181 agcgagaggc agagggagcg agcgggcggc cggctagggt ggaagagccg ggcgagcaga
 241 gctgcgctgc gggcgtcctg ggaagggaga tccggagcga atagggggct tcgcctctgg
 301 cccagccctc ccgctgatcc cccagccagc ggtccgcaac ccttccgca tccacgaaac
 361 tttgcccata gcagcgggcg ggcactttgc actggaactt acaacacccg agcaaggacg
 421 cgactctccc gacgcgggga ggctattctg cccatttggg gacacttccc cgccgctgcc
 481 aggacccgct tctctgaaag gctctccttg cagctgctta gacgctggat ttttttcggg
 541 tagtggaaaa ccagcagcct cccgcgacga tgcccctcaa cgttagcttc accaacagga
 601 actatgacct cgactacgac tcggtgcagc cgtatttcta ctgcgacgag gaggagaact
 661 tctaccagca gcagcaagag agcgagctgc agccccgcggc gcccagcgag gatatctgga
 721 agaaattcga gctgctgccc accccgcccc tgtccctag ccgccgctcc gggctctgct
 781 cgccctccta cgttgcggtc acacccttct cccttcgggg agacaacgac gccggtggcg
 841 ggagcttctc cacggccgac cagctggaga tggtgaccga gctgctggga ggagacatgg
 901 tgaaccagag tttcatctgc gacccggacg acgagacctt catcaaaaac atcatcatcc
 961 aggactgtat gtggagcggc ttctcggccg ccgccaagct cgtctcagag aagctggcct
1021 cctaccaggc tgcgcgcaaa gacagcggca gcccgaaccc cgcccgcggc cacagcgtct
1081 gctccacctc cagcttgtac ctgcaggatc tgagcgccgc cgcctcagag tgcatcgacc
1141 cctcggtggt cttccctac cctctcaacg acagcagctc gcccaagtcc tgcgcctcgc
1201 aagactccag cgccttctct ccgtcctcgg attctctgct ctcctcgacg gagtcctccc
1261 cgcagggcag ccccgagccc ctggtgctcc atgaggagac accgcccacc accagcagcg
1321 actctgagga ggaacaagaa gatgaggaag aaatcgatgt tgtttctgtg gaaaagaggc
1381 aggctcctgg caaaaggtca gagtctggat caccttctgc tggaggccac agcaaacctc
1441 ctcacagccc actggtcctc aagaggtgcc acgtctccac acatcagcac aactacgcag
1501 cgcctcccct cactcggaag gactatcctg ctgccaagag ggtcaagttg acagtgtca
1561 gagtcctgag acagatcagc aacaaccgaa aatgcaccag ccccaggtcc tggacaccg
1621 aggagaatgt caagaggcga acacacaacg tcttggagcg ccagaggagg aacgagctaa
1681 aacggagctt ttttgccctg cgtgaccaga tcccggagtt ggaaaacaat gaaaaggccc
1741 ccaaggtagt tatccttaaa aaagccacag catacatcct gtccgtccaa gcagaggagc
1801 aaaagctcat ttctgaagag gacttgttgc ggaaacgacg agaacgttg aaacacaaac
1861 ttgaacagct acggaactct tgtgcgtaag gaaagtaag gaaaacgatt ccttctaaca
1921 gaaatgtcct gagcaatcac ctatgaactt gtttcaaatg catgatcaaa tgcaacctca
1981 caaccttggc tgagtcttga gactgaaaga tttagccata atgtaaactg cctcaaattg
2041 gactttgggc ataaaagaac ttttttatgc ttaccatctt ttttttttct ttaacagatt
2101 tgtatttaag aattgttttt aaaaaattt aagatttaca caatgtttct ctgtaaatat
2161 tgccattaaa tgtaaataac tttaataaaa cgtttatagc agttacacag aatttcaatc
2221 ctagtatata gtacctagta ttataggtac tataaacct aattttttt atttaagtac
2281 attttgcttt ttaaagttga ttttttcta ttgttttag aaaaataaa ataactggca
2341 aatatatcat tgagccaaaa aaaaaaaaa aaaaaa (SEQ ID NO:8)
```

FIG 1. (cont'd)

LNK

MNGPALQPSSPSSAPSASPAAAPRGWSEFCELHAVAAARELARQYWLFAREHPQHAPLRAELVSLQFTDLFQRYFCR
EVRDGRAPGRDYRDTGRGPPAKAEASPEPGPGPAAPGLPKARSSEELAPPRPPGPCSFQHFRRSLRHIFRRRSAGEL
PAAHTAAAPGTPGEAAETPARPGLAKKFLPWSLAREPPPEALKEAVLRYSLADEASMDSGARWQRGRLALRRAPGPD
GPDRVLELFDPPKSSRPKLQAACSSIQEVRWCTRLEMPDNLYTFVLKVKDRTDIIFEVGDEQQLNSWMAELSECTGR
GLESTEAEMHIPSALEPSTSSSPRGSTDSLNQGASPGGLLDPACQKTDHFLSCYPWFHGPISRVKAAQLVQLQGPDA
HGVFLVRQSETRRGEYVLTFNFQGIAKHLRLSLTERGQCRVQHLHFPSVVDMLHHFQRSPIPLECGAACDVRLSSYV
VVVSQPPGSCNTVLFPFSLPHWDSESLPHWGSELGLPHLSSSGCPRGLSPEGLPGRSSPPEQIFHLVPSPEELANSL
QHLEHEPVNRARDSDYEMDSSSRSHLRAIDNQYTPL (SEQ ID NO:9)

```
   1 cccgggccac cgcctccgcc cggctgcccg cccggactgt cgcggcccgc ggtggcgacg
  61 gcggccgctg caaagtttcc ccggcggcgg cggcccgggg gcgcatcctc ccgcaactgt
 121 caagcgctgg cggcggaaat gatgaggcgc tggccatttt ccgagcccgg gtttcctgcc
 181 tgagccccgc tcgagcgagc cgcgagcgag gagccggcgg gcgggagagg acgcgcccag
 241 ggcggggggcc cgcccgcccc ctcgggattt cgagggcccg ggggcgcgcg acgccatggg
 301 ccggccgggc ccagagctcc tgtctctcag cccggccgca ccacctgggt ctccgccatg
 361 aacgggcctg ccctgcagcc ctcctcgccc tcttccgcgc cctcagcctc cccggcggcg
 421 gccccgcggg gctggagcga gttctgtgag ttgcacgccg tagcggcggc ccgggagctg
 481 gcccgccagt actggctgtt cgcccgggag catccgcagc acgcgccgct gcgcgccgag
 541 ctggtgtcgc tgcagttcac cgacctcttc cagcgctact ctgccgcga ggtgcgcgac
 601 ggacgggcgc cgggccgcga ctaccgggac acaggccgtg ggccccagc caaggccgag
 661 gcgtccccgg agccaggccc cggcccgcc gcccctggcc tgcccaaggc ccgcagctct
 721 gaggagctgg ccccgccgcg gccgcccggg cctgctcct tccagcactt cgccgcagc
 781 ctccgccaca tcttccgccg ccgctcggcc ggggagctgc cagcggccca caccgctgcc
 841 gcccccggga ccccggaga ggctgctgag acccccgccc ggcctggcct ggccaagaag
 901 ttcctgccct ggagcctggc ccgggagccg ccacccgagg cgctgaagga ggcggtgctg
 961 cgctacagcc tggccgacga ggcctccatg gacagcgggg cacgctggca gcgcggggagg
1021 ctggcgctgc gccgggcccc gggccccgat ggccccgacc gcgtgctgga gctcttcgac
1081 ccacccaaga gttcaaggcc caagctacaa gcagcttgct ccagcatcca ggaggtccgg
1141 tggtgcacac ggcttgagat gcctgacaac ctttacacct tgtgctgaa ggtgaaggac
1201 cggacagaca tcatctttga ggtgggagac gagcagcagc tgaattcatg gatggctgag
1261 ctctcggagt gcacaggccg agggctggag agcacagaag cagagatgca tattccctca
1321 gccctagagc ctagcacgtc cagctcccca aggggcagca cagattccct taaccaaggt
1381 gcttctcctg gggggctgct ggacccggcc tgccagaaga cggaccattt cctgtcctgc
1441 taccctggt tccacggccc catctccaga gtgaaagcag ctcagctggt tcagctgcag
1501 ggcctgatg ctcatggagt gttcctggtg cggcagagcg agacgcggc tggggaatac
1561 gtgctcactt tcaactttca ggggatagcc aagcacctgc gcctgtcgct gacagagcgg
1621 ggccagtgcc gtgtgcagca cctccacttt cctcggtcg tggacatgct ccaccacttc
1681 cagcgctcgc ccatcccact cgagtgcggc gcgcctgtg atgtccggct ctccagctac
1741 gtggtagtcg tctcccaacc accaggttcc tgcaacacgg tcctcttccc tttctccctt
1801 cctcactggg attcagagtc ccttcctcac tggggttcag agttgggcct tccccacctt
1861 agttcttctg gctgtcccgc ggggctcagc ccagagggtc tccagggcg atcctcaccc
1921 cccgagcaga tcttccacct ggtgccttcg cccgaagaac tggccaacag cctgcagcac
1981 ctggagcatg agcctgtgaa tgagcccgg actcggact acgaaatgga ctcatcctcc
2041 cggagccacc tgcgggccat agacaatcag tacacacctc tctgaccagt gaggaattcc
2101 aggcctcaac agctgccctt gaggagcaca ggcagaagtg tgaacttgtg aatgtaattg
2161 atctttcctt ccttccagag aaagatttaa gggacactgt taactgctcg tgccagtttg
2221 gaagtgaccc ttctattagg cctgttgaag ggcctcctg taggtttcat ctatccacct
2281 ggctttctcc ttattgttta cagatgtagt tcttgttaga ggatgccgct agctcctgcc
```

FIG. 1 (cont'd)

```
2341 cggggtccct atgcccagtc cccgttactc ttagagaaag gagttggggt gagggccaga
2401 gctggcagtg gaaacttgtt ctcttttca ctgacactgt cacagcggat gacagactt
2461 ctacggggag gagggggga tcatcaggaa gcccagaaca ctaacaagcg gttctcccat
2521 ctaccgtcag tccacatggc aggtctgctg tgtccacacc acagatgacc acatctaatc
2581 ctgcttctac tctcagcttt aggacaaaag ctctgtcaga ggcacaagct gaaggtcaaa
2641 aatgatttaa aacattttac ctcagactaa tttctttaaa ggattcaggt tcaaaactta
2701 accactgctt atttcagtgc actgtttcaa ctaacaccca tgctatttt gtagtcagaa
2761 acagctatgc aaaccctacc taatttacag tctgagccag catgctggct tgtctactgc
2821 atcctcggga cagtcacctg ccactgagtg gccactgtcc ttcctaaatg tcaagaagtg
2881 aagtatgtca cccttcagg gaaattcagg caattactga aataggaagg tggcaagaac
2941 agttctatcc tggtgcctta cgaataaaaa actggattct ggtttacagc agctttacag
3001 tgatagttaa attaactggg gctaggggaa aagcaaccaa aaagggaaaa aggactccta
3061 ggccctttct attaaatcct tcagcaacaa ggctggcttg gtgccctcca agcatctaat
3121 ggcttattaa attatcccac aattgggttt taggctcctt tttgaccca aaatggaagc
3181 tgggaatctg gtgccataac taatgagaaa ctcctttaat accccacaat cagtgttctg
3241 ttctacctgg ctactgcttc actggattga aaatctatct atctccttgc acacatgggc
3301 acacacaatc tccaccatcc agggaggtcc tgaattcaaa tctctatcta tccaagtgat
3361 acaattcata gggggctggc tcctcccaga acctgtctgg aggctcagaa acggggcag
3421 tgacagtgga gtcagctgct cttgggtgcc agcagagcca ttcagtacaa cccccaggct
3481 cacacagtg gcttctagga aactgggagt ttagatcagc tttacagata catcgatcag
3541 aggctaaaat gaaacctcag cctaaaactc ataggactga ctgcctggga ggagggttag
3601 gtctgcttct tccacttata cttagtctct gtgctccaag aggtcaaatt tttgcttcta
3661 gaatttcctt ggggtctttc agagggtggg ggaacaaacc cctatgcact tttcttttt
3721 tttttttgaga tggagtttct cttgtcaacc gggctggagt gcagtggtgc aatcttggct
3781 cactgcaacc tccaccttcc tggttcaagc gattctgcct cgacctctca agtagctggg
3841 attacaagca ccagccacca tgcctggcta attttgtatt tttagtagag acagggttc
3901 accatgttgg ccaggctggt ctcgaatgtc tgacctcagg tgatccaccc gccttggcct
3961 cccaaagtgc tgggattaca ggcgcgagcc accgcgccca gcctacacca cttttagtac
4021 caacactctt gggtgatttc atggacccta aagcagacct gacactgatc cagatttgca
4081 gtccatttt aaggacacct gtctttattt cctcaaagtc aagcagcttt ctctgaaaaa
4141 tgaatgctaa ttagtgtgaa ccaaaagagt aagtaagagt ctgaagtttt tttaaaggag
4201 aaagcttatt atggaaagtc actggtcctc ccctccgcac aggaaaggta cccagtagat
4261 aatgaaccaa attaagttcc ctccctccag ccagaagtta aacatctggg atatgacgtc
4321 ttcatgccag gggcactcat ttcttagcag cctctctaca tacatctctc aggtggtgcc
4381 aagaggcaca ccaggtagag caaacttagc agctctgact aacaggctgc aaagtgcaag
4441 ttcagattct gtggcagaga tttggagggc acccacgtcc agactgcttc ccgtccaagt
4501 taccaggaca gctcaaaaac atgctgacag aaaactccca tggctctagg aaaagtgac
4561 actaagccaa caccttctt tatgtgggag caaaatcagc tgatgaaggg gtgggcacca
4621 ttgtggggca ggcaccccac tggctgcagc tagcccacca taggcacagc acatcccacc
4681 actctccttc cagtcctgac caggccccag ccggcaactt ctaccgagag ccatggctca
4741 acaccaaact ggacagtaga catcatgatc cctccagtta gctctaatta cagaccccac
4801 cagtacagct tgacagctcc cggcaccatc ccttccttca tctgacttat tgaactttta
4861 caaactaaca gtcaccagca ccaaagaatt aagtcaacta acctgccttg aattttaaac
4921 cagcaatcca tatggcttta tctggtataa atcttctgcc tttgatcatt tctggaccgt
4981 aggaaaaagg aatagcaatc attaaaatct tgggccagag aacactattt ttacataaca
5041 gtttcttaac ctaaagtcaa ggccttggac tcttccctga gggttgcctg aaattccttc
5101 atgctttcta ttcaggacta attcccttac tgcaaatgtg ttagctctaa catctcccac
5161 aagctaaagg aacttgcaag tatattaaca aggacacatc tgacatcctg tgtttggtta
5221 aaatatacag cacattgtga taacataaag tggatccatc ttgtatcatt ataggcaaaa
5281 ggtatttggc aaatttttat gtatggtttt atgtactgta caagtaactt attcttgaat
```

FIG 1. (cont'd)

```
5341 aatgcaaatt tgctataat gtacaaattg ctatatgtga attaaaaagt ttccaaaatc
5401 ttgaaaaaaa aaaaaaaaaa aaa (SEQ ID NO:10)
```

ETV5

MDGFYDQQVPFMVPGKSRSEECRGRPVIDRKRKFLDTDLAHDSEELFQDLSQLQEAWLAEAQVPDDEQFVPDFQSDN
LVLHAPPPTKIKRELHSPSSELSSCSHEQALGANYGEKCLYNYCAYDRKPPSGFKPLTPPTTPLSPTHQNPLFPPPQ
ATLPTSGHAPAAGPVQGVGPAPAPHSLPEPGPQQQTFAVPRPPHQPLQMPKMMPENQYPSEQRFQRQLSEPCHPFPP
QPGVPGDNRPSYHRQMSEPIVPAAPPPPQGFKQEYHDPLYEHGVPGMPGPPAHGFQSPMGIKQEPRDYCVDSEVPNC
QSSYMRGGYFSSSHEGFSYEKDPRLYFDDTCVVPERLEGKVKQEPTMYREGPPYQRRGSLQLWQFLVTLLDDPANAH
FIAWTGRGMEFKLIEPEEVARRWGIQKNRPAMNYDKLSRSLRYYYEKGIMQKVAGERYVYKFVCDPDALFSMAFPDN
QRPFLKAESECHLSEEDTLPLTHFEDSPAYLLDMDRCSSLPYAEGFAY (SEQ ID NO:11)

```
   1 gagtccagcc gctggtgcgc ggagcggttc accgtcttcg gagcggttcg gcccagcctt
  61 tcgcccaggc gcccaggccc gctgcgcgcg tgcgtgagcg cgcctgcgcc gccagggccg
 121 ctgcaagggg aggagagcgg ccgcctcagg aggatccctt ttccccagaa aattactcaa
 181 tgctgaaacc tctcaaagtg gtattagaga cgctgaaagc accatggacg ggttttatga
 241 tcagcaagtc ccttttatgg tcccagggaa atctcgatct gaggaatgca gagggcggcc
 301 tgtgattgac agaaagagga gttttttgga cacagatctg gctcacgatt ctgaagagct
 361 atttcaggat ctcagtcaac ttcaagaggc ttggttagct gaagcacaag ttcctgatga
 421 tgaacagttt gtcccagatt tcagtctga taacctggtg cttcatgccc cacctccaac
 481 caagatcaaa cgggagctgc acagccctc ctctgagctg tgtcttgta gccatgagca
 541 ggctcttggt gctaactatg gagaaaagtg cctctacaac tattgtgcct atgataggaa
 601 gcctcccctct gggttcaagc cattaacccc tctacaacc cccctctcac ccacccatca
 661 gaatccccta tttcccccac ctcaggcaac tctgcccacc tcagggcatg cccctgcagc
 721 tggcccagtt caaggtgtgg gccccgcccc cgccccccat tcgcttccag agcctggacc
 781 acagcagcaa acatttgcgg tccccccgacc accacatcag ccctgcaga tgccaaagat
 841 gatgcctgaa aaccagtatc catcagaaca gagatttcag agacaactgt ctgaaccctg
 901 ccaccccttc cctcctcagc caggagttcc tggagataat cgccccagtt accatcggca
 961 aatgtcagaa cctattgtcc ctgcagctcc ccgcccct cagggattca acaagaata
1021 ccatgaccca ctctatgaac atggggtccc gggcatgcca gggcccccag cacacgggtt
1081 ccagtcacca atgggaatca agcaggagcc tcgggattac tgcgtcgatt cagaagtgcc
1141 taactgccag tcatcctaca tgagggggg ttattctcc agcagccatg aaggttttc
1201 atatgaaaaa gatcccgat tatactttga cgacacttgt gttgtgcctg agagactgga
1261 aggcaaagtc aaacaggagc ctaccatgta tcgagagggg ccccccttacc agaggcgagg
1321 ttcccttcag ctgtggcagt tcctggtcac ccttcttgat gacccagcca atgcccactt
1381 cattgcctgg acaggtcgag gcatggagtt caagctgata gaaccggaag aggttgctcg
1441 gcgctgggc atccagaaga accggccagc catgaactat gacaagctga gccgctctct
1501 ccgctattac tatgaaaagg gcatcatgca aaggtggct ggagagcgat acgtctacaa
1561 atttgtctgt gacccagatg ccctcttctc catggctttc ccggataacc agcgtccgtt
1621 cctgaaggca gagtccgagt gccacctcag cgaggaggac accctgccgc tgacccactt
1681 tgaagacagc cccgcttacc tcctggacat ggaccgctgc agcagcctcc cctatgccga
1741 aggctttgct tactaagttt ctgagtggcg gagtggccaa acctagagc tagcagttcc
1801 cattcaggca acaagggca gtggttttgt ttgtgttttt ggttgttcct aaagcttgcc
1861 ctttgagtat tatctggaga acccaagctg tctctggatt ggcacccta agacagata
1921 cattggctgg ggagtgggaa cagggagggg cagaaaacca ccaaaaggcc agtgcctcaa
1981 ctcttgattc tgatgaggtt tctgggaaga gatcaaaatg gagtctcctt accatggaca
2041 atacatgcaa agcaatatct tgttcaggtt agtacccgca aacgggaca tgatgtgaca
```

FIG 1. (cont'd)

```
2101 atctcgatcg atcatggact actaaatggc ctttacatag aagggctctg atttgcacaa
2161 tttgttgaaa aatcacaaac ccatagaaaa gtgagtaggc taagttgggg aggctcaaac
2221 cattaagggt taaaaataca tcttaaacat tggaaagctc ttctagctga atctgaaata
2281 ttaccccttg tctagaaaaa gggggcagt cagaacagct gttccccact ccgtgttctc
2341 aaaatcataa accatggcta ctcttgggaa ccacccggcc atgtggtcgc caagtagagc
2401 aagcccctt tctcttccca atcacgtggc tgagtgtgga tgactttat tttaggagaa
2461 gggcgattaa cacttttgac agtattttgt tttgccctga tttgggggat tgttttgttt
2521 tggtggttgt tttggaaaaa cagtttataa actgatttt gtagttttgg tatttaaagc
2581 aaaaaaacga aaaacaaaaa acaaaaacaa acctttggt aatgtgcact gtgtctttag
2641 ccagggccgt gcaacttatg aagacactgc agcttgagag gggctttgct gaggcttccc
2701 cttggccatg tgaaagcccg ccttgttgcc tgctttgtgc tttctgcacc agacaacctg
2761 atggaacatt tgcacctgag ttgtacattt ttgaagtgtg cagggcagcc tggacacaag
2821 cttagattct ctatgtatag ttccccgtgt tcactaacat gccctctctg gaaagcatat
2881 gtatataaca tgtgtcatgt cctttggaaa cctggtcacc tggtgaaaac ccttgggatt
2941 cttccctggg catgactgat gacaatttcc atttcatcag tttgttttgt tttccttttt
3001 ctttaaatct tggacttta accctacctg tgtgattcag tagggtttga gacttagctg
3061 tgatactgac aggtaagcaa cagtgctagc attctagatt cctgcctttt tttaaaaaga
3121 aattattctc attgctgtat tatattggaa aagttttaaa caaccaagct aaagctatgt
3181 gaaagttgag ctcaaagtag aggaaaagtt actggtggta ccttgctgcc tgctctgctg
3241 gtagaattct gtgctccccg tgacacttag tacattaaga atgactacac tgttcctcgt
3301 atgtgaagga ggcagtgctg actccgtgag tgtgagacac gtgctttgaa ctgcttttct
3361 attcatggag cactccatag tctcaaactg tccccttat gaccaacagc acatttgtga
3421 agaggttcgc agggataagg ggtgcactt aaacatgaga ttctcctcta
3481 ttggaagcta attagcccac aaggtggta aacctgtaga ttgggcctta attagcattg
3541 tactctaatc aaaggactct ttctaaacca tatttatagc tttcttaacc tacacatagt
3601 ctatacatag atgcatattt taccccagc tggctagaga tttatttgtt gtaaatgctg
3661 tatagatttg gttttccttt ctttacttac cctggtttgg attttttttt ttttttttt
3721 tgaatggatt tatgctgtct tagcaatatg acaataatcc tctgtagctt gagctacccc
3781 tcccctgctg taacttacgt gacctgtgct gtcactgggc ataggacagc ggcatcacgg
3841 ttgcattccc attggactca tgcacctccc ggatggtttt tgttttttc gggggttctt
3901 tggggtttgt ttgtttgctt cttttccaga gtgtggaaag tctacagtgc agaaaggctt
3961 gaacctgcca gctgatttga aatactttca ccctgcgcag ggccgtatgc atcctgccaa
4021 gctgcgttat attctgtact gtgtacaata aagaagtttg cttttcgttt a (SEQ ID
NO:12)
```

HES1

MAAVRVLVASRLAAASAFTSLSPGGRTPSQRAALHLSVPRPAARVALVLSGCGVYDGTEIHEASAILVHLSRGGAEV
QIFAPDVPQMHVIDHTKGQPSEGESRNVLTESARIARGKITDLANLSAANHDAAIFPGGFGAAKNLLCCIAPVLAAK
VLRGVEVTVGHEQEEGGKWPYAGTAEAIKALGAKHCVKEVVEAHVDQKNKVVTTPAFMCETALHYIHDGIGAMVRKV
LELTGK (SEQ ID NO:13)

```
  1 agtcccgacg agcaacgcgt tgtagaggg gtgggtgcgc acgctctgtc cctgcgtgac
 61 cttccgaccc cgctgtcctc accgcaatgg cggctgtgag ggtcctggtg gcctcgaggc
121 tcgctgcggc atctgcattc acgtccctgt ccccggcgg tcggacgcct cccagcgcg
181 cagcccttca cctctccgtg ccgcgccccg cggccagggt cgcgctggtg ctgtctggat
241 gcggagtcta cgatgggacc gagatccacg aggcctcggc gatcctggtg cacctgagcc
301 gtgagggggc tgaagtccag atctttgctc ctgacgtccc tcagatgcac gtgattgacc
```

FIG 1. (cont'd)

```
 361 acaccaaggg gcagccgtcc gaaggcgaga gcaggaatgt tttgaccgag tctgcgagga
 421 tcgccgtgg caaaatcaca gacctggcca acctcagtgc agccaaccat gatgctgcca
 481 tctttccagg aggctttgga gcggctaaaa acctcttgtg ctgcattgca cctgtcctcg
 541 cggccaaggt gctcagaggc gtcgaggtga ctgtgggcca cgagcaggag gaaggtggca
 601 agtggcctta tgccgggacc gcagaggcca tcaaggccct gggtgccaag cactgcgtga
 661 aggaagtggt cgaagctcac gtggaccaga aaacaaggt ggtcacgacc ccagccttca
 721 tgtgcgagac ggcactccac tacatccatg atgggatcgg agccatggtg aggaaggtgc
 781 tggaactcac tggaaagtga cgcgcatgga cggggcccag ctaggcgcca ggacttggcc
 841 tcaccctctg gctgaggagc tgtcggctgc tttccatcca gctgggagtc tggcaggccc
 901 tttttttttt ttctttgccg aaacctgcag gcgttctctc tctaaggagg atgtgctgca
 961 gtgcatgggg gatgtttctt cctgggtgtg gctgggctgc tctcacatac agaggccgag
1021 gggccaattc gttctctgcc acagggactt gcctcactgt gtcccaaaaa caaatcgcag
1081 ccagcttttc cagaaataga aaattctgcc gtctgaggtt ttatacttca ggttagttag
1141 ttttggaag gaagaacatt tttaggtttg caagcctcct gatcaggaaa ccagaaatac
1201 cacatttatg gaccatgaaa ggttggttct tgactctgaa gggacttttg agttaatcag
1261 cgtaagggga tttctaaagc aggcaatccc tgtagccgca gagaataaac gccttcccaa
1321 aatggcaact tcccacagcc acatttcaga cctgctgaga ctgctgagtg aggaatggca
1381 gtgaggtttc ttcaattagt ctcagttctc ttaattttca ggaagaaagg gaaattgcag
1441 ccctcagcc cccaggattg acctctgggg agtgatggta gcgttggtgc caggccgtgg
1501 gttcaggtgt ggcagaagct tgcagatgcg tccgaaggga aataaagtgt gttggcgtta
1561 gactttgtgc tgcaaa (SEQ ID NO:14)
```

SPRY2

MEARAQSGNGSQPLLQTPRDGGRQRGEPDPRDALTQQVHVLSLDQIRAIRNTNEYTEGPTVVPRPGLKPAPRPSTQH
KHERLHGLPEHRQPPRLQHSQVHSSARAPLSRSISTVSSGSRSSTRTSTSSSSEQRLLGSSFSSGPVADGIIRVQP
KSELKPGELKPLSKEDLGLHAYRCEDCGKCKCKECTYPRPLPSDWICDKQCLCSAQNVIDYGTCVCCVKGLFYHCSN
DDEDNCADNPCSCSQSHCCTRWSAMGVMSLFLPCLWCYLPAKGCLKLCQGCYDRVNRPGCRCKNSNTVCCKVPTVPP
RNFEKPT (SEQ ID NO:15)

```
    1 gtaaggccgt tttcttttcc cattcgctca tctgccagga aaagggactt gccgttggcg
   61 cttcggcctc ttgttcattg agaaaaaaga ggaaatactc cgcgtgcgct tgtagaaggg
  121 gagtcgtctc cagctccgaa ccccggagtg ttcatcagcg gggaatctgg ctccgaattc
  181 tctttttttc tcccgccgat tgctcggaag ttggtctaaa gcagaggttg aaagaaagg
  241 aaaaaagttt gcatcgagac tggatttatt tgcacatcgc agaaagaaga gaatccaagg
  301 gagaggggtt ggtgcaaagc cgcgatcacg gagttcagat gtgttctaag cctgctggag
  361 tgaccacact tccaagacct gatggaggcc agagctcaga gtggcaacgg tcgcagccc
  421 ttgctgcaga cgccccgtga cggtggcaga cagcgtgggg agcccgaccc agagacgcc
  481 ctcacccagc aggtacatgt cttgtctctg gatcagatca gagccatccg aaacaccaat
  541 gagtacacag aggggcctac tgtcgtccca agacctgggc tcaagcctgc tcctcgcccc
  601 tccactcagc acaaacacga gagactccac ggtctgcctg agcaccgcca gcctcctagg
  661 ctccagcact cgcaggtcca ttcttctgca cgagcccctc tgtccagatc cataagcacg
  721 gtcagctcag ggtcgcggag cagtacgagg acaagtacca gcagcagctc ctctgaacag
  781 agactgctag gatcatcctt ctcctccggg cctgttgctg atgcataat ccgggtgcaa
  841 cccaaatctg agctcaagcc aggtgagctt aagccactga gcaaggaaga tttgggcctg
  901 cacgcctaca ggtgtgagga ctgtggcaag tgcaaatgta aggagtgcac ctacccaagg
  961 cctctgccat cagactggat ctgcgacaag cagtgccttt gctcggccca gaacgtgatt
 1021 gactatggga cttgtgtatg ctgtgtgaaa ggtctcttct atcactgttc taatgatgat
```

FIG 1. (cont'd)

```
1081 gaggacaact gtgctgacaa cccatgttct tgcagccagt ctcactgttg tacacgatgg
1141 tcagccatgg gtgtcatgtc cctcttttg ccttgtttat ggtgttacct tccagccaag
1201 ggttgcctta aattgtgcca ggggtgttat gaccgggtta acaggcctgg ttgccgctgt
1261 aaaaactcaa acacagtttg ctgcaaagtt cccactgtcc cccctaggaa ctttgaaaaa
1321 ccaacatagc atcattaatc aggaatatta cagtaatgag gattttttct ttctttttt
1381 aatacacata tgcaaccaac taaacagtta taatcttggc actgttaata gaaaggtggg
1441 atagtctttg ctgtttgcgg tgaaatgctt tttgtccatg tgccgtttta actgatatgc
1501 ttgttagaac tcagctaatg gagctcaaag tatgagatac agaacttggt gacccatgta
1561 ttgcataagc taaagcaaca cagacactcc taggcaaagt ttttgtttgt gaatagtact
1621 tgcaaaactt gtaaattagc agatgacttt ttttccattgt tttctccaga gagaatgtgc
1681 tatatttttg tatatacaat aatatttgca actgtgaaaa acaagttgtg ccatactaca
1741 tggcacagac acaaaatatt atactaatat gttgtacatt cggaagaatg tgaatcaatc
1801 agtatgtttt tagattgtat tttgcctac agaaagcctt tattgtaaga ctctgatttc
1861 cctttggact tcatgtatat tgtacagtta cagtaaaatt caacctttat tttctaattt
1921 tttcaacata ttgtttagtg taaagaatat ttatttgaag ttttattatt ttataaaaaa
1981 gaatatttat tttaagaggc atcttacaaa ttttgccct tttatgagga tgtgatagtt
2041 gctgcaaatg aggggttaca gatgcatatg tccaatataa aatagaaaat atattaacgt
2101 ttgaaattaa aaaaaaaaa aaaaaa (SEQ ID NO:16)
```

DUSP4

MVTMEELREMDCSVLKRLMNRDENGGGAGGSGSHGTLGLPSGGKCLLLDCRPFLAHSAGYILGSVNVRCNTIVRRRA
KGSVSLEQILPAEEEVRARLRSGLYSAVIVYDERSPRAESLREDSTVSLVVQALRRNAERTDICLLKGGYERFSSEY
PEFCSKTKALAAIPPPVPPSATEPLDLGCSSCGTPLHDQGGPVEILPFLYLGSAYHAARRDMLDALGITALLNVSSD
CPNHFEGHYQYKCIPVEDNHKADISSWFMEAIEYIDAVKDCRGRVLVHCQAGISRSATICLAYLMMKKRVRLEEAFE
FVKQRRSIISPNFSFMGQLLQFESQVLATSCAAEAASPSGPLRERGKTPATPTSQFVFSFPVSVGVHSAPSSLPYLH
SPITTSPSC (SEQ ID NO:17)

```
   1 gctgagcgcc ggaggagcgt aggcagggca gcgctggcgc cagtggcgac aggagccgcg
  61 cgaccggcaa aaatacacgg gaggccgtcg ccgaaaagag tccgcggtcc tctctcgtaa
 121 acacactctc ctccaccggc gcctcccct ccgctctgcg cgccgcccgg ctgggcgccc
 181 gaggccgctc cgactgctat gtgaccgcga ggctgcggga ggaaggggac aggaagaag
 241 aggctctccc gcgggagccc ttgaggacca gtttgcggc cacttctgca ggcgtccctt
 301 cttagctctc gcccgccct tctgcagcc taggcggccc gggttctctt ctcttcctcg
 361 cgcgccagc cgcctcggtt cccggcgacc atggtgacga tggaggagct gcgggagatg
 421 gactgcagtg tgctcaaaag gctgatgaac cgggacgaga atggcggcgg cgcgggcggc
 481 agcggcagcc acggcacct ggggctgccg agcggcggca agtgcctgct gctggactgc
 541 agaccgttcc tggcgcacag cgcgggctac atcctaggtt cggtcaacgt gcgctgtaac
 601 accatcgtgc ggcggcgggc taagggctcc gtgagcctgg agcagatcct gcccgccgag
 661 gaggaggtac gcgcccgctt gcgctccggc ctctactcgg cggtcatcgt ctacgacgag
 721 cgcagcccgc gcgccgagag cctccgcgag gacagcaccg tgtcgctggt ggtgcaggcg
 781 ctgcgccgca acgccgagcg caccgacatc tgcctgctca aggcggcta tgagaggttt
 841 tcctccgagt acccagaatt ctgttctaaa accaaggccc tggcagccat cccaccccg
 901 gttccccca gtgccacaga gcccttggac ctgggctgca gctcctgtgg acccacta
 961 cacgaccagg ggggtcctgt ggagatcctc ccttcctct acctcggcag tgcctaccat
1021 gctgcccgga gagacatgct ggacgcctg gcatcacgg ctctgttgaa tgtctcctcg
1081 gactgcccaa accactttga aggacactat cagtacaagt gcatcccagt ggaagataac
1141 cacaaggccg acatcagctc ctggttcatg gaagcctag agtacatcga tgccgtgaag
```

FIG 1. (cont'd)

```
1201 gactgccgtg ggcgcgtgct ggtgcactgc caggcgggca tctcgcggtc ggccaccatc
1261 tgcctggcct acctgatgat gaagaaacgg gtgaggctgg aggaggcctt cgagttcgtt
1321 aagcagcgcc gcagcatcat ctcgcccaac ttcagcttca tggggcagct gctgcagttc
1381 gagtcccagg tgctggccac gtcctgtgct gcggaggctg ctagcccctc gggacccctg
1441 cgggagcggg gcaagacccc cgccaccccc acctcgcagt tcgtcttcag ctttccggtc
1501 tccgtgggcg tgcactcggc ccccagcagc ctgccctacc tgcacagccc catcaccacc
1561 tctcccagct gttagagccg ccctggggc cccagaacca gagctggctc ccagcaaggg
1621 taggacgggc cgcatgcggg cagaaagttg ggactgagca gctgggagca ggcgaccgag
1681 ctccttcccc atcatttctc cttggccaac gacgaggcca gccagaatgg caataaggac
1741 tccgaataca taataaaagc aaacagaaca ctccaactta gagcaataac ggctgccgca
1801 gcagccaggg aagaccttgg tttggtttat gtgtcagttt cacttttccg atagaaattt
1861 cttacctcat ttttttaagc agtaaggctt gaagtgatga acccacaga tcctagcaaa
1921 tgtgcccaac cagctttact aaagggggag gaagggaggg caaggggatg agaagacaag
1981 tttcccagaa gtgcctggtt ctgtgtactt gtccctttgt tgtcgttgtt gtagttaaag
2041 gaatttcatt ttttaaaaga aatcttcgaa ggtgtggttt tcatttctca gtcaccaaca
2101 gatgaataat tatgcttaat aataaagtat ttattaagac tttcttcaga gtatgaaagt
2161 acaaaaagtc tagttacagt ggatttagaa tatatttatg ttgatgtcaa acagctgagc
2221 accgtagcat gcagatgtca aggcagttag gaagtaaatg gtgtcttgta gatatgtgca
2281 aggtagcatg atgagcaact tgagtttgtt gccactgaga agcaggcggg ttgggtggga
2341 ggaggaagaa agggaagaat taggtttgaa ttgcttttta aaaaaaaag aaaagaaaaa
2401 gacagcatct cactatgttg ccaaggctca tcttgagaag caggcgggtt gggtgggagg
2461 aggaagaaag ggaagaatta ggtttgaatt gcttttt (SEQ ID NO:18)
```

FOSL1

MFRDFGEPGPSSGNGGGYGGPAQPPAAAQAAQQKFHLVPSINTMSGSQELQWMVQPHFLGPSSYPRPLTYPQYSPPQ
PRPGVIRALGPPPGVRRRPCEQISPEEEERRRVRRERNKLAAAKCRNRRKELTDFLQAETDKLEDEKSGLQREIEEL
QKQKERLELVLEAHRPICKIPEGAKEGDTGSTSGTSSPPAPCRPVPCISLSPGPVLEPEALHTPTLMTTPSLTPFTP
SLVFTYPSTPEPCASAHRKSSSSSGDPSSDPLGSPTLLAL (SEQ ID NO:19)

```
   1 acgggccaag gcggcgcgtc tcgggggtgg agcctggagg tgaccgcgcc gctgcaacgc
  61 cccaccccc cgcggtcgca gtggttcagc ccgagaactt ttcattcata aaaagaaaag
 121 actccgcacg gcgcgggtga gtcagaaccc agcagccgtg taccccgcag agccgccagc
 181 cccgggcatg ttccgagact cggggaacc cggcccgagc tccgggaacg gcggcgggta
 241 cggcggcccc gcgcagcccc cggccgcagc gcaggcagcc cagcagaagt tccacctggt
 301 gccaagcatc aacaccatga gtggcagtca ggagctgcag tggatggtac agcctcattt
 361 cctggggccc agcagttacc ccaggcctct gacctaccct cagtacagcc cccacaacc
 421 ccggccagga gtcatccggg ccctggggcc gctccaggg gtacgtcgaa ggccttgtga
 481 acagatcagc ccggaggaag aggagcgccg ccgagtaagg cgcgagcgga acaagctggc
 541 tgcggccaag tgcaggaacc ggaggaagga actgaccgac ttcctgcagg cggagactga
 601 caaactggaa gatgagaaat ctggctgca gcgagagatt gaggagctgc agaagcagaa
 661 ggagcgccta gagctggtgc tggaagccca ccgacccatc tgcaaaatcc cggaaggagc
 721 caaggagggg gacacaggca gtaccagtgg caccagcagc ccaccagccc ctgccgccc
 781 tgtaccttgt atctcccttt cccagggcc tgtgcttgaa cctgaggcac tgcacacccc
 841 cacactcatg accacaccct ccctaactcc tttcacccc agcctggtct tcacctaccc
 901 cagcactcct gagccttgtg cctcagctca tcgcaagagt agcagcagca gcggagaccc
 961 atcctctgac ccccttggct ctccaaccct cctcgctttg tgaggcgcct gagccctact
1021 ccctgcagat gccacccag ccaatgtctc ctccccttcc cccaccggtc cagctggcct
```

FIG 1. (cont'd)

```
1081 ggacagtatc ccacatccaa ctccagcaac ttcttctcca tccctctaat gagactgacc
1141 atattgtgct tcacagtaga gccagcttgg ggccaccaaa gctgcccact gtttctcttg
1201 agctggcctc tctagcacaa tttgcactaa atcagagaca aaatatttcc catttgtgcc
1261 agaggaatcc tggcagccca gagactttgt agatccttag aggtcctctg agccctaac
1321 cccttccaga tcactgccac actctccatc accctcttcc tgtgatccac ccaaccctat
1381 ctcctgacag aaggtgccac tttacccacc tagaacacta actcaccagc cccactgcca
1441 gcagcagcag gtgattggac caggccattc tgccgccccc tcctgaaccg cacagctcag
1501 gaggcgccct tggcttctgt gatgcggtca tctgcggatc tcagctttga gaagccttca
1561 gctccaggga atccaagcct ccacagcgag ggcagctgct atttattttc ctaaagagag
1621 tatttttata caaacctacc aaaatggaat aaaaggcttg aagctgtgaa aaaaaaaaa
1681 aaaaaaaaaa aaa (SEQ ID NO:20)
```

PLK3

MEPAAGFLSPRPFQRAAAAPAPPAGPGPPPSALRGPELEMLAGLPTSDPGRLITDPRSGRTYLKGRLLGKGGFARCY
EATDTETGSAYAVKVIPQSRVAKPHQREKILNEIELHRDLQHRHIVRFSHHFEDADNIYIFLELCSRKSLAHIWKAR
HTLLEPEVRYYLRQILSGLKYLHQRGILHRDLKLGNFFITENMELKVGDFGLAARLEPPEQRKKTICGTPNYVAPEV
LLRQGHGPEADVWSLGCVMYTLLCGSPPFETADLKETYRCIKQVHYTLPASLSLPARQLLAAILRASPRDRPSIDQI
LRHDFFTKGYTPDRLPISSCVTVPDLTPPNPARSLFAKVTKSLFGRKKKSKNHAQERDEVSGLVSGLMRTSVGHQDA
RPEAPAASGPAPVSLVETAPEDSSPRGTLASSGDGFEEGLTVATVVESALCALRNCIAFMPPAEQNPAPLAQPEPLV
WVSKWVDYSNKFGFGYQLSSRRVAVLFNDGTHMALSANRKTVHYNPTSTKHFSFSVGAVPRALQPQLGILRYFASYM
EQHLMKGGDLPSVEEVEVPAPPLLLQWVKTDQALLMLFSDGTVQVNFYGDHTKLILSGWEPLLVTFVARNRSACTYL
ASHLRQLGCSPDLRQRLRYALRLLRDRSPA (SEQ ID NO:21)

```
   1 cctgggcgcc agcgcagcgt agcaaatcca ggcagcgcca cgcgcggccg ggccgggcg
  61 gaaccgagaa gccgggaccg cgctgcgacg cgccggccgc atggagcctg ccgccggttt
 121 cctgtctccg cgccccttcc agcgtgcggc cgcgcgcgcc gctccccgg ccggggcccgg
 181 gccgcctccg agtgccttgc gcggacctga gctggagatg ctggccgggc taccgacgtc
 241 agaccccggg cgcctcatca cggacccgcg cagcggccgc acctacctca aaggccgctt
 301 gttgggcaag ggggcttcg cccgctgcta cgaggccact gacacagaga ctggcagcgc
 361 ctacgctgtc aaagtcatcc cgcagagccg cgtcgccaag ccgcatcagc gcgagaagat
 421 cctaaatgag attgagctgc accgagacct gcagcaccgc cacatcgtgc gttttcgca
 481 ccactttgag gacgctgaca acatctacat tttcttggag ctctgcagcc gaaagtccct
 541 ggcccacatc tggaaggccc ggcacaccct gttgagccca gaagtgcgct actacctgcg
 601 gcagatcctt tctggcctca gtacttgca ccagcgcggc atcttgcacc gggacctcaa
 661 gttgggaaat ttttcatca ctgagaacat ggaactgaag gtgggggatt ttgggctggc
 721 agcccggttg gagcctccgg agcagaggaa gaagaccatc tgtggcaccc ccaactatgt
 781 ggctccagaa gtgctgctga cagggccag cggccctgag gcggatgtat ggtcactggg
 841 ctgtgtcatg tacacgctgc tctgcgggag ccctcccttt gagacggctg acctgaagga
 901 gacgtaccgc tgcatcaagc aggttcacta cgctgcct gccagcctct cactgcctgc
 961 ccggcagctc ctggccgcca tccttcgggc ctcacccga accgcccct ctattgacca
1021 gatcctgcgc catgacttct ttaccaaggg ctacaccccc gatcgactcc ctatcagcag
1081 ctgcgtgaca gtcccagacc tgacaccccc caacccagct aggagtctgt ttgccaaagt
1141 taccaagagc ctctttggca gaaagaagaa gagtaagaat catgcccagg agagggatga
1201 ggtctccggt ttggtgagcg gcctcatgcg cacatccgtt ggccatcagg atgccaggcc
1261 agaggctcca gcagcttctg gccagcccc tgtcagcctg gtagagacag cacctgaaga
1321 cagctcaccc cgtgggacac tggcaagcag tggagatgga tttgaagaag gtctgactgt
1381 ggccacagta gtggagtcag ccctttgtgc tctgagaaat tgtatagcct tcatgccccc
```

FIG 1. (cont'd)

```
1441 agcggaacag aacccggccc ccctggccca gccagagcct ctggtgtggg tcagcaagtg
1501 ggttgactac tccaataagt tcggctttgg gtatcaactg tccagccgcc gtgtggctgt
1561 gctcttcaac gatggcacac atatggccct gtcggccaac agaaagactg tgcactacaa
1621 tcccaccagc acaaagcact tctccttctc cgtgggtgct gtgccccggg ccctgcagcc
1681 tcagctgggt atcctgcggt acttcgcctc ctacatggag cagcacctca tgaagggtgg
1741 agatctgccc agtgtggaag aggtagaggt acctgctccg cccttgctgc tgcagtgggt
1801 caagacggat caggctctcc tcatgctgtt tagtgatggc actgtccagg tgaacttcta
1861 cggggaccac accaagctga ttctcagtgg ctgggagccc ctccttgtga cttttgtggc
1921 ccgaaatcgt agtgcttgta cttacctcgc ttcccacctt cggcagctgg gctgctctcc
1981 agacctgcgg cagcgactcc gctatgctct gcgcctgctc cgggaccgca gcccagccta
2041 ggacccaagc cctgaggcct gaggcctgtg cctgtcaggc tctggccctt gcctttgtgg
2101 ccttcccct tcctttggtg cctcactggg ggctttgggc cgaatccccc agggaatcag
2161 ggaccagctt tactggagtt gggggcggct tgtcttcgct ggctcctacc ccatctccaa
2221 gataagcctg agccttagct cccagctagg gggcgttatt tatggaccac ttttatttat
2281 tgtcagacac ttatttattg ggatgtgagc cccagggggg cctcctccta ggataataaa
2341 caattttgca gaattggaaa aaaaaaaa (SEQ ID NO:22)
```

GJB1

MNWTGLYTLLSGVNRHSTAIGRVWLSVIFIFRIMVLVVAAESVWGDEKSSFICNTLQPGCNSVCYDQFFPISHVRLW
SLQLILVSTPALLVAMHVAHQQHIEKKMLRLEGHGDPLHLEEVKRHKVHISGTLWWTYVISVVFRLLFEAVFMYVFY
LLYPGYAMVRLVKCDVYPCPNTVDCFVSRPTEKTVFTVFMLAASGICIILNVAEVVYLIIRACARRAQRRSNPPSRK
GSGFGHRLSPEYKQNEINKLLSEQDGSLKDILRRSPGTGAGLAEKSDRCSAC (SEQ ID NO:23)

```
   1 gcggtgatga attgggacgc aggcgcggag cccagggacc actcccctg cacagacatg
  61 agaccatagg ggacctgtct gggtggcctc agggataggc gctccccaag gtgtgaatga
 121 ggcaggatga actggacagg tttgtacacc ttgctcagtg gcgtgaaccg gcattctact
 181 gccattggcc gagtatggct ctcggtcatc ttcatcttca gaatcatggt gctggtggtg
 241 gctgcagaga gtgtgtgggg tgatgagaaa tcttccttca tctgcaacac actccagcct
 301 ggctgcaaca gcgtttgcta tgaccaattc ttccccatct cccatgtgcg gctgtggtcc
 361 ctgcagctca tcctagtttc caccccagct ctcctcgtgg ccatgcacgt ggctcaccag
 421 caacacatag agaagaaaat gctacggctt gagggccatg ggaccccct acacctggag
 481 gaggtgaaga ggcacaaggt ccacatctca gggacactgt ggtggaccta tgtcatcagc
 541 gtggtgttcc ggctgttgtt tgaggccgtc ttcatgtatg tcttttatct gctctaccct
 601 ggctatgcca tggtgcggct ggtcaagtgc gacgtctacc cctgcccaa cacagtggac
 661 tgcttcgtgt cccgccccac cgagaaaacc gtcttcaccg tcttcatgct agctgcctct
 721 ggcatctgca tcatcctcaa tgtggccgag gtggtgtacc tcatcatccg ggcctgtgcc
 781 cgccgagccc agcgccgctc caatccacct tcccgcaagg gctcgggctt cggccaccgc
 841 ctctcacctg aatacaagca gaatgagatc aacaagctgc tgagtgagca ggatggctcc
 901 ctgaaagaca tactgcgccc cagccctggc accggggctg gctggctga aagagcgac
 961 cgctgctcgg cctgctgatg ccacatacca ggcaacctcc catcccaccc ccgaccctgc
1021 cctgggcgag cccctccttc tccctgccg gtgcacaggc ctctgcctgc tgggattac
1081 tcgatcaaaa ccttccttcc ctggctactt cccttcctcc cggggccttc cttttgagga
1141 gctggagggg tggggagcta gaggccacct atgccagtgc tcaaggttac tgggagtgtg
1201 ggctgccctt gttgctgca ccttccctc ttccctctcc ctctctctgg gaccactggg
1261 tacaagagat gggatgctcc gacagcgtct ccaattatga aactaatctt aaccctgtgc
1321 tgtcagatac cctgtttctg gagtcacatc agtgaggagg gatgtgggta agaggagcag
1381 agggcagggg tgctgtggac atgtgggtgg agaagggagg gtggccagca ctagtaaagg
```

FIG 1. (cont'd)

```
1441 aggaatagtg cttgctggcc acaaggaaaa ggaggaggtg tctggggtga gggagttagg
1501 gagagagaag caggcagata agttggagca ggggttggtc aaggccacct ctgcctctag
1561 tccccaaggc ctctctctgc ctgaaatgtt acacattaaa caggatttta cagccaaaaa
1621 aaaaaaaaaa aaaaaaaa (SEQ ID NO:24)
```

CD3EAP

MEEPQAGDAARFSCPPNFTAKPPASESPRFSLEALTGPDTELWLIQAPADFAPECFNGRHVPLSGSQIVKGKLAGKR
HRYRVLSSCPQAGEATLLAPSTEAGGGLTCASAPQGTLRILEGPQQSLSGSPLQPIPASPPPQIPPGLRPRFCAFGG
NPPVTGPRSALAPNLLTSGKKKKEMQVTEAPVTQEAVNGHGALEVDMALGSPEMDVRKKKKKKNQQLKEPEAAGPVG
TEPTVETLEPLGVLFPSTTKKRKKPKGKETFEPEDKTVKQEQINTEPLEDTVLSPTKKRKRQKGTEGMEPEEGVTVE
SQPQVKVEPLEEAIPLPPTKKRKKEKGQMAMMEPGTEAMEPVEPEMKPLESPGGTMAPQQPEGAKPQAQAALAAPKK
KTKKEKQQDATVEPETEVVGPELPDDLEPQAAPTSTKKKKKKKERGHTVTEPIQPLEPELPGEGQPEARATPGSTKK
RKKQSQESRMPETVPQEEMPGPPLNSESGEEAPTGRDKKRKQQQQQPV (SEQ ID NO:25)

```
   1 aagttctgaa cttgtgaggc atctgggcct ccccagaaga catttaacac agaaagcaca
  61 gccctactaa ctagtattct tacctgtctc ttcaagaatt tcagaccaat cgaccgtcct
 121 gtctctttaa ggcttaggaa gagcagtgtg gctgcccctt aaggaggcg ttgcaacaaa
 181 ccatattgga cagacgatgg gggcgaccca tcgggacccg acgggcctct gactccagca
 241 atacagcgaa tcagcggctt tcgggaatac attttcgga aaaagacttc ttcctcggtt
 301 ttctgctctg cacacgttga aatttcccc agttttcct gcagatcggg agtcgagcaa
 361 tgcctacccc cgcgctccg caccagttgg gcgctcccgg atgatgccct acccctttgg
 421 atccacgtgg tctgcaacct ggtgcagca gcccgggcta cagggttgcc tgaggtgtgg
 481 gtcccaggat ggaggagccc caggccggcg atgctgctcg gttctcttgt cccccccaact
 541 ttaccgcgaa gccccccagcc tcagagtccc ctcgtttctc cttgaggcg ctgacgggtc
 601 cagatacgga gctgtggctt attcaggccc ctgcagactt tgccccagaa tgcttcaatg
 661 ggcggcatgt gcctctctct ggctcccaga tcgtcaaggg caaattggca ggcaagcggc
 721 accgctatcg agtcctcagc agctgtcccc aagctggaga agcgaccctg ctggccccct
 781 caacggaggc aggaggtgga ctcacctgtg cctcagcccc ccagggcacc ctaaggatcc
 841 ttgagggtcc ccagcaatcc ctgtcaggga gcctctgca gcccatccca gcaagtcccc
 901 caccacagat ccctcctggc ctgaggcctc ggttctgtgc cttgggggc aacccaccag
 961 tcacagggcc taggtcagcc ttggcccca acctgctcac ctcagggaag aagaaaaagg
1021 agatgcaggt gacagaggcc ccagtcactc aggaggcagt gaatgggcac ggggccctgg
1081 aggtggacat ggctttgggg tcgccagaaa tggatgtgcg gaagaagaag aagaaaaaaa
1141 atcagcagct gaaagaacca gaggcagcag ggcctgtggg gacagagccc acagtggaga
1201 cactggagcc tctgggagtg ctgttccgt ccaccaccaa gaagaggaag aagcccaaag
1261 ggaaagaaac cttcgagcca gaagacaaga cagtgaagca ggaacagatt aacactgagc
1321 ctctagaaga cacagtcctg tccccgacca aaaagaaaga gaggcaaaag gggacggaag
1381 ggatgagcc agagaggggg gtgacagttg agtctcagcc acaggtgaag gtggagccac
1441 tggaggaagc catccctctg cccctacga agaagaggaa aaagaaaag ggacagatgg
1501 caatgatgga gccagggacg gaggcgatgg agccagtgga gccggagatg aagcctctgg
1561 agtccccagg ggggaccatg gcgcctcaac agccagaagg agcgaagcct caggcccagg
1621 cagctctggc agctcccaaa aagaagacga agaagaaaa acagcaagat gccacagtgg
1681 agccagagac agaggtggtg gggcctgagc tgccggatga ccttgagcct caggcagctc
1741 ccacatccac caagaagaag aagaagaaga agagagagg tcacacagtg actgagccaa
1801 ttcagccact agagcctgaa ctgccagggg agggacagcc tgaagccagg caactccgg
1861 gatccaccaa gaagaggaag aagcagagtc aggaagccg gatgccagag acagtgcccc
1921 aagaggagat gccagggccg ccactgaatt cagagtctgg ggaggaggct cccacaggcc
1981 gggacaagaa gcggaagcag cagcagcagc agcctgtgta gtctgccccc gggaaactga
```

FIG 1. (cont'd)

```
2041 ggaactaaag aaagctgaag gtgcccacct gggccaccag aaggtgacac ccccagaatc
2101 cctccccaga gactgcacca gcgcagccag caggagcctg gcctgggagg acgatttatt
2161 attacactgg gggtttcctt ggcagctggg gtcatcaggg tactttcaag aagggctcgt
2221 gcaggacatc aaacagcctc cgggcctgga tgggagggag aaaaaaatga ggaaccagtc
2281 attaaaggag ctgtttcctg ggtaaatcta gagtgggggtt ttggttcttt attttcccct
2341 ataccctcaa gcatttatcc attgagttac aaacaatcca gttacaatct ttttaagtta
2401 ttattattat tattatttt tttttttttg agatggagtc tcgctctgtc gcccaggttg
2461 gagtgcagtg gcgcaatctc ggctcactgc aagctccgcc tcccgggttc acgccattct
2521 cctgcctcag cctcctgagt agctgggact acaggcccct gccagctaa ttttttgtat
2581 ttttttttag tagagatggg gtttcaccac gttagccagg atggtctcga tctcctgacc
2641 tccctgatgcg cctgcctcag cctcccagtg ctgggattat aggtgtgagc cactgcgcct
2701 ggctaagtta ttattatttt tttgagacag tctcctggtg tcacccaggc tggagtgcag
2761 tggtgtgatc ttggctcact gcaacctccg cctcctgggt tccaacgatt ctcctgcctc
2821 agcctcccga gtagctgggc taaaggtgc ccaccactat acccggctaa ttttgtatt
2881 tttagtagag acaggggttt caccatattg gccaggctgg tctcgaactc ctgacctcgt
2941 gatccacctg ccttgacctc ccaaagtgct aggataacag tgtgagcca ccgcaccctg
3001 ccaagttatt taaaatgta ccattattat tgactatagt cacctggttg tgttatcaaa
3061 tagtatgtct tattcattct ttctttgtgt gtgtgtgtgt gtgtgtgtgt gtgtgtggta
3121 cccattaacc ttccccatct ccctgccagc cctaactac cctccccagc ctccaggaac
3181 tatccatcca ctcttatctc catgagttca attgttttga tttttagata cacaaataaa
3241 taagaacatg caatgtttgt ctttctgtgc ctggcttatt tcactt (SEQ ID NO:26)
```

SLC4A7

MERFRLEKKLPGPDEEAVVDLGKTSSTVNTKFEKEELESHRAVYIGVHVPFSKESRRRHRHRGHKHHHRRRKDKESD
KEDGRESPSYDTPSQRVQFILGTEDDDEEHIPHDLFTEMDELCYRDGEEYEWKETARWLKFEEDVEDGGDRWSKPYV
ATLSLHSLFELRSCILNGTVMLDMRASTLDEIADMVLDNMIASGQLDESIRENVREALLKRHHHQNEKRFTSRIPLV
RSFADIGKKHSDPHLLERNGEGLSASRHSLRTGLSASNLSLRGESPLSLLLGHLLPSSRAGTPAGSRCTTPVPTPQN
SPPSSPSISRLTSRSSQESQRQAPELLVSPASDDIPTVVIHPPEEDLEAALKGEEQKNEENVDLTPGILASPQSAPG
NLDNSKSGEIKGNGSGGSRENSTVDFSKVDMNFMRKIPTGAEASNVLVGEVDFLERPIIAFVRLAPAVLLTGLTEVP
VPTRFLFLLLGPAGKAPQYHEIGRSIATLMTDEIFHDVAYKAKDRNDLLSGIDEFLDQVTVLPPGEWDPSIRIEPPK
SVPSQEKRKIPVFHNGSTPTLGETPKEAAHHAGPELQRTGRLFGGLILDIKRKAPFFLSDFKDALSLQCLASILFLY
CACMSPVITFGGLLGEATEGRISAIESLFGASLTGIAYSLFAGQPLTILGSTGPVLVFEKILYKFCRDYQLSYLSLR
TSIGLWTSFLCIVLVATDASSLVCYITRFTEEAFAALICIIFIYEALEKLFDLGETYAFNMHNNLDKLTSYSCVCTE
PPNPSNETLAQWKKDNITAHNISWRNLTVSECKKLRGVFLGSACGHHGPYIPDVLFWCVILFFTTFFLSSFLKQFKT
KRYFPTKVRSTISDFAVFLTIVIMVTIDYLVGVPSPKLHVPEKFEPTHPERGWIISPLGDNPWWTLLIAAIPALLCT
ILIFMDQQITAVIINRKEHKLKKGAGYHLDLLMVGVMLGVCSVMGLPWFVAATVLSISHVNSLKVESECSAPGEQPK
FLGIREQRVTGLMIFILMGLSVFMTSVLKFIPMPVLYGVFLYMGVSSLKGIQLFDRIKLFGMPAKHQPDLIYLRYVP
LWKVHIFTVIQLTCLVLLWVIKVSAAAVVFPMMVLALVFVRKLMDLCFTKRELSWLDDLMPESKKKKEDDKKKKEKE
EAERMLQDDDDTVHLPFEGGSLLQIPVKALKYSPDKPVSVKISFEDEPRKKYVDAETSL (SEQ ID NO:27)

```
   1 ctcactgtcc ctggaatctt caagggagtt actgcattac atcatcagaa acaaggcatt
  61 tctatattac tatggaaaga tttcgtctgg agaagaagtt acctggtcct gatgaagaag
 121 ctgttgtgga tcttggcaaa actagctcaa ctgtgaacac caagtttgaa aaagaagaac
 181 tagaaagtca tagagctgta tatattggtg ttcacgtccc gtttagtaaa gagagtcgtc
 241 ggcgtcatag gcatcgcgga cacaaacatc accaccggag aagaaagat aagaatcag
 301 ataaagaaga tggacgggaa tctccttctt atgatacacc atcccagaga gttcagttta
 361 tccttggtac tgaagatgat gatgaagaac atattcccca tgatctcttc acggaaatgg
```

FIG 1. (cont'd)

```
 421 atgaactgtg ttacagagat ggagaagaat atgaatggaa agaaactgct agatggctga
 481 aatttgaaga ggatgttgaa gatggcggtg accgatggag taaaccttat gtggcaactc
 541 tctctttgca cagtctttt gaactaagga gttgcatcct caatggaaca gtcatgctgg
 601 atatgagagc aagcactcta gatgaaatag cagatatggt attagacaac atgatagctt
 661 ctggccaatt agacgagtcc atacgagaga atgtcagaga agctcttctg aagagacatc
 721 atcatcagaa tgagaaaaga ttcaccagtc ggattcctct tgttcgatct tttgcagata
 781 taggcaagaa acattctgac cctcacttgc ttgaaaggaa tggggaaggc ctttcagcct
 841 cccgccactc tttgcgaaca ggtctgtctg cctcaaacct ttccttgaga ggagaatcac
 901 ctttatctct tcttcttggt catcttcttc cttcttcaag agctggaacc cctgcaggct
 961 caaggtgtac aaccccagta cccacccctc aaaacagtcc tccttctagc cctagcatca
1021 gccgcctgac ctccagaagt tcccaagaga gtcagcgtca ggccccagaa ctactggttt
1081 cacctgccag tgatgatatt cccacagtag taattcatcc gcctgaggaa gacttagaag
1141 cagcgctgaa aggcgaggag cagaagaatg aggaaaatgt tgacttaact ccaggtattt
1201 tggcctctcc ccagtctgct cctggaaact tggacaatag taaaagtgga gaaattaaag
1261 gtaatggaag tggtggaagc agagaaaata gtactgttga cttcagcaag gttgatatga
1321 atttcatgag aaaaattcct acgggtgctg aggcatccaa cgtcctggtg ggcgaagtag
1381 acttttgga aaggccaata attgcatttg tgagactggc tcctgctgtc ctccttacag
1441 ggttgactga ggtccctgtt ccaaccaggt ttttgttttt gttattgggt ccagcgggca
1501 aggcaccaca gtaccatgaa attggacgat caatagccac tctcatgaca gatgagattt
1561 tccatgatgt agcttataaa gcaaaagaca gaaatgacct cttatctgga attgatgaat
1621 ttttagatca agtaactgtc ctacctccag gagagtggga tccttctata cgcatagaac
1681 caccaaaaag tgtcccttct caggaaaaga gaaagattcc tgtgtttcac aatggatcta
1741 cccccacact gggtgagact cctaagagg ccgctcatca tgctgggcct gagctacaga
1801 ggactggacg gcttttggt ggtttgatac ttgacatcaa aaggaaagca ccttttttct
1861 tgagtgactt caaggatgca ttaagcctgc agtgcctggc ctcgattctt ttcctatact
1921 gtgcctgtat gtctcctgta atcacttttg gagggctgct tggagaagct acagaaggca
1981 gaataagtgc aatagagtct cttttggag catcattaac tgggattgcc tattcattgt
2041 ttgctgggca acctctaaca atattgggga gcacaggtcc agttctagtg tttgaaaaaa
2101 ttttatataa attctgcaga gattatcaac tttcttatct gtctttaaga accagtattg
2161 gtctgtggac ttctttttg tgcattgttt tggttgcaac agatgcaagc agccttgtgt
2221 gttatattac tcgatttaca gaagaggctt ttgcagccct tatttgcatc atattcatct
2281 acgaggcttt ggagaagctc tttgatttag gagaaacata tgcatttaat atgcacaaca
2341 acttagataa actgaccagc tactcagtta tatgtactga acctccaaac cccagcaatg
2401 aaactctagc acaatggaag aaagataata taacagcaca caatatttcc tggagaaatc
2461 ttactgtttc tgaatgtaaa aaacttcgtg gtgtattctt ggggtcagct tgtggtcatc
2521 atggaccttta tattccagat gtgctctttt ggtgtgtcat cttgttttc acaacatttt
2581 ttctgtcttc attcctcaag caatttaaga ccaagcgtta ctttcctacc aaggtgcgat
2641 cgacaatcag tgattttgct gtatttctca aatagtaat aatggttaca attgactacc
2701 ttgtaggagt tccatctcct aaacttcatg ttcctgaaaa atttgagcct actcatccag
2761 agagagggtg gatcataagc ccactgggag ataatccttg gtggacctta ttaatagctg
2821 ctattcctgc tttgctttgt accattctca tctttatgga tcaacaaatc acagctgtaa
2881 ttataaacag aaaggaacac aaattgaaga aaggagctgg ctatcacctt gatttgctca
2941 tggttggcgt tatgttggga gtttgctctg tcatgggact tccatggttt gtggctgcaa
3001 cagtgttgtc aataagtcat gtcaacagct taaagttga atctgaatgt tctgctccag
3061 gggaacaacc caagttttg ggaattcgtg aacagcgggt tacagggcta atgattttta
3121 ttctaatggg cctctctgtg ttcatgactt cagtcctaaa gtttattcca atgcctgttc
3181 tgtatggtgt ttcctttat atgggagttt cctcattaaa aggaatccag ttatttgacc
3241 gtataaaatt atttggaatg cctgctaagc atcagcctga tttgatatac ctccgttatg
3301 tgccgctctg gaaggtccat attttcacag tcattcagct tacttgtttg gtccttttat
3361 gggtgataaa agtttcagct gctgcagtgg ttttcccat gatggttctt gcattagtgt
```

FIG 1. (cont'd)

```
3421  ttgtgcgcaa actcatggac ctgtgtttca cgaagagaga acttagttgg cttgatgatc
3481  ttatgccaga aagtaagaaa aagaaagaag atgacaaaaa gaaaaaagag aaagaggaag
3541  ctgaacggat gcttcaagat gatgatgata ctgtgcacct tccatttgaa gggggaagtc
3601  tcttgcaaat tccagtcaag gccctaaaat atagtcctga taaacctgtg agtgtgaaaa
3661  taagttttga agatgaacca agaaagaaat acgtggatgc tgaaacttca ttatagaatt
3721  gaaccaagag gcattataca tatagatata tacatatgta atgtgtgcgt atcatgtcac
3781  tatatataag aatattgtat gtcatgctgt ttatgtgtga ctaccgggtt tttaaaagta
3841  gtgtctggag tttgtaatga gcaccgtgga gactatgtat ttaatgaaat gctctctttg
3901  aagtgaggta catggttctt aactattcaa atatttattc tgttagaaaa aaaaattttc
3961  tgttttgcaa tagaaggatg tggagaaatg ctttcagtct acttttctta aatctctgtt
4021  catcagtggc aattcgtaaa aaccttaagt gatactttgt ttatatgttt ataattttta
4081  ggtgtttcct gaaattttca catattattt cactttttgtt agtgcttttat gggaagaata
4141  gggagtctat accagtgctg tgggaaaaat ggtaacattt cagggcttct ctatttgtgt
4201  ttcatttctg tagatgtcca tcgtgtttca ctaactggcg ttttcttagc catagagatg
4261  actgtagaac aatagaaact ttaataatga tagttttaa cttttatgtt taaatttttt
4321  ttaaatctta aaaccttcat atctaggtat ccattgtgac agacaagtaa aattgcaggt
4381  gatttgataa ttaagcaccc ataccattta taacttctga atttaaaaag ttatacaatg
4441  ccagtttgca atagttgatt ttgatgcctt tgtagaatat ttttctgaa tccttatgct
4501  cttttaaagc caatgattcc cactctgttc tctgccttgt ctctctttgt cttaaaatgc
4561  tttagtttcc atcaggttca agttcttgac tattattctc ttataagtag taggcgtaaa
4621  taatcaggag ttagaattct ctcagaaggg tctatgatca gtattacttt attaagaatt
4681  acctttcatt ttctctttat gttattcttt cactttttgta gattacattt aatagcttgt
4741  tacctgtgat tttattttaa aatatttatt ttgatatgat gcttaaatat tatataaaca
4801  tttggaaaag taacaaatag agtaaattgt taatgtaaat agttggtgct tactttcatt
4861  tatgtttatt atcttaaagc aattgataga ttttacatct ttgatataaa gcactgccat
4921  atttatattt taaaaggaaa ttagacattt tatatgtagc tcagattaat gacatttta
4981  ttttgtgtat tagttttttgc ttttctgagc ttttttaaagt ctaacaaatc ttttttagtca
5041  tcttttatat acttttagtt ccacatgaaa taaatgttgt taagcctgta ggactggatg
5101  aatggggttg tgaaactgat ttgacaagag aataatttac aaaaatcaaa tgagtattga
5161  gaagccacag aaatatcaaa aatggtgaca tcactattag gatgaaaatt ttatgaaatt
5221  ccaatgctcc cttttaaccat ataattaaat tacaaggta tacataatta atctaataaa
5281  ggatcatgag gaatgccaaa agctgaaatt ttagcaagtc tggtgtttta aattcattat
5341  aaactattta ttaactaatg taatgtcctc ctctaagacc atattgtaag agtcttgtta
5401  aaatgatgga ttcaacttct gcctcggatg agaggttgga aatgtagctg cttttcttta
5461  gaaaatatgt agctgtcatc atttggtact gcctaaaaag agttagactc tattggcaat
5521  tgatagagta ttacccacgg tgcttattat tgtttatgag cttccattgt aatgattcct
5581  ttttatttgt agcagcataa ttatttccaa agacccagt atttgctgct attttttaaaa
5641  ctcccctgat gtacctgaac aagaggattt cctcacatca tttccttgtg tctggacatc
5701  aggggtaaca actgtactta ctttacagga agaaatttta aaactgaaaa ctacctggga
5761  tcatagtgtt tctgtgattt tatttaattg tgtatagtaa ttatccagtg ccagaaaaac
5821  cgtcacttgc aaaatacttt gcactcaaaa tgtttttaca atgcttctaa atgttactgg
5881  tttctgcttt cttttgacta cttgactgac aaaatgatct gactactcca tttaagagca
5941  aaggtaactc atgtttaggt aattaactgc ttgttttaag tgattatatt tcttccactg
6001  ttttgaaaa ataatcaaag atagcattca ttgagagaca gtgacagata taatttacta
6061  catatattga ttttttaaata aagttgcctt aataagtgt atgtaagcag tagtagttgc
6121  tatgtactga tttacctcaa ggtgcaaaat aattaaacct gtacatattc catttacaaa
6181  ataaattcag ccctgcactt tctttagatg ccttgatttc cagaatggag cttagtgcta
6241  ctgaataccc tggccacaga gccacctcag gatattcttt tctccaccct agtttattta
6301  tttatagata tctgttttaca aagtctgtag taaatcctga tgctgaccat ctgaaatgta
6361  ctttttttct gaatgctgtt tcaatctaaa atagcagctt tgagaaaac aatgatgtaa
```

FIG 1. (cont'd)

```
6421 attccttatg ataaaaggat gattctatat attctttaat gatattaaat atgccgaagc
6481 caagcacaca gtctttctaa agtgtgtgta tgtttgtgtg aatgtgaatg atactgatct
6541 tatatctgtt aaaagttgtt ttaaaaagct gtggcatccc attgttcata tttgccaagt
6601 cttctgtaaa gatgtctagg acgaaatatt ttatgtgcta atgcatgtat ttgtaaacca
6661 gatttgttta ccactcaaaa ttaacttgtt ttcttcatcc aaaaaagttt atttcttcca
6721 cgtacttaaa ttttctgtgt gggtataata tagctttcta atttttttct ttcacaaagg
6781 caggttcaaa attctgttga aagaaaaatg ctttctgaaa ctgaggtata acaccagagc
6841 ttgctgttta aaggattata tgatgtacat cagttctata aatgtgctca gcagtttaac
6901 atgtgaatcc tgttttaaag tgctcagatt tcaactgtgt aagccattga tataacgctg
6961 taattaaaaa tgtttatatg aaataactta atgttttaaa tttatttatg tagatcacat
7021 catttttatc gtatgcagtg caaatatgtg aaatgtcttt tggtttattc caacaattat
7081 ttatttaga aagtaagttt aaagacttta aggacattca aagtttaaaa tagtgttcaa
7141 attgcaaaat ttggcaatct tcatataaat tggtttcttt tctaacttt caaaaactaa
7201 cattaaatgt caattatagg aaaacatagt tggaaatgta atcatccaaa gatcattttt
7261 aaaatgaaat ttaattagca catattgaac atttgactta attgttaaac ccagttttg
7321 tttttgttttt taatcagat ttttgcacac tgattagttt ttgtgttgtg gcttttgttg
7381 cttattatt caaggttttt ttttttttc ttccccatgg gggagattgt cttccaatgt
7441 ttaactacgt ttaaataaat aaaaattgaa ttttattgtt catttatata aaatctgata
7501 ccttgatgta atttcacaat acagttccaa tttttatggc ttttataatt acaatgatat
7561 tttcttctat aataaaatcc aaagtaaaca tttaaattgt agaactgata tttttcattt
7621 atatgaagta taagcctcta ctgggtctat attgtgaatc atcctgcctt tcaaatttgt
7681 ttcataattg ttagatgaaa actattttt tggagatgtt actgaagttg attgagcaat
7741 aaaagtctac ttaatta (SEQ ID NO:28)
```

CCND1

MEHQLLCCEVETIRRAYPDANLLNDRVLRAMLKAEETCAPSVSYFKCVQKEVLPSMRKIVATWMLEVCEEQKCEEEV
FPLAMNYLDRFLSLEPVKKSRLQLLGATCMFVASKMKETIPLTAEKLCIYTDNSIRPEELLQMELLLVNKLKWNLAA
MTPHDFIEHFLSKMPEAEENKQIIRKHAQTFVALCATDVKFISNPPSMVAAGSVVAAVQGLNLRSPNNFLSYYRLTR
FLSRVIKCDPDCLRACQEQIEALLESSLRQAQQNMDPKAAEEEEEEEEEVDLACTPTDVRDVDI (SEQ ID
NO:29)

```
  1 gtagcagcga gcagcagagt ccgcacgctc cggcgagggg cagaagagcg cgagggagcg
 61 cggggcagca gaagcgagag ccgagcgcgg acccagccag gacccacagc cctccccagc
121 tgcccaggaa gagccccagc catggaacac cagctcctgt gctgcgaagt ggaaaccatc
181 cgccgcgcgt accccgatgc caacctcctc aacgacgggt gctgcgggc catgctgaag
241 gcggaggaga cctgcgcgcc ctcggtgtcc tacttcaaat gtgtgcagaa ggaggtcctg
301 ccgtccatgc ggaagatcgt cgccacctgg atgctggagg tctgcgagga acagaagtgc
361 gaggaggagg tcttcccgct ggccatgaac tacctggacc gcttcctgtc gctggagccc
421 gtgaaaaaga gccgcctgca gctgctgggg gccacttgca tgttcgtggc ctctaagatg
481 aaggagacca tccccctgac ggccgagaag ctgtgcatct acaccgacaa ctccatccgg
541 cccgaggagc tgctgcaaat ggagctgctc ctggtgaaca agctcaagtg gaacctggcc
601 gcaatgaccc cgcacgattt cattgaacac ttcctctcca aatgccaga ggcggaggag
661 aacaaacaga tcatccgcaa acacgcgcag accttcgttg ccctctgtgc cacagatgtg
721 aagttcattt ccaatccgcc ctccatggtg gcagcgggga gcgtggtggc cgcagtgcaa
781 ggcctgaacc tgaggagccc caacaacttc ctgtcctact accgcctcac acgcttcctc
841 tccagagtga tcaagtgtga cccggactgc ctccgggcct gccaggagca gatcgaagcc
901 ctgctggagt caagcctgcg ccaggcccag cagaacatgg accccaaggc cgccgaggag
```

FIG 1. (cont'd)

```
 961 gaggaagagg aggaggagga ggtggacctg gcttgcacac ccaccgacgt gcgggacgtg
1021 gacatctgag ggcgccaggc aggcgggcgc caccgccacc cgcagcgagg gcggagccgg
1081 ccccaggtgc tccactgaca gtccctcctc tccggagcat tttgatacca gaagggaaag
1141 cttcattctc cttgttgttg gttgtttttt cctttgctct ttcccccttc catctctgac
1201 ttaagcaaaa gaaaagatt acccaaaaac tgtctttaaa agagagagag agaaaaaaaa
1261 aatagtattt gcataaccct gagcggtggg ggaggagggt tgtgctacag atgatagagg
1321 attttatacc ccaataatca actcgttttt atattaatgt acttgtttct ctgttgtaag
1381 aataggcatt aacacaaagg aggcgtctcg ggagaggatt aggttccatc ctttacgtgt
1441 ttaaaaaaaa gcataaaaac attttaaaaa catagaaaaa ttcagcaaac cattttaaa
1501 gtagaagagg gttttaggta gaaaaacata ttcttgtgct tttcctgata aagcacagct
1561 gtagtggggt tctaggcatc tctgtacttt gcttgctcat atgcatgtag tcactttata
1621 agtcattgta tgttattata ttccgtaggt agatgtgtaa cctcttcacc ttattcatgg
1681 ctgaagtcac ctcttggtta cagtagcgta gcgtggccgt gtgcatgtcc tttgcgcctg
1741 tgaccaccac cccaacaaac catccagtga caaccatcc agtggaggtt tgtcgggcac
1801 cagccagcgt agcagggtcg ggaaaggcca cctgtcccac tcctacgata cgctactata
1861 aagagaagac gaaatagtga cataatatat tctatttta tactcttcct attttgtag
1921 tgacctgttt atgagatgct ggttttctac ccaacggccc tgcagccagc tcacgtccag
1981 gttcaaccca cagctacttg gtttgtgttc ttcttcatat tctaaaacca ttccatttcc
2041 aagcactttc agtccaatag gtgtaggaaa tagcgctgtt tttgttgtgt gtgcagggag
2101 ggcagttttc taatggaatg gtttgggaat atccatgtac ttgtttgcaa gcaggacttt
2161 gaggcaagtg tgggccactg tggtggcagt ggaggtgggg tgtttgggag gctgcgtgcc
2221 agtcaagaag aaaaaggttt gcattctcac attgccagga tgataagttc cttttcctttt
2281 ctttaaagaa gttgaagttt aggaatcctt tggtgccaac tggtgtttga aagtagggac
2341 ctcagaggtt tacctagaga acaggtggtt tttaagggtt atcttagatg tttcacaccg
2401 gaaggttttt aaacactaaa atatataatt tatagttaag gctaaaaagt atatttattg
2461 cagaggatgt tcataaggcc agtatgattt ataaatgcaa tctccccttg atttaaacac
2521 acagatacac acacacacac acacacacac acaaaccttc tgcctttgat gttacagatt
2581 taatacagtt tattttaaa gatagatcct tttataggtg agaaaaaaac aatctggaag
2641 aaaaaaacca cacaaagaca ttgattcagc ctgtttggcg tttcccagag tcatctgatt
2701 ggacaggcat gggtgcaagg aaaattaggg tactcaacct aagttcggtt ccgatgaatt
2761 cttatcccct gccccttcct ttaaaaaact tagtgacaaa atagacaatt tgcacatctt
2821 ggctatgtaa ttcttgtaat ttttatttag gaagtgttga agggaggtgg caagagtgtg
2881 gagctgacg tgtgagggag gacaggcggg aggaggtgtg aggaggaggc tcccgagggg
2941 aaggggcggt gcccacaccg gggacaggcc gcagctccat tttcttattg cgctgctacc
3001 gttgacttcc aggcacggtt tggaaatatt cacatcgctt ctgtgtatct ctttcacatt
3061 gtttgctgct attggaggat cagttttttg ttttacaatg tcatatactg ccatgtacta
3121 gttttagttt tctcttagaa cattgtatta cagatgcctt ttttgtagtt tttttttttt
3181 ttttatgtga tcaattttga cttaatgtga ttactgctct attccaaaaa ggttgctgtt
3241 tcacaatacc tcatgcttca cttagccatg gtggacccag cgggcaggtt ctgcctgctt
3301 tggcgggcag acacgcgggc gcgatcccac acaggctggc ggggccggc cccgagccg
3361 cgtgcgtgag aaccgcgccg gtgtcccag agaccaggct gtgtccctct tctcttccct
3421 gcgcctgtga tgctgggcac ttcatctgat cggggcgta gcatcatagt agttttaca
3481 gctgtgttat tctttgcgtg tagctatgga agttgcataa ttattattat tattattata
3541 acaagtgtgt cttacgtgcc accacggcgt tgtacctgta ggactctcat tcgggatgat
3601 tggaatagct tctggaattt gttcaagttt tgggtatgtt taatctgtta tgtactagtg
3661 ttctgtttgt tattgttttg ttaattacac cataatgcta atttaaagag actccaaatc
3721 tcaatgaagc cagctcacag tgctgtgtgc cccggtcatc tagcaagctg ccgaaccaaa
3781 agaatttgca ccccgctgcg ggcccacgtg gttggggccc tgccctggca gggtcatcct
3841 gtgctcggag gccatctcgg gcacaggccc accccgcccc acccctccag aacacggctc
3901 acgcttacct caaccatcct ggctgcggcg tctgtctgaa ccacgcgggg gccttgaggg
```

FIG 1. (cont'd)

```
3961 acgctttgtc tgtcgtgatg gggcaagggc acaagtcctg gatgttgtgt gtatcgagag
4021 gccaaaggct ggtggcaagt gcacggggca cagcggagtc tgtcctgtga cgcgcaagtc
4081 tgagggtctg ggcggcgggc ggctgggtct gtgcatttct ggttgcaccg cggcgcttcc
4141 cagcaccaac atgtaaccgg catgtttcca gcagaagaca aaaagacaaa catgaaagtc
4201 tagaaataaa actggtaaaa c (SEQ ID NO:30)
```

DUSP6

MIDTLRPVPFASEMAISKTVAWLNEQLELGNERLLLMDCRPQELYESSHIESAINVAIPGIMLRRLQKGNLPVRALF
TRGEDRDRFTRRCGTDTVVLYDESSSDWNENTGGESLLGLLLKKLKDEGCRAFYLEGGFSKFQAEFSLHCETNLDGS
CSSSSPPLPVLGLGGLRISSDSSSDIESDLDRDPNSATDSDGSPLSNSQPSFPVEILPFLYLGCAKDSTNLDVLEEF
GIKYILNVTPNLPNLFENAGEFKYKQIPISDHWSQNLSQFFPEAISFIDEARGKNCGVLVHCLAGISRSVTVTVAYL
MQKLNLSMNDAYDIVKMKKSNISPNFNFMGQLLDFERTLGLSSPCDNRVPAQQLYFTTPSNQNVYQVDSLQST
(SEQ ID NO:31)

```
   1 cttggaggga gggattagaa gccgctagac ttttttttcct cccctctcag tagcacggag
  61 tccgaattaa ttggatttca ttcactgggg aggaacaaaa actatctggg cagcttcatt
 121 gagagagatt cattgacact aagagccagc ggctgcagct gggtgcagag agaacctccg
 181 gctttacttc tgtctcgtct gccccaaccg ctagcctcgg cttgggtaag gcgaggcgga
 241 attaaacccc gctccgagag cggcagcttc gcgcgcggtg cgctcggcct atgcctgccc
 301 cgagggcgt ctggtaggca ccccgccctc tcccgcagct cgacccccat gatagatacg
 361 ctcagacccg tgcccttcgc gtcggaaatg gcgatcagca agacggtggc gtggctcaac
 421 gagcagctgg agctgggcaa cgagcggctg ctgctgatgg actgccggcc gcaggagcta
 481 tacgagtcgt cgcacatcga gtcggccatc aacgtggcca tcccgggcat catgctgcgg
 541 cgcctgcaga agggtaacct gccggtgcgc gcgctcttca cgcgcggcga ggaccgggac
 601 cgcttcaccc ggcgctgtgg caccgacaca gtggtgctct acgacgagag cagcagcgac
 661 tggaacgaga atacgggcgg cgagtcgttg ctcgggctgc tgctcaagaa gctcaaggac
 721 gagggctgcc gggcttctta cctggaaggt ggcttcagta agttccaagc cgagttctcc
 781 ctgcattgcg agaccaatct agacggctgc tgtagcagca gctcgccgcc gttgccagtg
 841 ctggggctcg gggcctgcg gatcagctct gactcttcct cggacatcga gtctgacctt
 901 gaccgagacc ccaatagtgc aacagactcg gatggtagtc cgctgtccaa cagccagcct
 961 tccttcccag tggagatctt gcccttcctc tacttgggct gtgccaaaga ctccaccaac
1021 ttggacgtgt tggaggaatt cggcatcaag tacatcttga acgtcacccc caatttgccg
1081 aatctctttg agaacgcagg agagtttaaa tacaagcaaa tccccatctc ggatcactgg
1141 agccaaaacc tgtcccagtt ttttcctgag gccatttctt tcatagatga agcccggggc
1201 aagaactgtg gtgtcttggt acattgcttg gctggcatta gccgctcagt cactgtgact
1261 gtggcttacc ttatgcagaa gctcaatctg tcgatgaacg atgcctatga cattgtcaaa
1321 atgaaaaaat ccaacatatc ccctaacttc aacttcatgg gtcagctgct ggacttcgag
1381 aggacgctgg gactcagcag cccatgtgac aacagggttc cagcacagca gctgtatttt
1441 accaccccctt ccaaccagaa tgtataccag gtggactctc tgcaatctac gtgaaagacc
1501 ccacatccct ccttgctgga atgtgtctgg cccttcagca gtttctcttg gcagcatcag
1561 ctgggctgct ttctttgtgt gtggcccag gtgtcaaaat gacaccagct gtctgtacta
1621 gacaaggtta ccaagtgcgg aattggttaa tactaacaga gagatttgct ccattctctt
1681 tggaataaca ggacatgctg tatagataca ggcagtaggt ttgctctgta cccatgtgta
1741 cagcctaccc atgcagggac tgggattcga ggacttccag cgcataggg tagaaccaaa
1801 tgataggta ggagcatgtg ttctttaggg ccttgtaagg ctgtttcctt ttgcatctgg
1861 aactgactat ataattgtct tcaatgaaga ctaattcaat tttgcatata gaggagccaa
1921 agagagattt cagctctgta tttgtggtat cagtttggaa aaaaaaatct gatactccat
```

FIG 1. (cont'd)

```
1981 ttgattattg taaatatttg atcttgaatc acttgacagt gtttgtttga attgtgtttg
2041 ttttttcctt tgatgggctt aaaagaaatt atccaagggg agaaagagca gtatgccact
2101 tcttaaaaca gaacaaaaca aaaaaagaaa attgtgctct tttctaatcc aaagggtata
2161 tttgcagcat gcttgacttt accaattctg atgacatctt tacggacact attatcacta
2221 agaccttgtt atggcgaagt ctttagtctt tttcatgtat tttcctcatg attttttctc
2281 tttatgtagt ttgactatgc cttacctttg taaatatttt tgcttgtgtt gtcgcaaagg
2341 ggataatctg ggaaagacac caaatcatgg gctcactta aaaaaagaaa gaataaaaaa
2401 accttcagct gtgctaaaca gtatattacc tctgtataaa attcttcagg gagtgtcacc
2461 tcaaatgcaa tactttgggt tggtttcttt cctttaaaaa aatttgtata aactggaag
2521 tgtgtgtgtg tgagcatggg tacccatttg ataagagaaa tgcatttgat tgtgaagaag
2581 ggagagttaa attctccatt atgttcgtgg tgtaaagttt agagctggaa tttattataa
2641 gaatgtaaaa ccttaaatta ttaataaata actattttgg ctattgaaaa aaaaaaaaaa
2701 aaaaaaaaaa (SEQ ID NO:32)
```

POLR1C

MAASQAVEEMRSRVVLGEFGVRNVHTTDFPGNYSGYDDAWDQDRFEKNFRVDVVHMDENSLEFDMVGIDAAIANAFR
RILLAEVPTMAVEKVLVYNNTSIVQDEILAHRLGLIPIHADPRLFEYRNQGDEEGTEIDTLQFRLQVRCTRNPHAAK
DSSDPNELYVNHKVYTRHMTWIPLGNQADLFPEGTIRPVHDDILIAQLRPGQEIDLLMHCVKGIGKDHAKFSPVATA
SYRLLPDITLLEPVEGEAAEELSRCFSPGVIEVQEVQGKKVARVANPRLDTFSREIFRNEKLKKVVRLARVRDHYIF
SVESTGVLPPDVLVSEAIKVLMGKCRRFLDELDAVQMD (SEQ ID NO:33)

```
   1 gagagagaga agatggcggc ttctcaggcg gtggaggaaa tgcggagccg cgtggttctg
  61 ggggagtttg gggttcgcaa tgtccatact actgactttc ccggtaacta ttccggttat
 121 gatgatgcct gggaccagga ccgcttcgag aagaatttcc gtgtggatgt agtacacatg
 181 gatgaaaact cactggagtt tgacatggtg ggaattgacg cagccattgc caatgctttt
 241 cgacgaattc tgctagctga ggtgccaact atggctgtgg agaaggtcct ggtgtacaat
 301 aatacatcca ttgttcagga tgagattctt gctcaccgtc tggggctcat tcccattcat
 361 gctgatcccc gtcttttga gtatcggaac caaggagatg aagaaggcac agagatagat
 421 actctacagt ttcgtctcca ggtcagatgc actcggaacc ccatgctgc taaagattcc
 481 tctgacccca acgaactgta cgtgaaccac aaagtgtata ccaggcatat gacatggatc
 541 cccctgggga accaggctga tctcttttca gagggcacta tccgaccagt gcatgatgat
 601 atcctcatcg ctcagctgcg gcctggccaa gaaattgacc tgctcatgca ctgtgtcaag
 661 ggcattggca agatcatgc aagttttca ccagtggcaa cagccagtta caggctcctg
 721 ccagacatca ccctgcttga gcccgtggaa ggggaggcag ctgaggagtt gagcaggtgc
 781 ttctcacctg gtgttattga ggtgcaggaa gtccaaggta aaaaggtggc cagagttgcc
 841 aaccccggc tggataccct cagcagagaa atcttccgga atgagaagct aaagaaggtt
 901 gtgaggcttg cccgggttcg agatcattat atcttctctg ttgagtcaac gggggtgttg
 961 ccaccagatg tgctggtgag tgaagccatc aaagtactga tggggaagtg ccggcgcttc
1021 ttgatgaac tagatgcggt tcagatggac tgagcttgga tgcttctgag gcaagctgaa
1081 gctttgggtt ctgactgacc caccctacag gactgctgaa cagagagccc agtgtgacta
1141 gggatcctga gttttctggg acaattccag ctttaatcaa tacattttgt taaatgtgcc
1201 ataaaatgag acttttacg cctttataag gcttagatg taaataaact cacccaaaca
1261 aaaaaaaaa aaaaaa (SEQ ID NO:34)
```

FIG 1. (cont'd)

RRS1

MEGQSVEELLAKAEQDEAEKLQRITVHKELELQFDLGNLLASDRNPPTGLRCAGPTPEAELQALARDNTQLLINQLW
QLPTERVEEAIVARLPEPTTRLPREKPLPRPRPLTRWQQFARLKGIRPKKKTNLVWDEVSGQWRRRWGYQRARDDTK
EWLIEVPGNADPLEDQFAKRIQAKKERVAKNELNRLRNLARAHKMQLPSAAGLHPTGHQSKEELGRAMQVAKVSTAS
VGRFQERLPKEKVPRGSGKKRKFQPLFGDFAAEKKNQLELLRVMNSKKPQLDVTRATNKQMREEDQEEAAKRRKMSQ
KGKRKGGRQGPGGKRKGGPPSQGGKRKGGLGGKMNSGPPGLGGKRKGGQRPGGKRRK (SEQ ID NO:35)

```
   1 cacgtggtta tgctgccgga gtttgggccg ccactgtagg aaaagtaact tcagctgcag
  61 ccccaaagcg agtgagccga gccggagcca tggagggcca gagcgtggag gagctgctcg
 121 caaaggcaga gcaggacgag gcagagaagt tgcaacgcat cacggtgcac aaggagctgg
 181 agctgcagtt tgacctgggc aacctgctgg cgtcggaccg gaaccccccg accgggctgc
 241 ggtgcgccgg acccacgccg gaggccgagc tacaggccct ggcgcgggac aacacgcaac
 301 tgctcatcaa ccagctgtgg cagctgccca cggagcgcgt ggaagaggcg atagtggcgc
 361 ggctgccgga gcccaccaca cgcctgccgc gagagaagcc tctgccccga ccgcggccac
 421 ttacacgctg gcagcagttc gcgcgcctca agggcatccg tcccaagaag aagaccaacc
 481 tggtgtggga cgaggtgagt ggccagtggc ggcggcgctg gggctaccag cgcgcccggg
 541 acgacaccaa agaatggctg attgaggtgc ccggcaatgc cgacccttg gaggaccagt
 601 tcgccaagcg gattcaggcc aagaaggaaa gggtggccaa gaacgagctg aaccggctgc
 661 gtaacctggc ccgcgcgcac aagatgcagc tgcccagcgc ggccggcttg caccctaccg
 721 gacaccagag taaggaggag ctgggccgcg ccatgcaagt ggccaaggtc tccaccgcct
 781 ctgtggggcg cttccaggag cgcctcccca aggagaaggt gccccggggc tccggcaaga
 841 aaaggaagtt tcaacccctt ttcggggact tgcagccga gaaaaagaac cagttggagc
 901 tgcttcgtgt catgaacagc aagaagcctc agctggatgt gactagggcc accaataagc
 961 agatgaggga ggaggaccag gaggaggccg ccaagaggag gaaaatgagc cagaagggca
1021 agagaaaggg aggccggcag gggcctgggg gcaagaggaa aggggcccg cccagccagg
1081 gagggaagag gaaaggggc ttgggaggca agatgaattc tgggccgcct ggcttgggtg
1141 gcaagagaaa aggaggacag cgcccaggag gaaagaggag gaagtaatag tttctaactg
1201 tcggacccgt ctgtaaacca aggactatga atactaaatg ttaagttcta ggcaattata
1261 cggggactca gaaggacctg gccgctgcct tcattgagtt taagggaca ggattgccct
1321 tccgtcaaga aagtatgtaa gtgttggact gcacaaatta atgttttcc cacaaccgag
1381 actttggaga ttaagaactt atttgaggat ttaagaatta gggaataat ttggtggaaa
1441 ccgggaatga gttctattct taaacagcct ttttttttct ttttaatgtt ggatatacgg
1501 cgaggtagag ttggccatat ttcagagact tagattacg tatatgtttc tgcattattt
1561 ttacaacaag tttgtgtatc agagcgggag tgcgggggag ggaaagaaaa caaacagttt
1621 cagaattgaa taggcaagtg actgttttaa agattaagta ataaagatgt cttatctagt
1681 gtgacttta aaaaaaaaa aaaaaaaa (SEQ ID NO:36)
```

PHLDA2

MKSPDEVLREGELEKRSDSLFQLWKKKRGVLTSDRLSLFPASPRARPKELRFHSILKVDCVERTGKYVYFTIVTTDH
KEIDFRCAGESCWNAAIALALIDFQNRRALQDFRSRQERTAPAAPAEDAVAAAAAPSEPSEPSRPSPQPKPRTP
(SEQ ID NO:37)

```
   1 agagccggcg ccgtcaccgc ccgcattgcc gctcccagtc ccgcgctcgg cacgacatga
  61 aatccccga cgaggtgcta cgcgagggcg agttggagaa gcgcagcgac agcctcttcc
 121 agctatggaa gaagaagcgc ggggtgctca cctccgaccg cctgagcctg ttccccgcca
 181 gccccgcgc gcgccccaag gagctgcgct ccactccat cctcaaggtg gactgcgtgg
```

FIG 1. (cont'd)

```
241 agcgcacggg caagtacgtg tacttcacca tcgtcaccac cgaccacaag gagatcgact
301 tccgctgcgc gggcgagagc tgctggaacg cggccatcgc gctggcgctc atcgatttcc
361 agaaccgccg cgccctgcag gactttcgca gccgccagga acgcaccgca cccgccgcac
421 ccgccgagga cgccgtggct gccgcggccg ccgcaccctc cgagccctcg gagccctcca
481 ggccatcccc gcagcccaaa ccccgcacgc catgagcccg ccgcgggcca tacgctggac
541 gagtcggacc gaggctagga cgtggccggc gctctccagc cctgcagcag aagaacttcc
601 cgtgcgcgcg gatcctcgct ccgttgcacg ggcgccttaa gttattggac tatctaatat
661 ctatgtattt atttcgctgg ttctttgtag tcacatattt tatagtctta atatcttgtt
721 tttgcatcac tgtgcccatt gcaaataaat cacttggcca (SEQ ID NO:38)
```

ST8SIA1

MAVLAWKFPRTRLPMGASALCVVVLCWLYIFPVYRLPNEKEIVQGVLQQGTAWRRNQTAARAFRKQMEDCCDPAHLF
AMTKMNSPMGKSMWYDGEFLYSFTIDNSTYSLFPQATPFQLPLKKCAVVGNGGILKKSGCGRQIDEANFVMRCNLPP
LSSEYTKDVGSKSQLVTANPSIIRQRFQNLLWSRKTFVDNMKIYNHSYIYMPAFSMKTGTEPSLRVYYTLSDVGANQ
TVLFANPNFLRSIGKFWKSRGIHAKRLSTGLFLVSAALGLCEEVAIYGFWPFSVNMHEQPISHHYYDNVLPFSGFHA
MPEEFLQLWYLHKIGALRMQLDPCEDTSLQPTS (SEQ ID NO:39)

```
  1 tccgctgcca cttcgcctag ctttgtgctg aggccccggc ccccgccccct gggacgccgg
 61 ggctgcgatg agccctgcg ggcgggcccg gcgacaaacg tccagagggg ccatggctgt
121 actggcgtgg aagttccgc ggacccggct gccatggga gccagtgccc tctgtgtcgt
181 ggtcctctgt tggctctaca tcttccccgt ctaccggctg cccaacgaga aagagatcgt
241 gcagggggtg ctgcaacagg gcacggcgtg gaggaggaac cagaccgcgg ccagagcgtt
301 caggaaacaa atggaagact gctgcgaccc tgcccatctc tttgctatga ctaaaatgaa
361 ttcccctatg gggaagagca tgtggtatga cggggagttt ttatactcat tcaccattga
421 caattcaact tactctctct cccacaggc aaccccattc cagctgccat tgaagaaatg
481 cgcggtggtg ggaaatggtg ggattctgaa gaagagtggc tgtggccgtc aaatagatga
541 agcaaatttt gtcatgcgat gcaatctccc tccttttgtca agtgaataca ctaaggatgt
601 tggatccaaa agtcagttag tgacagctaa tcccagcata attcggcaaa ggtttcagaa
661 ccttctgtgg tccagaaaga catttgtgga caacatgaaa atttataacc acagttacat
721 ctacatgcct gccttttcta tgaagacagg aacagagcca tcttttgaggg tttattatac
781 actgtcagat gttggtgcca atcaaacagt gctgtttgcc aaccccaact ttctgcgtag
841 cattggaaag ttctggaaaa gtagaggaat ccatgccaag cgcctgtcca caggacttt
901 tctggtgagc gcagctctgg gtctctgtga agaggtggcc atctatggct tctggcccctt
961 ctctgtgaat atgcatgagc agcccatcag ccaccactac tatgacaacg tcttacccctt
1021 ttctggcttc catgccatgc ccgaggaatt tctccaactc tggtatcttc ataaaatcgg
1081 tgcactgaga atgcagctgg acccatgtga agatacctca ctccagccca cttcctagga
1141 acaatggaag aagaaaggac tgaaccaggg tattttttgtt aggttttcta tgtgactcca
1201 agagggaatg gtcaagttgt ttcatgagtt tgcatgggcc cttggaaaaa caggaaagga
1261 gcaatgaaga tccaagcaaa actttacttt cagcgttggc ttggaggaca aataagaaat
1321 gaaacatcct atgaaatact ttatagcaca tggcagattt gcaactagta aaatgctggt
1381 gaaatgctgt tggtaaagca catggtccaa atctagaaga tgcagttcaa aaacaagaca
1441 gactcgagtt gttagggctg aggaaccaat caaggtagaa caaagaaaat gttggggtaa
1501 aagtgttgct gattgtcaac acaaactggc ttaataatat taataagaac ctgtcttatt
1561 aagactggct ttagaaccgt aggttttttt aaaaaattat tatttatttt tgccctcttt
1621 ggggaagtgg gtgggtagat ttaaaaaatc (SEQ ID NO:40)
```

FIG 1. (cont'd)

GRIN1

MSTMRLLTLALLFSCSVARAACDPKIVNIGAVLSTRKHEQMFREAVNQANKRHGSWKIQLNATSVTHKPNAIQMALS
VCEDLISSQVYAILVSHPPTPNDHFTPTPVSYTAGFYRIPVLGLTTRMSIYSDKSIHLSFLRTVPPYSHQSSVWFEM
MRVYSWNHIILLVSDDHEGRAAQKRLETLLEERESKAEKVLQFDPGTKNVTALLMEAKELEARVIILSASEDDAATV
YRAAAMLNMTGSGYVWLVGEREISGNALRYAPDGILGLQLINGKNESAHISDAVGVVAQAVHELLEKENITDPPRGC
VGNTNIWKTGPLFKRVLMSSKYADGVTGRVEFNEDGDRKFANYSIMNLQNRKLVQVGIYNGTHVIPNDRKIIWPGGE
TEKPRGYQMSTRLKIVTIHQEPFVYVKPTLSDGTCKEEFTVNGDPVKKVICTGPNDTSPGSPRHTVPQCCYGFCIDL
LIKLARTMNFTYEVHLVADGKFGTQERVNNSNKKEWNGMMGELLSGQADMIVAPLTINNERAQYIEFSKPFKYQGLT
ILVKKEIPRSTLDSFMQPFQSTLWLLVGLSVHVVAVMLYLLDRFSPFGRFKVNSEEEEEDALTLSSAMWFSWGVLLN
SGIGEGAPRSFSARILGMVWAGFAMIIVASYTANLAAFLVLDRPEERITGINDPRLRNPSDKFIYATVKQSSVDIYF
RRQVELSTMYRHMEKHNYESAAEAIQAVRDNKLHAFIWDSAVLEFEASQKCDLVTTGELFFRSGFGIGMRKDSPWKQ
NVSLSILKSHENGFMEDLDKTWVRYQECDSRSNAPATLTFENMAGVFMLVAGGIVAGIFLIFIEIAYKRHKDARRKQ
MQLAFAAVNVWRKNLQQYHPTDITGPLNLSDPSVSTVV (SEQ ID NO:41)

```
   1 gcccgcggcc cgagcccatg agcaccatgc gcctgctgac gctcgccctg ctgttctcct
  61 gctccgtcgc ccgtgccgcg tgcgacccca agatcgtcaa cattggcgcg gtgctgagca
 121 cgcggaagca cgagcagatg ttccgcgagg ccgtgaacca ggccaacaag cggcacggct
 181 cctggaagat tcagctcaat gccacctccg tcacgcacaa gcccaacgcc atccagatgg
 241 ctctgtcggt gtgcgaggac ctcatctcca gccaggtcta cgccatccta gttagccatc
 301 cacctacccc caacgaccac ttcactccca ccctgtctc ctacacagcc ggcttctacc
 361 gcatacccgt gctggggctg accaccgca tgtccatcta tcggacaag agcatccacc
 421 tgagcttcct gcgcaccgtg ccgccctact ccaccagtc cagcgtgtgg tttgagatga
 481 tgcgtgtcta cagctggaac cacatcatcc tgctggtcag cgacgaccac gagggccggg
 541 cggctcagaa acgcctggag acgctgctgg aggagcgtga gtccaaggca gagaaggtgc
 601 tgcagtttga cccagggacc aagaacgtga cggccctgct gatggaggcg aaagagctgg
 661 aggcccggt catcatcctt tctgccagcg aggacgatgc tgccactgta taccgcgcag
 721 ccgcgatgct gaacatgacg ggctccgggt acgtgtggct ggtcggcgag cgcgagatct
 781 cggggaacgc cctgcgctac gccccggacg gcatcctcgg gctgcagctc atcaacggca
 841 agaacgagtc ggcccacatc agcgacgccg taggcgtggt ggcccaggcc gtgcacgagc
 901 tcctcgagaa ggagaacatc accgacccgc cgcggggctg cgtgggcaac accaacatct
 961 ggaagaccgg gccgctcttc aagagagtgc tgatgtcttc caagtatgcg gatggggtga
1021 ctggtcgcgt ggagttcaat gaggatgggg accggaagtt cgccaactac agcatcatga
1081 acctgcagaa ccgcaagctg gtgcaagtgg gcatctacaa tggcacccac gtcatcccta
1141 atgacaggaa gatcatctgg ccaggcggag agacagagaa gcctcgaggg taccagatgt
1201 ccaccagact gaagattgtg acgatccacc aggagccctt cgtgtacgtc aagcccacgc
1261 tgagtgatgg gacatgcaag gaggagttca cagtcaacgg cgacccagtc aagaaggtga
1321 tctgcaccgg gcccaacgac acgtcgccgg gcagccccg ccacacggtg cctcagtgtt
1381 gctacggctt ttgcatcgac ctgctcatca gctggcacg gaccatgaac ttcacctacg
1441 aggtgcacct ggtggcagat ggcaagttcg gcacacagga gcgggtgaac aacagcaaca
1501 agaaggagtg gaatgggatg atgggcgagc tgctcagcgg gcaggcagac atgatcgtgg
1561 cgccgctaac cataaacaac gagcgcgcgc agtacatcga gttttccaag cccttcaagt
1621 accagggcct gactattctg gtcaagaagg agattccccg gagcacgctg gactcgttca
1681 tgcagccgtt ccagagcaca ctgtggctgc tggtggggct gtcggtgcac gtggtggccg
1741 tgatgctgta cctgctggac cgcttcagcc ccttcggccg gttcaaggtg aacagcgagg
1801 aggaggagga ggacgcactg accctgtcct cggccatgtg gttctcctgg ggcgtcctgc
1861 tcaactccgg catcgggaa ggcgccccca agcttctc agcgcgcatc ctgggcatgg
1921 tgtgggccgg ctttgccatg atcatcgtgg cctcctacac cgccaacctg cggccttcc
1981 tggtgctgga ccggccgag gagcgcatca cgggcatcaa cgaccctcgg ctgaggaacc
2041 cctcggacaa gtttatctac gccacggtga agcagagctc cgtggatatc tacttccggc
```

FIG. 1 (cont'd)

```
2101 gccaggtgga gctgagcacc atgtaccggc atatggagaa gcacaactac gagagtgcgg
2161 cggaggccat ccaggccgtg agagacaaca agctgcatgc cttcatctgg gactcggcgg
2221 tgctggagtt cgaggcctcg cagaagtgcg acctggtgac gactggagag ctgttttcc
2281 gctcgggctt cggcataggc atgcgcaaag acagccctg gaagcagaac gtctccctgt
2341 ccatcctcaa gtcccacgag aatggcttca tggaagacct ggacaagacg tgggttcggt
2401 atcaggaatg tgactcgcgc agcaacgccc tgcgaccct tactttgag aacatggccg
2461 gggtcttcat gctggtagct ggggcatcg tggccgggat cttcctgatt ttcatcgaga
2521 ttgcctacaa gcggcacaag gatgctcgcc ggaagcagat gcagctggcc tttgccgccg
2581 ttaacgtgtg gcggaagaac ctgcagcagt accatcccac tgatatcacg ggcccgctca
2641 acctctcaga tccctcggtc agcaccgtgg tgtgaggccc ccggaggcgc ccacctgccc
2701 agttagcccg gccaaggaca ctgatgggtc ctgctgctcg ggaaggcctg agggaagccc
2761 accgcccca gagactgccc accctgggcc tcccgtccgt ccgccgccc accccgctgc
2821 ctggcgggca gcccctgctg gaccaaggtg cggaccggag cggctgagga cggggcagag
2881 ctgagtcggc tgggcagggc cgcagggcgc tccggcagag gcagggccct ggggtctctg
2941 agcagtgggg agcggggcct aactggcccc aggcggaggg gcttggagca gagacggcag
3001 ccccatcctt cccgcagcac cagcctgagc cacagtgggg cccatggccc cagctggctg
3061 ggtcgcccct cctcgggcgc ctgcgctcct ctgcagcctg agctccaccc tcccctcttc
3121 ttgcggcacc gcccacccac accccgtctg ccccttgacc ccacacgccg gggctggccc
3181 tgccctcccc cacggccgtc cctgacttcc cagctgcagc gcctcccgcc gcctcgggcc
3241 gcctc (SEQ ID NO:42)
```

NFKB2

MESCYNPGLDGIIEYDDFKLNSSIVEPKEPAPETADGPYLVIVEQPKQRGFRFRYGCEGPSHGGLPGASSEKGRKTY
PTVKICNYEGPAKIEVDLVTHSDPPRAHAHSLVGKQCSELGICAVSVGPKDMTAQFNNLGVLHVTKKNMMGTMIQKL
QRQRLRSRPQGLTEAEQRELEQEAKELKKVMDLSIVRLRFSAFLRASDGSFSLPLKPVISQPIHDSKSPGASNLKIS
RMDKTAGSVRGGDEVYLLCDKVQKDDIEVRFYEDDENGWQAFGDFSPTDVHKQYAIVFRTPPYHKMKIERPVTVFLQ
LKRKRGGDVSDSKQFTYYPLVEDKEEVQRKRRKALPTFSQPFGGGSHMGGGSGGAAGGYGGAGGGGSLGFFPSSLAY
SPYQSGAGPMGCYPGGGGGAQMAATVPSRDSGEEAAEPSAPSRTPQCEPQAPEMLQRAREYNARLFGLAQRSARALL
DYGVTADARALLAGQRHLLTAQDENGDTPLHLAIIHGQTSVIEQIVYVIHHAQDLGVVNLTNHLHQTPLHLAVITGQ
TSVVSFLLRVGADPALLDRHGDSAMHLALRAGAGAPELLRALLQSGAPAVPQLLHMPDFEGLYPVHLAVRARSPECL
DLLVDSGAEVEATERQGGRTALHLATEMEELGLVTHLVTKLRANVNARTFSAS (SEQ ID NO:43)

```
  1 atggagagtt gctacaaccc aggtctggat ggtattattg aatatgatga tttcaaattg
 61 aactcctcca ttgtggaacc caaggagcca gccccagaaa cagctgatgg cccctacctg
121 gtgatcgtgg aacagcctaa gcagagaggc ttccgatttc gatatggctg tgaaggcccc
181 tccatggag gactgcccgg tgcctccagt gagaagggcc gaaagaccta tcccactgtc
241 aagatctgta actacgaggg accagccaag atcgaggtgg acctggtaac acacagtgac
301 ccacctcgtg ctcatgccca cagtctggtg ggcaagcaat gctcggagct ggggatctgc
361 gccgtttctg tggggcccaa ggacatgact gcccaattta caacctgggg tgtcctgcat
421 gtgactaaga gaacatgat ggggactatg atacaaaaac ttcagaggca gcggctccgc
481 tctaggcccc agggccttac ggaggccgag cagcgggagc tggagcaaga ggccaaagaa
541 ctgaagaagg tgatggatct gagtatagtg cggctgcgct tctctgcctt ccttagagcc
601 agtgatggct ccttctccct gcccctgaag ccagtcatct cccagcccat ccatgacagc
661 aaatctccgg gggcatcaaa cctgaagatt tctcgaatgg acaagacagc aggctctgtg
721 cggggtggag atgaagttta tctgctttgt gacaaggtgc agaaagatga cattgaggtt
781 cggttctatg aggatgatga aatggatgg caggcctttg gggacttctc tccacagat
841 gtgcataaac agtatgccat tgtgttccgg acaccccct atcacaagat gaagattgag
901 cggcctgtaa cagtgtttct gcaactgaaa cgcaagcgag aggggacgt gtctgattcc
```

FIG 1. (cont'd)

```
 961 aaacagttca cctattaccc tctggtggaa gacaaggaag aggtgcagcg gaagcggagg
1021 aaggccttgc ccaccttctc ccagcccttc ggggtggct cccacatggg tggaggctct
1081 gggggtgcag ccggggggcta cggaggagct ggaggaggtg gcagcctcgg tttcttcccc
1141 tcctccctgg cctacagccc ctaccagtcc ggcgcgggcc ccatgggctg ctacccggga
1201 ggcgggggcg gggcgcagat ggccgccacg gtgcccagca gggactccgg ggaggaagcc
1261 gcggagccga gcgcccccct caggacccc cagtgcgagc cgcaggcccc ggagatgctg
1321 cagcgagctc gagagtacaa cgcgcgcctg ttcggcctgc cgcagcgcag cgcccgagcc
1381 ctactcgact acggcgtcac cgcggacgcg cgcgcgctgc tggcggggaca gcgccacctg
1441 ctgacggcgc aggacgagaa cggagacaca ccactgcacc tagccatcat ccacgggcag
1501 accagtgtca ttgagcagat agtctatgtc atccaccacg cccaggacct cggcgttgtc
1561 aacctcacca accacctgca ccagacgccc ctgcacctgg cggtgatcac ggggcagacg
1621 agtgtggtga gctttctgct gcgggtaggt gcagacccag ctctgctgga tcggcatgga
1681 gactcagcca tgcatctggc gctgcgggca ggcgctggtg ctcctgagct gctgcgtgca
1741 ctgcttcaga gtggagctcc tgctgtgccc cagctgttgc atatgcctga ctttgaggga
1801 ctgtatccag tacacctggc ggtccgagcc gaagccctg agtgcctgga tctgctggtg
1861 gacagtgggg ctgaagtgga ggccacagag cggcagggg gacgaacagc cttgcatcta
1921 gccacagaga tggaggagct ggggttggtc acccatctgg tcaccaagct ccgggccaac
1981 gtgaacgctc gcacctttc agcctcctga (SEQ ID NO:44)
```

ETV4

MASTDYSTYSQAAAQQGYSAYTAQPTQGYAQTTQAYGQQSYGTYGQPTDVSYTQAQTTATYGQTAYATSYGQPPTGY
TTPTAPQAYSQPVQGYGTGAYDTTTATVTTTQASYAAQSAYGTQPAYPAYGQQPAATAPTRPQDGNKPTETSQPQSS
TGGYNQPSLGYGQSNYSYPQVPGSYPMQPVTAPPSYPPTSYSSTQPTSYDQSSYSQQNTYGQPSSYGQQSSYGQQSS
YGQQPPTSYPPQTGSYSQAPSQYSQQSSSYGQQNVTGCASMYLHTEGFSGPSPGDGAMGYGYEKPLRPFPDDVCVVP
EKFEGDIKQEGVGAFREGPPYQRRGALQLWQFLVALLDDPTNAHFIAWTGRGMEFKLIEPEEVARLWGIQKNRPAMN
YDKLSRSLRYYYEKGIMQKVAGERYVYKFVCEPEALFSLAFPDNQRPALKAEFDRPVSEEDTVPLSHLDESPAYLPE
LAGPAQPFGPKGGYSY (SEQ ID NO:45)

```
   1 agagggagac ggacgttgag agaacgagga ggaaggagag aaaatggcgt ccacggatta
  61 cagtacctat agccaagctg cagcgcagca gggctacagt gcttacaccg cccagcccac
 121 tcaaggatat gcacagacca cccaggcata tgggcaacaa agctatggaa cctatggaca
 181 gcccactgat gtcagctata cccaggctca gaccactgca acctatgggc agaccgccta
 241 tgcaacttct tatggacagc ctcccactgg ttatactact ccaactgccc cccaggcata
 301 cagccagcct gtccaggggt atggcactgg tgcttatgat accaccactg ctacagtcac
 361 caccacccag gcctcctatg cagctcagtc tgcatatggc actcagcctg cttatccagc
 421 ctatggcag cagccagcag ccactgcacc tacaagaccg caggatggaa acaagcccac
 481 tgagactagt caacctcaat ctagcacagg gggttacaac cagcccagcc taggatatgg
 541 acagagtaac tacagttatc ccaggtacc tgggagctac cccatgcagc cagtcactgc
 601 acctccatcc taccctccta ccagctattc ctctacacag ccgactagtt atgatcagag
 661 cagttactct cagcagaaca cctatgggca accgagcagc tatggacagc agagtagcta
 721 tggtcaacaa agcagctatg gcagcagcc tccactagt tacccacccc aaactggatc
 781 ctacagccaa gctccaagtc aatatagcca acagagcagc agctacgggc agcagaatgt
 841 caccgggtgc gcatcaatgt acctccacac agagggcttc tctgggccct ctccaggtga
 901 cggggccatg ggctatggct atgagaaacc tctgcgacca ttcccagatg atgtctgcgt
 961 tgtccctgag aaatttgaag gagacatcaa gcaggaaggg gtcggtgcat tcgagaggg
```

FIG. 1 (cont'd)

```
1021 gccgccctac cagcgccggg gtgccctgca gctgtggcaa tttctggtgg ccttgctgga
1081 tgacccaaca aatgcccatt tcattgcctg gacgggccgg ggaatggagt tcaagctcat
1141 tgagcctgag gaggtcgcca ggctctgggg catccagaag aaccggccag ccatgaatta
1201 cgacaagctg agccgctcgc tccgatacta ttatgagaaa ggcatcatgc agaaggtggc
1261 tggtgagcgt tacgtgtaca agtttgtgtg tgagcccgag gccctcttct ctttggcctt
1321 cccggacaat cagcgtccag ctctcaaggc tgagtttgac cggcctgtca gtgaggagga
1381 cacagtccct ttgtcccact tggatgagag ccccgcctac ctcccagagc tggctggccc
1441 cgcccagcca tttggcccca agggtggcta ctcttactag ccccagcgg ctgttccccc
1501 tgccgcaggt gggtgctgcc ctgtgtacat ataaatgaat ctggtgttgg ggaaaccttc
1561 atctgaaacc cacagatgtc tctgggcag atccccactg tcctaccagt tgccctagcc
1621 cagactctga gctgctcacc ggagtcattg ggaaggaaaa gtggagaaat ggcaagtcta
1681 gagtctcaga actcccctg ggggtttcac ctgggccctg gaggaattca gctcagcttc
1741 ttcctaggtc caagccccc acaccttttc cccaaccaca gagaacaaga gtttgttctg
1801 ttctggggga cagagaaggc gcttcccaac ttcatactgg caggagggtg aggaggttca
1861 ctgagctccc cagatctccc actgcgggga cacagaagcc tggactctgc cccacgctgt
1921 ggcctggag ggtcccggtt tgtcagttct tggtgctctg tgttcccaga ggcaggcgga
1981 ggttgaagaa aggaacctgg gatgaggggt gctgggtata agcagagagg gatgggttcc
2041 tgctccaagg gaccctttgc ctttcttctg ccctttccta ggcccaggcc tgggtttgta
2101 tcccatt (SEQ ID NO:46)
```

SPRED2

MTEETHPDDDSYIVRVKAVVMTRDDSSGGWFPQEGGGISRVGVCKVMHPEGNGRSGFLIHGERQKDKLVVLECYVRK
DLVYTKANPTFHHWKVDNRKFGLTFQSPADARAFDRGVRKAIEDLIEGSTTSSSTIHNEAELGDDDVFTTATDSSSN
SSQKREQPTRTISSPTSCEHRRIYTLGHLHDSYPTDHYHLDQPMPRPCRQVSFPDDDEEIVRINPREKIWMTGYEDY
RHAPVRGKYPDPSEDADSSYVRFAKGEVPKHDYNYPYVDSSDFGLGEDPKGRGGSVIKTQPSRGKSRRRKEDGERSR
CVYCRDMFNHEENRRGHCQDAPDSVRTCIRRVSCMWCADSMLYHCMSDPEGDYTDPCSCDTSDEKFCLRWMALIALS
FLAPCMCCYLPLRACYHCGVMCRCCGGKHKAAA (SEQ ID NO:47)

```
   1 cacgaggtgc acccottccc ccaaaccota tcccgcgccc tgcttcccct tctgctgcgg
  61 cgccctcttc atctctagcc gcccccctc cccaaatcag gcgatctccg gagatgtgaa
 121 gaaggggggc gagcggacag gaagatgaag ggagcaaagc tgcccgccgc gggacaggcg
 181 tctaggtaac aagaaaatga ccgaagaaac acaccagac gatgacagct atattgtgcg
 241 tgtcaaggct gtggttatga ccagagatga ctccagcggg gatggttcc cacaggaagg
 301 aggcgggatc agtcgcgtcg ggtctgtaa ggtcatgcac ccgaaggca atggacgaag
 361 cggctttctc atccatggtg aacgacagaa agacaaactg gtggtattgg aatgctatgt
 421 aagaaaggac ttggtctaca ccaaagccaa tccaacgttt catcactgga aggtcgataa
 481 taggaagttt ggacttactt tccaaagccc tgctgatgcc cgagcctttg acaggggagt
 541 aaggaaagca atcgaagacc ttatagaagg ttcaacaacg tcatcttcca ccatccataa
 601 tgaagctgag cttggcgatg atgacgtttt tacaacagct acagacagtt cttctaattc
 661 ctctcagaag agagagcaac ctactcggac aatctcctct cccacatcct gtgagcaccg
 721 gaggatttat accctgggcc acctccacga ctcatacccc acagaccact atcacctcga
 781 tcagccgatg ccaaggcct gccgccaggt gagcttcccg gacgacgacg aggagatcgt
 841 gcgcatcaac cccgggaga agatctggat gacggggtac gaggattacc ggcacgcacc
 901 cgtcagggc aagtacccgg accctcgga ggacgcggac tcctcctacg tgcgcttcgc
 961 caagggcgag gtccccaagc atgactacaa ctaccctac gtggactcct cagactttgg
1021 cctaggcgag gaccccaaag gccgcggggg cagcgtgatc aagacgcagc cctcccgggg
1081 caagtcgcgg cggcggaagg aggacggaga gcgctcgcgg tgcgtgtact gcagggacat
1141 gttcaaccac gaggagaacc gccgggccca ctgccaggac gcccccgact ccgtgagaac
```

FIG. 1 (cont'd)

```
1201 ttgcatccgc cgggtgagct gcatgtggtg cgcggacagc atgctctatc actgtatgtc
1261 ggaccccgag ggagactata cagacccttg ctcgtgcgat actagcgacg agaagttttg
1321 cctccggtgg atggctctta ttgccttgtc tttcctggcc cctgtatgt gctgttacct
1381 gccccttcgg gcctgctacc actgcggagt gatgtgcagg tgctgtggcg ggaagcacaa
1441 agcggccgcg tgactcagtt tccctccctt ctccctccat ccgcagccac aggggaactc
1501 gtctcttaca tactctcatc ttctcccccg ctcccttcca ctccaaggag cgaggagggc
1561 aagcggcctc ccagctccct ggtacctcga ggaccattc cagccaggga cgctgccggg
1621 tagactctcc actcccctg ccgccacac tgcagcagcc atccatac acacacgctc
1681 gcacagtgtt ctgaggaagg aaccttcgcc acagactcct gtactattaa caatctgtaa
1741 ccaagctaac tgtctcatcc atgtgttgat ttcctgtttc ctcctccccc gcctcttcca
1801 gttcaaagga gtctgcaatt ggaactgctg attttcggtg ggttttgtag ttgattttc
1861 caagagcgtc gaagactctc tttctcttgg ttcaccttgc ctgtcgctag caagcatctg
1921 gttcagcgga aatgggatgt gagaatgatg aaacccgaca gaagtatctc agcctgcagt
1981 cagttattat gtataggagg tgagctagtt aacaaacttg taccacaaaa caatatcgct
2041 ttaactttc taaagccaaa tttcccatgt aagctgcagt ttctatcttt agcccatcat
2101 cattttctgc ccccccaaaa tctgttgaaa tgattcactg atgcaaaaca ttcacccgta
2161 atagactgag aattgagcct taacttcaga ttaacttgtg agaatcagga aaattccttc
2221 aactgcattg catcctcttg gaccagggct agaatgggga tttcaggttt ctatgagcct
2281 ccccattacc cctaaagtag aacatttttt aaattgtgtt gccaccactt ctaaaaattt
2341 agcaatatta gaataggata ctagtgaagt aagaaatttt gcttgttgtt ttgcaaacca
2401 aatagtttcc tcaaacacaa atcagtgttc ccacgaacaa gttccagttg agaaacacta
2461 aggtatggt gaataaaacc atagggagct tcttcccccc aacccctggc tattttatat
2521 taatggggag aggggatttt taaatgtcat aaatttgaag agtggtgggt tgcattttct
2581 tcatgggttt atgttttcgt ttcattttgg actcaatttc acatcaccaa attcctcatt
2641 tatacttggg gaaaaaacaa ggccatatgt aaaaacccctt ccaatgccta agtgtctttc
2701 tcctgcaact ccaaacccag actcgccact ttgggtgcac aggtggttag gtcagccaac
2761 tggttctgcc tgtcgccttg ccacggagga ggcttctaat tagctggaaa agagtatttt
2821 tctaatacgt tgcaaggatt agccaaatct tcttattgaa gaaagaagaa aagtgaagag
2881 tggttaccta tacctagcat agtacaatca gaacctcgtg gagaccaccg gggacaggct
2941 tgcggacgcc ggctgttctt cccgccacga tcttctgtg gtagcggcca gcagaagaca
3001 tggcctgctc cccactccct ttcccactc cttctttatt gcacacagga caccagtctt
3061 caaggaaagg gacttttttc cagtctgcca atcatattgg gaaagtgcta gctgtgctca
3121 ccttcatggg gctgtttcca gctcgtccac aagctcatcg atttttcttta gtagattacc
3181 ggtgtaaata cccagtgtgc ttatgagtca gttagtagac gtcttcattc attggagtaa
3241 ctggtttagg cttttccagtt tggaaaagga gcagagagct gtccatctgg attgatggaa
3301 gaaaagagaa cctcatccat gctggagaa catctagaaa accttcagcc agcctccagt
3361 gctgtcgaga gaccaccttc cccgacccg gaggcacttc cttggggtct ttctctaggg
3421 tctcctctct acaaagcaca acactaatgt tcgtttcctt agacctcagt tcaagtgccc
3481 ctatttattt caataagaac gcacatatcc cagctgtttt ttgtttgtca cctctattta
3541 gttgttacct gtttctctct tctttcaccc cctgtccttt tccacccttt taagagttac
3601 gctagcagat cttactccac gtatactttt tggtttgtga aggcatcggt taagggcaca
3661 aagacagcca tgggacatt tatgtaaata cgtctctaat tgccacactg cagctgaaca
3721 gtgtgtagta ttttcccagt cagctttgcc atactgacgt caatcatttg agagaaatta
3781 ttcagatttt attttgtat ctgtggtaac aaaacattaa ccaaaagatt ttctgtccag
3841 aagcctcccc gacccccaa gctatttgct cacattaaca aattaaagtg cctgaagcat
3901 aattcattct ttacctgtat actaaaaacc ctgttgtatt gatttttta taataagcct
3961 ttttacctct gtgtaaaaaa tatatataca agtgtatgat gtacattta gttcttaact
4021 ttttttttat ggtttctaat atgtatgacc aatgtagcca ttgctttaaa atgtaccgtg
4081 taaatataaa cacatcctat cagaaaaaaa aaaaaaaa (SEQ ID NO:48)
```

FIG. 1 (cont'd)

ARID5A

RSGQPRAEGLGAGAAGPLRAMAAPVKGNRKQSTEGDALDPPASPKPAGKQNGIQNPISLEDSPEAGGEREEEQEREE
EQAFLVSLYKFMKERHTPIERVPHLGFKQINLWKIYKAVEKLGAYELVTGRRLWKNVYDELGGSPGSTSAATCTRRH
YERLVLPYVRHLKGEDDKPLPTSKPRKQYKMAKENRGDDGATERPKKAKEERRMDQMMPGKTKADAADPAPLPSQEP
PRNSTEQQGLASGSSVSFVGASGCPEAYKRLLSSFYCKGTHGIMSPLAKKKLLAQVSKVEALQCQEEGCRHGAEPQA
SPAVHLPESPQSPKGLTENSRHRLTPQEGLQAPGGSLREEAQAGPCPAAPIFKGCFYTHPTEVLKPVSQHPRDFFSR
LKDGVLLGPPGKEGLSVKEPQLVWGGDANRPSAFHKGGSRKGILYPKPKACWVSPMAKVPAESPTLPPTFPSSPGLG
SKRSLEEEGAAHSGKRLRAVSPFLKEADAKKCGAKPAGSGLVSCLLGPALGPVPPEAYRGTMLHCPLNFTGTPGPLK
GQAALPFSPLVIPAFPAHFLATAGPSPMAAGLMHFPPTSFDSALRHRLCPASSAWHAPPVTTYAAPHFFHLNTKL
(SEQ ID NO:49)

```
   1 cggtccggac agccgcgcgc tgagggtctc ggggcgggcg ccgcgggacc tctccgggcc 61 atggcagccc ctgtcaaagg gaacaggaag cagtccacgg agggtgacgc cctagaccca
 121 cctgcatccc ccaaacctgc tggcaagcag aacggaatcc agaacccat ctcgctggag
 181 gactcccccg aggcaggcgg ggagcggcag ggagagcagg agcgggagga ggagcaggcc
 241 ttcctggtca gcctctacaa gttcatgaag gagcgacaca cgcccatcga gagggtgccc
 301 catctcggct tcaagcagat taacctgtgg aagatctaca agcagtggag aagctggggg
 361 gcctatgagc tggtgaccgg cgccgcctc tggaagaacg tgtacgacga gctgggggc
 421 agcccaggca gcaccagcgc ggccacgtgc acgcgccgcc actacgagag gctggtcctg
 481 ccatacgtgc ggcacctgaa gggggaggat gacaagccgc tgcccacctc aagcccagg
 541 aaacagtaca agatggctaa ggagaacagg ggggatgatg gggccaccga gaggccgaag
 601 aaggccaagg aggagcggcg catggaccag atgatgccag aaagaccaa agcagatgct
 661 gctgacccag caccacttcc cagccaggag ccccccagga acagcacaga acagcagggc
 721 ctggcctctg gtcttctgt gtcctttgtg ggtgccagcg gctgtcctga ggcctacaag
 781 cggctcctat ccagcttcta ctgcaagggg acacacggca tcatgtcacc actggccaaa
 841 aagaagctcc tggcccaggt gagcaaggtg gaggccttgc agtgccagga ggagggctgc
 901 cgccatgggg cagagcccca ggcgtcccca gctgttcacc tcccagagag tccccagagc
 961 cccaaaggcc tgactgagaa ctccaggcac cggctgaccc ctcaggaggg attgcaggcc
1021 ccaggtggca gcctcagaga ggaggcgcag gcaggccct gcccggcagc cccatcttc
1081 aagggctgct ctacaccca ccccaccgag gtgctgaagc ctgtcagcca gcaccccagg
1141 gacttcttct ctagacttaa agatggggtg ctattggggc ctcctggcaa agaggggctg
1201 tcagtgaaag agccccagct ggtgtggggc ggagacgcta accgccttc tgcgttccat
1261 aaaggtggct ccagaaaggg catcctctac cccaagccca agcctgctg ggtgtcccc
1321 atgccaaagg tcccagccga gagcccacg ctcccgccca cttccccag tagcccaggc
1381 ctgggcagca agcgcagcct ggaggaagag ggtgctgccc acagtgggaa agagactgcgg
1441 gccgtgtctc cctttcttaa ggaggcggat gccaagaagt gtggggccaa acctgcaggg
1501 tccggcctgg tctcctgcct ctgggccca gcctggggc ctgtgccccc agaggcctac
1561 aggggcacca tgctgcactg cccgctgaac ttcactggca cccgggccc cttgaagggc
1621 caggctgcac tccccttcag cccctggtc atcccggcct tccggcca cttcctggcc
1681 accgcaggcc cctcgcccat ggccgctggc ctgatgcact cccccaac gtccttcgac
1741 agtgccctcc gccacagact tgcccggcc tcatctgcct ggcacgcacc accagtcaca
1801 acctatgcag cgccccactt cttccacctc aacaccaagc tgtaggccag cccatggtgt
1861 tgtgtacact gtggagtcga caggggccta acaggcag gtactgctgc caggggctc
1921 tgaactagtg cctgctaccc aggacacccg ggccatgccc ctggctgggc agcctggcac
```

FIG. 1 (cont'd)

```
1981 aagtgaagaa gaaggcagtg ggaaaactgg gtttatctca aggcagcagc ctgagcccag
2041 gagcagagga cccagttgtt ataaggcgct gggagaggat gggcagctcc cactgcccca
2101 gagcggasst cgaagcaccc aggttgccca cggaaaatcc aataaaaaga caccagtgtg
2161 aatccaaaaa aaa (SEQ ID NO:50)
```

SH3BP1

MMKRQLHRMRQLAQTGSLGRTPETAEFLGEDLLQVEQRLEPAKRAAHNIHKRLQACLQGQSGADMDKRVKKLPLMAL
STTMAESFKELDPDSSMGKALEMSCAIQNQLARILAEFEMTLERDVLQPLSRLSEEELPAILKHKKSLQKLVSDWNT
LKSRLSQATKNSGSSQGLGGSPGSHSHTTMANKVETLKEEEEELKRKVEQCRDEYLADLYHFVTKEDSYANYFIRLL
EIQADYHRRSLSSLDTALAELRENHGQADHSPSMTATHFPRVYGVSLATHLQELGREIALPIEACVMMLLSEGMKEE
GLFRLAAGASVLKRLKQTMASDPHSLEEFCSDPHAVAGALKSYLRELPEPLMTFDLYDDWMRAASLKEPGARLQALQ
EVCSRLPPENLSNLRYLMKFLARLAEEQEVNKMTPSNIAIVLGPNLLWPPEKEGDQAQLDAASVSSIQVVGVVEALI
QSADTLFPGDINFNVSGLFSAVTLQDTVSDRLASEEELPSTAVPTPATTPAPAPAPAPAPAPALASAATKERTESEVP
PRPASPKVTRSPPETAAPVEDMARRTKRPAPARPTMPPPQVSGSRSSPPAPPLPPGSGSPGTPQALPRRLVGSSLRA
PTVPPPLPPTPPQPARRQSRRSPASPSPASPGPASPSPVSLSNPAQVDLGAATAEGGAPEAISGVPTPPAIPPQPRP
RSLASETN (SEQ ID NO:51)

```
   1 cgcccaccca tccggggcaa gagccgcgcc gcaggagagg caggctggac cggggctcc
  61 ccgggccgc gaccccgcc gtgaccccgc agccccagc tgcccccaa gatgatgaag
 121 aggcagctgc accgcatgcg gcagctggcc cagacgggca gcttgggacg caccccggag
 181 accgctgagt tcctgggtga ggacctgctg caggtagaac agcggctgga gccggccaag
 241 cgggcagccc acaacatcca caagcggctg caggcctgtc tgcagggcca gagcggggca
 301 gacatggaca gcggtgaa gaagcttccc ctcatggctc tgtccaccac gatggctgag
 361 agcttcaagg agctggaccc tgattccagc atggggaagg ccttggagat gagctgtgcc
 421 atccagaatc agctggcccg catcctggcc gagtttgaga tgaccctgga gagggacgtc
 481 ctgcagccac tcagcaggct gagtgaggag gagctgccag ccatcctcaa acacaagaaa
 541 agcctccaga agctcgtgtc cgactggaac acactcaaga gcaggctcag tcaggcaacc
 601 aagaattcag gcagcagtca aggcctagga ggcagcccgg gtagtcacag ccatacgacc
 661 atggccaaca aggtggagac gctgaaggag gaggaggagg agctgaagag gaaagtggag
 721 caatgcaggg acgagtactt ggctgacctg taccactttg ttaccaagga ggactcctat
 781 gccaactact tcattcgtct cctggagatt caggccgatt accatcgcag gtcactgagc
 841 tcgctggaca cagccctggc tgagctgagg gagaaccacg gccaagcaga ccactcccct
 901 tcgatgacag ccacccactt ccccagggtg tatggggtgt cgctggcaac ccacctgcaa
 961 gagctgggcc gggagattgc cctgcccatc gaggcctgcg tcatgatgct gctttctgag
1021 ggcatgaagg aagagggtct cttccgtctg gctgctgggg cctcggtgct gaagcgtctc
1081 aagcagacaa tggcctcgga ccccacagc ctggaggagt tctgctccga cccgcacgct
1141 gtggcaggtg ccctcaagtc ctatctgcgg gagctgccag agcctctgat gaccttcgac
1201 ctctatgatg actggatgag ggcagccagc ctgaaggagc caggggcccg gctgcaggcc
1261 ctccaagagg tgtgcagccg cctaccccc gagaacctca gcaacctcag gtacctgatg
1321 aagttcctgg cacggctggc cgaggagcag gaggtgaaca agatgacacc cagcaacatc
1381 gccatagtcc tgggacccaa cttgctgtgg ccacctgaga aagaaggga ccaggcccag
1441 ctggatgcag cctccgtgtc ttccatccag gtggtgggcg tcgtcgaggc gctgatccag
1501 agcgcagaca ccctcttccc tggagacatc aacttcaacg tgtcaggcct cttctcagct
1561 gttaccctcc aggacacagt cagtgacagg ctggcctctg aggaacttcc gtccactgcc
1621 gtgccaccc cagccaccac cccggctccg gctccggctc cagctccagc tccggcccca
1681 gccttggctt cagcagctac caaggaaagg acagagtctg aggtgcctcc cagaccagcc
1741 tccccaagg tcaccaggag tccccggag acagctgccc cagtggagga catggctcgg
1801 aggaccaagc gcccggcgcc agcccggccc accatgccgc cccccaggt ctccggctcc
```

FIG. 1 (cont'd)

```
1861 cgctcctccc ctccagcccc gcccttgccc cctggctctg gcagccctgg gaccccccaa
1921 gccctgcccc gacgtctggt tggcagcagc ctccgagccc ccacagtgcc accccgtta
1981 cccccacac ccctcagcc tgcccggcgc caaagccggc gttcaccagc ctccccagc
2041 ccggcctccc caggtccagc ctcccccagc ccagtctctt tgagtaaccc tgcacaggtg
2101 gacctggggg ctgccacagc agagggagga gcccctgagg ctatcagtgg ggtcccact
2161 ccccagcta tcccccctca gccccgcccc aggagccttg cctcagagac caactgagtg
2221 gctggtttct ccctaagcag ccctcagcac ccctccctc cccacctggc cctcccagga
2281 cagctctcgc ccccacaaa ggggcatggg cctccagcct ttgcccacaa gtgcctcagt
2341 gcccactggg tcggccccca tggccaggag ggctcaggac aatcctctat ttcctgacct
2401 tttcctcgtc caccctgggc ttggggaccc ccccaccgga ctctccactc tccggcaggt
2461 cctagggag ccaccggaag gaaggagagg tttgcctgct cctacgggac tgattcttct
2521 cttgccgaca tgttttttgt aaggctggta aataaattat tttggacaaa actggaaaaa
2581 aaaaaaaaaa aa (SEQ ID NO:52)
```

MAP2K3

MESPASSQPASMPQSKGKSKRKKDLRISCMSKPPAPNPTPPRNLDSRTFITIGDRNFEVEADDLVTISELGRGAYGV
VEKVRHAQSGTIMAVKRIRATVNSQEQKRLLMDLDINMRTVDCFYTVTFYGALFREGDVWICMELMDTSLDKFYRKV
LDKNMTIPEDILGEIAVSIVRALEHLHSKLSVIHRDVKPSNVLINKEGHVKMCDFGISGYLVDSVAKTMDAGCKPYM
APERINPELNQKGYNVKSDVWSLGITMIEMAILRFPYESWGTPFQQLKQVVEEPSPQLPADRFSPEFVDFTAQCLRK
NPAERMSYLELMEHPFFTLHKTKKTDIAAFVKEILGEDS (SEQ ID NO:53)

```
   1 cggcgccgcc cgtcgcggac tcgtccttgc tgcagtcgcc gccgcagtcc tcgccgcagt
  61 cgccgccgcc gccgccgccg ccgccgctgc tcctccgcct ggcctgggca gtctgcccgc
 121 agccatgagc gtgctcggcc cggtggagc ccgcagtcct ctagattagt ctccaccgcc
 181 gtccaggacc cacttgcagc atggagtcgc ccgcctcgag ccagcccgcc agcatgcccc
 241 agtccaaagg aaaatccaag aggaagaagg atctacggat atcctgcatg tccaagccac
 301 ccgcacccaa ccccacaacc cccgaacc tggactcccg gaccttcatc accattggag
 361 acagaaactt tgaggtggag gctgatgact tggtgaccat ctcagaactg ggccgtggag
 421 cctatggggt ggtagagaag gtgcggcacg cccagagcgg caccatcatg gccgtgaagc
 481 ggatccgggc caccgtgaac tcacaggagc agaagcggct gctcatggac ctggacatca
 541 acatgcgcac ggtcgactgc ttctacactg tcaccttcta cggggcacta ttcagagagg
 601 gagacgtgtg gatctgcatg gagctcatgg acacatcctt ggacaagttc taccggaagg
 661 tgctggataa aacatgaca attccagagg acatccttgg ggagattgct gtgtctatcg
 721 tgcgggccct ggagcatctg cacagcaagc tgtcggtgat ccacagagat gtgaagccct
 781 ccaatgtcct tatcaacaag gagggccatg tgaagatgtg tgactttggc atcagtggct
 841 acttggtgga ctctgtggcc aagacgatgg atgccggctg caagccctac atggccctg
 901 agaggatcaa cccagagctg aaccagaagg gctacaatgt caagtccgac gtctggagcc
 961 tgggcatcac catgattgag atggccatcc tgcggttccc ttacgagtcc tgggggaccc
1021 cgttccagca gctgaagcag gtggtggagg agccgtcccc ccagctccca gccgaccgtt
1081 tctcccccga gtttgtggac ttcactgctc agtgcctgag gaagaacccc gcagagcgta
1141 tgagctacct ggagctgatg gagcacccct tcttcacctt gcacaaaacc aagaagacgg
1201 acattgctgc cttcgtgaag gagatcctgg agaagactc atagggctg ggcctcggac
1261 cccactccgg ccctccagag ccccacagcc ccatctgcgg gggcagtgct cacccacacc
1321 ataagctact gccatcctgg cccagggcat ctgggaggaa ccgaggggc tgctcccacc
1381 tggctctgtg gcgagccatt tgtcccaagt gccaaagaag cagaccattg gggctcccag
1441 ccaggccctt gtcggcccca ccagtgcctc tccctgctgc tcctaggacc cgtctccagc
1501 tgctgagatc ctggactgag ggggcctgga tgcccctgt ggatgctgct gccctgcac
1561 agcaggctgc cagtgcctgg gtggatgggc caccgccttg cccagcctgg atgccatcca
```

FIG. 1 (cont'd)

```
1621 agttgtatat ttttttaatc tctcgactga atggactttg cacactttgg cccagggtgg
1681 ccacacctct atcccggctt tggtgcgggg tacacaagag gggatgagtt gtgtgaatac
1741 cccaagactc ccatgaggga gatgccatga gccgcccaag gccttcccct ggcactggca
1801 aacagggcct ctgcggagca cactggctca cccagtcctg cccgccaccg ttatcggtgt
1861 cattcacctt tcgtgttttt tttaatttat cctctgttga ttttttcttt tgctttatgg
1921 gtttggcttg ttttcttgc atggtttgga gctgatcgct tctcccccac ccccctaggt
1981 accagcaggc agagccttgc cctctgctca ggctggggtc cagtgggagg ggcccaagat
2041 ctctgctcag agaagtgcag ggggagcctt ccagctcact ctccctgagg actggcttga
2101 cagggctat gggtttgctt tggtgttgtt tttaaaaaaa gaaaatatat tttttttgaaa
2161 aaacgactgc ccatcccggg tcctttccct gatgggttgg ggcagttacc tggttgctgt
2221 tttaattaaa aaaaaaaaaa aaaaaaaaaa aa (SEQ ID NO:54)
```

TNC

MGAMTQLLAGVFLAFLALATEGGVLKKVIRHKRQSGVNATLPEENQPVVFNHVYNIKLPVGSQCSVDLESASGEKDL
APPSEPSESFQEHTVDGENQIVFTHRINIPRRACGCAAAPDVKELLSRLEELENLVSSLREQCTAGAGCCLQPATGR
LDTRPFCSGRGNFSTEGCGCVCEPGWKGPNCSEPECPGNCHLRGRCIDGQCICDDGFTGEDCSQLACPSDCNDQGKC
VNGVCICFEGYAGADCSREICPVPCSEEHGTCVDGLCVCHDGFAGDDCNKPLCLNNCYNRGRCVENECVCDEGFTGE
DCSELICPNDCFDRGRCINGTCYCEEGFTGEDCGKPTCPHACHTQGRCEEGQCVCDEGFAGLDCSEKRCPADCHNRG
RCVDGRCECDDGFTGADCGELKCPNGCSGHGRCVNGQCVCDEGYTGEDCSQLRCPNDCHSRGRCVEGKCVCEQGFKG
YDCSDMSCPNDCHQHGRCVNGMCVCDDGYTGEDCRDRQCPRDCSNRGLCVDGQCVCEDGFTGPDCAELSCPNDCHGQ
GRCVNGQCVCHEGFMGKDCKEQRCPSDCHGQGRCVDGQCICHEGFTGLDCGQHSCPSDCNNLGQCVSGRCICNEGYS
GEDCSEVSPPKDLVVTEVTEETVNLAWDNEMRVTEYLVVYTPTHEGGLEMQFRVPGDQTSTIIQELEPGVEYFIRVF
AILENKKSIPVSARVATYLPAPEGLKFKSIKETSVEVEWDPLDIAFETWEIIFRNMNKEDEGEITKSLRRPETSYRQ
TGLAPGQEYEISLHIVKNNTRGPGLKRVTTTRLDAPSQIEVKDVTDTTALITWFKPLAEIDGIELTYGIKDVPGDRT
TIDLTEDENQYSIGNLKPDTEYEVSLISRRGDMSSNPAKETFTTGLDAPRNLRRVSQTDNSITLEWRNGKAAIDSYR
IKYAPISGGDHAEVDVPKSQQATTKTTLTGLRPGTEYGIGVSAVKEDKESNPATINAATELDTPKDLQVSETAETSL
TLLWKTPLAKFDRYRLNYSLPTGQWVGVQLPRNTTSYVLRGLEPGQEYNVLLTAEKGRHKSKPARVKASTEQAPELE
NLTVTEVGWDGLRLNWTAADQAYEHFIIQVQEANKVEAARNLTVPGSLRAVDIPGLKAATPYTVSIYGVIQGYRTPV
LSAEASTGETPNLGEVVVAEVGWDALKLNWTAPEGAYEYFFIQVQEADTVEAAQNLTVPGGLRSTDLPGLKAATHYT
ITIRGVTQDFSTTPLSVEVLTEEVPDMGNLTVTEVSWDALRLNWTTPDGTYDQFTIQVQEADQVEEAHNLTVPGSLR
SMEIPGLRAGTPYTVTLHGEVRGHSTRPLAVEVVTEDLPQLGDLAVSEVGWDGLRLNWTAADNAYEHFVIQVQEVNK
VEAAQNLTLPGSLRAVDIPGLEAATPYRVSIYGVIRGYRTPVLSAEASTAKEPEIGNLNVSDITPESFNLSWMATDG
IFETFTIEIIDSNRLLETVEYNISGAERTAHISGLPPSTDFIVYLSGLAPSIRTKTISATATTEALPLLENLTISDI
NPYGFTVSWMASENAFDSFLVTVVDSGKLLDPQEFTLSGTQRKLELRGLITGIGYEVMVSGFTQGHQTKPLRAEIVT
EAEPEVDNLLVSDATPDGFRLSWTADEGVFDNFVLKIRDTKKQSEPLEITLLAPERTRDLTGLREATEYEIELYGIS
KGRRSQTVSAIATTAMGSPKEVIFSDITENSATVSWRAPTAQVESFRITYVPITGGTPSMVTVDGTKTQTRLVKLIP
GVEYLVSIIAMKGFEESEPVSGSFTTALDGPSGLVTANITDSEALARWQPAIATVDSYVISYTGEKVPEITRTVSGN
TVEYALTDLEPATEYTLRIFAEKGPQKSSTITAKFTTDLDSPRDLTATEVQSETALLTWRPPRASVTGYLLVYESVD
GTVKEVIVGPDTTSYSLADLSPSTHYTAKIQALNGPLRSNMIQTIFTTIGLLYPFPKDCSQAMLNGDTTSGLYTIYL
NGDKAQALEVFCDMTSDGGGWIVFLRRKNGRENFYQNWKAYAAGFGDRREEFWLGLDNLNKITAQGQYELRVDLRDH
GETAFAVYDKFSVGDAKTRYKLKVEGYSGTAGDSMAYHNGRSFSTFDKDTDSAITNCALSYKGAFWYRNCHRVNLMG
RYGDNNHSQGVNWFHWKGHEHSIQFAEMKLRPSNFRNLEGRRKRA (SEQ ID NO:55)

```
  1 accggccaca gcctgcctac tgtcacccgc ctctcccgcg cgcagataca cgccccgcc
 61 tccgtgggca caaagccagc gctgctgggg aactcgggg aacgcgcacg tgggaaccgc
121 cgcagctcca cactccaggt acttcttcca aggaccctagg tctctcgccc atcggaaaga
181 aaataattct ttcaagaaga tcagggacaa ctgatttgaa gtctactctg tgcttctaaa
241 tccccaattc tgctgaaagt gaatccctag agccctagag ccccagcagc acccagccaa
```

FIG. 1 (cont'd)

```
 301 acccacctcc accatggggg ccatgactca gctgttggca ggtgtctttc ttgctttcct
 361 tgccctcgct accgaaggtg gggtcctcaa gaaagtcatc cggcacaagc gacagagtgg
 421 ggtgaacgcc accctgccag aagagaacca gccagtggtg tttaaccacg tttacaacat
 481 caagctgcca gtgggatccc agtgttcggt ggatctggag tcagccagtg gggagaaaga
 541 cctggcaccg ccttcagagc ccagcgaaag ctttcaggag cacacagtag atggggaaaa
 601 ccagattgtc ttcacacatc gcatcaacat ccccgccgg gcctgtggct gtgccgcagc
 661 ccctgatgtt aaggagctgc tgagcagact ggaggagctg gagaacctgg tgtcttccct
 721 gagggagcaa tgtactgcag gagcaggctg ctgtctccag cctgccacag gccgcttgga
 781 caccaggccc ttctgtagcg gtcggggcaa cttcagcact gaaggatgtg gctgtgtctg
 841 cgaacctggc tggaaaggcc ccaactgctc tgagcccgaa tgtccaggca actgtcacct
 901 tcgaggccgg tgcattgatg ggcagtgcat ctgtgacgac ggcttcacgg gcgaggactg
 961 cagccagctg gcttgcccca gcgactgcaa tgaccagggc aagtgcgtga atggagtctg
1021 catctgtttc gaaggctacg ccggggctga ctgcagccgt gaaatctgcc cagtgccctg
1081 cagtgaggag cacggcacat gtgtagatgg cttgtgtgtg tgccacgatg gctttgcagg
1141 cgatgactgc aacaagcctc tgtgtctcaa caattgctac aaccgtggac gatgcgtgga
1201 gaatgagtgc gtgtgtgatg agggtttcac gggcgaagac tgcagtgagc tcatctgccc
1261 caatgactgc ttcgaccggg gccgctgcat caatggcacc tgctactgcg aagaaggctt
1321 cacaggtgaa gactgcggga aacccacctg cccacatgcc tgccacaccc agggccggtg
1381 tgaggagggg cagtgtgtat gtgatgaggg cttttgccggt ttggactgca gcgagaagag
1441 gtgtcctgct gactgtcaca atcgtggccg ctgtgtagac gggcggtgtg agtgtgatga
1501 tggtttcact ggagctgact gtggggagct caagtgtccc aatggctgca gtggccatgg
1561 ccgctgtgtc aatgggcagt gtgtgtgtga tgagggctat actggggagg actgcagcca
1621 gctacggtgc cccaatgact gtcacagtcg gggccgctgt gtcgagggca atgtgtatg
1681 tgagcaaggc ttcaagggct atgactgcag tgacatgagc tgccctaatg actgtcacca
1741 gcacggccgc tgtgtgaatg gcatgtgtgt ttgtgatgac ggctacacag gggaagactg
1801 ccgggatcgc caatgcccca gggactgcag caacagggc ctctgtgtgg acggacagtg
1861 cgtctgtgag gacggcttca ccggccctga ctgtgcagaa ctctcctgtc caaatgactg
1921 ccatggccag ggtcgctgtg tgaatgggca gtgcgtgtgc catgaaggat ttatgggcaa
1981 agactgcaag gagcaaagat gtcccagtga ctgtcatggc cagggccgct gcgtggacgg
2041 ccagtgcatc tgccacgagg gcttcacagg cctggactgt ggccagcact cctgccccag
2101 tgactgcaac aacttaggac aatgcgtctc gggccgctgc atctgcaacg agggctacag
2161 cggagaagac tgctcagagg tgtctcctcc caaagacctc gttgtgacag aagtgacgga
2221 agagacggtc aacctggcct gggacaatga gatgcgggtc acagagtacc ttgtcgtgta
2281 cacgcccacc cacgagggtg gtctggaaat gcagttccgt gtgcctgggg accagacgtc
2341 caccatcatc caggagctgg agcctggtgt ggagtacttt atccgtgtat ttgccatcct
2401 ggagaacaag aagagcattc ctgtcagcgc cagggtggcc acgtacttac ctgcacctga
2461 aggcctgaaa ttcaagtcca tcaaggagac atctgtggaa gtggagtggg atcctctaga
2521 cattgctttt gaaacctggg agatcatctt ccggaatatg aataaagaag atgagggaga
2581 gatcaccaaa agcctgagga ggccagagac ctcttaccgg caaactggtc tagctcctgg
2641 gcaagagtat gagatatctc tgcacatagt gaaaaacaat acccggggcc ctggcctgaa
2701 gagggtgacc accacacgct ggatgcccc cagccagatc gaggtgaaag atgtcacaga
2761 caccactgcc ttgatcacct ggttcaagcc cctggctgag atcgatggca ttgagctgac
2821 ctacggcatc aaagacgtgc caggagaccg taccaccatc gatctcacag aggacgagaa
2881 ccagtactcc atcgggaacc tgaagcctga cactgagtac gaggtgtccc tcatctcccg
2941 cagaggtgac atgtcaagca cccagccaa agagaccttc acaacaggcc tcgatgctcc
3001 caggaatctt cgacgtgttt cccagacaga taacagcatc accctggaat ggaggaatgg
3061 caaggcagct attgacagtt acagaattaa gtatgccccc atctctggag gggaccacgc
3121 tgaggttgat gttccaaaga gccaacaagc cacaaccaaa accacactca caggtctgag
3181 gccgggaact gaatatggga ttggagtttc tgctgtgaag gaagacaagg agagcaatcc
3241 agcgaccatc aacgcagcca cagagttgga cacgcccaag gaccttcagg tttctgaaac
```

FIG. 1 (cont'd)

```
3301 tgcagagacc agcctgaccc tgctctggaa gacaccgttg gccaaatttg accgctaccg
3361 cctcaattac agtctcccca caggccagtg ggtgggagtg cagcttccaa gaaacaccac
3421 ttcctatgtc ctgagaggcc tggaaccagg acaggagtac aatgtcctcc tgacagccga
3481 gaaaggcaga cacaagagca agcccgcacg tgtgaaggca tccactgaac aagcccctga
3541 gctggaaaac ctcaccgtga ctgaggttgg ctgggatggc ctcagactca actggaccgc
3601 ggctgaccag gcctatgagc actttatcat tcaggtgcag gaggccaaca aggtggaggc
3661 agctcggaac ctcaccgtgc ctggcagcct tcgggctgtg gacataccgg cctcaaggc
3721 tgctacgcct tatacagtct ccatctatgg ggtgatccag ggctatagaa caccagtgct
3781 ctctgctgag gcctccacag gggaaactcc caatttggga gaggtcgtgg tggccgaggt
3841 gggctgggat gccctcaaac tcaactggac tgctccagaa ggggcctatg agtacttttt
3901 cattcaggtg caggaggctg acacagtaga ggcagcccag aacctcaccg tccaggagg
3961 actgaggtcc acagacctgc ctgggctcaa agcagccact cattatacca tcaccatccg
4021 cggggtcact caggacttca gcacaacccc tctctctgtt gaagtcttga cagaggaggt
4081 tccagatatg ggaaacctca cagtgaccga ggttagctgg gatgctctca gactgaactg
4141 gaccacgcca gatggaacct atgaccagtt tactattcag gtccaggagg ctgaccaggt
4201 ggaagaggct cacaatctca cggttcctgg cagcctgcgt tccatgaaaa tcccaggcct
4261 cagggctggc actccttaca cagtcaccct gcacggcgag gtcaggggcc acagcactcg
4321 accccttgct gtagaggtcg tcacagagga tctcccacag ctgggagatt tagccgtgtc
4381 tgaggttggc tgggatggcc tcagactcaa ctggaccgca gctgacaatg cctatgagca
4441 ctttgtcatt caggtgcagg aggtcaacaa agtggaggca gcccagaacc tcacgttgcc
4501 tggcagcctc agggctgtgg acatcccggg cctcgaggct gccacgcctt atagagtctc
4561 catctatggg gtgatccggg gctatagaac accagtactc tctgctgagg cctccacagc
4621 caaagaacct gaaattggaa acttaaatgt ttctgacata actcccgaga gcttcaatct
4681 ctcctggatg gctaccgatg ggatcttcga gacctttacc attgaaatta ttgattccaa
4741 taggttgctg gagactgtgg aatataatat ctctggtgct gaacgaactg cccatatctc
4801 agggctaccc cctagtactg attttattgt ctacctctct ggacttgctc ccagcatccg
4861 gaccaaaacc atcagtgcca cagccacgac agaggccctg ccccttctgg aaaacctaac
4921 catttccgac attaatccct acgggttcac agtttcctgg atggcatcgg agaatgcctt
4981 tgacagcttt ctagtaacgg tggtggattc tgggaagctg ctggaccccc aggaattcac
5041 actttcagga acccagagga agctggagct tagaggcctc ataactggca ttggctatga
5101 ggttatggtc tctggcttca cccaagggca tcaaaccaag cccttgaggg ctgagattgt
5161 tacagaagcc gaaccggaag ttgacaacct tctggtttca gatgccaccc cagacggttt
5221 ccgtctgtcc tggacagctg atgaagtggt cttcgacaat tttgttctca aaatcagaga
5281 taccaaaaag cagtctgagc cactggaaat aaccctactt gcccccgaac gtaccaggga
5341 cttaacaggt ctcagagagg ctactgaata cgaaattgaa ctctatggaa taagcaaagg
5401 aaggcgatcc cagacagtca gtgctatagc aacaacagcc atgggctccc caaaggaagt
5461 catttctca gacatcactg aaaattcggc tactgtcagc tggagggcac ccacggccca
5521 agtggagagc ttccggatta cctatgtgcc cattacagga ggtacaccct ccatggtaac
5581 tgtggacgga accaagactc agaccaggct ggtgaaactc atacctggcg tggagtacct
5641 tgtcagcatc atcgccatga agggctttga ggaaagtgaa cctgtctcag ggtcattcac
5701 cacagctctg gatggcccat ctggcctggt gacagccaac atcactgact cagaagcctt
5761 ggccaggtgg cagccagcca ttgccactgt ggacagttat gtcatctcct acacaggcga
5821 gaaagtgcca gaaattacac gcacggtgtc cgggaacaca gtggagtatg ctctgaccga
5881 cctcgagcct gccacggaat acacactgag aatctttgca gagaaggggc cccagaagag
5941 ctcaaccatc actgccaagt tcacaacaga cctcgattct ccaagagact tgactgctac
6001 tgaggttcag tcggaaactg cctccttac ctggcgaccc ccccgggcat cagtcaccgg
6061 ttacctgctg gtctatgaat cagtggatgg cacagtcaag gaagtcattg tgggtccaga
6121 taccacctcc tacagcctgg cagacctgag cccatccacc cactacacag ccaagatcca
6181 ggcactcaat gggcccctga ggagcaatat gatccagacc atcttcacca caattggact
6241 cctgtacccc ttccccaagg actgctccca agcaatgctg aatggagaca cgacctctgg
```

FIG. 1 (cont'd)

```
6301 cctctacacc atttatctga atggtgataa ggctcaggcg ctggaagtct tctgtgacat
6361 gacctctgat gggggtggat ggattgtgtt cctgagacgc aaaaacggac gcgagaactt
6421 ctaccaaaac tggaaggcat atgctgctgg atttggggac cgcagagaag aattctggct
6481 tgggctggac aacctgaaca aaatcacagc ccaggggcag tacgagctcc gggtggacct
6541 gcgggaccat ggggagacag cctttgctgt ctatgacaag ttcagcgtgg agatgccaa
6601 gactcgctac aagctgaagg tggagggta cagtgggaca gcaggtgact ccatggccta
6661 ccacaatggc agatccttct ccacctttga caaggacaca gattcagcca tcaccaactg
6721 tgctctgtcc tacaaagggg ctttctggta caggaactgt caccgtgtca acctgatggg
6781 gagatatggg gacaataacc acagtcaggg cgttaactgg ttccactgga agggccacga
6841 acactcaatc cagtttgctg agatgaagct gagaccaagc aacttcagaa atcttgaagg
6901 caggcgcaaa cgggcataaa ttgagggac cactgggtga gagaggaata aggcggccca
6961 gagcgaggaa aggattttac caaagcatca atacaaccag cccaaccatc ggtccacacc
7021 tgggcatttg gtgagaatca aagctgacca tggatccctg gggcaacgg caacagcatg
7081 ggcctcacct cctctgtgat ttctttcttt gcaccaaaga catcagtctc caacatgttt
7141 ctgttttgtt gtttgattca gcaaaaatct cccagtgaca acatcgcaat agttttttac
7201 ttctcttagg tggctctggg atgggagagg ggtaggatgt acaggggtag tttgttttag
7261 aaccagccgt attttacatg aagctgtata attaattgtc attatttttg ttagcaaaga
7321 ttaaatgtgt cattggaagc catccctttt tttacatttc atacaacaga aaccagaaaa
7381 gcaatactgt ttccatttta aggatatgat taatattatt aatataataa tgatgatgat
7441 gatgatgaaa actaaggatt tttcaagaga tctttctttc caaacatttt ctggacagta
7501 cctgattgta tttttttttt aaataaaagc acaagtactt ttgaaaaaaa accggaattc
(SEQ ID NO:56)
```

RKHD2

MMAAMLSHAYGPGGCGAAAAALNGEQAALLRRKSVNTTECVPVPSSEHVAEIVGRQGCKIKALRAKTNTYIKTPVRG
EEPIFVVTGRKEDVAMAKREILSAAEHFSMIRASRNKNGPALGGLSCSPNLPGQTTVQVRVPYRVVGLVVGPKGATI
KRIQQQTHTYIVTPSRDKEPVFEVTGMPENVDRAREEIEMHIAMRTGNYIELNEENDFHYNGTDVSFEGGTLGSAWL
SSNPVPPSRARMISNYRNDSSSSLGSGSTDSYFGSNRLADFSPTSPFSTGNFWFGDTLPSVGSEDLAVDSPAFDSLP
TSAQTIWTPFEPVNPLSGFGSDPSGNMKTQRRGSQPSTPRLSPTFPESIEHPLARRVRSDPPSTGNHVGLPIYIPAF
SNGTNSYSSSNGGSTSSSPPESRRKHDCVICFENEVIAALVPCGHNLFCMECANKICEKRTPSCPVCQTAVTQAIQI
HS (SEQ ID NO:57)

```
  1 ggccgagctg gagctggaag aggacgagga ggaggggag gaagcggagc tggacggaga
 61 cctgctggag gaggaggagc tggaggaagc agaggaggag gaccggtcgt cgctgctgct
121 gctgtcgccg cccgcggcca ccgcctctca gacccagcag atcccaggcg ggtccctggg
181 gtctgtgctg ctgccagccg ccaggttcga tgcccgggag gcggcggccg cggcggcggc
241 ggcggggtg ctgtacggag ggacgatgc ccagggcatg atggcggcga tgctgtccca
301 cgcctacggc cccggcggtt gtggggcgg ggcggccgcc ctgaacgggg agcaggcggc
361 cctgctccgg agaaagagcg tcaacaccac cgagtgcgtc ccggtgccca gctccgagca
421 cgtcgccgag atcgtcggcc gccagggttg taaaattaaa gcactgagag ccaagacaaa
481 cacgtatatc aagactcctg ttcgtggtga gagcccatt tttgttgtca ctggaaggaa
541 agaagatgtt gccatggcca aagagagat cctctcagct gcagagcact ctccatgat
601 tcgtgcatct cgaaacaaaa atgggcctgc cctggaggga ttatcatgta gtcctaatct
661 gcccggtcaa accaccgtcc aagtcaggt cccttatcgt gtggtaggat tagtggttgg
721 acccaaagga gcaactatta aagaattca gcagcagacc cacacctaca tagtaactcc
781 gagcagagat aaggaacctg tcttttgaagt gacagggatg cctgaaaatg ttgaccgagc
841 acgggaagaa atagaaatgc atattgccat gcgtacagga aactatatag agctcaatga
901 agagaatgat ttccattaca atggtaccga tgtaagcttt gaaggtggca ctcttggctc
```

FIG. 1 (cont'd)

```
 961 tgcgtggctc tcctccaatc ctgttcctcc tagccgcgca agaatgatat ccaattatcg
1021 aaatgatagt tccagttctc taggaagtgg ctctacagat tcctactttg gaagcaatag
1081 gctggctgac tttagtccaa caagcccatt tagcacagga aacttctggt ttggagatac
1141 actaccatct gtaggctcag aagacctagc agttgactct cctgcctttg actctttacc
1201 aacatctgct caaactatct ggactccatt tgaaccagtt aacccactct ctggctttgg
1261 gagtgatcct tctggtaaca tgaagactca gcgcagagga agtcagccat ctactcctcg
1321 tctgtctcct acatttcctg agagcataga acatccactt gctcggaggg ttaggagcga
1381 cccacctagt acaggcaacc atgttggcct tccaatatat atccctgctt tttctaatgg
1441 taccaatagt tactcctctt ccaatggtgg ttccacctct agctcacctc cagaatcaag
1501 acgaaagcac gactgtgtga tttgctttga aatgaggtt attgctgccc tagttccatg
1561 tggccacaac ctcttctgca tggaatgtgc caacaagatc tgtgaaaaga aacgccatc
1621 atgtccagtt tgccagacag ctgttactca ggcaatccaa attcactctt aactatatat
1681 atatacataa atactatatc tctatatgga ctcgtaaagg catgggtata atggtacccc
1741 ccagtaaact tcctaatgat ttcttatgac tgttatcagg ctttattggg attaggctaa
1801 agttgttagt aaacttataa aaggctgcta tggtaacact aaacctaagt ggtctcttgt
1861 ctattagttt ggtttgaatt attagtacta tcctgtagac ccagagacat agtttatata
1921 agaattgcta aagctgaagt tcaacttgcc tgagtgaaga taatcatagg ttgtgtgagc
1981 ctatgaaaaa gtgtatacgt ctaagatttc aaaacaatgg gtcccaaagc ctaaccactt
2041 taagagttta tggagggtac ttggcattac agacgattca tacacttcca gtgctgcctt
2101 ctttacactg ccagttttga caaaacaggt ttgttttta ttttacaaca acatatgcct
2161 aattctgcag gattgcaagt aacttttaa tgcattgtga ttacttattg gtaatgatag
2221 ggctgatggc agtttactag atcactggtt ataatttggg acaaaaactg ctacatcaac
2281 tttcatctcg cccagagtgc tcaaggctgg tatgatcagt ggatcaggaa tgcaattgtg
2341 aattcctgcc cattgcctct cttggtgaat gtggaaatgg ccacctgggt tttcccatat
2401 caggaagggc tttgggatgg cacctatatt ggctgataat tgaggatgca aacattccat
2461 tcattagtgt gatcgagctg ttaattttta gactatagat caaaatgtga aacattttat
2521 gttcaatcca tatttgtctt gcacattata aatatatttt tatttttag taatttaggg
2581 gagggaggag ggagaaaggg ataatgatgc ccttggcata attcacaaaa gcagctgtga
2641 caacctccaa tcagtttact tcatttcaaa actatttcca atcacaagga aagatttatt
2701 taaaatatac tcgtacattt cacctgtgga tgtctataac ttcatcctca gtatgttccc
2761 aaatctgctgc tggcattgaa aggacaaaac attatactag tgggtttttc tactaattat
2821 tttttgaagc attattttcc caacacaaaa gagctttttt ctcggtataa tgaaaattga
2881 aatcctatgt gtattcaata gtaaatagac aaatttattt tttttatttcc acttgaagag
2941 ttacatttcg tataaaagtt tacaaataac ggttttttat ttgattttt cagtataaaa
3001 aaagttgcct tgatggcata ttatgatgta atgctaattg cttgtaggat agtaaatggt
3061 cagtattgaa acctaatctc tagctgccgt cttgtagata tgaacgaatg ttcaccaagc
3121 atgtattttg tattttgttg cattgtacac tgcaactaat aagccaagga atcgacatat
3181 attaggtgcg tgtactgttt ctaaaaacca caaactaaga atgataaatt atcaatatag
3241 tttagtattt gctaatttta ctacactctt ttgttatgta tatgtaggga agtcataggg
3301 attataaatt caatttgagt aaaatttaaa accatatatt ttatgataaa gggcctttaa
3361 cttaagatgg ccaaagcact gatattatat atttgctgta aagagaatta taagagtttt
3421 attttctga tattaaaagt tacttgataa agacttgttt ccattaactt gaaaaaaaaa
3481 aaaaaaaaaa aaa (SEQ ID NO:58)
```

HEY1

MKRAHPEYSSSDSELDETIEVEKESADENGNLSSALGSMSPTTSSQILARKRRRGIIEKRRRDRINNSLSELRRLVP
SAFEKQGSAKLEKAEILQMTVDHLKMLHTAGGKGYFDAHALAMDYRSLGFRECLAEVARYLSIIEGLDASDPLRVRL

FIG. 1 (cont'd)

VSHLNNYASQREAASGAHAGLGHIPWGTVFGHHPHIAHPLLLPQNGHGNAGTTASPTEPHHQGRLGSAHPEAPALRA
PPSGSLGPVLPVVTSASKLSPPLLSSVASLSAFPFSFGSFHLLSPNALSPSAPTQAANLGKPYRPWGTEIGAF
(SEQ ID NO:59)

```
   1 ttccccactc ccccgccctc cccagggccc tgggaagggg ctcagcgtgg gaaaggatgg
  61 ttgagtttta accagaggca aagcgtgagc gggatcagtg tgtgcggaac gcaagcagcc
 121 gagagcggag aggcgccgct gtagttaact cctccctgcc cgccgcgccg accctcccca
 181 ggaaccccca gggagccagc atgaagcgag ctcaccccga gtacagctcc tcggacagcg
 241 agctggacga gaccatcgag gtggagaagg agagtgcgga cgagaatgga aacttgagtt
 301 cggctctagg ttccatgtcc ccaactacat cttcccagat tttggccaga aaagacgga
 361 gaggaataat tgagaagcgc cgacgagacc ggatcaataa cagtttgtct gagctgagaa
 421 ggctggtacc cagtgctttt gagaagcagg gatctgctaa gctagaaaaa gccgagatcc
 481 tgcagatgac cgtggatcac ctgaaaatgc tgcatacggc aggagggaaa ggttactttg
 541 acgcgcacgc ccttgctatg gactatcgga gtttgggatt tcgggaatgc ctggcagaag
 601 ttgcgcgtta tctgagcatc attgaaggac tagatgcctc tgacccgctt cgagttcgac
 661 tggtttcgca tctcaacaac tacgcttccc agcgggaagc cgcgagcggc gcccacgcgg
 721 gcctcggaca cattccctgg gggaccgtct tcggacatca cccgcacatc gcgcacccgc
 781 tgttgctgcc ccagaacggc cacgggaacg cgggcaccac ggcctcaccc acggaaccgc
 841 accaccaggg caggctgggc tcggcacatc cggaggcgcc tgctttgcga gcgcccccta
 901 gcggcagcct cggaccggtg ctccctgtgg tcacctccgc ctccaaactg tcgccgcctc
 961 tgctctcctc agtggcctcc ctgtcggcct tcccttctc tttcggctcc ttccacttac
1021 tgtctcccaa tgcactgagc ccttcagcac ccacgcaggc tgcaaacctt ggcaagccct
1081 atagaccttg ggggacggag atcggagctt tttaaagaac tgatgtagaa tgagggaggg
1141 gaaagtttaa aatcccagct gggctggact gttgccaaca tcaccttaaa gtcgtcagta
1201 aaagtaaaaa ggaaaaaggt acactttcag ataattttt ttttaaagac taaaggtttg
1261 ttggtttact tttatctttt ttaatgtttt tttcatcatg tcatgtatta gcagttttta
1321 aaaactagtt gttaaatttt gttcaagaca ttaaattgaa atagtgagta taagccaaca
1381 ctttgtgata ggtttgtact gtgcctaatt tactttgtaa accagaatga ttccgttttt
1441 gcctcaaaat tggggaatc ttaacattta gtattttttg tctgttttc tccttgtata
1501 gttatggtct gttttagaa ttaatttttcc aaaccactat gcttaatgtt aacatgattc
1561 tgtttgttaa tattttgaca gattaaggtg ttgtataaat aatattcttt tggggggagg
1621 ggaactatat tgaattttat atttctgagc aaagcgttga caaatcagat gatcagcttt
1681 atccaagaaa gaagactagt aaattgtctg cctcctatag cagaaaggtg aatgtacaaa
1741 ctgttggtgg ccctgaatcc atctgaccag ctgctggtat ctgccaggac tggcagttct
1801 gatttagtta ggagagagcc gctgataggt taggtctcat ttggagtgtt ggtggaaagg
1861 aaactgaagg taattgaata gaatacgcct gcatttacca gcccagcaa cacaaagaat
1921 ttttaatcac acggatctca aattcacaaa tgttaacatg gataagtgat catggtgtgc
1981 gagtggtcaa ttgagtagta cagtggaaac tgttaaatgc ataacctaat ttcctggga
2041 ctgccatatt ttcttttaac tggaaatttt tatgtgagtt ttccttttgg tgcatggaac
2101 tgtggttgcc aaggtattta aaagggcttt cctgcctcct tctctttgat ttatttaatt
2161 tgatttgggc tataaatat catttttcag gttattctt ttagcaggtg tagttaaacg
2221 acctccactg aactgggttt gacctctgtt gtactgatgt gttgtgacta aataaaaaag
2281 aaagaacaaa gtaaaaaaaa aaaaaaaaa aaaaaaaaa (SEQ ID NO:60)
```

FIG. 1 (cont'd)

PYCRL

MAAAEPSPRRVGFVGAGRMAGAIAQGLIRAGKVEAQHILASAPTDRNLCHFQALGCRTTHSNQEVLQSCLLVIFATK
PHVLPAVLAEVAPVVTTEHILVSVAAGVSLSTLEELLPPNTRVLRVLPNLPCVVQEGAIVMARGRHVGSSETKLLQH
LLEACGRCEEVPEAYVDIHTGLSGSGVAFVCAFSEALAEGAVKMGMPSSLAHRIAAQTLLGTAKMLLHEGQHPAQLR
SDVCTPGGTTIYGLHALEQGGLRAATMSAVEAATCRAKELSRK (SEQ ID NO:61)

```
   1 agcgcagcgg cgtccgaggc aacaagatgg cagctgcgga gccgtctccg cggcgcgtgg
  61 gcttcgtggg cgcggccgc atggcggggg ccatcgcgca gggcctcatc agagcaggaa
 121 aagtggaagc tcagcacata ctggccagtg caccaacaga caggaaccta tgtcactttc
 181 aagctctggg ttgccggacc acgcactcca accaggaggt gctacagagc tgcctgctcg
 241 tcatctttgc caccaagcct catgtgctgc cagctgtcct ggcagaggtg gctcctgtgg
 301 tcaccactga acacatcttg gtgtccgtgg ctgctggggt gtctctgagc accctggagg
 361 agctgctgcc cccaaacaca cgggtgctgc gggtcttgcc caacctgccc tgtgtggtcc
 421 aggaaggggc catagtgatg gcgcggggcc gccacgtggg gagcagcgag accaagctcc
 481 tgcagcatct gctggaggcc tgtgggcggt gtgaggaggt gcctgaagcc tacgtcgaca
 541 tccacactgg cctcagtggc agtggcgtgg ccttcgtgtg tgcattctcc gaggccctgg
 601 ctgaaggagc cgtcaagatg ggcatgccca gcagcctggc caccgcatc gctgcccaga
 661 ccctgctggg gacggccaag atgctgctgc acgagggcca acccagcc cagctgcgct
 721 cagacgtgtg caccccgggt ggcaccacca tctatggact ccacgccctg gagcagggcg
 781 ggctgcgagc agccaccatg agcgccgtgg aggctgccac ctgccgggcc aaggagctca 841 gcagaaagta ggctgggctc tggccatcct ttcctgcctc tgtgcccctg cctctccctg
 901 tgtcccttcc cctgaggact gcggctccct ccctcctgca tgagggtctc ctactgctcc
 961 ttctcccctt gcacagggaa atgcaggggg caggacttgg gaggttccag caggcggggg
1021 agccccgacc agtggggaca ctcctccctc cccagtgagc agaaggcacc gtggtggtgg
1081 ctctgcccct tgctgcagtg agcccacctt gctgaacat tggttctgag gggcccaaga
1141 gatggcgtct tggtcatttg cccgcatggt tgggcagttg gttgaggcca tgaacagaac
1201 ttacggtaac aggcacggct ggcccaatgc ctggtctgga gctggagctt gcctttggct
1261 ttccaggtgg ctccgtgcag ctacagccag gccggctgcc tcatctcagc tctaggggc
1321 acgagccata tggggtctgc acaagagacc ctctcccctg cagtaaagcc aggggccctg
1381 gcctgatggg gcccccatgg ggagctggag cctgccctgc agcctggaga gagggtggc
1441 tgtggtgggc gtgctcatcc cctgctaagg agcaggagct gctgggccag gtctgcggca
1501 gtgctggggt ggcaccaggt gggcagtggt aggtggggtg gcttgaggtc tgggagggtg
1561 gccctggcca gccaggacac atgcagaccc ctggcttagt ctggatacag gctccctctt
1621 tcctcccaat cctaagctcc tgacaagtgg ccaggtggct ctgggcctc ctgccccgtg
1681 cctaggtcag gggtcctgga atacccgta gctctggcac caccactg gcctctgatg
1741 gcaagacttg gcccctccac ctgtccctaa cggacggcag gtcaggaaag ccaggactca
1801 ggggagaagc aaaccccag gattgaaggc tagggttcta ggcctttgg gtggggaggg
1861 cccgggccgg acagcctcag ctccgtcccc tgcccacaa gattcacctg gcctccagt
1921 cccacgctgg ccccaactgc tgcagctctc ggcttccgcc aacagcctc tggaggtgag
1981 gcgggagcat gccctcagcg aggctgggcg gcgggtcctg ctgtgccatc tccctgtgcg
2041 cctgagcaga tcaatccacc agtgcaaaac agggctaacg gcacctgcag gacagcagca
2101 cgctccatcc ctcatgctca gctgcctctg cggccacgga cttctgccct tcatctgctc
2161 tctcttactc tcctgagcct agcccgtccg taagctccct ccctgcctg gttcccaggg
2221 caggctgact cagttgactg cttggtccaa gcctggccct ggcacttgtc agggtcagcc
2281 taaggagatg ggaataaaga ggccagagag caccaagtga gctcatgttt c (SEQ ID
NO:62)
```

FIG. 1 (cont'd)

HYDIN

MTSRRLEESMGAVQMGLVNMFKGFQSKVLPPLSPKVVTEEEVNRMLTPSEFLKEMSLTTEQRLAKTRLMCRPQIIEL
LDMGETTHQKFSGIDLDQALFQPFPSEIIFQNYTPCEVYEVPLILRNNDKIPRLVKVVEESSPYFKVISPKDIGHKV
APGVPSIFRILFTPEENKDYAHTLTCVTEREKFIVPIKARGARAILDFPDKLNFSTCPVKYSTQKILLVRNIGNKNA
VFHIKTCRPFSIEPAIGTLNVGESMQLEVEFEPQSVGDHSGRLIVCYDTGEKVFVSLYGAAIDMNIRLDKNSLTIEK
TYISLANQRTITIHNRSNIIAHFLWKVFATQQEEDREKYRACDDLIKEEKDETDEFFEECITDPLLREHLSVLSRTF
ANQRRLVQGDSKLFFNNVFTVEPLEGDVWPNSSAEITVYFNPLEAKLYQQTIYCDILGREIRLPLRIKGEGMGPKIH
FNFELLDIGKVFTGSAHCYEAILYNKGSIDALFNMTPPTSALGACFVFSPKEGIIEPSGVQAIQISFSSTILGNFEE
EFLVNVNGSPEPVKLTIRGCVIGPTFHFNVPALHFGDVSFGFPHTLICSLNNTSLIPMTYKLRIPGDGLGHKSISYC
EQHVDYKRPSWTKEEISSMKPKEFTISPDCGTIRPQGFAAIRVTLCSNTVQKYELALVVDVEGIGEEVLALLITARC
VVPALHLVNTEVDFGHCFLKYPYEKTLQLANQDDLPGFYEVQPQVCEEVPTVLFSSPTPSGVISPSSTIHIPLVLET
QVTGEHRSTVYISIFGSQDPPLVCHLKSAGEGPVIYVHPNQVDFGNIYVLKDSSRILNLCNQSFIPAFFQAHMAHKK
SLWTIEPNEGMVPPETDVQLALTANLNDTLTFKDCVILDIENSSTYRIPVQASGTGSTIVSDKPFAPELNLGAHFSL
DTHYYHFKLINKGRRIQQLFWMNDSFRPQAKLSKKGRVKKGHAHVQPQPSGSQEPRDPQSPVFHLHPASMELYPGQA
IDVILEGYSATPRVRG (SEQ ID NO:63)

```
   1 aagctgggta tggagcccct cagcggcggc ggggtctgtg agttggacgc ggggtcttgg
  61 cggggaatgg aggtagaata aacgtgggac ccggagtgca ccaagaaaaa aaaattacta
 121 aaaatgacaa gtagaagact tgaggagtcc atggggctg ttcagatggg attggtcaat
 181 atgttcaaag gatttcaaag caaggttttg ccacccctga gtccaaaggt ggttacagaa
 241 gaagaagtaa accgaatgct tacaccctca gagttcctga aggaaatgtc cctgaccacc
 301 gagcagagac tggcaaaaac acgtttgatg tgccgaccac agatcatcga actcttagat
 361 atggggaaa caacacatca gaagttttca ggaattgacc tggatcaggc attattccag
 421 ccctttccat cagaaattat atttcagaac tacactccct gtgaagtcta tgaagttcca
 481 ctgattttga ggaacaatga caaaattcca ggttggtga agttgtgga agaaagttcg
 541 ccttactta aagtaatcag ccccaaagat attggccaca aagtggctcc tggagtgcct
 601 tccatattcc gaatcctctt tactccagag gagaacaagg attacgccca tacgttgacc
 661 tgtgttactg aaagagaaaa gtttattgta cccatcaaag ctagagggc acgagccatt
 721 ctcgattttc ctgacaagct gaatttttcc acttgtcctg tcaaatacag cacccagaag
 781 attctgctgg tacgaaacat tggcaacaaa aatgctgtat ttcacatcaa aacttgtagg
 841 ccttctctcta tagaaccagc tattggaact cttaatgtgg gagagtccat gcaactggaa
 901 gtggagtttg agccacagag tgtgggcgat cacagtggaa gacttatcgt gtgttatgac
 961 acaggtgaaa aggtgtttgt atctctctat ggagctgcca tagacatgaa tataaggctg
1021 gataagaatt ccttgaccat cgagaaaacc tacatatctc tggccaatca gcgaactata
1081 accattcaca atcgcagtaa tatcattgcc catttcctgt ggaaggtatt tgctacccag
1141 caagaagagg acagagaaaa atatagggcc tgtgatgatc tgatcaaaga ggagaaggat
1201 gagactgatg agttttttga agagtgcatt actgatcctt tactccgaga acatctttct
1261 gttctgtccc gaacctttgc gaatcagagg aggctggtgc agggagacag caagctgttc
1321 ttcaataacg ttttcactgt ggagcccctg gaaggtgatg tctggcccaa ctcatcagct
1381 gaaatcaccg tgtactttaa cccactagaa gccaagctct atcaacagac catttactgc
1441 gacattttag gccgagaaat ccgtctgccc ctccgaatca aaggggaagg catgggacct
1501 aagattcact tcaactttga attgctggat attgggaaag ttttcactgg atctgcacat
1561 tgttatgagg cgatactgta caacaaaggc agcatcgatg ctctcttcaa catgaccct
1621 ccaacttcag ctttgggcgc ctgctttgtt ttcagtccca aggaaggcat cattgaacca
1681 agtggagtcc aagctatcca gatctccttc agctctacca tcctgggaaa ctttgaagaa
1741 gagttcctgg tcaatgtcaa tgggtcacct gagcctgtga aactgaccat tagaggctgt
1801 gtcattggac ctaccttcca ttttaatgtt ccagctctgc actttggtga tgtttccttt
1861 gggtttcctc ataccttgat atgttccctc aataatacct ctttgatccc catgacttac
1921 aaactgcgta tccctgggga tggccttggc cataaaagca tttcatattg tgagcagcat
```

FIG. 1 (cont'd)

```
1981 gtggactaca aaagaccatc ttggaccaag gaagaaatat cctcaatgaa accaaaagaa
2041 ttcaccatct ctcctgactg tggcaccatt cgcccccagg gatttgctgc tatcagggtg
2101 acattatgct ccaacactgt gcagaaatac gagctggcac tcgtggtgga cgtggagggc
2161 atcggagaag aggtgctggc gctcttaatt acagcaaggt gtgttgtacc tgccctccac
2221 ctggtcaata cagaggtgga ctttgggcac tgcttcctga agtacccgta tgagaaaaca
2281 ctccagcttg ccaatcaaga tgacctccca ggattctatg aggtccagcc tcaggtgtgt
2341 gaggaggtgc ctactgtgct gttttccagc cccaccccca gcggggtcat ctccccaagc
2401 agcaccatcc acataccact ggtcctggag acccaggtca ctggagaaca cagatccacg
2461 gtttacatct caatctttgg gagccaggac cccctttgg tatgtcactt aaagagcgct
2521 ggagaaggcc cagttatcta cgtccatccc aatcaagtgg acttcgggaa tatctacgtc
2581 ctaaaagact cttccaggat tctcaaccta tgcaaccagt ccttcattcc cgcattttc
2641 caggcacaca tggcacacaa aaaatccctt tggacgattg aacccaatga aggcatggtt
2701 cctccagaaa ctgatgttca actggcactg accgccaacc tgaatgacac actgacattc
2761 aaggactgtg ttattttgga cattgaaaat agcagtacct atcggattcc tgttcaggct
2821 tccggaactg gttccactat tgtttcagat aagcccttg ctccagaact caatttgggg
2881 gcacatttta gcctggatac ccactattac cactttaagt tgatcaacaa gggacgtcgg
2941 atccaacagt tgttctggat gaatgatagc ttccgacccc aggccaagct gagtaagaag
3001 ggccgggtta agaagggaca tgctcatgtc caaccccagc ccagtggctc tcaggagccc
3061 agggatccac agagcccgt gtttcatctc caccccgcca gcatggagct gtacccaggc
3121 caggcaattg atgtgatact cgaaggctat tctgctactc ccagggtaag gggatagcac
3181 atttggaagc tattgttttt tcctaaataa atctctactg tatctatttc ttaggaaagt
3241 cccttgacat ttatctgagg aaggatatgg tttctcaagg attgtgtaca atcctgagtt
3301 accatagtag catccgtgc tttcggggtg cagctctgct cagtcttcaa tttgtttctg
3361 tagctactgt gaacccaatc ttaaaggagg ttctcatgct cagggtccac agtgaccagc
3421 cagcaagtct ctggtagaaa aacacccagt ttttagccaa agcaaattct cctattaaca
3481 cttagcagga tgaatttaat attcattcaa aaagggtgtt tatatcgaca ctctgggctg
3541 cctctcctat tcaggtattg ggacatccct gttcctttct ttccagcctg actgcaactc
3601 acatttcaaa acatcttctt tttatgcatt aataaaagag ccacatttat cttcagcaa
```
(SEQ ID NO:64)

SORBS2

MNTGRDSQSPDSAKGFRSVRPNLQDKRSPTQAPPPPERKESFHSSLITSHTKGVILDQLVTNTQIPSSTEYFANKKP
LQGTMYSNEDSRQTIVYSEESNTTMSYTQKITNPLPAASSTDPAPFANINTPVLQEDYRQDSQTRRISTLKLTHNQD
LGSSSPISTPQVLQICRSTVISQKARSLTPNPVPETHTASLSIQIAPLSGQDLESHKQLPELSPETAKIPLQQERQK
SAVAAASQSSDCRVSQITVNGNSGGAVSPMSYYQRPFSPSAYSLPASLNSSIVMQHGTSLDSTDTYPQHAQSLDGTT
SSSIPLYRSSEEEKRVTVIKAPHYPGIGPVDESGIPTAIRTTVDRPKDWYKTMFKQIHMVHKPDDDTDMYNTPYTYN
AGLYNPPYSAQSHPAAKTRTYRPLSKSHSDNSPNAFKDASSPVPPPHVPPPVPPLRPRDRSSTEKHDWDPPDRKVDT
RKFRSEPRSIFEYEPGKSSILQHERPTDRINPDDIDLENEPWYKFFSELEFGRPPPKKPLDYVQDHSSGVFNEASLH
QSSIDRSLERPMSSASMASDFRKRRKSEPAVGPPRGLGDQSASRTSPGRVDLPGSSTTLTKSFTSSSPSSPSRAKDR
ESPRSYSSTLTDMGRSAPRERRGTPEKEKLPAKAVYDFKAQTSEELSFKKGDTVYILRKIDQNWYEGEHHGRVGIFP
ISYVEKLTPPEKAQPARPPPPAQPGEIGEAIAKYNFNADTNVELSLRKGDRVILLKRVDQNWYEGKIPGTNRQGIFP
VSYVEVVKKNTKGAEDYPDPPIPHSYSSDRIHSLSSNKPQRPVFTHENIQGGGEPFQALYNYTPRNEDELELRESDV
IDVVEKCDDGWFVGTSRRAKFFGTFPGNYVKRL (SEQ ID NO:65)

```
   1 tgtacaaaaa agcaggctcc accatgaaca cagggcgtga ttctcagtca ccagactcag
  61 caaaaggttt tagaagcgtt cgaccaaacc tacaagataa aagatcacca actcaggcac
 121 cccctccacc agaaagaaaa gagagctttc atagctcttt gataaccagt cacacaaagg
 181 gtgtcatttt agaccagtta gtaactaaca cacaaattcc ctccagtaca gagtactttg
```

FIG. 1 (cont'd)

```
 241 ctaacaaaaa acctcttcag ggaactatgt attccaatga agattcgaga cagacaattg
 301 tatattctga agaatctaac acaaccatgt catatacaca aaaaatcact aatcctctac
 361 cagcagcttc cagcacggat cctgcaccat tcgctaacat caacacccca gttctacaag
 421 aggactacag gcaagattct caaactcgga ggatttctac cttgaaacta acccataacc
 481 aggatctagg aagtagcagc cccattagta ctccacaggt tctccaaatc tgtcgaagta
 541 ccgtcatttc tcaaaaggcc cgctcactga ccctaatcc agtgcctgag acacacacag
 601 catctctttc cattcagata gctccccttt caggacagga tcttgaaagc cacaaacagc
 661 tacctgagct ttctccagag actgcaaaga tacctcttca gcaagagaga caaaaatctg
 721 cagttgcagc ggcctctcag tcctcagact gcagagtgag ccagataaca gtgaatggaa
 781 actcaggagg tgccgtgagt cccatgagtt actatcagag gccgtttcc cctcggcat
 841 attctctccc agcctcactc aactccagca ttgtcatgca gcacggcaca tccctcgatt
 901 ccacagacac atatccccag catgcgcagt ctctggatgg caccaccagc agctctatcc
 961 ccctgtaccg atcctcagag gaagagaaga gagtgacagt catcaaagcc ccgcattacc
1021 cagggatcgg gcccgtggat gaatccggaa tccccacagc aattagaacg acagtcgacc
1081 ggcccaagga ctggtacaag acgatgttta agcagattca catggtgcac aagccggatg
1141 atgacacaga catgtataat actccttata catacaatgc aggtctgtac aacccaccct
1201 acagtgctca gtcacaccct gctgcaaaga cccgaaccta cagacctctt tccaaaagcc
1261 actccgacaa cagcccaat gcctttaagg atgcgtcctc cccagtgcct ccccacatg
1321 ttccacctcc agtcccgccg cttcgaccaa gagatcggtc ttcaacagaa aagcatgact
1381 gggatcctcc agacagaaaa gtggacacaa gaaaatttcg gtctgagcca aggagtattt
1441 ttgaatatga acctggcaag tcatcaattc ttcagcatga aagaccaact gatcgcataa
1501 atccagatga catagattta gaaaatgagc cctggtataa attcttttca gaactggagt
1561 ttggacgccc gcctcctaaa aagcctctgg actatgttca agatcattct tctggtgttt
1621 tcaatgaggc ctccttgcat cagtcctcta tagacagaag cctggaaaga cccatgagtt
1681 ctgcaagcat ggccagtgac ttcaggaagc ggaggaagag cgagcctgca gtgggtccac
1741 cacggggctt gggagatcaa agtgcgagca ggactagccc aggccgagtg gacctcccag
1801 gatcaagcac cactcttaca aagtctttca ctagctcttc tcttcttcc ccatcaagag
1861 caaaagaccg tgagtcccct agaagttact catccacttt gactgacatg gggagaagtg
1921 caccaaggga aagaagagga actccagaaa aagagaaatt gcctgcaaaa gctgtttatg
1981 attttaaggc tcagacatct gaggagttgt catttaagaa aggagatact gtctacatcc
2041 tcaggaaaat tgatcaaaat tggtatgagg gagaacacca cgggagagtg ggcatcttcc
2101 cgatctcata cgtagaaaaa ctcacacctc ctgagaaagc acagcctgca agaccacctc
2161 cgccagccca gcccggagaa atcggagaag ctatagccaa atacaacttc aacgcagaca
2221 caaatgtgga gctgtcactg agaaagggag atagagttat tcttcttaaa agagttgatc
2281 aaaactggta tgaaggtaaa atcccaggaa ccaacagaca aggcatcttc cctgtttcct
2341 atgtggaggt cgtcaagaag aacacaaaag gtgctgagga ctaccctgac cctccaatac
2401 cccacagcta ttctagtgat aggattcaca gcttgagctc aaataagcca cagcgtcctg
2461 tgtttactca tgaaaatatt caaggtgggg gggaaccgtt tcaggctctg tataactata
2521 ctcccaggaa tgaagatgag ctggagctca gagaaagtga tgtcattgat gtcgtggaaa
2581 agtgtgatga cggctggttt gtgggggacct caagaagagc caaattcttt ggtactttcc
2641 ccggaaacta cgtcaagagg ctgtagcttg acccagcttt cttgtaca (SEQ ID NO:66)
```

SPRY4

MEPPIPQSAPLTPNSVMVQPLLDSRMSHSRLQHPLTILPIDQVKTSHVENDYIDNPSLALTTGPKRTRGGAPELAPT
PARCDQDVTHHWISFSGRPSSVSSNSSTSSDQRLLDHMAPPPVADQASPRAVRIQPKVVHCQPLDLKGPAVPPELDK
HFLLCEACGKCKCKECASPRTLPSCWVCNQECLCSAQTLVNYGTCMCLVQGIFYHCTNEDDEGSCADHPCSCSRSNC
CARWSFMGALSVVLPCLLCYLPATGCVKLAQRGYDRLRRPGCRCKHTNSVICKAASGDAKTSRPDKPF (SEQ ID
NO:67)

FIG. 1 (cont'd)

```
   1 gccccggctt caggatttac acagacgtgg ggcgatgctt gtgaccctgc agctcctcaa
  61 aggcccctag aagcctgttt ctccgtacag tccaggacct ccagccccat ggagccccg
 121 atcccacaga gcgccccctt gactcccaac tcagtcatgg tccagcccct tcttgacagc
 181 cggatgtccc acagccggct ccagcaccca ctcaccatcc tacccattga ccaggtgaag
 241 accagccatg tggagaatga ctacatagac aaccctagcc tggccctgac caccggccca
 301 aagcggaccc ggggcggggc cccagagctg gccccgacgc ccgcccgctg tgaccaggat
 361 gtcacccacc attggatctc cttcagcggg cgcccagct ctgtgagcag caacagcagc
 421 acatcctctg accaacggct cttagaccac atggcaccac cacccgtggc tgaccaggcc
 481 tcaccaaggg ctgtgcgcat ccagcccaag gtggtccact gccagccgct ggacctcaag
 541 ggcccggcgg tcccacccga gctggacaag cacttcttgc tgtgcgaggc ctgtgggaag
 601 tgtaaatgca aggagtgtgc atcccccgg acgttgcctt cctgctgggt ctgcaaccag
 661 gagtgcctgt gctcagccca gactctggtc aactatggca cgtgcatgtg tttggtgcag
 721 ggcatcttct accactgcac gaatgaggac gatgagggct cctgcgctga ccaccctgc
 781 tcctgctccc gctccaactg ctgcgccgc tggtccttca tgggtgctct ctccgtggtg
 841 ctgccctgcc tgctctgcta cctgcctgcc accggctgcg tgaagctggc ccagcgtggc
 901 tacgaccgtc tgcgccgccc tggttgccgc tgcaagcaca cgaacagcgt catctgcaaa
 961 gcagccagcg gggatgccaa gaccagcagg cccgacaagc ctttctgaca gtttgtgtcg
1021 aagccccagt gctctgcctg gaaacctggt tctcttctga catctaagaa gactgcagca
1081 aggtcagagg ttttagcctc ctgaggctga ccttgctagt ctgcccactc cctaccccca
1141 gcttcggaaa atacagagac caccaccacg taccctgtat tcccaagat gatgaagaag
1201 cactttgggg cttttttttca gggtcctgaa actttgtgtc aaacagacaa tgcaggggca
1261 gggtgtggtt tggggggaaa ttttttcttt tcagaagaca gaacacagat gtggacacat
1321 atccggaaac tgcagctgct tgaatgcctt cccagccct ccttctccct ccctccctcc
1381 gcaccccct tcctcttttc cattgtcttt ggctctcaca ggagctagct gcctgggagg
1441 aattgttaac tgagtaccag ggtacctta aagaagaccc ttggagtctt ctataccttc
1501 ttctccttcc ccatctcact ccacccact ttgtccctga tgtcttgggg aaggtgtaga
1561 acaccctagc agttcctatt gtatatactt gggagccact gagaacagag gacggccagt
1621 gagtccaagc ctcgttcctc cttctgcctc cccggagcca caggatggat ttaggagcca
1681 ctgctcagtg cacttctccc ttccaactgc atcaactaac tctcggggt gttctgctca
1741 ccacaccgtc cttcggttct tactgagtca cagactcgcc tgcccactac gtgtcctggg
1801 ttctctctac tcagatccct tccagaaact ttatatgggt agaggaagcc agggcggcaa
1861 atgcgagacc aaatatcatt tgccaatga gtctgaggct gtggtctctg gatccagtca
1921 ttatgttttt atagaataat taaaccggat gctaacggtg ttttaaaaaa taataataaa
1981 acaacttgtt tcctttttggc caccccagg aagggctgat ttcaaaatct ggggcgagc
2041 aacctcaagg aacacaattt ccctccctat caacaagagg atttttaacag caaagaagag
2101 aggcagcacc tcccattggc agaatgaccg ctgagccagg ctgggtttgg gtttcttctc
2161 ttctgattct gctgctcact gtcatagcct tttgtgtata gtgatgtgtc tgtatctttta
2221 atgtaaatag agagatgatg aaaaagagt ctattttagt gttaggaagc cccagcaggg
2281 gagtcggaag agcttggaag agctggggag agggtagggg aaaggttttt ccaggggcca
2341 ctgggtttga gccctgcttc tgtgcacagc cacaccaccc tctcccgaca gccctcaaag
```
(SEQ ID NO:68)

FIG. 1 (cont'd)

ETV1

MDGFYDQQVPYMVTNSQRGRNCNEKPTNVRKRKFINRDLAHDSEELFQDLSQLQETWLAEAQVPDNDEQFVPDYQAE
SLAFHGLPLKIKKEPHSPCSEISSACSQEQPFKFSYGEKCLYNVSAYDQKPQVGMRPSNPPTPSSTPVSPLHHASPN
STHTPKPDRAFPAHLPPSQSIPDSSYPMDHRFRRQLSEPCNSFPPLPTMPREGRPMYQRQMSEPNIPFPPQGFKQEY
HDPVYEHNTMVGSAASQSFPPPLMIKQEPRDFAYDSEVPSCHSIYMRQEGFLAHPSRTEGCMFEKGPRQFYDDTCVV
PEKFDGDIKQEPGMYREGPTYQRRGSLQLWQFLVALLDDPSNSHFIAWTGRGMEFKLIEPEEVARRWGIQKNRPAMN
YDKLSRSLRYYYEKGIMQKVAGERYVYKFVCDPEALFSMAFPDNQRPLLKTDMERHINEEDTVPLSHFDESMAYMPE
GGCCNPHPYNEGYVY (SEQ ID NO:69)

```
    1 gttgatagaa gtccagatcc tgaggaaatc tccagctaaa tgctcaaaat ataaaatact
   61 gagctgagat ttgcgaagag cagcagcatg gatggatttt atgaccagca agtgccttac
  121 atggtcacca atagtcagcg tgggagaaat tgtaacgaga accaacaaa tgtcaggaaa
  181 agaaaattca ttaacagaga tctggctcat gattcagaag aactctttca agatctaagt
  241 caattacagg aaacatggct tgcagaagct caggtacctg acaatgatga gcagtttgta
  301 ccagactatc aggctgaaag tttggctttt catggcctgc cactgaaaat caagaaagaa
  361 ccccacagtc catgttcaga aatcagctct gcctgcagtc aagaacagcc ctttaaattc
  421 agctatggag aaaagtgcct gtacaatgtc agtgcctatg atcagaagcc acaagtggga
  481 atgaggccct ccaacccccc cacaccatcc agcacgccag tgtccccact gcatcatgca
  541 tctccaaact caactcatac accgaaacct gaccgggcct tccagctca cctccctcca
  601 tcgcagtcca taccagatag cagctacccc atggaccaca gatttcgccg ccagcttcct
  661 gaaccctgta actcctttcc tcctttgccg acgatgccaa gggaaggacg tcctatgtac
  721 caacgccaga tgtctgagcc aaacatcccc ttcccaccac aaggctttaa gcaggagtac
  781 cacgacccag tgtatgaaca caacaccatg gttggcagtg cggccagcca aagctttccc
  841 cctcctctga tgattaaaca ggaacccaga gattttgcat atgactcaga agtgcctagc
  901 tgccactcca tttatatgag gcaagaaggc ttcctggctc atcccagcag aacagaaggc
  961 tgtatgtttg aaaagggccc caggcagttt tatgatgaca cctgtgttgt cccagaaaaa
 1021 ttcgatggag acatcaaaca gagccagga atgtatcggg aaggacccac ataccaacgg
 1081 cgaggatcac ttcagctctg cagttttttg gtagctcttc tggatgaccc ttcaaattct
 1141 cattttattg cctggactgg tcgaggcatg gaatttaaac tgattgagcc tgaagaggtg
 1201 gcccgacgtt gggcattca gaaaaacagg ccagctatga actatgataa acttagccgt
 1261 tcactccgct attactatga gaaggaatt atgcaaaagg tggctggaga gagatatgtc
 1321 tacaagtttg tgtgtgatcc agaagccctt ttctccatgg cctttccaga taatcagcgt
 1381 ccactgctga agacagacat ggaacgtcac atcaacgagg aggacacagt gcctctttct
 1441 cactttgatg agagcatggc ctacatgccg gaagggggct gctgcaaccc ccacccctac
 1501 aacgaaggct acgtgtatta acacaagtga cagtcaagca gggcgttttt gcgcttttcc
 1561 tttttttctgc aagatacaga gaattgctga atcttttgttt tatttctgtt gtttgtattt
 1621 tatttttaaa taataataca caaaaagggg cttttcctgt tgcattattc tatggtctgc
 1681 catggactgt gcactttatt tgagggtggg tgggagtaat ctaaacatttt attctgtgta
 1741 acaggaagct aatgggtgaa tgggcagagg gatttgggga ttactttta cttaggcttg
 1801 ggatggggtc ctacaagttt tgagtatgat gaaactatat catgtctgtt tgatttcata
 1861 acaacataag ataatgttta ttttatcggg gtatctatgg tacagttaat ttcacgttgt
 1921 gtaaatatcc acttggagac tatttgcctt gggcattttc ccctgtcatt tatgagtctc
 1981 tgcaggtgta caaaaaaacc caatctact gtaaatggca gtttaattgt tagaaatgac
 2041 tgttttttgca ccacttgtaa aaaggtattt agcgattgca tttgctgttt gttgttttat
 2101 tttgctttat atatgacttg cagaggataa ccataaaatg ggtaattctc tctgaagttg
 2161 aataatcacc atgactgtaa atgagggca caattttgga ctctggcgcc aaactgagtc
 2221 ataggccagt agcattacgt gtatctggtg ccaccttgct gtttagatac aaatcatacc
 2281 gtcttttaaa tattttgaag cccatttcag ttaaataatg acatgtcatg gtcctttgga
 2341 atcttcattt aaatgttaaa tctggaatca aaatgaagca aaaatatct gtctcctttt
```

FIG. 1 (cont'd)

```
2401 cactttcttc agtacataaa tacattattt aatcaataag aattaactgt actaaatcat
2461 gtattatgct gttctagtta cagcaaacac tctttaagaa aaatatccaa tacactaaat
2521 aggtactata gtaattttta gacatggtac ccattgatat gcatttaaac cttttactgc
2581 tgtgttatgt tgataacata tataaatatt agataatgct aatgcttctg ctgctgtctt
2641 ttctgtaata ttctctttca tgctgaattt actatgacca tttataagca gtgcagttaa
2701 ctacagatag catttcagga caaaatagat gactcaaacc atttattgct taaaaaatag
2761 cttacgccat gctatgctat aagcagcttt tatgcacatt gacaaatgaa gagtaagctt
2821 cagcttgcta aaggaaactg tggaaccttt tgtaactttt ggtgatatgg aaaattattt
2881 acaaaccgtc aaagaatatg aggaagttgc tgtatgacat agtgctggca ctgatattat
2941 ccatcatctc tttttggaca cttctgtaaa tgtgattgga ttgtttgaaa gaagatttaa
3001 agtttcaaag ttttttgttc tgttttgct ttgcatttgg agaaaatatt gaaagcaggg
3061 tatgttgttt cattcacctt gaaaaaacca tgagtaaatg gggatataga atctctgaat
3121 agctcgctaa aagattcaag caagggacat gaattttgtt ccatctatca ataatatcca
3181 gaagaacaac ttttttaaag agtctatagc aaaaagcaaa aaaaaaaaaa aattctaaac
3241 acaaagtcaa aataaaccta ttgtaaaagc atttcgtgat gagcatgaaa aagattgttt
3301 aaagatgatc cccccagcta cccatttcc aaaactacac agatcacagc tcatttctct
3361 aagtggagca gttatcaaga aacccaaaca ccaaaattgc tactcttcac atttaatcct
3421 acaaaaagta ctccaatttc aaaatatgta tgtaacctgc gatttcaatg attgttgttc
3481 atatacatca tgtattattt tggcccattt tgggcctaaa aagaaaaact atgccttaaa
3541 aatcagaacc ttttctcccc actatgctta tgtggccatc tacagcactt agaataaaaa
3601 cagatgttaa aatattcagt gaaagtttta ttggaaaaag gaattgagat atataattga
3661 gatttggtga aattgaagga gaaatttaa gtgagtcttt aaaatatatt ctgaatgaaa
3721 actgtattga ggattcattt ttgttccttt tttttctttt tctcttttct ccttttcctt
3781 cttttaata gtctagtttt agtcagtcag tgaggaagaa ttgggccatg ctaacgttat
3841 cacaagagaa caatggcaga atggtatta gttatataat atttaaggac aaactatatg
3901 ttttgctgtt ttaacgtagt gactcactga actaaataca taattgacca acattaagtg
3961 tatttccaat acagaagggt tgaaaatatt acattataaa ctcttttgaa aaatgtatct
4021 aaaatttttt aagttctgtt ttgattccac ttttttggttg agttttatg ttttttgtttt
4081 caggtagatt aataaatctg gcagctgatt tctgcaagat tcttgtgttt tgaatttctc
4141 attgaattgg ctactcaaac atagaaatca tttgttaatg atgtaatgtc ttctctcagc
4201 ttttatcttc actgctgttt gctgtctctt gatgatgaca tgttaatacc caatagatta
4261 attgcaacaa acacttatac tcaaataact aagtaaaaat aattttttct gttatgtcca
4321 tgaaaagtgc ttcagaataa aaatccacaa gactgacagt gcagaacatt tttctcaaat
4381 catgggcgga tcttggaggt ctagtttccc gtagatgctg taaccaatta ccacaacttc
4441 agtaatttac acaaatttat cttatagttc tggaggcaga agttcaaaag aagccttaag
4501 agactaaaac caagatgtcc ttaggtctgg ttccttctgg aggctccagg ggagattctt
4561 ccagctttca cttctagagt ctgctgacat tccttggctc ctggctacat cacttcaatc
4621 tctgcttcca tggtcacata ctcttctact atagtcaaat ttccttcctg cctcttataa
4681 ggatgcttgt gattacattt aggggatgct cagataatcc aggacaatct ctccatctca
4741 agatccttaa cttaatgacg tgtgccaagt cccttggct agataattat tcataggtcc
4801 cagggattag gacatggatg taaggggtga gggcagggct gttattcaga acaccgcacg
4861 gaggaggaag actgtgtagc aaagactcta attgatttac tcaggaacag tggagttctg
4921 ctgagggatc taggatttga aagtactaga gtttgctttt atttaccact gagatatttt
4981 cccttattc tgcataaata attttgaaaa ctttctatat taaatttcaa ctattccact
5041 aaaatgtctg gtaatcacat caagccttta gattattcaa atccttcccc agccccagg
5101 aaaacactaa gtcatgaaac agaaaaacag aaggtatgat aataatagta ataacagtta
5161 aatcagtggt ctaatccaga ttttattttt taatacattt cttttggtgt taatatgggt
5221 tactatgtga tcttatcatt tgctagtgat tattacttat taggtaagaa caatgtgtaa
5281 aatatgtcta ttactcaaaa gaacaattgc aaaatgagtc aacttatctt tatataacca
5341 ggaaagaaat atattgccag aagctacaga attttgccag atgatagggt tttctaaaat
```

FIG. 1 (cont'd)

```
5401 gagccacttt gtctatcatg cagcctttc  agagcttgta atgagaaaac attacagagg
5461 agaaggtcat ttggatgttt gttacttgga atcctagaaa acaaaaacta aaatttaaaa
5521 ataagaagtg agtaagctat tttccatttg cgatttggta tggagaagag aggaaataga
5581 attattaaaa aaatacaaat tgggtaaaag tgatggtgga aaaaatataa agaaggcaaa
5641 tgtacatatt aagcaattct actaagaatt ggaaaaatca agtttcaaaa agatggtaat
5701 agttgggcat gatactagaa aatttcaccc agtttattca gagctcaact agtactttta
5761 ggacttctt ttttatatac atgagactca ctttgacata cttaaaaaaa aaacagttta
5821 tggaaagtac agtttaagag gagaatttga ttagactaag tggatatctt tatagaaata
5881 ttaatgattt cagaattttc agttacaagt gtatataccg tggctattgt ttatggattc
5941 atatgtaagg tagggtcttt tttgcatata gactccagta ttagttactt tcattctaaa
6001 attatattta tgcttctatg gggaagaaaa tttttaattc acttggttgt attaaaatta
6061 tacttacggt ttgagaaaac atgctatgaa aatcatgatt atagcaaatt aaatatgctc
6121 aaaatttaaa tctaaaataa aagcccagaa actgaaaa  (SEQ ID NO:70)
```

Figure 7

| Gene Symbol | OMIM | Ensembl | UniGene ID | Entrez Gene | Representative Public ID |
|---|---|---|---|---|---|
| IER3 | 602996 | ENSG00000137331 | 591785 | 8870 | NM_003897 |
| EGR1 | 128990 | --- | 326035 | 1958 | NM_001964 |
| IER2 | --- | ENSG00000160888 | 501629 | 9592 | NM_004907 |
| MYC | 113970 /// 190080 | ENSG00000136997 | 202453 | 4609 | NM_002467 |
| LNK | 605093 | --- | 506784 | 10019 | NM_005475 |
| ETV5 | 601600 | ENSG00000171656 | 43697 | 2119 | BF060791/NM_004454 |
| HES1 | 139605 | ENSG00000114315 | 250666 | 3280 | BE973687/NM_198155 |
| SPRY2 | 602466 | ENSG00000136158 | 18676 | 10253 | NM_005842 |
| DUSP4 | 602747 | ENSG00000120875 | 417962 | 1846 | NM_001394 |
| FOSL1 | 136515 | ENSG00000175592 | 283565 | 8061 | BG251266/NM_005438 |
| PLK3 | 602913 | ENSG00000173846 | 632415 | 1263 | NM_004073 |
| GJB1 | 302800 /// 304040 | ENSG00000169562 | 333303 | 2705 | NM_000166 |
| CD3EAP | 107325 | ENSG00000117877 | 646358 | 10849 | NM_012099 |
| SLC4A7 | 603353 | ENSG00000033867 | 250072 | 9497 | NM_003615 |
| CCND1 | 151400 /// 168461 /// 193300 /// 254500 | ENSG00000110092 | 523852 | 595 | M73554 |
| DUSP6 | 602748 | ENSG00000139318 | 298654 | 1848 | BC003143 |
| POLR1C | 610060 | ENSG00000171453 | 584839 | 9533 | AF008442 |
| RRS1 | --- | ENSG00000179041 | 71827 | 23212 | BC001811 |
| PHLDA2 | 602131 | ENSG00000181649 | 154036 | 7262 | AF001294 |
| ST8SIA1 | 601123 | ENSG00000111728 | 408614 | 6489 | L32867 |
| GRIN1 | 138249 | ENSG00000176884 | 558334 | 2902 | L05666 |
| NFKB2 | 164012 | --- | 73090 | 4791 | U09609 |
| ETV4 | 600711 | ENSG00000175832 | 434059 | 2118 | U35622 |
| SPRED2 | 609292 | ENSG00000198369 | 59332 | 200734 | AW138902/NM_181784 |
| ARID5A | --- | ENSG00000196843 | 920 | 10865 | M62324 |
| SH3BP1 | --- | ENSG00000100092 | 601143 | 23616 | NM_018957 |
| MAP2K3 | 602315 | ENSG00000034152 | 514012 | 5606 | AA780381/BC032478 |
| TNC | 187380 | --- | 143250 | 3371 | BF434846/NM_002160 |
| RKHD2 | --- | ENSG00000176624 | 465144 | 51320 | NM_016626 |
| HEY1 | 602953 | --- | 234434 | 23462 | NM_012258 |
| PYCRL | --- | ENSG00000104524 | 165186 | 65263 | NM_023078 |
| HYDIN | --- | ENSG00000157423 | 461229 | 54768 | NM_017558 |
| SORBS2 | --- | --- | 481342 | 8470 | NM_014133/AM392656 |
| SPRY4 | 607984 | ENSG00000187678 | 323308 | 81848 | W48843/BC125096 |
| ETV1 | 600541 | ENSG00000006468 | 22634 | 2115 | BE881590/NM_004956 |

US 7,812,143 B2

BIOMARKERS FOR CANCER TREATMENT

CROSS-REFERENCE TO RELATED APPLICATIONS/PATENTS & INCORPORATION BY REFERENCE

This application claims priority to U.S. Provisional Application Ser. No. 60/788,014, filed Mar. 31, 2006, the contents of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

One approach to the study of cancer is genetic profiling, an effort aimed at identifying perturbations in gene expression that lead to the malignant phenotype. However, cancers differ widely in their genetic "signature", leading to difficulty in diagnosis and treatment, as well as in the development of effective therapeutics.

Genetic profiling of tumors may provide a more effective approach to cancer management and/or treatment. Accordingly, there is a need in the art to better understand the genetic profile of specific classes of tumors, in an effort to provide improved therapeutics, diagnostics and screening methods.

The kinase pathway comprising RAS, RAF, mitogen-activated protein kinase kinase (MEK) and extracellular signal regulated kinase (ERK) is activated in most human tumours, often through gain-of-function mutations of RAS and RAF family members (Davies, H. et al. 2002 Nature 417, 949-954). It has previously been shown that mutation of BRAF is associated with enhanced and selective sensitivity to MEK inhibition. This MEK dependency was observed in BRAF mutant cells regardless of tissue lineage. Since BRAF is a serine/threonine kinase that is commonly activated by somatic point mutation in human cancer, it may provide new therapeutic opportunities in malignant melanoma and other cancers.

SUMMARY OF THE INVENTION

Biomarkers whose levels change depending on cancer status following treatment with a therapeutic drug have been identified and characterized herein. Profiles based on the same have been generated, and methods of using such profiles for qualification of cancer status defined.

In one aspect, the invention provides a biomarker indicative of the therapeutic efficacy of a Ras/Raf/MEK/ERK pathway inhibitor comprising one or more of Markers 1-35. In one embodiment of the invention, the biomarker is selected from the group consisting of SPRY2, ETV1, ETV4, ETV5, and DUSP6. In further embodiments of the invention, the Ras/Raf/MEK/ERK pathway inhibition is inhibition of MEK or Raf.

In another aspect, the invention provides a panel of biomarkers indicative of the therapeutic efficacy of a Ras/Raf/MEK/ERK pathway inhibitor comprising two or more of Markers 1-35. In one embodiment of the invention, the two or more biomarkers are selected from the group consisting of SPRY2, ETV1, ETV4, ETV5, and DUSP6. In further embodiments of the invention, the Ras/Raf/MEK/ERK pathway inhibition is inhibition of MEK or Raf.

In another aspect, the invention provides a method for selecting an individual for treatment with a Ras/Raf/MEK/ERK pathway inhibitor, comprising: obtaining a cancerous tumor sample from the individual; measuring the amount of a biomarker in the tumor sample, wherein the biomarker is selected from the group consisting of DUSP6 (Marker 1, Table 1), SPRY2 (Marker 15), ETV4 (Marker 23), ETV5 (Marker 21), PLK3 (Marker 12), and MAP2K3 (Marker 7); and selecting the individual for treatment with a Ras/Raf/MEK/ERK pathway inhibitor based on the measured amount of the biomarker. In one embodiment of the invention, the cancerous tumor is from an organ selected from the group consisting of skin, colon, thyroid, ovarian, lung, and pancreas. In another embodiment of the invention, the skin tumor is a melanoma. In further embodiments of the invention, cells of the tumor comprise an activated Ras/Raf/MEK/ERK pathway or a B-Raf mutation. In still further embodiments of the invention, the step of measuring comprises measuring the amount of nucleic acid encoding the biomarker in the sample or measuring the amount of a biomarker polypeptide.

In another aspect, the invention provides a method of qualifying cancer status in a subject comprising: measuring the amount of at least one biomarker in a tumor sample obtained from the subject, wherein the biomarker is selected from the group consisting of Markers 1-35; and correlating the measurement with cancer status, thereby qualifying cancer status in a subject. In one embodiment of the invention, the step of measuring comprises measuring the amount of at least one biomarker in a tumor sample obtained from the subject after treatment with a therapeutic drug, and comparing the amount to an amount of the biomarker in a tumor sample from the subject prior to treatment with the therapeutic drug. In one embodiment, the invention further comprise managing treatment of the subject based on cancer status. In an additional embodiment, the invention comprises obtaining the tumor sample.

In yet another embodiment of the invention, the subject is human. In further embodiments of the invention, cells of the tumor comprise an activated Ras/Raf/MEK/ERK pathway or have a B-Raf mutation. In another embodiment of the invention, the cancerous tumor is from an organ selected from the group consisting of skin, colon, thyroid, ovarian, lung, and pancreas. In a specific embodiment, the skin tumor is a melanoma. In another embodiment of the invention, the tumor is selected from the group consisting of: prostate carcinoma, lung carcinoma, glioma, acute myelogenous leukemia, pancreatic carcinoma, head and neck carcinomas. In further embodiments of the method of the invention, the step of measuring comprises measuring the amount of nucleic acid encoding the biomarker in the sample or measuring the amount of a biomarker polypeptide.

In another aspect, the invention provides a method for identifying an anti-tumor response in a subject exposed to a therapeutic drug, the method comprising determining the amount of a biomarker selected from the group consisting of Markers 1-35, or combinations thereof, in a tumor, wherein an increase in the amount of Markers 32-35, or a decrease in the amount of Markers 1-31, or combinations thereof, after exposure to the drug identifies an anti-tumor response in the subject.

In yet another aspect, the invention provides a method of monitoring the efficacy of a therapeutic drug in a subject comprising determining the amount of a biomarker selected from the group consisting of Markers 1-35, or combinations thereof, in a tumor, wherein an increase in the amount of Markers 32-35, or a decrease in the amount of Markers 1-31, or combinations thereof, after exposure to the drug indicates that the drug is effective.

In one embodiment of the invention, the subject is human. In further embodiments of the invention, cells of the tumor have a B-Raf mutation or an activated Ras/Raf/MEK/ERK pathway. In another embodiment of the invention, the cancerous tumor is from an organ selected from the group consisting of skin, colon, thyroid, ovarian, lung, and pancreas. In a specific embodiment, the skin tumor is a melanoma.

In one embodiment of the invention, the tumor is selected from the group consisting of: prostate carcinoma, lung carcinoma, glioma, acute myelogenous leukemia, pancreatic carcinoma, head and neck carcinomas. In yet another embodiment of the invention the therapeutic drug is an inhibitor of the Ras/Raf/MEK/ERK pathway. In further embodiments of the invention, the therapeutic drug is selected from the group consisting of: Ras, Raf, MEK or MAPK inhibitors. In another embodiment of the method of the invention, the step of measuring comprises measuring each of Markers 1-35.

In another aspect, the invention provides a method of identifying an agent useful in the treatment of a cancer, comprising: contacting a cancerous cell with a test agent; determining the amount of a biomarker selected from the group consisting of Markers 1-35; and comparing the amount of the biomarker with the amount of the biomarker in the cancerous cell prior to the step of contacting, wherein an increase in the amount of Markers 32-35, or a decrease in the amount of Markers 1-31, or combinations thereof, identifies the test agent as useful in the treatment of cancer. In one embodiment of the invention, the test agent is a Ras/Raf/MEK/ERK inhibitor. In specific embodiments, the test agent is a MEK inhibitor or a Raf inhibitor.

In another aspect, the invention provides a method for identifying a biomarker for determining the efficacy of a cancer treatment, comprising: contacting a cancer cell with a Ras, Raf, MEK or ERK inhibitor; measuring the amount of a candidate biomarker in the cancer cell; and comparing the amount of the biomarker to the amount of the biomarker in the cell prior to contacting the cancer cell with a Ras, Raf, MEK or MAPK inhibitor, wherein a difference identifies the candidate as a biomarker for determining the efficacy of a cancer treatment. In one embodiment of the invention, the cancer cell comprises a B-Raf mutation. In further embodiments of the invention, the inhibitor is a MEK inhibitor or a Raf inhibitor.

In another aspect, the invention provides a kit for determining the efficacy of a cancer therapy, comprising an adsorbent, wherein the adsorbent retains one or more biomarkers selected from one or more of Markers 1-35, and written instructions for use of the kit for determining the efficacy of a cancer therapy. In one embodiment of the invention, the adsorbent is an antibody, single or double stranded oligonucleotide, amino acid, protein, peptide or fragments thereof. In another embodiment of the invention, one or more biomarkers is detected using mass spectrometry, immunoassay, or PCR.

The invention also includes an biomarker profile derived from a biological sample exposed to a Ras/Raf/MEK/ERK pathway inhibitor, wherein the profile indicates therapeutic efficacy of a Ras/Raf/MEK/ERK pathway inhibitor, comprising an increased amount of a biomarker selected from the group consisting of Markers 32-35, and a decreased amount of a biomarker selected from the group consisting of Markers 1-31, or combinations thereof.

Other aspects of the invention are described in or are obvious from the following disclosure and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 1 shows the nucleic acid and amino acid sequences corresponding to Markers 1-35.

FIG. 7 shows a table providing sequence identifying information for the 35 biomarkers listed in Table 1.

DETAILED DESCRIPTION OF THE INVENTION

I. Definitions

Figure 2:
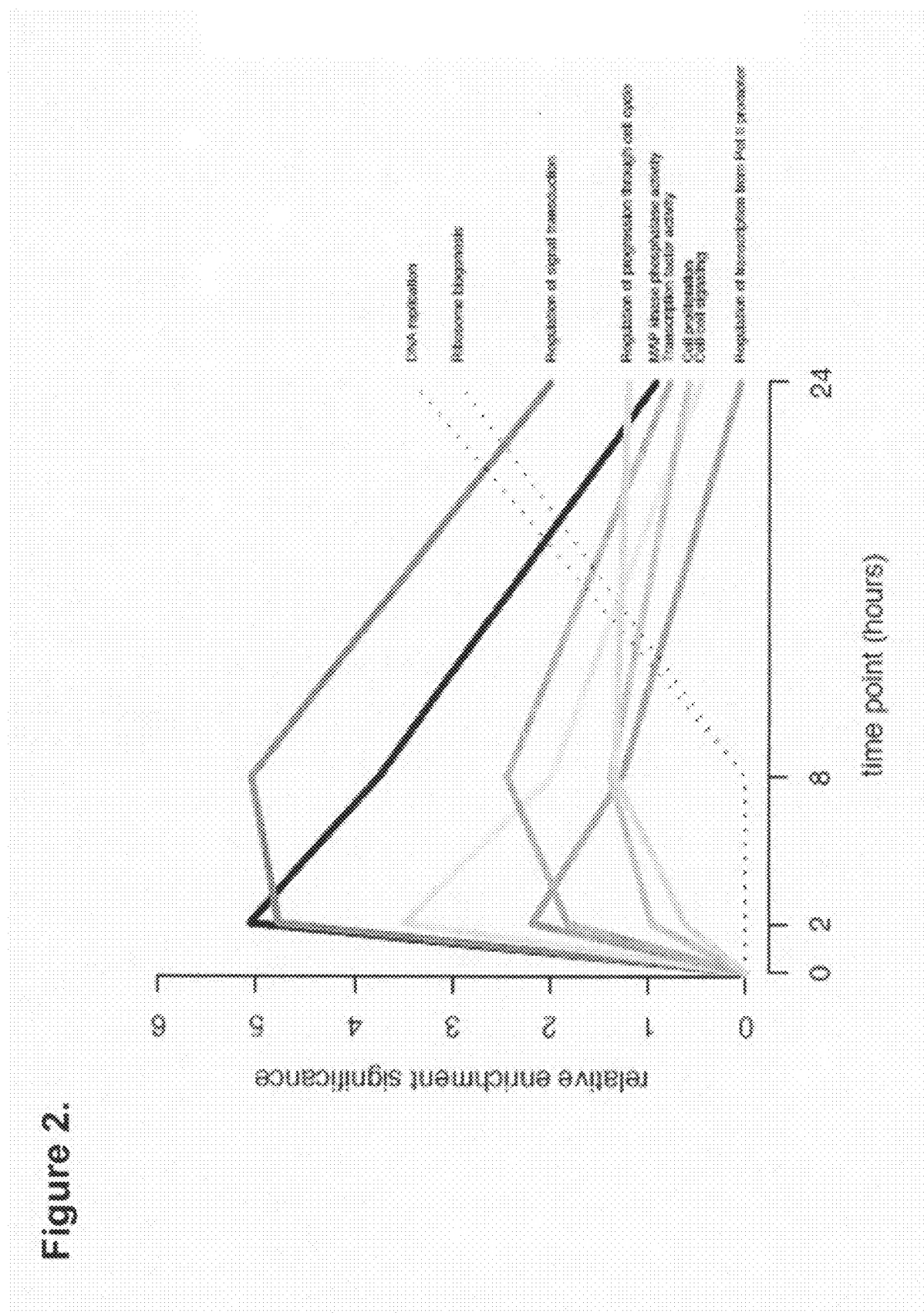
FIG. 2 shows a graph depicting the relative enrichment significance as a function of time of exposure to MEK inhibitor, with each line corresponding to genes of a functional class based on biological process according to Gene Ontology (GO) classification.

Unless defined otherwise, all technical and scientific terms used herein have the meaning commonly understood by a person skilled in the art to which this invention belongs. The following references provide one of skill with a general definition of many of the terms used in this invention: Lackie and Dow, *The Dictionary of Cell & Molecular Biology* (3 ed. 1999); Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the "Ras/Raf/MEK/ERK pathway" refers to the intracellular kinase cascade comprising RAS, RAF, mitogen-activated protein kinase kinase (MEK) and extracellular signal regulated kinase (ERK). The Ras/Raf/MEK/ERK signaling pathway is known in the art and described in McCormick F. 1993 *Nature* 363(6424):15-6. As used herein, an "activated Ras/Raf/MEK/ERK pathway" refers to a detectable increase in levels of phosphorylated MAPK, and/or increased expression and/or activation of its primary targets (Favres, G. 2006 *Bulletin du Cancer* 93(4):25-30; Kolch, W. 2000 *Biochem J* 351(2):289-305; Peysonnaux, C. and Eychece, A. 2001 *Biol Cell* 93:53-62; Satyamoorthy, K., et al. 2003 *Cancer Res* 63:756-759; Houben, M., et al. 2004 *J Carcinog* 3:6). An "activated Ras/Raf/MEK/ERK pathway is also defined as an increase in kinase activity of members of the pathway. Methods for measuring kinase activity of Ras/Raf/MEK/ERK pathway members are taught, for example, in Davies et al., 2002, Nature 417:949.

As used herein, an "inhibitor" of the Ras/Raf/MEK/ERK pathway refers to a compound, such as a small molecule, chemical compound, biologic compound, antibody, antisense, siRNA, or the like that reduces the level of Ras/Raf/MEK/ERK pathway activation by at least 10%. Where Ras/Raf/MEK/ERK pathway activation is determined by measuring the amount of phosphorylated MAPK, an inhibitor of the pathway is a compound that will decrease the amount of phosphorylated MAPK by 10%. Similarly, "inhibition" of the Ras/Raf/MEKIERK pathway refers to a decrease in pathway activity, as measured by phosphorylated MAPK levels, by at least 10%.

A "subject" is a vertebrate, preferably a mammal, more preferably a primate and still more preferably a human. Mammals include, but are not limited to, primates, humans, farm animals, sport animals, and pets.

As used herein, "sample" or "biological sample" refers to a tumor sample.

As used herein, the term "panel" refers to a composition, such as an array, comprising one or more biomarkers. A "panel" can also refer to a profile or index of expression patterns of one or more biomarkers described herein. For example, a panel can refer to a solid surface comprising biomarker nucleic acid or polypeptide molecules. A panel can also be a description of the expression of one or more biomarkers for a given tumor or cancer type, or for a given patient. That is, by way of example, a panel of biomarkers for a given patient or given tumor or cancer may be as follows: Marker 1: downregulated; Marker 2: downregulated; Marker 10: downregulated; Marker 20: downregulated; Marker 32: upregulated.

The term "qualifying cancer status" refers to the association of the expression level of a given biomarker, or the expression pattern of a plurality of biomarkers, with the status of a cancer, wherein "status" refers to stage, degree, severity, operability, or prognosis. Qualifying cancer status can include quantifying the amount of a given biomarker, or can include a qualitative analysis of an expression pattern of multiple biomarkers.

"Managing subject treatment" refers to the behavior of the clinician or physician subsequent to the determination of cancer status. For example, if the result of the methods of the present invention is inconclusive or there is reason that confirmation of status is necessary, the physician may order more tests. Alternatively, if the status indicates that treatment is appropriate, the physician may schedule the patient for treatment, e.g., surgery, administer one or more therapeutic agents or radiation. Likewise, if the status is negative, e.g., late stage cancer or if the status is acute, no further action may be warranted. Furthermore, if the results show that treatment has been successful, a maintenance therapy or no further management may be necessary. For example, detection of the differential presence of one or more biomarkers in a tumor sample from an individual may indicate to a clinician the efficacy of a therapeutic drug (such as a MEK inhibitor) and, based on that, the clinician can manage the subject's treatment by continuing treatment with the therapeutic drug.

"Monitoring" refers to observing, measuring, and/or recording changes in a varying parameter (e.g. monitoring the efficacy of a Ras/Raf/MEK/ERK pathway inhibitor in a subject).

As used herein, the phrase "prior to treatment" can refer to a time prior to the commencement of treatment, but can also refer to a time prior to the current treatment. That is, "prior to treatment" can refer to a prior treatment.

"Marker" or "biomarker" in the context of the present invention refer to a polypeptide (of a particular apparent molecular weight) or nucleic acid, which is differentially present in a sample taken from subjects having cancer as compared to a comparable sample taken from control subjects (e.g., a person with a negative diagnosis or undetectable cancer, normal or healthy subject); or which is differentially present in a sample taken from a subject having cancer, prior to treatment as compared to after exposure to a therapeutic drug. The term "biomarker" is used interchangeably with the term "marker." Polypeptide biomarkers can be identified by molecular mass in Daltons, and include the masses centered around the identified molecular masses for each marker. Nucleic acid biomarkers can be identified by sequence.

The term "measuring" means methods which include detecting or observing the presence or absence of marker(s) in the sample, quantifying the amount of marker(s) in the sample, and/or qualifying the type of biomarker. Measuring can be accomplished by methods known in the art and those further described herein, including but not limited to microarray analysis (with Significance Analysis of Microarrays (SAM) software), SELDI, PCR, and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry, atomic force microscopy, and PCR (including quantitative PCR).

"Detect" refers to identifying the presence, absence or amount of the object to be detected.

The phrase "differentially present" refers to differences in the quantity and/or the frequency of a marker present in a sample taken from subjects having cancer as compared to a control subject, or in a sample taken from cancer subjects prior to treatment as compared to after exposure to a therapeutic drug. For example, some markers described herein are present at an elevated level in samples of subjects compared to samples from control subjects, or in samples of cancer subjects before vs. after exposure to a therapeutic drug. In contrast, other markers described herein are present at a decreased level in samples of cancer subjects compared to samples from control subjects, or in samples of cancer subjects before vs. after exposure to a therapeutic drug.

A marker can be differentially present in terms of quantity, frequency or both.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the cancer subjects' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionucleides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm2 to 50 mJ/mm2. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons that ionize gas phase neutrals; (2) strong electric field to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Solid support" refers to a solid material that can be derivatized with, or otherwise attached to, a capture reagent. Exemplary solid supports include probes, microtiter plates and chromatographic resins.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Surface-enhanced laser desorption/ionization" or "SELDI" refers to a method of desorption/ionization gas phase ion spectrometry (e.g., mass spectrometry) in which the analyte is captured on the surface of a SELDI probe that engages the probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip).

"Surface-Enhanced Affinity Capture" or "SEAC" is a version of SELDI that involves the use of probes comprising an absorbent surface (a "SEAC probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001).

In some embodiments, a SEAC probe is provided as a pre-activated surface that can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Adsorption" refers to detectable non-covalent binding of an analyte to an adsorbent or capture reagent.

"Eluant" or "wash solution" refers to an agent, typically a solution, which is used to affect or modify adsorption of an analyte to an adsorbent surface and/or remove unbound materials from the surface. The elution characteristics of an eluant can depend on, for example, pH, ionic strength, hydrophobicity, degree of chaotropism, detergent strength and temperature.

"Analyte" refers to any component of a sample that one wishes to detect. The term can refer to a single component or a plurality of components in the sample.

The "complexity" of a sample adsorbed to an adsorption surface of an affinity capture probe means the number of different protein species that are adsorbed.

"Array," "microarray," or "Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. For a DNA microarray or polynucleotide array, one or more DNA molecules, preferably a collection of DNA spots, is attached to a solid surface. A DNA microarray can be used for expression profiling, monitoring expression levels for thousands of genes simultaneously, or for comparative genomic hybridization. A "protein biochip" refers to a biochip adapted for the capture of polypeptides.

"Protein biochip" refers to a biochip adapted for the capture of polypeptides. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000). Protein biochips produced by Ciphergen Biosystems comprise surfaces having chromatographic or biospecific adsorbents attached thereto at addressable locations. Biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application US20030032043A1 (Pohl and Papanu, "Latex Based Adsorbent Chip," Jul. 16, 2002) and U.S. patent application 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

"Immunoassay" is an assay that uses an antibody to specifically bind an antigen (e.g., a marker). The immunoassay is characterized by the use of specific binding properties of a particular antibody to isolate, target, and/or quantify the antigen.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well-characterized fragments produced by digestion with various peptidases. This includes, e.g., Fab-" and F(ab)-" 2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

The term "obtaining" as in "obtaining the tumor sample" is intended to include any method of acquiring the tumor sample.

The terms "comprises", "comprising", and the like are intended to have the broad meaning ascribed to them in U.S. Patent Law and can mean "includes", "including" and the like.

It is to be understood that this invention is not limited to the particular component parts of a device described or process steps of the methods described, as such devices and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise.

Other definitions appear in context throughout the specification.

II. Biomarkers of the Invention

The present invention is based in part on the discovery that in cancers characterized by activation of the Ras/Raf/MEK/ERK pathway, inhibition of the pathway results in the differential presence of specific biomarkers. These biomarkers can then be correlated with disease status, be used to identify subjects as candidates for certain treatments, or be used to monitor treatment efficacy.

In one aspect, the present invention identifies biomarkers that are indicative of the therapeutic efficacy of a drug in a cancer subject. Indeed, it has been discovered that a number of genes are expressed at an increased or decreased level in tumor samples of cancer subjects after exposure to a therapeutic drug. These genes are involved in DNA replication, ribosome biogenesis, regulation of signal transduction, regulation of progression through the cell cycle, MAP kinase phosphatase activity, transcription factor activity, cell proliferation, cell-cell signaling, and regulation of transcription from PolII promoters (FIG. 2). Included are the biomarkers listed, without limitation, in Table 1, below.

TABLE 1

| Marker | |
|---|---|
| 1 | DUSP6 |
| 2 | ARID5A |
| 3 | BRS1 |
| 4 | MYC |
| 5 | FOSL1 |
| 6 | SPRED2 |
| 7 | MAP2K3 |
| 8 | EGR1 |
| 9 | CD3EAP |
| 10 | PHLDA2 |
| 11 | POLR1C |
| 12 | PLK3 |
| 13 | HES1 |
| 14 | PYCRL |
| 15 | SPRY2 |
| 16 | SH3BP1 |
| 17 | IER2 |
| 18 | CCND1 |
| 19 | IER3 |
| 20 | SPRY4 |
| 21 | ETV5 |
| 22 | ETV1 |
| 23 | ETV4 |
| 24 | SLC4A7 |
| 25 | RKHD2 |
| 26 | GJB1 |
| 27 | DUSP4 |
| 28 | LNK |
| 29 | HEY1 |
| 30 | TNC |
| 31 | ST8SIAI |
| 32 | HYDIN |
| 33 | NFKB2 |
| 34 | GRINI |
| 35 | SORBS2 |

While initially identified using genetic analysis, the biomarkers described herein include both nucleic acid and amino acid biomarker sequences. For example, the nucleic acid sequence (e.g., mRNA) a differentially present gene can be used as a biomarker, but the polypeptide sequence encoded thereby can also be used as a biomarker. Accordingly, reference to detection or measurement of a biomarker can refer to detection or measurement of either or both of a polynucleotide or polypeptide sequence (e.g., by using PCR or SELDI, respectively, to detect the biomarker).

While the present disclosure is focused on the biomarkers noted in Table 1, these markers can be classified based on function. For example, the biomarkers of Table 1 can be classified into functional groups including biomarkers involved in DNA replication, ribosome biogenesis, regulation of signal transduction, regulation of progression through the cell cycle, MAP kinase phosphatase activity, transcription factor activity, cell proliferation, cell-cell signaling, and regulation from a PolII promoter. Accordingly, it is contemplated, that additional genes and encoded proteins that fall within these functional classifications could be useful biomarkers according to the invention.

The biomarkers of the invention represent known genes, the sequences of which are available through public databases known to those of skill in the art. FIG. 7 provides exemplary accession numbers for the biomarkers of Table 1. Also contemplated within the scope of the instant invention are variants of the biomarkers of Table 1. Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent (e.g., an adsorbent) is bound to a solid phase, such as a bead, a plate, a membrane or a chip. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization (discussed further below).

Also included with the scope of the invention are variants of the nucleic acid or amino acid biomarker sequences, including, but not limited to amino acid or nucleic acid sequences having at least 30%, at least 35%, at least 40%, at least 45%, at least 50%, at least 55%, at least 60%, at least 65%, at least 70%, at least 75%, at least 80%, at least 85%, at least 90%, at least 95% or at least 99% sequence identity to the sequences shown in FIG. 1.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times. 100%). In one embodiment, the two sequences are the same length.

The determination of percent identity between two sequences can also be accomplished using a mathematical algorithm. A preferred, non-limiting example of a mathematical algorithm utilised for the comparison of two sequences is the algorithm of Karlin and Altschul, 1990, *Proc. Natl. Acad. Sci. U.S.A.* 87:2264-2268, modified as in Karlin and Altschul, 1993, *Proc. Natl. Acad. Sci. U.S.A.* 90:5873-5877. Such an algorithm is incorporated into the NBLAST and XBLAST programs of Altschul et al., 1990, *J. Mol. Biol.* 215:403. BLAST nucleotide searches can be performed with the NBLAST nucleotide program parameters set, e.g., for score=100, word length=12 to obtain nucleotide sequences homologous to a nucleic acid molecules of the present invention. BLAST protein searches can be performed with the XBLAST program parameters set, e.g., to score-50, word length=3 to obtain amino acid sequences homologous to a protein molecule of the present invention. To obtain gapped alignments for comparison purposes, Gapped BLAST can be utilised as described in Altschul et al., 1997, Nucleic Acids Res. 25:3389-3402. Alternatively, PSI-BLAST can be used to perform an iterated search, which detects distant relationships between molecules (Id.). When utilising BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilised for the comparison of sequences is the algorithm of Myers and Miller, 1988, CABIOS 4:11-17. Such an algorithm is incorporated in the ALIGN program (version 2.0) which is part of the GCG sequence alignment software package. When utilising the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

III. Methods of the Invention

The invention further provides that the biomarkers described herein, used individually or in combination with other biomarkers, can be employed in various methods. In the first, biomarkers of the invention are employed in methods for selecting subjects for treatment with a Ras/Raf/MEK/ERK pathway inhibitor. As such, the amount of at least one biomarker delineated herein may be predictive of a subject's response to treatment. Biomarkers particularly useful in such an aspect of the invention include, without limitation, DUSP6 (Marker 1, Table 1), SPRY2 (Marker 15), ETV4 (Marker 23), ETV5 (Marker 21), PLK3 (Marker 12), and MAP2K3 (Marker 7). A subject is identified as a candidate for treatment with a Ras/Raf/MEK/ERK pathway inhibitor if the one or more of the biomarkers are detected in an amount greater than twice the average value (of an unselected population of tumors or patient samples, or cell lines).

In another aspect, the amount of at least one biomarker delineated herein provides information for qualifying cancer status in a subject. The determination of status may be the result of an isolated measurement, or it may precede and follow exposure of the subject to a therapeutic drug, thus providing indication of a potentially changing cancer status in the subject. For example, isolated measurement of one or more biomarkers may be used to determine whether a patient's cancer is of a type that is amenable to treatment with a Ras/Raf/MEK/ERK pathway inhibitor, whereas a repeated measurement may be used to determine a patient's responsiveness to a treatment regime using a Ras/Raf/MEK/ERK pathway inhibitor.

The biomarkers of the invention find further use in methods for identifying anti-tumor response and for monitoring the efficacy of a therapeutic drug in a cancer subject. For example, the biomarkers described herein have been shown to be differentially present in cancer cells following treatment with inhibitors of the Ras/Raf/MEK/ERK pathway. Thus, the level of one or more biomarkers in a patient that has been treated with a Ras/Raf/MEK/ERK pathway inhibitor can be determined, wherein the differential presence of the biomarker can be indicative of the efficacy of the treatment. Based on this information, a physician or other medical professional, can manage treatment of the patient. Managing patient treatment refers to the behavior of the clinician or physician subsequent to the determination of cancer status. For example, if the result of the methods of the present invention is inconclusive or there is reason that confirmation of status is necessary, the physician may order more tests. Alternatively, if the status indicates that treatment is appropriate, the physician may schedule the patient for treatment, e.g., surgery, administer one or more therapeutic agents or radiation. Likewise, if the status is negative, e.g., late stage cancer or if the status is acute, no further action may be warranted. Furthermore, if the results show that treatment has been successful, a maintenance therapy or no further management may be necessary. For example, detection of the differentially presence of one or more biomarkers in a tumor sample from an individual may indicate to a clinician the efficacy of a therapeutic drug (such as a MEK inhibitor) and, based on that, the clinician may manage the subjects treatment by continuing treatment with the therapeutic drug.

Conversely, therapeutic agents useful in cancer treatment may be identified using methods employing the biomarkers delineated herein. For example, a patient or other subject with cancer may be treated with a Ras/Raf/MEK/ERK pathway inhibitor (such as a chemical or small molecule), for a given period of time. The amount of one or more biomarkers present in cancer cells can then be determined in the subject wherein the differential presence of the biomarker in the subject relative to some earlier time (e.g., prior to administration of the inhibitor, or an earlier time of inhibitor administration) indicates that the pathway inhibitor may be a useful therapeutic. For example, the presence (or differential presence) of a biomarker may be determined following treatment of a subject with a Ras/Raf/MEK/ERK using a biochip. Although the variability of genes across biochips can be large, an about 2-fold or greater change in the context of the entirety of 22,000 genes (on the chip) is significant, when the gene is scored in at least one of the two conditions as "present" (with a raw signal intensity about 100 or greater), and the difference between the two conditions (within the context of the whole microarray) is associated with a p-value of about $\leq 0.001$. Similarly, the presence (or differential presence) of a biomarker may be determined using PCR, wherein a candidate agent is identified where a 50% reduction or increase in mRNA levels for a given biomarker is observed.

Therapeutic Drugs

A "therapeutic drug," as used herein, refers to a compound (such as a small molecule, biologic compound, or chemical compound) that exerts an inhibitory effect on the Ras/Raf/MEK/ERK signaling pathway in a cell. Preferred therapeutic drugs contemplated herein include Ras inhibitors, Raf inhibitors, MEK inhibitors, and ERK inhibitor. Exemplary MEK inhibitors include, without limitation, AZD6244 (Astra Zeneca), PD0325901 (Pfizer), XL518 (Exelixis), hypothemycin, and anthrax lethal factor. Exemplary RAF inhibitors include, without limitation, RAF265 (Novartis), PLX4032 (Plexxikon), XL281 (Exelixis), and Bay 43-9006 (Bayer). Exemplary Ras inhibitors include farnesyl transferase inhibitors such as Zarnestra (Johnson & Johnson)

Therapeutic drugs useful in the invention, in addition to the foregoing, include compounds that may act on other components of the Ras/Raf/MEK/ERK pathway other than Ras, Raf, MEK, or ERK, and that ultimately result in a decrease in pathway activation, for example, by inhibiting an activator of Ras, Raf, MEK, or ERK, or by inhibiting an effector molecule downstream from Ras, Raf, MEK, or ERK, or by activating an inhibitory effector molecule downstream or upstream from Ras, Raf, MEK, or ERK.

Cancers

Cancers contemplated for the methods described herein are cancers characterized by BRAF mutations and/or an activated Ras/Raf/MEK/ERK pathway. In particular, such cancers include, without limitation, melanoma, colon cancer, thyroid cancer, ovarian cancer, breast cancer, lung cancer, and pancreatic cancer.

Tumors/cancers sampled for the methods described herein constitute any tumor (cancer) with an activating mutation or lesion in the pathway that results in MAPK activation. This includes, without limitation, sarcomas, carcinomas and other solid tumor cancers, including, but not limited to germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma, renal cancer, bladder cancer, esophageal cancer, cancer of the larynx, cancer of the parotid, cancer of the biliary tract, rectal cancer, endometrial cancer, squamous cell carcinomas, adenocarcinomas, small cell carcinomas, neuroblastomas, mesotheliomas, adrenocortical carcinomas, epithelial carcinomas, desmoid tumors, desmoplastic small round cell tumors, endocrine tumors, Ewing sarcoma family tumors, germ cell tumors, hepatoblastomas, hepatocellular carcinomas, lymphomas, melanomas, non-rhabdomyosarcome soft tissue sarcomas, osteosarcomas, peripheral primative neuroectodermal tumors, retinoblastomas, rhabdomyosarcomas, Wilms tumors, and the like.

A. Sample Collection and Preparation

The biomarkers can be measured in tumor samples from cancer subjects before and after exposure of the subject to a therapeutic drug. Accordingly, tumor samples may be collected from a subject over a period of time. Furthermore, obtaining numerous samples from a subject over a period of time can be used to verify results from earlier detections and/or identify a differential expression as a result of exposure to a therapeutic drug. Generally, tumor samples are typically collected from a subject via biopsy, but may be collected using other known clinical methods specific for particular types of cancers, such as the collection of peripheral blood or bone marrow for hematological malignancies, or the collection of peripheral blood mononuclear cells for surrogate assays of target inhibition/biomarker measurement.

In one embodiment of the invention, the tumor samples are analyzed without additional preparation and/or separation procedures. In another embodiment of the invention, sample preparation and/or separation can involve, without limitation, any of the following procedures, depending on the type of sample collected and/or types of biomarkers searched: removal of high abundance polypeptides; addition of preservatives and calibrants, desalting of samples; concentration of sample substances; protein digestions; and fraction collection. In yet another embodiment of the invention, sample preparation techniques concentrate information-rich biomarkers and deplete polypeptides or other substances that would carry little or no information such as those that are highly abundant in or native to the tumor.

In another embodiment of the invention, sample preparation takes place in a manifold or preparation/separation device. Such a preparation/separation device may be, for example, be a microfluidics device. In yet another embodiment of the invention, the preparation/separation device interfaces directly or indirectly with a detection device. Such a preparation/separation device may, for example, be a fluidics device.

In another embodiment of the invention, the removal of undesired polypeptides (e.g., high abundance, uninformative, or undetectable polypeptides) can be achieved using high affinity reagents, high molecular weight filters, column purification, ultracentrifugation and/or electrodialysis. High affinity reagents include antibodies that selectively bind to high abundance polypeptides or reagents that have a specific pH, ionic value, or detergent strength. High molecular weight filters include membranes that separate molecules on the basis of size and molecular weight. Such filters may further employ reverse osmosis, nanofiltration, ultrafiltration and microfiltration.

Ultracentrifugation constitutes another method for removing undesired polypeptides. Ultracentrifugation is the centrifugation of a sample at about 60,000 rpm while monitoring with an optical system the sedimentation (or lack thereof) of particles. Finally, electrodialysis is an electromembrane process in which ions are transported through ion permeable membranes from one solution to another under the influence of a potential gradient. Since the membranes used in electrodialysis have the ability to selectively transportions having positive or negative charge and reject ions of the opposite charge, electrodialysis is useful for concentration, removal, or separation of electrolytes.

In another embodiment of the invention, the manifold or microfluidics device performs electrodialysis to remove high molecular weight polypeptides or undesired polypeptides. Electrodialysis can be used first to allow only molecules under approximately 30 kD to pass through into a second chamber. A second membrane with a very small molecular weight (roughly 500 D) allows smaller molecules to egress the second chamber.

Upon preparation of the samples, biomarkers of interest may be separated in another embodiment of the invention. Separation can take place in the same location as the preparation or in another location. In one embodiment of the invention, separation occurs in the same microfluidics device where preparation occurs, but in a different location on the device. Samples can be removed from an initial manifold location to a microfluidics device using various means, including an electric field. In another embodiment of the invention, the samples are concentrated during their migration to the microfluidics device using reverse phase beads and an organic solvent elution such as 50% methanol. This elutes the molecules into a channel or a well on a separation device of a microfluidics device.

Chromatography constitutes another method for separating subsets of substances. Chromatography is based on the differential absorption and elution of different substances. Liquid chromatography (LC), for example, involves the use of fluid carrier over a non-mobile phase. Conventional LC columns have an in inner diameter of roughly 4.6 mm and a flow rate of roughly 1 ml/min. Micro-LC has an inner diameter of roughly 1.0 mm and a flow rate of roughly 40 ul/min. Capillary LC utilizes a capillary with an inner diameter of roughly 300 im and a flow rate of approximately 5 ul/min. Nano-LC is available with an inner diameter of 50 um-1 mm and flow rates of 200 nl/min. The sensitivity of nano-LC as compared to HPLC is approximately 3700 fold. Other types of chromatography contemplated for additional embodiments of the invention include, without limitation, thin-layer chromatography (TLC), reverse-phase chromatography, high-performance liquid chromatography (HPLC), and gas chromatography (GC).

In another embodiment of the invention, the samples are separated using capillary electrophoresis separation. This will separate the molecules based on their eletrophoretic mobility at a given pH (or hydrophobicity).

In another embodiment of the invention, sample preparation and separation are combined using microfluidics technology. A microfluidic device is a device that can transport liquids including various reagents such as analytes and elutions between different locations using microchannel structures.

A biomarker can be modified before analysis to improve its resolution or to determine its identity. For example, the biomarker may be subject to proteolytic digestion before analysis. Any protease can be used. Proteases, such as trypsin, that are likely to cleave the biomarkers into a discrete number of fragments are particularly useful. The fragments that result from digestion function as a fingerprint for the products, thereby enabling their detection indirectly. This is particularly useful where there are biomarkers with similar molecular masses that might be confused for the product in question. Also, proteolytic fragmentation is useful for high molecular weight products, because smaller products are more easily resolved by mass spectrometry. In specific embodiments, the proteases occur or naturally exist in the tumor sample.

To improve detection resolution of the biomarkers, neuraminidase can, for instance, be used to remove terminal sialic acid residues from glycoproteins to improve binding to an anionic adsorbent (e.g., cationic exchange ProteinChip® arrays) and to improve detection resolution. In another example, the biomarkers can be modified by the attachment of a tag of particular molecular weight that specifically bind to molecular markers, further distinguishing them. Optionally, after detecting such modified products, the identity of the products can be further determined by matching the physical and chemical characteristics of the modified products in a protein database (e.g., SwissProt).

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. Modified forms of any biomarker of this invention also may be used, themselves, as biomarkers in the profiles. In certain cases, the modified forms may exhibit better discriminatory power in diagnosis than the specific forms set forth herein.

For some of the method embodiments of the invention, it may be helpful to purify the biomarker whose differential presence has been detected by the methods disclosed herein prior to subsequent analysis. Nearly any means known to the art for the purification and separation of small molecular weight substances, e.g., anion or cation exchange chromatography, gas chromatography, liquid chromatography or high pressure liquid chromatography may be used. Methods of selecting suitable separation and purification techniques and means of carrying them out are known in the art (see, e.g., Labadarious et. al., *J Chromatography* (1984) 310:223-231, and references cited therein; and Shahrokhin and Gehrke, *J. Chromatography* (1968) 36:31-41, and Niessen *J. Chromatography* (1998) 794:407-435). To the extent that it is desired to determine the differential presence of a nucleic acid biomarker, the biomarker may be purified using known methods including, slab or capillary gel electrophoresis.

In another embodiment of the method of the invention, purification of the biomarker comprises fractioning a sample comprising one or more protein products by size-exclusion chromatography and collecting a fraction that includes the one or more products; and/or fractioning a sample comprising the one or more products by anion exchange chromatography and collecting a fraction that includes the one or more products. Fractionation is monitored for purity on normal phase and immobilized nickel arrays. Generating data on immobilized biomarker fractions on an array is accomplished by subjecting the array to laser ionization and detecting intensity of signal for mass/charge ratio; and transforming the data into computer readable form. Preferably, fractions are subjected to gel electrophoresis and correlated with data generated by mass spectrometry. In one aspect, gel bands representative of potential biomarkers are excised and subjected to enzymatic treatment and are applied to biochip arrays for peptide mapping.

B. Detection and Quantitation of Biomarkers

Any suitable method can be used to detect (a differential presence of) one or more of the biomarkers described herein. Successful practice of the invention can be achieved with one or a combination of methods that can detect and, preferably, quantify the biomarkers. These methods include, without limitation, hybridization-based methods including those employed in biochip arrays, mass spectrometry (e.g., laser desorption/ionization mass spectrometry), fluorescence (e.g. sandwich immunoassay), surface plasmon resonance, ellipsometry and atomic force microscopy. For nucleic acid biomarkers, methods for detection and quantitation include PCR, quantitative PCR, northern blot analysis, southern blot analysis, mass spectrometry and the like.

Methods may further include, by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero. Spectroscopic methods for detecting and quantifying protein biomarkers are known in the art and are described, for example in U.S. Pat. Nos. 5,719,060; 6,225,047; 5,719,060; 6,124,137 and PCT International Publication No. WO 03/64594.

In another embodiment of the invention, the biomarkers of the invention are measured by a method other than mass spectrometry or other than methods that rely on a measurement of the mass of the biomarker. In one such embodiment that does not rely on mass, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

In one embodiment, the biomarker can be a nucleic acid, wherein the nucleic acid can be detected and/or quantified using methods known in the art. For example, nucleic acid biomarkers may be detected using PCR (disclosed in U.S. Pat. No. 4,683,195, U.S. Pat. No. 4,683,202 and U.S. Pat. No. 4,965,188 and others in detail). In one embodiment, a real time PCR method is used to enable a convenient and reliable quantitative measurement of biomarker nucleic acids having a wide dynamic range. The real time PCR technique includes the method by using a TaqMan probe using ABI-PRISM7700.™. (Applied Biosystems) and the method by using LightCycler.™. (Ropche Diagnostics). Particularly in the latter case, in a high rate reaction cycle in which a temperature cycle of PCR is completed for some 10 minutes, a change of an amplified amount of a DNA synthesized for every cycle can be detected in a real time. DNA detection method of the real time PCR method includes 4 methods using a DNA-binding pigment (intercalator), a hybridization probe (kissing probe), TaqMan probe, or Sunrise Uniprimer (molecular beacon). On the other hand, the expression level of a biomarker gene can be analyzed by using a DNA-binding pigment such as SYBR GreenI. SYBR GreenI is a binding pigment specific to a double strand of the DNA and, when bound to a double strand, an inherent fluorescence intensity is reinforced. By adding SYBR GreenI at the PCR reaction and measuring the fluorescence intensity at the end of each cycle of an elongation reaction, the increase in a PCR product can be detected. For detection of a biomarker gene, similar to normal PCR, a primer is designed by using a commercialized gene analysis software on the basis of a sequence of the biomarker gene. SYBR GreenI detects a nonspecific product and, thus, requires designing an optimal primer. Required designing standards are a length of an oligomer, a base composition of the sequence, a GC content, and a Tm value.

Microarray-/Biochip-Based Methods

Detection methods may include use of a microarray/biochip array. Biochip arrays useful in the invention include protein and nucleic acid arrays. One or more biomarkers are captured on the biochip array and subjected to laser ionization to detect the molecular weight of the products. Analysis of the products is, for example, by molecular weight of the one or more biomarkers against a threshold intensity that is normalized against total ion current.

The biochip surfaces may, for example, be ionic, anionic, hydrophobic; comprised of immobilized nickel or copper ions, comprised of a mixture of positive and negative ions; and/or comprised of one or more antibodies, single or double stranded nucleic acids, proteins, peptides or fragments thereof, amino acid probes, or phage display libraries. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Biomarkers may be captured with capture reagents immobilized to a solid support, such as a biochip, a multiwell microtiter plate, a resin, or nitrocellulose membranes that are subsequently probed for the presence of proteins. Capture can be on a chromatographic surface or a biospecific surface. For example, a tumor sample containing the biomarkers may be placed on the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. Also of interest is the use of mass spectrometry, for example, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

C. Qualification of Cancer Status

As indicated above, the invention provides methods for qualifying cancer status in a subject using a biomarker profile, as specified herein. The biomarkers can be used alone or in combination with other products. The biomarkers are differentially present in tumor samples of a cancer patient before and after exposure to a therapeutic drug. For example, some of the markers are expressed at an elevated level and/or are present at a higher frequency after treatment, while some of the products are expressed at a decreased level and/or are present at a lower frequency after treatment. Therefore, generating a biomarker profile for a subject would provide useful information regarding cancer status.

In some embodiments, isolated (i.e., not before and after treatment, but, rather, at a single timepoint) quantitation of a biomarker is useful and can be correlated with a qualification of cancer status. Thus, the amount of the biomarker detected in a subject being tested may qualify cancer status.

In certain embodiments of the methods of qualifying cancer status, the methods further comprise managing subject treatment based on the status. The invention also provides for such methods where the biomarkers (or specific combination of biomarkers) are measured again after such subject management. In these cases, the methods are used to monitor the status of the cancer, e.g., candidacy for treatment with a Ras/Raf/MEK/ERK pathway inhibitor, response to cancer treatment, remission of the disease or progression of the disease.

The biomarkers of the present invention have a number of other uses. For example, identification of an anti-tumor response or monitoring the efficacy of a therapeutic drug in a cancer subject takes into account the amount of the biomarker(s) in a tumor sample before and after exposure of the subject to a therapeutic drug (up or down regulation of the biomarker(s)). The amounts are measured under the same or substantially similar experimental conditions but at different time periods preceding and following treatment. The biomarkers of the invention can also be used to identify an agent useful in the treatment of cancer.

The detection of a differential presence of a plurality of biomarkers in a tumor sample may improve the indication of therapeutic efficacy of a therapeutic drug in the treatment of a cancer.

In another embodiment of the invention, the output from a detection device can subsequently be processed, stored, and further analyzed or assayed using a bio-informatics system. A bio-informatics system may include one or more of the following, without limitation: a computer; a plurality of computers connected to a network; a signal processing tool(s); a pattern recognition tool(s); a tool(s) to control flow rate for sample preparation, separation, and detection.

The data processing utilizes mathematical foundations. In another embodiment of the invention, dynamic programming is used to align a separation axis with a standard separation profile. Intensities may be normalized, for example, by fitting roughly 90% of the intensity values into a standard spectrum. The data sets can then be fitted using wavelets designed for separation and mass spectrometer data. In yet another embodiment of the invention, data processing filters out some of the noise and reduces spectrum dimensionality, potentially allowing for pattern recognition.

Following data processing, pattern recognition tools can be utilized to identify subtle differences between phenotypic states. Pattern recognition tools are based on a combination of statistical and computer scientific approaches, which provide dimensionality reduction. Such tools are scalable. Data so obtained may be stored on a computer readable medium.

D. Kits

In one aspect, the invention provides kits for qualifying cancer status in a subject, wherein the kits can be used to detect the differential presence of the biomarkers described herein. For example, the kits can be used to detect a differential presence of any combination of the biomarkers in tumor samples of cancer subjects before and after exposure to a therapeutic drug. The kits of the invention have many applications. For example, the kits can be used to monitor efficacy of a therapeutic drug in a cancer subject. The kits can also be used to identify agents useful in the treatment of cancer.

In specific embodiments, kits of the invention contain a biomarker, which is optionally isotopically or fluorescently labeled.

The kits of the invention may include instructions, reagents, testing equipment (test tubes, reaction vessels, needles, syringes, etc.), standards for calibration, and/or equipment. Reagents may include acids, bases, oxidizing agents, and marker species. The instructions provided in a kit according to the invention may be directed to suitable operational parameters in the form of a label or a separate insert.

The kits may also include an adsorbent, wherein the adsorbent retains one or more biomarkers described herein (polynucleotide or polypeptide), and written instructions for use of the kit for qualification of cancer status in a subject. Such a kit could, for example, comprise: (a) a substrate comprising an adsorbent thereon, wherein the adsorbent is suitable for binding a biomarker, and (b) instructions to detect the biomarker(s) by contacting a tumor sample with the adsorbent and detecting the product(s) retained by the adsorbent. Accordingly, the kit could comprise (a) a DNA probe that specifically binds to a biomarker; and (b) a detection reagent. Such a kit could further comprise an eluant (as an alternative or in combination with instructions) or instructions for making an eluant, wherein the combination of the adsorbent and the eluant allows detection of the biomarker using, for example, gas phase ion spectrometry.

This invention is further illustrated by the following examples, which should not be construed as limiting. A skilled artisan should readily understand that other similar instruments with equivalent function/specification, either commercially available or user modified, are suitable for practicing the instant invention. Rather, the invention should be construed to include any and all applications provided herein and all equivalent variations within the skill of the ordinary artisan.

EXAMPLES

Example 1

Response of BRAF Mutant and Wild Type Cell Lines to MEK Inhibitor

Tumors with high MAPK activity due to activating BRAF mutations demonstrate sensitivity to pharmacologic inhibition by MEK (Solit, et al. Nature. January 19; 439(7074):358-62). Eleven cells lines, including five BRAF mutants, are characterized by their tissue of lineage and mechanism of MAPK activation, were used for the experiments described herein, and are listed in Table 2. All the cell lines have high levels of MAPK activity.

TABLE 2

Characteristics of cell lines used on experiments

| Cell line | Tissue of origin | BRAF status | Alteration of Receptor tyrosine kinase |
|---|---|---|---|
| SkMel 1 | Melanoma | V600E | |
| SkMel 5 | Melanoma | V600E | |
| SkMel 19 | Melanoma | V600E | |
| SkMel 28 | Melanoma | V600E | |
| MALME 3M | Melanoma | V600E | |
| Colo205 | Colorectal carcinoma | V600E | |
| HT29 | Colorectal carcinoma | V600E | |
| SkMel 31 | Melanoma | WT | Increase in copy number of EGFR |
| BT474 | Breast cancer | WT | HER2 amplification |
| SkBr3 | Breast cancer | WT | HER2 amplification |
| MDA-468 | Breast cancer | WT | EGFR amplification |
| A431 | Squamous cell carcinoma | WT | EGFR amplification |
| H1650 | Non-small cell lung cancer | WT | EGFR mutation |

Tumors in which high MAPK activity is due to activating mutations in B-RAF ($^{V600E}$BRAF, the most common activating mutation of RAF serine/threonine kinases) are sensitive to pharmacologic inhibition by MEK. Treatment of tumor cell lines and xenograft models with small molecule inhibitors of MEK (CI-1040, PD0325901, Pfizer) caused a decline in cyclin D levels and hypophosphorylation of RB, resulting in G1 arrest and inhibition of proliferation. Tumor growth delay was achieved, compared to vehicle-treated mice, in several $^{V600E}$ B-RAF xenograft models of melanoma and colon carcinoma, and analysis of tumor samples by western blot and immunohistochemistry revealed decline in both cyclin D and Ki-67, a marker of proliferation. In contrast, tumors with high MAPK activity under the control of activated receptors were resistant to MEK inhibition in both in vitro assays and xenograft models. Although effectiveness of the drug at its expected target, phosphorylated MAPK, was not measurably different in this group, an accompanying decline in cyclin D, change in cell cycle distribution, or anti-proliferative response in the HER2/EGFR (WT BRAF) tumors was not observed.

Example 2

Enrichment Significance of Genes Altered in Response to MEK Inhibition as a Function of Time in a MEK Inhibitor Sensitive V600E BRAF Melanoma Cell Line SkMel 28 cells (a melanoma cell line with the V600E BRAF mutation) were treated with the MEK inhibitor, PD0325901 (50 nM), for 2, 8, or 24 hours, or no treatment at all (=time 0 hours). Total cellular RNA was analyzed using an Affymetrix U133A 2.0 platform. Pairwise comparisons of gene expression at each individual time point to reference sample (time 0 hours) were performed, and genes were selected using a threshold of two-fold or greater change in either direction. The number of genes changing significantly increased as a function of time following exposure to MEK inhibitor (2 hours—91 genes; 8 hours—327 genes; 24 hours—1191 genes).

Thus, genes which changed greater than or equal to two-fold in either direction in response to PD0325901 compared to control were identified at three time points following MEK inhibition. All genes were assigned to a functional class based on biological process, according to Gene Ontology (GO) classification (FIG. 2). The number of genes changing in each functional classification was assigned a p-value based on the significance of the number of genes changing given the total number of genes changed at that time point, compared to the total number of genes in the GO functional class, and the total number of genes on the chip. An enrichment score was assigned to each functional class, and was defined as the –log 10(p-value).

As an example, for MAPK phosphatase genes at 2 hours, 3 were found to be changed, of 63 unique genes changed at this timepoint. There are 9 genes representing this functional class out of a total of 13,116 genes on the chip, so fewer genes would have been expected to have changed due to chance alone. Their deviation from expected is highly significant, with a p-value of $8.69 \times 10^{-6}$ (fisher's exact test), and, therefore, is assigned an enrichment score of 5.06).

The genes most significantly enriched at early time points include those whose roles include regulation of signal transduction and MAP kinase phosphatase activity. Also highly enriched are genes whose functions include transcription factor activity, cell proliferation, and regulation of progression through the cell cycle. At the later time point (24 hours), these functional classifications lose their significance, whereas other functional classes of genes not expected to result from direct consequences of MEK inhibition, are increased in their enrichment. These data form the justification for examining the profiles of genes changed in response to MEK inhibition in a large panel of cell lines at 8 hours.

Example 3

Determination of Genes Whose Expression Changes in Response to MEK Inhibition in a Panel of Cell Lines with V600E BRAF Mean expression of genes was determined for a panel of V600E BRAF cell lines in each of two conditions, MEK-inhibited (PD0325901 50 nM) or DMSO control, both at 8 hours. The panel of V600E BRAF cell lines included 5 melanoma cell lines (SkMel 1, SkMel 5, SkMel 19, SkMel 28, and MALME 3M) and two colorectal carcinoma cell lines (Colo205 and HT29).

Significance analysis of microarray (SAM) methods were used to determine the significance of difference between the two groups of genes (using a false discovery rate of 9%). 45 probe sets (closed red circles) were identified, representing 35 genes which change significantly in either direction in response to MEK inhibition (FIG. 3A). Of these, 31 genes are downregulated, and 4 genes are upregulated, in response to MEK inhibition. Expression of the genes was also presented as a heatmap representation (FIG. 3B).

Figure 5:
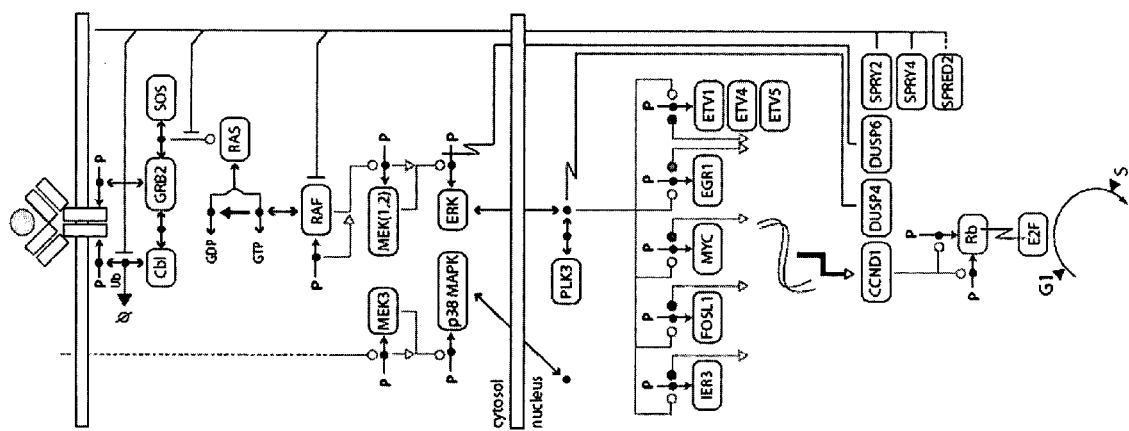
FIG. 5 schematically depicts a molecular interaction map of the Ras/Raf/MEK/ERK signaling pathway, which was constructed for the major components of the pathway, including RAS, RAF, MEK and MAPK, and the primary downstream targets of MAPK signaling. Of note, those genes identified in FIG. 3, which have associations with MAPK signaling are also shown, and are highlighted. At least 15 of the genes delineated in Table 1 are directly implicated as effectors of MAPK signaling.

Of note, all 35 genes are known to be associated with MAPK signaling (i.e., are effectors of MAPK activity) (FIG. 5), indicating a highly non-random signature.

Example 4

Figure 3:
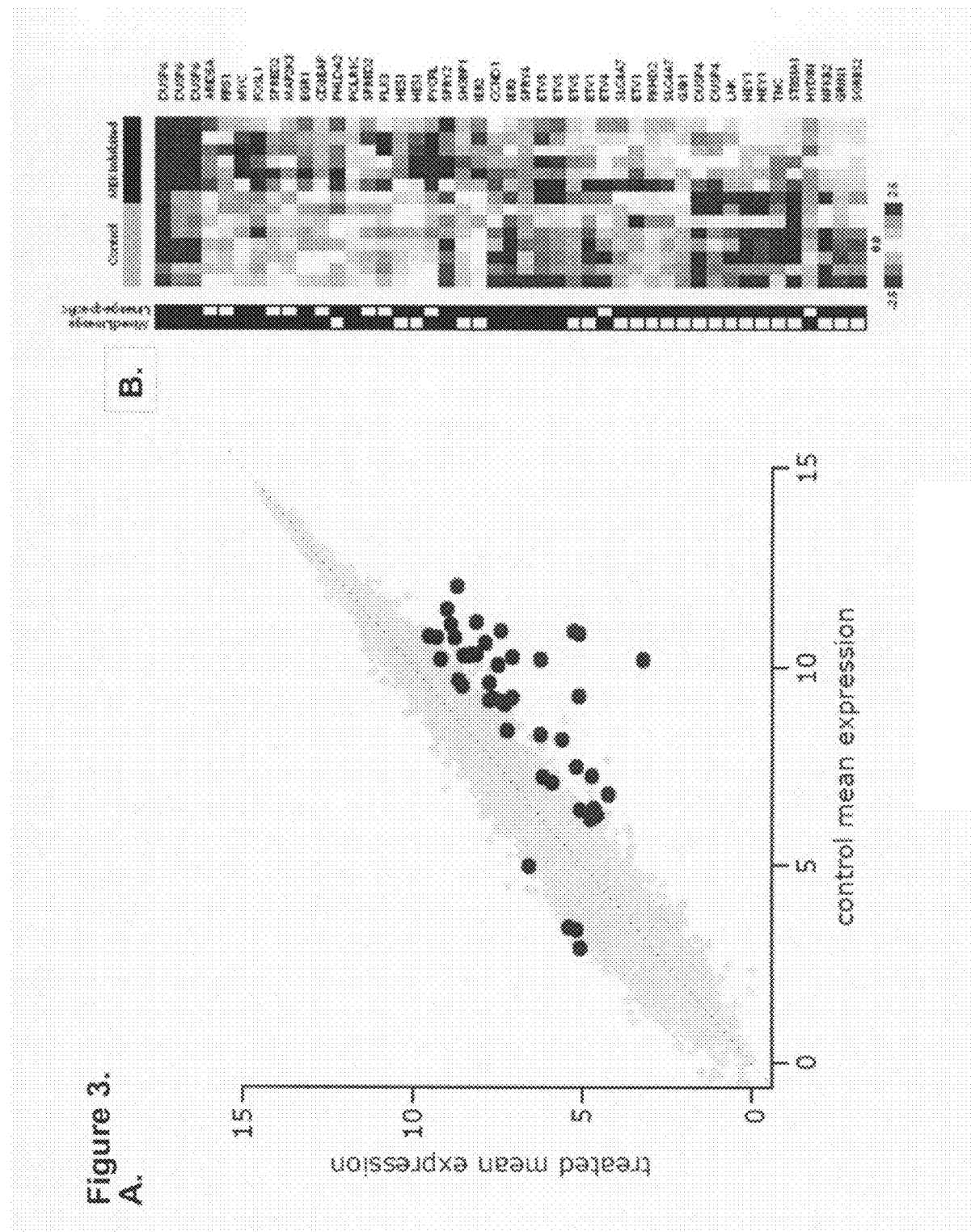
FIG. 3 shows (A) a graph depicting the significance of difference between the two groups (control and MEK-inhibited) of genes, with the identified 45 probe sets (closed red circles) representing 35 genes which change significantly in either direction in response to MEK inhibition. Of these, 31 genes are downregulated (to the right of the 45 degree angle dotted line), and 4 genes are upregulated (to the left of the 45 degree angle dotted line) in response to MEK inhibition; and (B) a heatmap representation of expression of those genes represented by the red filled circles in A in individual cell lines in the two conditions (control, MEK inhibited), where red represents higher expression and blue represents lower gene expression.

RNA and Protein Levels of a Subset of Genes Identified in FIG. 3 as a Function of Time Following MEK Inhibition Quantitative RT-PCR was used to determine relative levels of mRNA in cells as a function of time following exposure to the MEK inhibitor (PD0325901 50 nM). SkMel 5 cells were treated with MEK inhibitor (PD0325901 50 nM) for the times indicated (2 hrs, 4 hrs, 8 hrs, and 24 hrs). Following total RNA extraction and an in vitro reverse transcription step, synthesized cDNA was used in a PCR reaction containing pre-designed probe-primer sets purchased from Applied Biosystems and run on an ABI 7500 RT-PCR machine, using software supplied by Applied Biosystems. Relative levels of mRNA compared to the reference sample (time 0) were determined using the ΔΔCT calculation, using HPRT as a housekeeping gene for normalization.

In brief, each gene for each sample is assigned a value based on the number of PCR amplification cycles required for the amplified gene product to cross a detection threshold (i.e., a gene detectable at 25 amplification cycles is present in greater starting quantity than a gene product detectable at 30 cycles). The cycle value for each sample for the gene of interest is subtracted from the cycle value for a reference sample (untreated, or time 0), and this value is the delta CT for the gene of interest. The same is performed for a housekeeping gene (such as GAPDH or HPRT), the expression of which is not expected to change significantly by the perturbation (i.e. addition of the MEK inhibitor). This is the delta CT for the housekeeping gene. The delta CT (housekeeping gene) is subtracted from the delta CT (gene of interest), and this is the delta delta CT. Thus, a small difference in the expression of the housekeeping gene from sample to sample is taken into account to minimize differences due to sample preparation.

Figure 4:
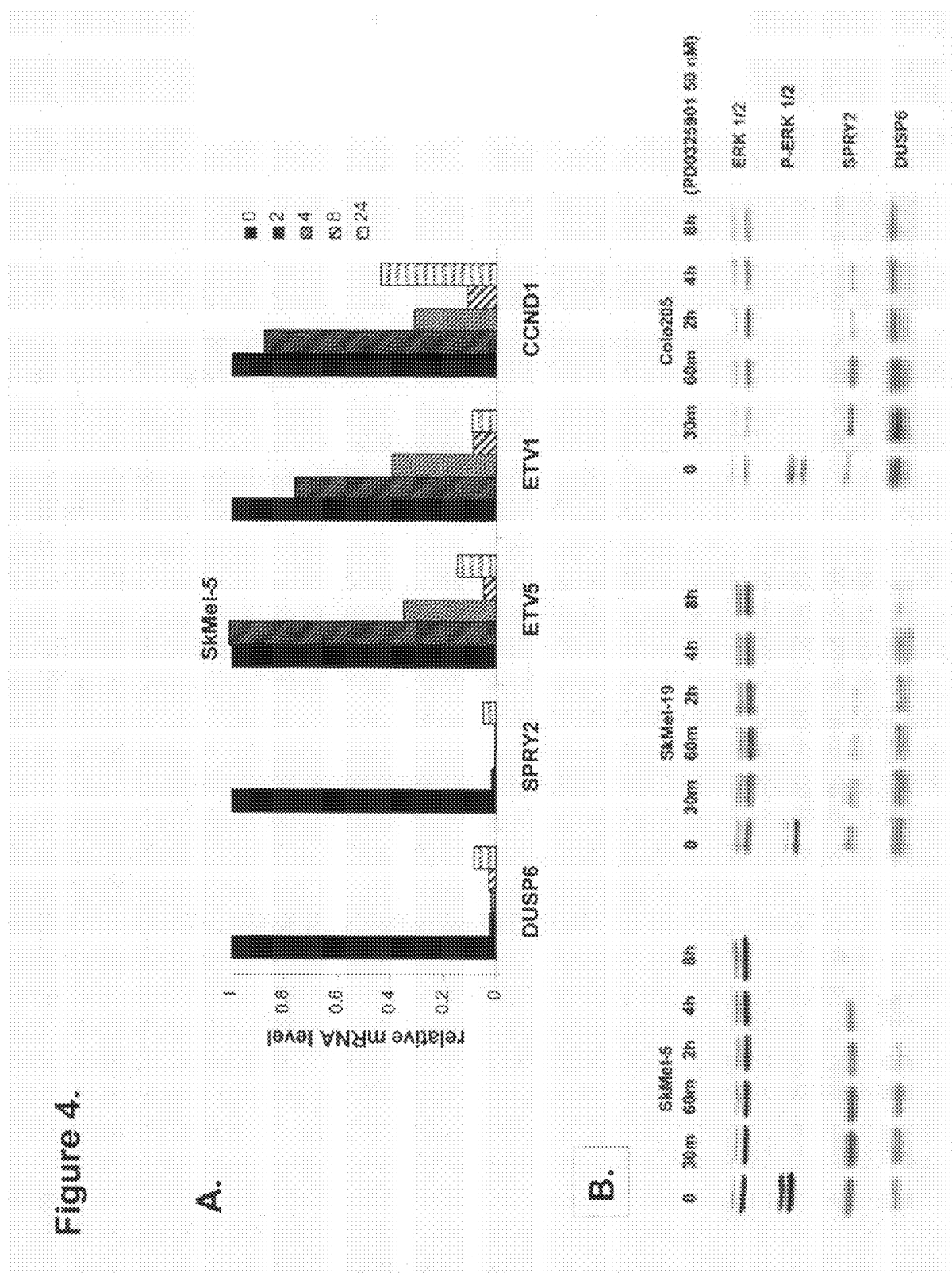
FIG. 4A shows bar graphs depicting the relative levels of mRNA in cells as a function of time (2 hrs, 4 hrs, 8 hrs, and 24 hrs) following exposure to the MEK inhibitor (PD0325901). Decrease in mRNA levels are seen for five of the target genes, including DUSP6, SPRY2, ETV1, ETV5, and CCND1, in the cell line SkMel 5 (V600E BRAF).
FIG. 4B shows the relative protein expression in cells as a function of time following exposure to MEK inhibitor (PD0325901 50 nM).

Decreases in mRNA levels were seen for five of the target genes, including DUSP6, SPRY2, ETV1, ETV5, and CCND1, in the cell line SkMel 5 (V600E BRAF) (FIG. 4A).

Following protein isolation using NP40 1% lysis buffer, Western blot analysis was used to determine relative protein expression in cells as a function of time following exposure to MEK inhibitor (PD0325901 50 nM). A decrease in protein expression was seen for two of the target genes, including DUSP6 and SPRY2, in three cell lines, SkMel 5, SkMel 19, and Colo205, all harboring the V600E BRAF mutation (FIG. 4B). For the Western Blot analysis, DUSP6 antibody (SantaCruz (#8598)), and SPRY2 antibody (Upstate Cell Signaling Solutions).

Example 5

A Multi-Gene Vector of Expression Shared Between Cell Line and Xenograft Models

Figure 6:
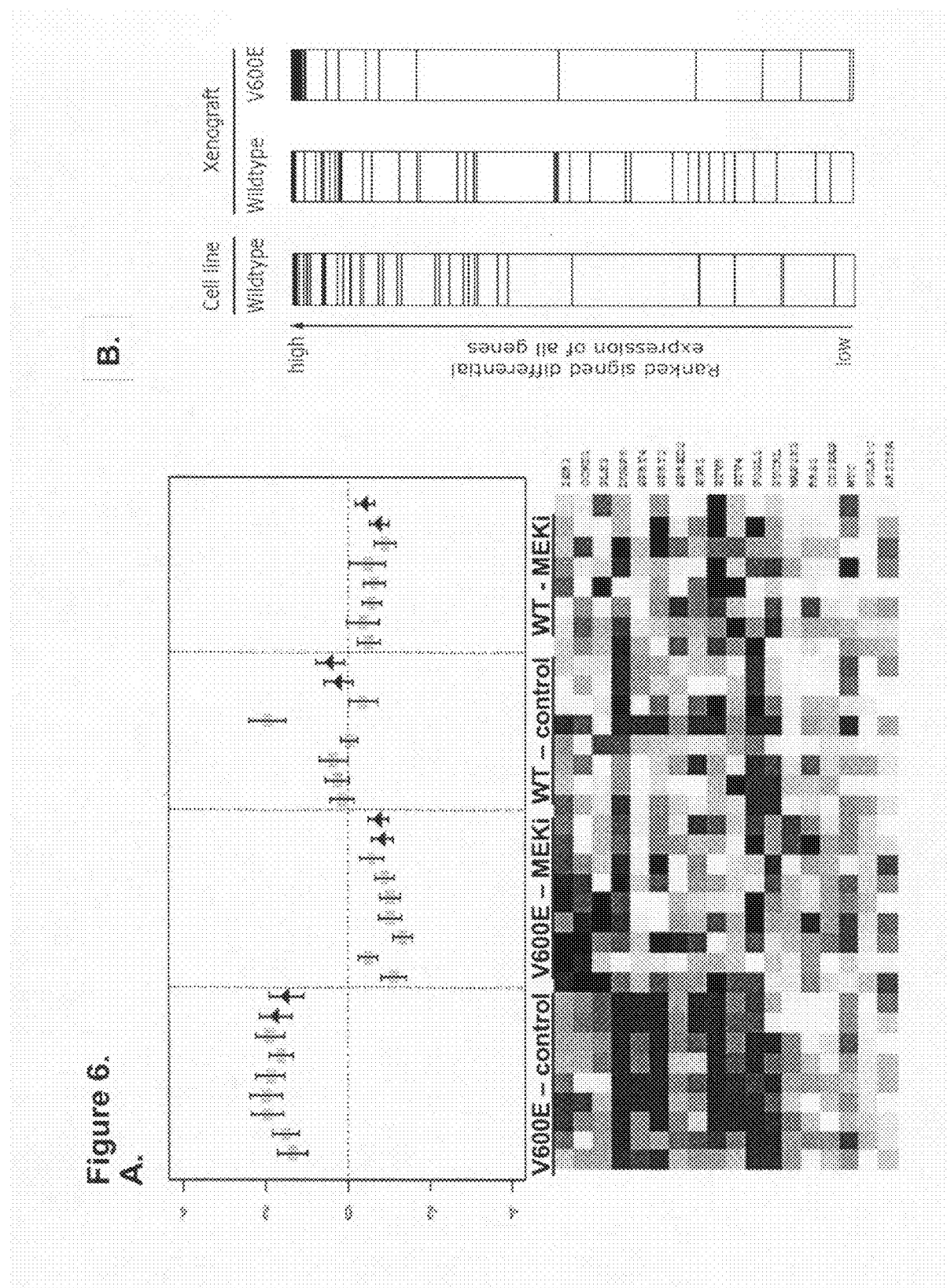
In FIG. 6A, each cell line or xenograft tumor is represented as a single vertical lane (7+2) or (6+2) for each of the four conditions as identified. The last two lanes in each condition are the xenografts (SkMel 28 tumors for the V600E BRAF, and BT474 tumors for the WT BRAF). Plotted above is the shared vector of expression across 18 genes in four independent conditions, between wild-type and mutant BRAF status and control versus MEK inhibition. Data is represented as mean±SEM of the 18 genes per sample. Boxes represent cell lines, while triangles represent xenografts. Below is the heatmap representation of individual gene expression stratified by sample membership in the given conditions (center).
FIG. 6B shows the ranked signed differential expression of all genes.

An 18 gene subset of the 35 genes from FIG. 3 was defined, comprised of those genes present in a mixed lineage (colon plus melanoma) analysis of mean expression across cell lines in MEK inhibited and control conditions. Expression of this gene profile was extracted from Affymetrix U133A gene chips for 7 cell lines with V600E BRAF, 2 xenograft tumors with V600E BRAF, 6 cell lines with WT BRAF, and 2 xenograft tumors with WT BRAF, each in the two conditions—control (untreated) or MEK-inhibited (PD0325901 50 nM for 8 hours for cell lines, or 25 mg/kg for 8 hours for murine xenografts) (FIG. 6A).

Those 35 genes identified as most significantly changed in V600E BRAF cell lines were ranked among the entire profile of 22,000 genes on the microarray with regard to the degree to which they change in response to MEK inhibition, in each of three other conditions: WT BRAF cell lines, V600E BRAF xenografts, and WT BRAF xenografts. The 35 genes, which cluster at the top in the V600E BRAF cell lines (not shown), are widely distributed in the rank of their change in the WT BRAF cell lines and xenografts, whereas they cluster among the most significantly changed genes in the V600E BRAF xenografts, suggesting a high degree of concordance between cell line and xenograft data for the V600E BRAF class (p-value=$10^{-36}$) (FIG. 6B).

Example 6

Predicting Candidacy for Ras/Raf/MEK/ERK Pathway Inhibitor Treatment

The following experiments were performed to identify biomarkers useful to identify promising candidates for treatment with Ras/Raf/MEK/ERK pathway inhibitor. These studies were conducted to determine whether the greater magnitude in change in the B-RAF mutant cell lines for this select group of genes was due to higher basal expression in B-RAF mutant cells compared to B-RAF WT/RTK activated cells. In a test of significance on each of the 23 probes generated in the B-RAF mutant mixed lineage analysis of cell lines upon MEK inhibition, we evaluated the background difference in expression between wild-type and mutant BRAF independent of MEK inhibition. Six of these, including DUSP6, SPRY2, ETV4 and ETV5, MAP2K3 and PLK3, had higher expression in the B-RAF mutant group, with fold change difference between 2.17 and 6.09 (p≦0.02; one-tailed Student's t-test). Both SPRY4 and SPRED2, as well as MYC, were also significant yet with reduced fold change difference (fold change of 1.77 to 1.92; p=0.018 to 0.057), and the balance did not show differential expression between BRAF status uncoupled from MEK inhibition (0.57<FC<1.23 and 0.057≦p≦0.49; not shown). Relative expression, shown as mean log transformed expression values, for 14 most significant probe sets, representing 10 unique genes, are shown in Table 3, and illustrate the differences in expression in B-RAF mutant and B-RAF wild-type in a MEK-independent fashion.

TABLE 3

| | | log expression | | | |
|---|---|---|---|---|---|
| Probe set ID | Gene symbol | V600E | WT | fold diff | p-value |
| 203348_s_at | ETV5 | 10.904 | 7.491 | 6.086 | 0.004 |
| 211603_s_at | ETV4 | 9.229 | 6.481 | 5.957 | 0.001 |
| 208893_s_at | DUSP6 | 10.175 | 5.404 | 5.288 | 0.005 |
| 203349_s_at | ETV5 | 11.119 | 8.201 | 4.781 | 0.004 |
| 220098_at | HYDIN | 2.919 | 4.169 | 3.664 | 0.047 |
| 208892_s_at | DUSP6 | 10.896 | 8.162 | 2.952 | 0.018 |
| 208891_at | DUSP6 | 10.826 | 8.188 | 2.930 | 0.022 |
| 204011_at | SPRY2 | 10.180 | 7.573 | 2.802 | 0.011 |
| 204958_at | PLK3 | 7.473 | 6.332 | 2.260 | 0.012 |
| 215498_s_at | MAP2K3 | 10.747 | 9.602 | 2.173 | 0.000 |
| 212466_at | SPRED2 | 6.417 | 5.087 | 1.919 | 0.057 |
| 221489_s_at | SPRY4 | 10.044 | 8.557 | 1.909 | 0.042 |
| 202431_s_at | MYC | 11.443 | 10.232 | 1.881 | 0.040 |
| 212458_at | SPRED2 | 10.288 | 9.309 | 1.768 | 0.018 |

Each of the 10 genes changes in response to MEK inhibition in each of the B-RAF mutant, MEK sensitive cell lines tested, but that only a subset of the genes are overexpressed in those cell lines compared to the RTK activated cells. When analyzed as a group, statistically significant differences upon MEK inhibition were not noted for the WT B-RAF group, but small changes were detected for individual cell line pairs. Thus we have functionally classified the genes which move in a MEK-ERK dependent fashion into at least three groups: 1) those that are both ERK dependent and B-RAF dependent for expression, 2) those that are ERK dependent only it the B-RAF mutant cells but not B-RAF dependent for expression, and 3) those that are B-RAF independent and ERK dependent in both groups of tumor cells. In other words, some genes tend to have higher expression in B-RAF mutant transformed cells, and are downregulated on exposure to MEK inhibition (DUSP6, ETV5). Others do not have higher expression in B-RAF mutant tumors compared to BRAF wild type, and thus their expression could be a result of transformation via a variety of molecular events (EER3), but they are ERK dependent in only MEK sensitive B-RAF mutant cell lines, whereas their expression does not change as a result of MEK inhibition in the WT B-RAF group of tumors. It is the former subset of genes which may be predictive of response to MEK inhibitors, in those tumors both with and without BRAF mutation. (i.e., the example of a WT BRAF melanoma without an identified lesion in the pathway, but with high expression of the output genes, would be expected to be MEK inhibitor sensitive even in the absence of the V600E BRAF mutation). So while these genes are markers of BRAF mutation, they may also be markers of cells with or without other mutations, that for some other reason (lineage/unidentified mutation/amplification of a WT kinase), have high output and are MEK dependent.

The invention claimed is:

1. A panel of isolated biomarkers consisting of DUSP6 (Marker 1), SPRY2 (Marker 15) and one or more biomarkers selected from the group consisting of Markers 2-14 and 16-35.

2. The panel of claim 1, wherein said one or more biomarkers are selected from the group consisting of ETV1, ETV4, and ETV5.

3. The panel of claim 1, wherein the differential expression of a biomarker in response to an agent is indicative of the therapeutic efficacy of the agent as an inhibitor of the Ras/Raf/MEK/ERK pathway.

4. The panel of claim 3, wherein said agent is a Raf inhibitor or MEK inhibitor.

5. The panel of claim 3, wherein said inhibitor is selected from the group consisting of AZD6244, PD0325901, XL518, hypothemycin, anthrax lethal factor, RAF265, PLX4032, XL281, Bay 43-9006, and a farnesyl transferase inhibitor.

6. A panel of isolated biomarkers consisting of DUSP6 (Marker 1), SPRY2 (Marker 15), ETV1 (Marker 22), ETV4 (Marker 23), and ETV5 (Marker 21) and one or more biomarkers selected from the group consisting of Markers 2-14, 16-20, and 24-35.

7. The panel of claim 6, wherein the differential expression of a biomarker in response to an agent is indicative of the therapeutic efficacy of the agent as an inhibitor of the Ras/Raf/MEK/ERK pathway.

8. The panel of claim 6, wherein said Ras/Raf/MEK/ERK pathway inhibitor is a Raf inhibitor or a MEK inhibitor.

9. The panel of claim 6, wherein said inhibitor is selected from the group consisting of AZD6244, PD0325901, XL518, hypothemycin, anthrax lethal factor, RAF265, PLX4032, XL281, Bay 43-9006, and a farnesyl transferase inhibitor.

* * * * *

UNITED STATES PATENT AND TRADEMARK OFFICE
CERTIFICATE OF CORRECTION

PATENT NO. : 7,812,143 B2
APPLICATION NO. : 11/732362
DATED : October 12, 2010
INVENTOR(S) : Christine Pratilas et al.

It is certified that error appears in the above-identified patent and that said Letters Patent is hereby corrected as shown below:

Column 1, Line 15, "paragraphing" should read --claiming--; Line 41, "tumours" should read --tumors--.

Column 4, Line 43, "are seen" should be changed to --is seen--.

Column 10, Lines 9-10, delete the sentence beginning with "A" and ending with "polypeptides."; Line 53, "voltametry" should be changed to --voltammetry--.

Column 12, Line 54, "(e.g., mRNA) a" should read --(e.g., mRNA) of a--.

Column 13, Line 50, "detect to useful" should read --detect the useful--; Line 59, delete the first occurrence of the word "also"; Line 66, "with" should read --within--.

Column 14, Line 1, "but not limited to amino acid" should read --but not limited to, amino acid--.

Column 15, Line 49, "differentially" should read --differential--.

Column 16, Line 1, "Ras/Raf/MEK/ERK using" should read --Ras/Raf/MEK/ERK pathway inhibitor using--; Line 19, "ERK inhibitor" should read --ERK inhibitors--.

Column 17, Line 55, "transportions" should read --transport ions--.

Column 19, Line 7, "slice variants" should read --splice variants--.

Column 20, Line 67, "at the PCR reaction" should read --to the PCR reaction--.

Column 22, Line 1, "voltametry" should read --voltammetry--.

Signed and Sealed this
First Day of March, 2011

David J. Kappos
*Director of the United States Patent and Trademark Office*

Column 28, Line 25, "it the B-RAF" should read --in the B-RAF--.

Column 28, Line 44, "BRAF" should read --B-RAF--.

SEQUENCE LISTING

```
<160> NUMBER OF SEQ ID NOS: 70

<210> SEQ ID NO 1
<211> LENGTH: 156
<212> TYPE: PRT
<213> ORGANISM: Homo sapiens

<400> SEQUENCE: 1

Met Cys His Ser Arg Ser Cys His Pro Thr Met Thr Ile Leu Gln Ala
 1               5                  10                  15

Pro Thr Pro Ala Pro Ser Thr Ile Pro Gly Pro Arg Arg Gly Ser Gly
             20                  25                  30
```

```
Pro Glu Ile Phe Thr Phe Asp Pro Leu Pro Glu Pro Ala Ala Ala Pro
         35                  40                  45

Ala Gly Arg Pro Ser Ala Ser Arg Gly His Arg Lys Arg Ser Arg Arg
     50                  55                  60

Val Leu Tyr Pro Arg Val Val Arg Arg Gln Leu Pro Val Glu Glu Pro
 65                  70                  75                  80

Asn Pro Ala Lys Arg Leu Leu Phe Leu Leu Leu Thr Ile Val Phe Cys
                 85                  90                  95

Gln Ile Leu Met Ala Glu Glu Gly Val Pro Ala Pro Leu Pro Pro Glu
                100                 105                 110

Asp Ala Pro Asn Ala Ala Ser Leu Ala Pro Thr Pro Val Ser Ala Val
                115                 120                 125

Leu Glu Pro Phe Asn Leu Thr Ser Glu Pro Ser Asp Tyr Ala Leu Asp
        130                 135                 140

Leu Ser Thr Phe Leu Gln Gln His Pro Ala Ala Phe
145                 150                 155

<210> SEQ ID NO 2
<211> LENGTH: 1254
<212> TYPE: DNA
<213> ORGANISM: Homo sapiens

<400> SEQUENCE: 2
ctcacttggc cttacactcc gctcggctca ccatgtgtca ctctcgcagc tgccacccga      60
ccatgaccat cctgcaggcc ccgaccccgg cccctccac catcccggga ccccggcggg     120
gctccggtcc tgagatcttc accttcgacc ctctcccgga gcccgcagcg gcccctgccg     180
ggcgccccag cgcctctcgc gggcaccgaa agcgcagccg cagggttctc taccctcgag     240
tggtccggcg ccagctgcca gtcgaggaac cgaacccagc caaaaggctt ctctttctgc     300
tgctcaccat cgtcttctgc cagatcctga tggctgaaga gggtgtgccg gcgcccctgc     360
ctccagagga cgcccctaac gccgcatccc tggcgcccac ccctgtgtcc gccgtcctcg     420
agccctttaa tctgacttcg gagccctcgg actacgctct ggacctcagc actttcctcc     480
agcaacaccc ggccgccttc taactgtgac tccccgcact cccaaaaaag aatccgaaaa     540
accacaaaga aacaccaggc gtacctggtg cgcgagagcg tatccccaac tgggacttcc     600
gaggcaactt gaactcagaa cactacagcg agacgccac ccggtgcttg aggcgggacc     660
gaggcgcaca gagaccgagg cgcatagaga ccgaggcaca gcccagctgg ggctaggccc     720
ggtgggaagg agagcgtcgt taatttattt cttattgctc ctaattaata tttatatgta     780
tttatgtacg tcctcctagg tgatggagat gtgtacgtaa tatttatttt aacttatgca     840
agggtgtgag atgttccccc tgctgtaaat gcaggtctct tggtatttat tgagctttgt     900
gggactggtg gaagcaggac acctggaact gcggcaaagt aggagaagaa atggggagga     960
ctcgggtggg ggaggacgtc ccggctggga tgaagtctgg tggtgggtcg taagtttagg    1020
aggtgactgc atcctccagc atctcaactc cgtctgtcta ctgtgtgaga cttcggcgga    1080
ccattaggaa tgagatccgt gagatccttc catcttcttg aagtcgcctt tagggtggct    1140
gcgaggtaga gggttggggg ttggtgggct gtcacggagc gactgtcgag atcgcctagt    1200
atgttctgtg aacacaaata aaattgattt actgtctgca aaaaaaaaaa aaaa          1254

<210> SEQ ID NO 3
<211> LENGTH: 543
<212> TYPE: PRT
<213> ORGANISM: Homo sapiens
```

<400> SEQUENCE: 3

```
Met Ala Ala Ala Lys Ala Glu Met Gln Leu Met Ser Pro Leu Gln Ile
 1               5                  10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
                180                 185                 190

Ala Val Pro Ser Asn Asp Ser Ser Pro Ile Tyr Ser Ala Ala Pro Thr
                195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
    275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
        355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
```

```
                405                 410                 415
Ile His Leu Arg Gln Lys Asp Lys Lys Ala Asp Lys Ser Val Val Ala
            420                 425                 430

Ser Ser Ala Thr Ser Ser Leu Ser Ser Tyr Pro Ser Pro Val Ala Thr
            435                 440                 445

Ser Tyr Pro Ser Pro Val Thr Thr Ser Tyr Pro Ser Pro Ala Thr Thr
        450                 455                 460

Ser Tyr Pro Ser Pro Val Pro Thr Ser Phe Ser Pro Gly Ser Ser
465                 470                 475                 480

Thr Tyr Pro Ser Pro Val His Ser Gly Phe Pro Ser Pro Ser Val Ala
                485                 490                 495

Thr Thr Tyr Ser Ser Val Pro Pro Ala Phe Pro Ala Gln Val Ser Ser
            500                 505                 510

Phe Pro Ser Ser Ala Val Thr Asn Ser Phe Ser Ala Ser Thr Gly Leu
            515                 520                 525

Ser Asp Met Thr Ala Thr Phe Ser Pro Arg Thr Ile Glu Ile Cys
        530                 535                 540

<210> SEQ ID NO 4
<211> LENGTH: 3136
<212> TYPE: DNA
<213> ORGANISM: Homo sapiens

<400> SEQUENCE: 4
gcgcagaact tggggagccg ccgccgccat ccgccgccgc agccagcttc cgccgccgca      60
ggaccggccc ctgccccagc tccgcagcc gcggcgcgtc cacgcccgcc cgcgcccagg     120
gcgagtcggg gtcgccgcct gcacgcttct cagtgttccc cgcgccccgc atgtaacccg     180
gccaggcccc cgcaactgtg tccctgcag ctccagcccc gggctgcacc ccccgcccc      240
gacaccagct ctccagcctg ctcgtccagg atggccgcgg ccaaggccga gatgcagctg     300
atgtccccgc tgcagatctc tgacccgttc ggatccttc ctcactcgcc caccatggac      360
aactaccca gctggagga gatgatgctg ctgagcaacg ggctccccca gttcctcggc      420
gccgccgggg ccccagaggg cagcggcagc aacagcagca gcagcagcag cggggggcggt     480
ggaggcggcg gggcggcag caacagcagc agcagcagca gcaccttcaa ccctcaggcg     540
gacacgggcg agcagcccta cgagcacctg accgcagagt cttttcctga catctctctg     600
aacaacgaga aggtgctggt ggagaccagt taccccagcc aaaccactcg actgccccc      660
atcacctata ctggccgctt ttccctggag cctgcaccca cagtggcaa caccttgtgg     720
cccgagcccc tcttcagctt ggtcagtggc ctagtgagca tgaccaaccc accggcctcc     780
tcgtcctcag caccatctcc agcggcctcc tccgcctccg cctcccagag cccaccctg      840
agctgcgcag tgccatccaa cgacagcagt cccatttact cagcggcacc caccttcccc     900
acgccgaaca ctgacatttt ccctgagcca caaagccagg ccttcccggg ctcggcaggg     960
acagcgctcc agtacccgcc tcctgcctac cctgccgcca agggtggctt ccaggttccc    1020
atgatccccg actacctgtt ccacagcag caggggggatc tgggcctggg caccccagac    1080
cagaagccct ccagggcct ggagagccgc acccagcagc cttcgctaac ccctctgtct     1140
actattaagg ccttttgccac tcagtcgggc tcccaggacc tgaaggccct caataccagc    1200
taccagtccc agctcatcaa acccagccgc atgcgcaagt accccaaccg gccagcaag     1260
acgccccccc acgaacgccc ttacgcttgc ccagtggagt cctgtgatcg ccgcttctcc    1320
cgctccgacg agctcacccg ccacatccgc atccacacag gccagaagcc cttccagtgc    1380
```

```
cgcatctgca tgcgcaactt cagccgcagc gaccacctca ccacccacat ccgcacccac    1440
acaggcgaaa agcccttcgc ctgcgacatc tgtggaagaa agtttgccag gagcgatgaa    1500
cgcaagaggc ataccaagat ccacttgcgg cagaaggaca agaaagcaga caaaagtgtt    1560
gtggcctctt cggccaccte ctctctctct tcctacccgt ccccggttgc tacctcttac    1620
ccgtccccgg ttactacctc ttatccatcc ccggccacca cctcataccc atccctgtg    1680 cccacctcct tctcctctcc cggctcctcg acctacccat ccctgtgca cagtggcttc    1740 ccctccccgt cggtggccac cacgtactcc tctgttcccc ctgctttccc ggcccaggtc    1800
agcagcttcc cttcctcagc tgtcaccaac tccttcagcg cctccacagg gctttcggac    1860 atgcagcaa ccttttctcc caggacaatt gaaatttgct aaagggaaag gggaaagaaa    1920
gggaaaaggg agaaaaagaa acacaagaga cttaaaggac aggaggagga gatggccata    1980
ggagaggagg gttcctctta ggtcagatgg aggttctcag agccaagtcc tccctctcta    2040
ctggagtgga aggtctattg ccaacaatc ctttctgccc acttccccttt ccccaattac    2100 tattcccttt gacttcagct gcctgaaaca gccatgtcca agttcttcac ctctatccaa    2160
agaacttgat ttgcatggat tttggataaa tcatttcagt atcatctcca tcatatgcct    2220
gaccccttgc tcccttcaat gctagaaaat cgagttggca aaatgggtt tgggccctc    2280 agagccctgc cctgcaccct tgtacagtgt ctgtgccatg gatttcgttt tcttggggt    2340 actcttgatg tgaagataat ttgcatattc tattgtatta tttggagtta ggtcctcact    2400
tgggggaaaa aaaaaaaga aaagccaagc aaaccaatgg tgatcctcta tttttgtgatg   2460 atgctgtgac aataagttg aaccttttt tttgaaacag cagtcccagt attctcagag    2520
catgtgtcag agtgttgttc cgttaacctt tttgtaaata ctgcttgacc gtactctcac    2580
atgtggcaaa atatggttg gttttctttt tttttttttt ttgaaagtgt tttttcttcg    2640
tccttttggt ttaaaaagtt tcacgtcttg gtgccttttg tgtgatgcgc cttgctgatg    2700
gcttgacatg tgcaattgtg agggacatgc tcacctctag ccttaagggg ggcagggagt    2760
gatgatttgg gggaggcttt gggagcaaaa taaggaagag ggctgagctg agcttcggtt    2820
ctccagaatg taagaaaaca aaatctaaaa caaaatctga actctcaaaa gtctatttt    2880 ttaactgaaa atgtaaattt ataaatatat tcaggagttg gaatgttgta gttacctact    2940
gagtaggcgg cgattttgt atgttatgaa catgcagttc attattttgt ggttctattt    3000
tactttgtac ttgtgtttgc ttaaacaaag tgactgtttg gcttataaac acattgaatg    3060
cgctttattg cccatgggat atgtggtgta tatccttcca aaaattaaa acgaaaataa    3120 agtagctgcg attggg                                                   3136
```

<210> SEQ ID NO 5
<211> LENGTH: 223
<212> TYPE: PRT
<213> ORGANISM: Homo sapiens

<400> SEQUENCE: 5

Met Glu Val Gln Lys Glu Ala Gln Arg Ile Met Thr Leu Ser Val Trp
1               5                   10                  15

Lys Met Tyr His Ser Arg Met Gln Arg Gly Gly Leu Arg Leu His Arg
            20                  25                  30

Ser Leu Gln Leu Ser Leu Val Met Arg Ser Ala Arg Glu Leu Tyr Leu
        35                  40                  45

Ser Ala Lys Val Glu Ala Leu Glu Pro Glu Val Ser Leu Pro Ala Ala

```
                50                     55                     60
Leu Pro Ser Asp Pro Arg Leu His Pro Pro Arg Glu Ala Glu Ser Thr
 65                     70                     75                     80

Ala Glu Thr Ala Thr Pro Asp Gly Glu His Pro Phe Pro Glu Pro Met
                85                     90                     95

Asp Thr Gln Glu Ala Pro Thr Ala Glu Glu Thr Ser Ala Cys Cys Ala
            100                    105                    110

Pro Arg Pro Ala Lys Val Ser Arg Lys Arg Ser Ser Ser Leu Ser
            115                    120                    125

Asp Gly Gly Asp Ala Gly Leu Val Pro Ser Lys Lys Ala Arg Leu Glu
130                    135                    140

Glu Lys Glu Glu Glu Glu Gly Ala Ser Ser Glu Val Ala Asp Arg Leu
145                    150                    155                    160

Gln Pro Pro Pro Ala Gln Ala Glu Gly Ala Phe Pro Asn Leu Ala Arg
                165                    170                    175

Val Leu Gln Arg Arg Phe Ser Gly Leu Leu Asn Cys Ser Pro Ala Ala
            180                    185                    190

Pro Pro Thr Ala Pro Pro Ala Cys Glu Ala Lys Pro Ala Cys Arg Pro
            195                    200                    205

Ala Asp Ser Met Leu Asn Val Leu Val Arg Ala Val Val Ala Phe
210                    215                    220

<210> SEQ ID NO 6
<211> LENGTH: 2088
<212> TYPE: DNA
<213> ORGANISM: Homo sapiens

<400> SEQUENCE: 6
ggtccgagtt cggaatttcg gttcaaggcc cagttcctcg gattgttcct gcgcaacttc       60
agtttccctt ccaggcacgg gcaatgagtg tttggccgcg acgagttgga aagcccggat      120
gcgtccttcg gttgggcggg gtgtctcagt gacgtcactg ggggtataaa agggcctggg      180
tggcgggcgc ctgggcagag cgtcctagca gtgtcactgc gtgggttggt ttgtgtagag      240
aggcgtgagc gagcccgttg tccggagtgc acctgctgcc tgttctgtcc ctcccgggag      300
cccccgccgc tgtcgccgtc gagtcgccat ggaagtgcag aaagaggcac agcgcatcat      360
gaccctgtcg gtgtggaaga tgtatcactc ccgcatgcag cgcggtggcc tgcggctgca      420
ccggagtctg cagctgtcgc tggtcatgcg cagcgcccgg gagctctacc tctcggccaa      480
ggtggaggcc ctcgagcccg aggtgtcgtt gccggccgcc ctcccctctg accctcgcct      540
gcacccgccc cgagaagccg agtccacggc gagacagcg accccgacg gtgagcaccc       600
gtttccggag ccaatggaca cgcaggaggc ccgacagcc gaggagacct ccgcctgctg      660
tgccccgcgc ccgccaaag tcagccgcaa acgacgcagc agcagcctga cgacggcgg       720
ggacgctgga ctggtcccga gcaagaaagc cgtctggaa gaaaggaag aagaggaggg       780
agcgtcatcc gaagtcgccg atcgcctgca gccccctccg gcgcaagcgg agggcgcctt      840
tcccaacctg gccgcgtcc tgcagaggcg cttctccggc ctcctgaact gcagccccgc      900
ggccccctccg acggcgccgc ccgcgtgcga ggcaaagccc gcttgccgcc cggcggacag      960
catgctcaac gtgctcgtgc gggccgtggt ggccttctga ggaccccgag cggcgctgcc     1020
ggagcccaga gcgcgcgtcg aacgtcggc ccgagggcgc agacctgagg cgaggccacc      1080
ccctccatc ctgggggaag cgcccgcgaa accgtggag agaagccgcc gcccgggctg      1140
ctgagaggcc cggagaggga ctctgtcccc ggggagccat cgccttcagt gtgcagggac     1200
```

-continued

```
ggcaccgagg agtctgagcc gggggcgcgg gcgccttccg cagagacctg cgcccacagg    1260
tgctgtctta gtggactggg acgtgaacct ttcgctctcc ttctggactg ggagaaggga    1320
ggcttgggtg ttgtgttttt tgttttgttt gtttgtttgt ttttaaagat ctcctcaggg    1380
tcggacttca ttttgtactg tgggctgtgc tggcccttc aaggttttc aagagttggt     1440 tttgcgtttc caacctcgga gaattccagg cactccccttt cccctccgc tgacatactt    1500 gtataagcgg tcatcgttgc gtcatggggc aggcgtgggg agcttcctgt cgccttgcgt    1560
gggtgtgggg cctgggagga ggtcctgggg cgtgcacccg ccctgggcag tggggaggag    1620
agtggcctga gttacttcac ccccgcgtgc tgctggttaa tgtcccgcgt ctctgcacct    1680
tcgggtggga gcggggactg atctactttc acattctcaa gttttttctca tctgcattag    1740 aggtgcccag taggttccca ggttccagcg tgcccctccc tcagacacac ggacacaatc    1800
agccgagaag ttcctggtct gaatcacgag aatgtgagg ggtgggggt gtcagtggaa      1860 aggcataagg ctgagctgag accagttgct ggtgaaactg ggccaatctg ggagggggaa    1920
catccttgcc agggagtttc tgagggtctg ctttgtttac ctttcgtgcg gtggattctt    1980
tttaactccg tctacctggc gttttgttag aaatgtcaga taggaaaata aaaaccattt    2040
gagtaaaaaa aaaaaaaaaa aaaaaaaaaa aaaaaaaaaa aaaaaaa                  2088
```

```
<210> SEQ ID NO 7
<211> LENGTH: 454
<212> TYPE: PRT
<213> ORGANISM: Homo sapiens

<400> SEQUENCE: 7

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
```

```
                210                 215                 220
Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
            245                 250                 255

Glu Glu Thr Pro Pro Thr Thr Ser Ser Asp Ser Glu Glu Gln Glu
        260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
    355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
    435                 440                 445

Leu Arg Asn Ser Cys Ala
    450

<210> SEQ ID NO 8
<211> LENGTH: 2377
<212> TYPE: DNA
<213> ORGANISM: Homo sapiens

<400> SEQUENCE: 8 accccccgagc tgtgctgctc gcggccgcca ccgccgggcc ccggccgtcc ctggctcccc      60
tcctgcctcg agaagggcag ggcttctcag aggcttggcg ggaaaaagaa cggagggagg     120
gatcgcgctg agtataaaag ccggttttcg gggctttatc taactcgctg tagtaattcc     180
agcgagaggc agagggagcg agcgggcggc cggctagggt ggaagagccg ggcgagcaga     240
gctgcgctgc gggcgtcctg ggaagggaga tccggagcga ataggggggct tcgcctctgg     300 cccagccctc ccgctgatcc cccagccagc ggtccgcaac ccttgccgca tccacgaaac     360
tttgcccata gcagcgggcg ggcactttgc actggaactt acaacacccg agcaaggacg     420
cgactctccc gacgcgggga ggctattctg cccatttggg gacacttccc cgccgctgcc     480
aggacccgct tctctgaaag gctctccttg cagctgctta gacgtggat tttttttcggg     540 tagtggaaaa ccagcagcct cccgcgacga tgccccctcaa cgttagcttc accaacagga     600
actatgacct cgactacgac tcggtgcagc cgtatttcta ctgcgacgag gaggagaact     660
tctaccagca gcagcagcag agcgagctgc agccccccggc gcccagcgag gatatctgga     720
```

-continued

```
agaaattcga gctgctgccc accccgcccc tgtcccctag ccgccgctcc gggctctgct      780
cgccctccta cgttgcggtc acaccttcct cccttcgggg agacaacgac ggcggtggcg      840
ggagcttctc cacggccgac cagctggaga tggtgaccga gctgctggga ggagacatgg      900
tgaaccagag tttcatctgc gacccggacg acgagacctt catcaaaaac atcatcatcc      960
aggactgtat gtggagcggc ttctcggccg ccgccaagct cgtctcagag aagctggcct     1020
cctaccaggc tgcgcgcaaa gacagcggca gcccgaaccc cgcccgcggc cacagcgtct     1080
gctccacctc cagcttgtac ctgcaggatc tgagcgccgc cgcctcagag tgcatcgacc     1140
cctcggtggt cttcccctac cctctcaacg acagcagctc gcccaagtcc tgcgcctcgc     1200
aagactccag cgccttctct ccgtcctcgg attctctgct ctcctcgacg gagtcctccc     1260
cgcagggcag ccccgagccc ctggtgctcc atgaggagac accgccacc accagcagcg     1320
actctgagga ggaacaagaa gatgaggaag aaatcgatgt tgtttctgtg gaaagaggc     1380
aggctcctgg caaaaggtca gagtctggat caccttctgc tggaggccac agcaaacctc     1440
ctcacagccc actggtcctc aagaggtgcc acgtctccac acatcagcac aactacgcag     1500
cgcctccctc cactcggaag gactatcctg ctgccaagag ggtcaagttg acagtgtca     1560
gagtcctgag acagatcagc aacaaccgaa atgcaccag ccccaggtcc tcggacaccg     1620
aggagaatgt caagaggcga cacacacaacg tcttggagcg ccagaggagg aacgagctaa     1680
aacggagctt ttttgccctg cgtgaccaga tcccggagtt ggaaaacaat gaaaaggccc     1740
ccaaggtagt tatccttaaa aaagccacag catacatcct gtccgtccaa gcagaggagc     1800
aaaagctcat ttctgaagag gacttgttgc ggaaacgacg agaacagttg aaacacaaac     1860
ttgaacagct acggaactct tgtgcgtaag gaaagtaag gaaaacgatt ccttctaaca     1920
gaaatgtcct gagcaatcac ctatgaactt gtttcaaatg catgatcaaa tgcaacctca     1980
caaccttggc tgagtcttga gactgaaaga tttagccata atgtaaactg cctcaaattg     2040
gactttgggc ataaaagaac ttttttatgc ttaccatctt tttttttct ttaacagatt     2100
tgtatttaag aattgttttt aaaaaatttt aagatttaca caatgtttct ctgtaaatat     2160
tgccattaaa tgtaaataac tttaataaaa cgtttatagc agttacacag aatttcaatc     2220
ctagtatata gtacctagta ttataggtac tataaaccct aatttttttt atttaagtac     2280
attttgcttt ttaaagttga ttttttttcta ttgtttttag aaaaaataaa ataactggca     2340
aatatatcat tgagccaaaa aaaaaaaaaa aaaaaa                                2377
```

<210> SEQ ID NO 9
<211> LENGTH: 575
<212> TYPE: PRT
<213> ORGANISM: Homo sapiens

<400> SEQUENCE: 9

```
Met Asn Gly Pro Ala Leu Gln Pro Ser Ser Pro Ser Ser Ala Pro Ser
  1               5                  10                  15

Ala Ser Pro Ala Ala Ala Pro Arg Gly Trp Ser Glu Phe Cys Glu Leu
             20                  25                  30

His Ala Val Ala Ala Ala Arg Glu Leu Ala Arg Gln Tyr Trp Leu Phe
         35                  40                  45

Ala Arg Glu His Pro Gln His Ala Pro Leu Arg Ala Glu Leu Val Ser
     50                  55                  60

Leu Gln Phe Thr Asp Leu Phe Gln Arg Tyr Phe Cys Arg Glu Val Arg
 65                  70                  75                  80
```

-continued

```
Asp Gly Arg Ala Pro Gly Arg Asp Tyr Arg Asp Thr Gly Arg Gly Pro
                85                  90                  95
Pro Ala Lys Ala Glu Ala Ser Pro Glu Pro Gly Pro Gly Pro Ala Ala
            100                 105                 110
Pro Gly Leu Pro Lys Ala Arg Ser Ser Glu Glu Leu Ala Pro Pro Arg
        115                 120                 125
Pro Pro Gly Pro Cys Ser Phe Gln His Phe Arg Arg Ser Leu Arg His
    130                 135                 140
Ile Phe Arg Arg Ser Ala Gly Glu Leu Pro Ala Ala His Thr Ala
145                 150                 155                 160
Ala Ala Pro Gly Thr Pro Gly Glu Ala Ala Glu Thr Pro Ala Arg Pro
                165                 170                 175
Gly Leu Ala Lys Lys Phe Leu Pro Trp Ser Leu Ala Arg Glu Pro Pro
            180                 185                 190
Pro Glu Ala Leu Lys Glu Ala Val Leu Arg Tyr Ser Leu Ala Asp Glu
        195                 200                 205
Ala Ser Met Asp Ser Gly Ala Arg Trp Gln Arg Gly Arg Leu Ala Leu
    210                 215                 220
Arg Arg Ala Pro Gly Pro Asp Gly Pro Asp Arg Val Leu Glu Leu Phe
225                 230                 235                 240
Asp Pro Pro Lys Ser Ser Arg Pro Lys Leu Gln Ala Ala Cys Ser Ser
                245                 250                 255
Ile Gln Glu Val Arg Trp Cys Thr Arg Leu Glu Met Pro Asp Asn Leu
            260                 265                 270
Tyr Thr Phe Val Leu Lys Val Lys Asp Arg Thr Asp Ile Ile Phe Glu
        275                 280                 285
Val Gly Asp Glu Gln Gln Leu Asn Ser Trp Met Ala Glu Leu Ser Glu
    290                 295                 300
Cys Thr Gly Arg Gly Leu Glu Ser Thr Glu Ala Glu Met His Ile Pro
305                 310                 315                 320
Ser Ala Leu Glu Pro Ser Thr Ser Ser Pro Arg Gly Ser Thr Asp
                325                 330                 335
Ser Leu Asn Gln Gly Ala Ser Pro Gly Gly Leu Leu Asp Pro Ala Cys
            340                 345                 350
Gln Lys Thr Asp His Phe Leu Ser Cys Tyr Pro Trp Phe His Gly Pro
        355                 360                 365
Ile Ser Arg Val Lys Ala Ala Gln Leu Val Gln Leu Gln Gly Pro Asp
    370                 375                 380
Ala His Gly Val Phe Leu Val Arg Gln Ser Glu Thr Arg Arg Gly Glu
385                 390                 395                 400
Tyr Val Leu Thr Phe Asn Phe Gln Gly Ile Ala Lys His Leu Arg Leu
                405                 410                 415
Ser Leu Thr Glu Arg Gly Gln Cys Arg Val Gln His Leu His Phe Pro
            420                 425                 430
Ser Val Val Asp Met Leu His His Phe Gln Arg Ser Pro Ile Pro Leu
        435                 440                 445
Glu Cys Gly Ala Ala Cys Asp Val Arg Leu Ser Ser Tyr Val Val Val
    450                 455                 460
Val Ser Gln Pro Pro Gly Ser Cys Asn Thr Val Leu Phe Pro Phe Ser
465                 470                 475                 480
Leu Pro His Trp Asp Ser Glu Ser Leu Pro His Trp Gly Ser Glu Leu
                485                 490                 495
Gly Leu Pro His Leu Ser Ser Ser Gly Cys Pro Arg Gly Leu Ser Pro
```

-continued

```
                500             505             510
      Glu Gly Leu Pro Gly Arg Ser Ser Pro Pro Glu Gln Ile Phe His Leu
              515                 520                 525

Val Pro Ser Pro Glu Glu Leu Ala Asn Ser Leu Gln His Leu Glu His
              530                 535                 540

Glu Pro Val Asn Arg Ala Arg Asp Ser Asp Tyr Glu Met Asp Ser Ser
      545                 550                 555                 560

Ser Arg Ser His Leu Arg Ala Ile Asp Asn Gln Tyr Thr Pro Leu
                      565                 570                 575
```

<210> SEQ ID NO 10
<211> LENGTH: 5423
<212> TYPE: DNA
<213> ORGANISM: Homo sapiens

<400> SEQUENCE: 10

```
cccgggccac cgcctccgcc cggctgcccg cccggactgt cgcggcccgc ggtggcgacg      60
gcggccgctg caaagtttcc ccggcggcgg cggcccgggg gcgcatcctc ccgcaactgt     120
caagcgctgg cggcggaaat gatgaggcgc tggccatttt ccgagcccgg gtttcctgcc     180
tgagccccgc tcgagcgagc cgcgagcgag gagccggcgg gcgggagagg acgcgcccag     240
ggcgggggcc cgcccgcccc ctcgggattt cgagggcccg ggggcgcgcg acgccatggg     300
ccggccgggc ccagagctcc tgtctctcag cccggccgca ccacctgggt ctccgccatg     360
aacgggcctg ccctgcagcc ctcctcgccc tcttccgcgc cctcagcctc cccggcggcg     420
gccccgcggg gctggagcga gttctgtgag ttgcacgccg tagcggcggc ccgggagctg     480
gcccgccagt actggctgtt cgcccggcag catccgcagc acgcgccgct gcgcgccgag     540
ctggtgtcgc tgcagttcac cgacctcttc cagcgctact tctgccgcga ggtgcgcgac     600
ggacgggcgc cgggccgcga ctaccgggac acaggccgtg gccccccagc caaggccgag     660
gcgtccccgg agccaggccc cggccccgcc gcccctggcc tgcccaaggc ccgcagctct     720
gaggagctgg ccccgccgcg gccgcccggg ccctgctcct ccagcacttt cgccgcagc      780
ctccgccaca tcttccgccg ccgctcggcc ggggagctgc cagcggccca caccgctgcc     840
gcccccggga ccccggaga ggctgctgag accccccgccc ggcctggcct ggccaagaag     900
ttcctgccct ggagcctggc ccgggagccg cacccgagg cgctgaagga ggcggtgctg     960
cgctacagcc tggccgacga ggcctccatg gacagcgggg cacgctggca gcgcgggagg    1020
ctggcgctgc gccgggcccc gggccccgat ggccccgacc gcgtgctgga gctcttcgac    1080
ccacccaaga gttcaaggcc caagctacaa gcagcttgct ccagcatcca ggaggtccgg    1140
tggtgcacac ggcttgagat gcctgacaac ctttacacct ttgtgctgaa ggtgaaggac    1200
cggacagaca tcatctttga ggtgggagac gagcagcagc tgaattcatg gatggctgag    1260
ctctcggagt gcaggccg agggctggag agcacagaag cagagatgca tattccctca     1320
gccctagagc ctagcacgtc cagctcccca aggggcagca cagattccct taaccaaggt    1380
gcttctcctg gggggctgct ggacccggcc tgccagaaga cggaccattt cctgtcctgc    1440
taccccctggt tccacggccc catctccaga gtgaaagcag ctcagctggt tcagctgcag    1500
ggccctgatg ctcatggagt gttcctggtg cggcagagcc agacgcggcg tgggaatac     1560
gtgctcactt tcaactttca ggggatagcc aagcacctgc cctgtcgct gacagagcgg    1620
ggccagtgcc gtgtgcagca cctccactt ccctcggtcg tggacatgct ccaccacttc    1680
cagcgctcgc ccatcccact cgagtgcggc gccgcctgtg atgtccggct ctccagctac    1740
```

```
gtggtagtcg tctcccaacc accaggttcc tgcaacacgg tcctcttccc tttctccctt   1800
cctcactggg attcagagtc ccttcctcac tggggttcag agttgggcct tccccacctt   1860
agttcttctg gctgtccccg ggggctcagc ccagagggtc tcccagggcg atcctcaccc   1920
cccgagcaga tcttccacct ggtgccttcg cccgaagaac tggccaacag cctgcagcac   1980
ctggagcatg agcctgtgaa tcgagcccgg gactcggact acgaaatgga ctcatcctcc   2040
cggagccacc tgcgggccat agacaatcag tacacacctc tctgaccagt gaggaattcc   2100
aggcctcaac agctgccctt gaggagcaca ggcagaagtg tgaacttgtg aatgtaattg   2160
atctttcctt ccttccagag aaagatttaa gggacactgt taactgctcg tgccagtttg   2220
gaagtgaccc ttctattagg cctgttgaag ggccctcctg taggtttcat ctatccacct   2280
ggctttctcc ttattgttta cagatgtagt tcttgttaga ggatgccgct agctcctgcc   2340
cggggtccct atgcccagtc cccgttactc ttagagaaag gagttggggt gagggccaga   2400
gctggcagtg gaaacttgtt ctcttttca ctgacactgt cacagcggat gacagacttt    2460
ctacggggag gaggggggga tcatcaggaa gcccagaaca ctaacaagcg gttctcccat   2520
ctaccgtcag tccacatggc aggtctgctg tgtccacacc acagatgacc acatctaatc   2580
ctgcttctac tctcagcttt aggacaaaag ctctgtcaga ggcacaagct gaaggtcaaa   2640
aatgatttaa aacattttac ctcagactaa tttctttaaa ggattcaggt tcaaaactta   2700
accactgctt atttcagtgc actgtttcaa ctaaccccca tgctattttt gtagtcagaa   2760
acagctatgc aaaccctacc taatttacag tctgagccag catgctggct tgtctactgc   2820
atcctcggga cagtcacctg ccactgagtg gccactgtcc ttcctaaatg tcaagaagtg   2880
aagtatgtca ccctttcagg gaaattcagg caattactga ataggaagg tggcaagaac     2940 agttctatcc tggtgcctta cgaataaaaa actggattct ggtttacagc agctttacag   3000
tgatagttaa attaactggg gctaggggaa aagcaaccaa aaagggaaaa aggactccta   3060
ggccctttct attaaatcct tcagcaacaa ggctggcttg gtgccctcca agcatctaat   3120
ggcttattaa attatcccac aattgggttt taggctcctt ttttgaccca aaatggaagc   3180
tgggaatctg gtgccataac taatgagaaa ctccttaat accccacaat cagtgttctg    3240
ttctacctgg ctactgcttc actggattga aaatctatct atctccttgc acacatgggc   3300
acacacaatc tccaccatcc agggaggtcc tgaattcaaa tctctatcta tccaagtgat   3360
acaattcata gggggctggc tcctcccaga acctgtctgg aggctcagaa acgggggcag   3420
tgacagtgga gtcagctgct cttgggtgcc agcagagcca ttcagtacaa cccccaggct   3480
cacagcagtg gcttctagga aactgggagt ttagatcagc tttacagata catcgatcag   3540
aggctaaaat gaaacctcag cctaaaactc ataggactga ctgcctggga ggagggttag   3600
gtctgcttct tccacttata cttagtctct gtgctccaag aggtcaaatt tttgcttcta   3660
gaatttcctt ggggtctttc agagggtggg ggaacaaacc cctatgcact tttcttttt    3720 tttttgaga tggagtttct cttgtcaacc gggctgagt gcagtggtgc aatcttggct     3780
cactgcaacc tccaccttcc tggttcaagc gattctgcct cgacctctca gtagctggg    3840 attacaagca ccagccacca tgcctggcta attttgtatt tttagtagag acagggtttc   3900
accatgttgg ccaggctggt ctcgaatgtc tgacctcagg tgatccaccc gccttggcct   3960
cccaaagtgc tgggattaca ggcgcgagcc accgcgccca gcctacacca ctttagtac   4020 caacactctt gggtgatttc atggacccta aagcagacct gacactgatc cagatttgca   4080
```

```
gtccattttt aaggacacct gtctttattt cctcaaagtc aagcagcttt ctctggaaaa    4140
tgaatgctaa ttagtgtgaa ccaaaagagt aagtaagagt ctgaagtttt tttaaaggag    4200
aaagcttatt atggaaagtc actggtcctc ccctccgcac aggaaaggta cccagtagat    4260
aatgaaccaa attaagttcc ctccctccag ccagaagtta acatctggg atatgacgtc    4320 ttcatgccag gggcactcat ttcttagcag cctctctaca tacatctctc aggtggtgcc    4380
aagaggcaca ccaggtagag caaacttagc agctctgact aacaggctgc aaagtgcaag    4440
ttcagattct gtggcagaga tttggagggc acccacgtcc agactgcttc ccgtccaagt    4500
taccaggaca gctcaaaaac atgctgacag aaaactccca tggctctagg aaaaagtgac    4560
actaagccaa caccttctt tatgtgggag caaaatcagc tgatgaaggg gtgggcacca    4620
ttgtggggca ggcaccccac tggctgcagc tagcccacca taggcacagc catcccacc    4680 actctccttc cagtcctgac caggccccag ccggcaactt ctaccgagag ccatggctca    4740
acaccaaact ggacagtaga catcatgatc cctccagtta gctctaatta cagaccccac    4800
cagtacagct tgacagctcc cggcaccatc ccttccttca tctgacttat tgaactttta    4860
caaactaaca gtcaccagca ccaaagaatt aagtcaacta acctgccttg aatttaaac     4920 cagcaatcca tatggcttta tctggtataa atcttctgcc tttgatcatt tctggaccgt    4980
aggaaaaagg aatagcaatc attaaaatct tgggccagag aacactattt ttacataaca    5040
gtttcttaac ctaaagtcaa ggccttggac tcttccctga gggttgcctg aaattccttc    5100
atgctttcta ttcaggacta attcccttac tgcaaatgtg ttagctctaa catctcccac    5160
aagctaaagg aacttgcaag tatattaaca aggacacatc tgacatcctg tgtttggtta    5220
aaatatacag cacattgtga taacataaag tggatccatc ttgtatcatt ataggcaaaa    5280
ggtatttggc aaattttat gtatggtttt atgtactgta caagtaactt attcttgaat      5340
aatgcaaatt ttgctataat gtacaaattg ctatatgtga attaaaaagt ttccaaaatc    5400
ttgaaaaaaa aaaaaaaaaa aaa                                            5423
```

<210> SEQ ID NO 11
<211> LENGTH: 510
<212> TYPE: PRT
<213> ORGANISM: Homo sapiens

<400> SEQUENCE: 11

```
Met Asp Gly Phe Tyr Asp Gln Gln Val Pro Phe Met Val Pro Gly Lys
  1               5                  10                  15

Ser Arg Ser Glu Glu Cys Arg Gly Arg Pro Val Ile Asp Arg Lys Arg
             20                  25                  30

Lys Phe Leu Asp Thr Asp Leu Ala His Asp Ser Glu Glu Leu Phe Gln
         35                  40                  45

Asp Leu Ser Gln Leu Gln Glu Ala Trp Leu Ala Glu Ala Gln Val Pro
     50                  55                  60

Asp Asp Glu Gln Phe Val Pro Asp Phe Gln Ser Asp Asn Leu Val Leu
 65                  70                  75                  80

His Ala Pro Pro Pro Thr Lys Ile Lys Arg Glu Leu His Ser Pro Ser
                 85                  90                  95

Ser Glu Leu Ser Ser Cys Ser His Glu Gln Ala Leu Gly Ala Asn Tyr
            100                 105                 110

Gly Glu Lys Cys Leu Tyr Asn Tyr Cys Ala Tyr Asp Arg Lys Pro Pro
        115                 120                 125

Ser Gly Phe Lys Pro Leu Thr Pro Pro Thr Thr Pro Leu Ser Pro Thr
```

```
            130                 135                 140
His Gln Asn Pro Leu Phe Pro Pro Gln Ala Thr Leu Pro Thr Ser
145                 150                 155                 160

Gly His Ala Pro Ala Ala Gly Pro Val Gln Val Gly Pro Ala Pro
                165                 170                 175

Ala Pro His Ser Leu Pro Glu Pro Gly Pro Gln Gln Gln Thr Phe Ala
                180                 185                 190

Val Pro Arg Pro Pro His Gln Pro Leu Gln Met Pro Lys Met Met Pro
            195                 200                 205

Glu Asn Gln Tyr Pro Ser Glu Gln Arg Phe Gln Arg Gln Leu Ser Glu
210                 215                 220

Pro Cys His Pro Phe Pro Pro Gln Pro Gly Val Pro Gly Asp Asn Arg
225                 230                 235                 240

Pro Ser Tyr His Arg Gln Met Ser Glu Pro Ile Val Pro Ala Ala Pro
                245                 250                 255

Pro Pro Pro Gln Gly Phe Lys Gln Glu Tyr His Asp Pro Leu Tyr Glu
                260                 265                 270

His Gly Val Pro Gly Met Pro Gly Pro Ala His Gly Phe Gln Ser
            275                 280                 285

Pro Met Gly Ile Lys Gln Glu Pro Arg Asp Tyr Cys Val Asp Ser Glu
    290                 295                 300

Val Pro Asn Cys Gln Ser Ser Tyr Met Arg Gly Gly Tyr Phe Ser Ser
305                 310                 315                 320

Ser His Glu Gly Phe Ser Tyr Glu Lys Asp Pro Arg Leu Tyr Phe Asp
                325                 330                 335

Asp Thr Cys Val Val Pro Glu Arg Leu Glu Gly Lys Val Lys Gln Glu
            340                 345                 350

Pro Thr Met Tyr Arg Glu Gly Pro Pro Tyr Gln Arg Arg Gly Ser Leu
        355                 360                 365

Gln Leu Trp Gln Phe Leu Val Thr Leu Leu Asp Asp Pro Ala Asn Ala
    370                 375                 380

His Phe Ile Ala Trp Thr Gly Arg Gly Met Glu Phe Lys Leu Ile Glu
385                 390                 395                 400

Pro Glu Glu Val Ala Arg Arg Trp Gly Ile Gln Lys Asn Arg Pro Ala
                405                 410                 415

Met Asn Tyr Asp Lys Leu Ser Arg Ser Leu Arg Tyr Tyr Glu Lys
                420                 425                 430

Gly Ile Met Gln Lys Val Ala Gly Glu Arg Tyr Val Tyr Lys Phe Val
            435                 440                 445

Cys Asp Pro Asp Ala Leu Phe Ser Met Ala Phe Pro Asp Asn Gln Arg
450                 455                 460

Pro Phe Leu Lys Ala Glu Ser Glu Cys His Leu Ser Glu Glu Asp Thr
465                 470                 475                 480

Leu Pro Leu Thr His Phe Glu Asp Ser Pro Ala Tyr Leu Leu Asp Met
                485                 490                 495

Asp Arg Cys Ser Ser Leu Pro Tyr Ala Glu Gly Phe Ala Tyr
            500                 505                 510

<210> SEQ ID NO 12
<211> LENGTH: 4071
<212> TYPE: DNA
<213> ORGANISM: Homo sapiens

<400> SEQUENCE: 12
```

```
gagtccagcc gctggtgcgc ggagcggttc accgtcttcg gagcggttcg gcccagcctt      60
tcgcccaggc gcccaggccc gctgcgcgcg tgcgtgagcg cgcctgcgcc gccagggccg     120
ctgcaagggg aggagagcgg ccgcctcagg aggatcccct ttcccccaga aattactcaa     180
tgctgaaacc tctcaaagtg gtattagaga cgctgaaagc accatggacg ggttttatga     240
tcagcaagtc cctttatgg tcccagggaa atctcgatct gaggaatgca gagggcggcc      300
tgtgattgac agaaagagga agttttttgga cacagatctg gctcacgatt ctgaagagct    360
atttcaggat ctcagtcaac ttcaagaggc ttggttagct gaagcacaag ttcctgatga     420
tgaacagttt gtcccagatt ttcagtctga taacctggtg cttcatgccc cacctccaac    480
caagatcaaa cgggagctgc acagcccctc ctctgagctg tcgtcttgta gccatgagca     540
ggctcttggt gctaactatg gagaaaagtg cctctacaac tatttgtgcct atgataggaa    600 gcctccctct gggttcaagc cattaaccc tcctacaacc ccctctcac ccacccatca       660 gaatccccta tttcccccac ctcaggcaac tctgcccacc tcagggcatg cccctgcagc     720
tggcccagtt caaggtgtgg gccccgcccc cgcccccat tcgcttccag agcctggacc      780
acagcagcaa acatttgcgg tcccccgacc accacatcag ccctgcaga tgccaaagat      840 gatgcctgaa aaccagtatc catcagaaca gagatttcag agacaactgt ctgaaccctg     900
ccaccccttc cctcctcagc caggagttcc tggagataat cgccccagtt accatcggca     960
aatgtcagaa cctattgtcc ctgcagctcc cccgcccct cagggattca aacaagaata     1020
ccatgaccca ctctatgaac atggggtccc gggcatgcca gggccccag cacacggggtt   1080 ccagtcacca atgggaatca agcaggagcc tcgggattac tgcgtcgatt cagaagtgcc   1140
taactgccag tcatcctaca tgagaggggg ttatttctcc agcagccatg aaggttttttc  1200 atatgaaaaa gatccccgat tatactttga cgacacttgt gttgtgcctg agagactgga   1260
aggcaaagtc aaacaggagc ctaccatgta tcgagagggg ccccccttacc agaggcgagg  1320 ttcccttcag ctgtggcagt tcctggtcac ccttcttgat gacccagcca atgcccactt   1380
cattgcctgg acaggtcgag gcatggagtt caagctgata gaaccggaag aggttgctcg  1440 gcgctgggggc atccagaaga accggccagc catgaactat gacaagctga gccgctctct  1500
ccgctattac tatgaaaagg gcatcatgca aaggtggct ggagagcgat acgtctacaa   1560
atttgtctgt gacccagatg ccctcttctc catggctttc ccggataacc agcgtccgtt   1620
cctgaaggca gagtccgagt gccacctcag cgaggaggac accctgccgc tgacccactt   1680
tgaagacagc cccgcttacc tcctggacat ggaccgctgc agcagcctcc cctatgccga   1740
aggctttgct tactaagttt ctgagtggcg gagtggccaa accctagagc tagcagttcc   1800
cattcaggca aacaagggca gtggttttgt ttgtgttttt ggttgttcct aaagcttgcc   1860
ctttgagtat tatctggaga acccaagctg tctctggatt ggcaccctta aagacagata   1920
cattggctgg ggagtgggaa cagggagggg cagaaaacca ccaaaaggcc agtgcctcaa   1980
ctcttgattc tgatgaggtt tctgggaaga gatcaaaatg gagtctcctt accatggaca   2040
atacatgcaa agcaatatct tgttcaggtt agtacccgca aaacgggaca tgatgtgaca   2100
atctcgatcg atcatggact actaaatggc ctttacatag aagggctctg atttgcacaa   2160
tttgttgaaa aatcacaaac ccatagaaaa gtgagtaggc taagtggggg aggctcaaac   2220
cattaagggt taaaaataca tcttaaacat tggaaagctc ttctagctga atctgaaata   2280
ttaccccttg tctagaaaaa ggggggcagt cagaacagct gttccccact ccgtgttctc   2340
aaaatcataa accatggcta ctcttgggaa ccacccggcc atgtggtcgc caagtagagc   2400
```

```
aagcccccttt tctcttccca atcacgtggc tgagtgtgga tgactttat tttaggagaa      2460 gggcgattaa cacttttgac agtatttgt tttgccctga tttggggat tgttttgttt       2520 tggtggttgt tttggaaaaa cagtttataa actgattttt gtagtttgg tatttaaagc       2580 aaaaaaacga aaacaaaaa acaaaaacaa acctttggt aatgtgcact gtgtctttag       2640
ccagggccgt gcaacttatg aagacactgc agcttgagag gggctttgct gaggcttccc      2700
cttggccatg tgaaagcccg ccttgttgcc tgctttgtgc tttctgcacc agacaacctg      2760
atggaacatt tgcacctgag ttgtacattt ttgaagtgtg cagggcagcc tggacacaag      2820
cttagattct ctatgtatag ttccccgtgt tcactaacat gccctctctg gaaagcatat      2880
gtatataaca tgtgtcatgt cctttggaaa cctggtcacc tggtgaaaac ccttgggatt      2940
cttccctggg catgactgat gacaatttcc atttcatcag tttgttttgt tttccttttt      3000 cttaaatct tggactttaa accctacctg tgtgattcag tagggtttga gcttagctg       3060 tgatactgac aggtaagcaa cagtgctagc attctagatt cctgcctttt tttaaaaga     3120 aattattctc attgctgtat tatattggaa agtttttaaa caaccaagct aaagctatgt    3180
gaaagttgag ctcaaagtag aggaaaagtt actggtggta ccttgctgcc tgctctgctg    3240
gtagaattct gtgctccccg tgacacttag tacattaaga atgactacac tgttcctcgt    3300
atgtgaagga ggcagtgctg actccgtgag tgtgagacac gtgctttgaa ctgcttttct    3360
attcatggag cactccatag tctcaaactg tccccttat gaccaacagc acatttgtga     3420
agaggttcgc agggataagg ggtgcacttt atagctatgg aaacatgaga ttctcctcta    3480
ttggaagcta attagcccac aaaggtggta aacctgtaga ttgggcctta attagcattg     3540
tactctaatc aaaggactct ttctaaacca tatttatagc tttcttaacc tacacatagt     3600
ctatacatag atgcatattt taccccccagc tggctagaga tttatttgtt gtaaatgctg    3660
tatagatttg gttttcctt ctttacttac cctggtttgg attttttttt ttttttttt      3720 tgaatggatt tatgctgtct tagcaatatg acaataatcc tctgtagctt gagctacccc    3780 tccctgctg taacttacgt gacctgtgct gtcactgggc ataggacagc ggcatcacgg     3840
ttgcattccc attggactca tgcacctccc ggatggtttt tgttttttc ggggttctt      3900 tggggtttgt ttgtttgctt cttttccaga gtgtggaaag tctacagtgc agaaaggctt    3960
gaacctgcca gctgatttga aatactttca ccctgcgcag ggccgtatgc atcctgccaa    4020
gctgcgttat attctgtact gtgtacaata aagaagtttg cttttcgttt a            4071
```

<210> SEQ ID NO 13
<211> LENGTH: 237
<212> TYPE: PRT
<213> ORGANISM: Homo sapiens

<400> SEQUENCE: 13

```
Met Ala Ala Val Arg Val Leu Val Ala Ser Arg Leu Ala Ala Ala Ser
  1               5                  10                  15

Ala Phe Thr Ser Leu Ser Pro Gly Gly Arg Thr Pro Ser Gln Arg Ala
                 20                  25                  30

Ala Leu His Leu Ser Val Pro Arg Pro Ala Ala Arg Val Ala Leu Val
             35                  40                  45

Leu Ser Gly Cys Gly Val Tyr Asp Gly Thr Glu Ile His Glu Ala Ser
         50                  55                  60

Ala Ile Leu Val His Leu Ser Arg Gly Gly Ala Glu Val Gln Ile Phe
     65                  70                  75                  80
```

```
Ala Pro Asp Val Pro Gln Met His Val Ile Asp His Thr Lys Gly Gln
            85                  90                  95

Pro Ser Glu Gly Glu Ser Arg Asn Val Leu Thr Glu Ser Ala Arg Ile
            100                 105                 110

Ala Arg Gly Lys Ile Thr Asp Leu Ala Asn Leu Ser Ala Ala Asn His
            115                 120                 125

Asp Ala Ala Ile Phe Pro Gly Gly Phe Gly Ala Ala Lys Asn Leu Leu
            130                 135                 140

Cys Cys Ile Ala Pro Val Leu Ala Ala Lys Val Leu Arg Gly Val Glu
145                 150                 155                 160

Val Thr Val Gly His Glu Gln Glu Gly Gly Lys Trp Pro Tyr Ala
            165                 170                 175

Gly Thr Ala Glu Ala Ile Lys Ala Leu Gly Ala Lys His Cys Val Lys
            180                 185                 190

Glu Val Val Glu Ala His Val Asp Gln Lys Asn Lys Val Val Thr Thr
            195                 200                 205

Pro Ala Phe Met Cys Glu Thr Ala Leu His Tyr Ile His Asp Gly Ile
            210                 215                 220

Gly Ala Met Val Arg Lys Val Leu Glu Leu Thr Gly Lys
225                 230                 235

<210> SEQ ID NO 14
<211> LENGTH: 1576
<212> TYPE: DNA
<213> ORGANISM: Homo sapiens

<400> SEQUENCE: 14
agtcccgacg agcaacgcgt ttgtagaggg gtgggtgcgc acgctctgtc cctgcgtgac      60
cttccgaccc cgctgtcctc accgcaatgg cggctgtgag ggtcctggtg gcctcgaggc     120
tcgctgcggc atctgcattc acgtcccgt ccccggcgg tcggacgcct tcccagcgcg      180
cagcccttca cctctccgtg ccgcgcccg cggccagggt cgcgctggtg ctgtctggat      240
gcggagtcta cgatgggacc gagatccacg aggcctcggc gatcctggtg cacctgagcc      300
gtggaggggc tgaagtccag atctttgctc ctgacgtccc tcagatgcac gtgattgacc      360
acaccaaggg gcagccgtcc gaaggcgaga gcaggaatgt tttgaccgag tctgcgagga      420
tcgcccgtgg caaaatcaca gacctggcca acctcagtgc agccaaccat gatgctgcca      480
tctttccagg aggctttgga gcggctaaaa acctcttgtg ctgcattgca cctgtcctcg      540
cggccaaggt gctcagaggc gtcgaggtga ctgtgggcca cgagcaggag aaggtggca      600 agtggcctta tgccgggacc gcagaggcca tcaaggccct gggtgccaag cactgcgtga      660
aggaagtggt cgaagctcac gtggaccaga aaaacaaggt ggtcacgacc ccagccttca      720
tgtgcgagac ggcactccac tacatccatg atgggatcgg agccatggtg aggaaggtgc      780
tggaactcac tggaaagtga cgcgcatgga cggggcccag ctaggcgcca ggacttggcc      840
tcaccctctg gctgaggagc tgtcggctgc tttccatcca gctgggagtc tggcaggccc      900
tttttttttt ttctttgccg aaacctgcag gcgttctctc tctaaggagg atgtgctgca      960
gtgcatgggg gatgtttctt cctgggtgtg gctgggctgc tctcacatac agaggccgag     1020
gggccaattc gttctctgcc acagggactt gcctcactgt gtcccaaaaa caaatcgcag     1080
ccagcttttc cagaaataga aaattctgcc gtctgaggtt ttatacttca ggttagttag     1140
tttttggaag gaagaacatt tttaggtttg caagcctcct gatcaggaaa ccagaaatac     1200
```

```
cacatttatg gaccatgaaa ggttggttct tgactctgaa gggacttttg agttaatcag    1260
cgtaagggga tttctaaagc aggcaatccc tgtagccgca gagaataaac gccttcccaa    1320
aatggcaact tcccacagcc acatttcaga cctgctgaga ctgctgagtg aggaatggca    1380
gtgaggtttc ttcaattagt ctcagttctc ttaattttca ggaagaaagg gaaattgcag    1440 ccccctcagcc cccaggattg acctctgggg agtgatggta gcgttggtgc caggccgtgg    1500
gttcaggtgt ggcagaagct tgcagatgcg tccgaaggga ataaagtgt gttggcgtta    1560 gactttgtgc tgcaaa                                                    1576
```

<210> SEQ ID NO 15
<211> LENGTH: 315
<212> TYPE: PRT
<213> ORGANISM: Homo sapiens

<400> SEQUENCE: 15

```
Met Glu Ala Arg Ala Gln Ser Gly Asn Gly Ser Gln Pro Leu Leu Gln
 1               5                  10                  15

Thr Pro Arg Asp Gly Gly Arg Gln Arg Gly Glu Pro Asp Pro Arg Asp
            20                  25                  30

Ala Leu Thr Gln Gln Val His Val Leu Ser Leu Asp Gln Ile Arg Ala
        35                  40                  45

Ile Arg Asn Thr Asn Glu Tyr Thr Glu Gly Pro Thr Val Val Pro Arg
    50                  55                  60

Pro Gly Leu Lys Pro Ala Pro Arg Pro Ser Thr Gln His Lys His Glu
65                  70                  75                  80

Arg Leu His Gly Leu Pro Glu His Arg Gln Pro Pro Arg Leu Gln His
                85                  90                  95

Ser Gln Val His Ser Ser Ala Arg Ala Pro Leu Ser Arg Ser Ile Ser
            100                 105                 110

Thr Val Ser Ser Gly Ser Arg Ser Ser Thr Arg Thr Thr Ser Ser
        115                 120                 125

Ser Ser Ser Glu Gln Arg Leu Leu Gly Ser Ser Phe Ser Ser Gly Pro
    130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Cys Val Lys Gly
    210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met
                245                 250                 255

Gly Val Met Ser Leu Phe Leu Pro Cys Leu Trp Cys Tyr Leu Pro Ala
            260                 265                 270

Lys Gly Cys Leu Lys Leu Cys Gln Gly Cys Tyr Asp Arg Val Asn Arg
        275                 280                 285

Pro Gly Cys Arg Cys Lys Asn Ser Asn Thr Val Cys Cys Lys Val Pro
    290                 295                 300
```

```
Thr Val Pro Pro Arg Asn Phe Glu Lys Pro Thr
305                 310                 315

<210> SEQ ID NO 16
<211> LENGTH: 2126
<212> TYPE: DNA
<213> ORGANISM: Homo sapiens

<400> SEQUENCE: 16
gtaaggccgt tttcttttcc cattcgctca tctgccagga aaagggactt gccgttggcg      60
cttcggcctc ttgttcattg agaaaaaaga ggaaatactc cgcgtgcgct tgtagaaggg     120
gagtcgtctc cagctccgaa ccccggagtg ttcatcagcg gggaatctgg ctccgaattc     180 tcttttttc tcccgccgat tgctcggaag ttggtctaaa gcagaggttg aaagaaagg      240 aaaaaagttt gcatcgagac tggatttatt tgcacatcgc agaaagaaga gaatccaagg     300
gagaggggtt ggtgcaaagc cgcgatcacg gagttcagat gtgttctaag cctgctggag     360
tgaccacact tccaagacct gatggaggcc agagctcaga gtggcaacgg tcgcagccc      420 ttgctgcaga cgccccgtga cggtggcaga cagcgtgggg agcccgaccc cagagacgcc     480
ctcacccagc aggtacatgt cttgtctctg gatcagatca gagccatccg aaacaccaat     540
gagtacacag aggggcctac tgtcgtccca gacctgggc tcaagcctgc tcctcgcccc     600
tccactcagc acaaacacga gagactccac ggtctgcctg agcaccgcca gcctcctagg     660
ctccagcact cgcaggtcca ttcttctgca cgagcccctc tgtccagatc cataagcacg     720
gtcagctcag ggtcgcggag cagtacgagg acaagtacca gcagcagctc ctctgaacag     780
agactgctag gatcatcctt ctcctccggg cctgttgctg atggcataat ccgggtgcaa     840
cccaaatctg agctcaagcc aggtgagctt aagccactga gcaaggaaga tttgggcctg     900
cacgcctaca ggtgtgagga ctgtggcaag tgcaaatgta aggagtgcac ctacccaagg     960
cctctgccat cagactggat ctgcgacaag cagtgccttt gctcggccca gaacgtgatt    1020
gactatggga cttgtgtatg ctgtgtgaaa ggtctcttct atcactgttc taatgatgat    1080
gaggacaact gtgctgacaa cccatgttct tgcagccagt ctcactgttg tacacgatgg    1140
tcagccatgg gtgtcatgtc cctcttttg ccttgtttat ggtgttacct tccagccaag    1200
ggttgcctta aattgtgcca ggggtgttat gaccgggtta acaggcctgg ttgccgctgt    1260
aaaaactcaa acacagtttg ctgcaaagtt cccactgtcc cccctaggaa ctttgaaaaa    1320
ccaacatagc atcattaatc aggaatatta cagtaatgag gatttttct ttcttttttt    1380 aatacacata tgcaaccaac taaacagtta taatcttggc actgttaata gaaaggtggg    1440
atagtctttg ctgtttgcgg tgaaatgctt tttgtccatg tgccgtttta actgatatgc    1500
ttgttagaac tcagctaatg gagctcaaag tatgagatac agaacttggt gacccatgta    1560
ttgcataagc taaagcaaca cagacactcc taggcaaagt ttttgtttgt gaatagtact    1620
tgcaaaactt gtaaattagc agatgacttt tttccattgt tttctccaga gagaatgtgc    1680 tatattttg tatatacaat aatatttgca actgtgaaaa acaagttgtg ccatactaca    1740
tggcacagac acaaaatatt atactaatat gttgtacatt cggaagaatg tgaatcaatc    1800
agtatgtttt tagattgtat tttgccttac agaaagcctt tattgtaaga ctctgatttc    1860
cctttggact tcatgtatat tgtacagtta cagtaaaatt caacctttat tttctaattt    1920
tttcaacata ttgtttagtg taaagaatat ttatttgaag ttttattatt ttataaaaaa    1980
gaatatttat tttaagaggc atcttacaaa ttttgcccct tttatgagga tgtgatagtt    2040
```

```
gctgcaaatg aggggttaca gatgcatatg tccaatataa aatagaaaat atattaacgt   2100
ttgaaattaa aaaaaaaaaa aaaaaa                                        2126
```

<210> SEQ ID NO 17
<211> LENGTH: 394
<212> TYPE: PRT
<213> ORGANISM: Homo sapiens

<400> SEQUENCE: 17

```
Met Val Thr Met Glu Glu Leu Arg Glu Met Asp Cys Ser Val Leu Lys
 1               5                  10                  15

Arg Leu Met Asn Arg Asp Glu Asn Gly Gly Ala Gly Gly Ser Gly
            20                  25                  30

Ser His Gly Thr Leu Gly Leu Pro Ser Gly Gly Lys Cys Leu Leu Leu
        35                  40                  45

Asp Cys Arg Pro Phe Leu Ala His Ser Ala Gly Tyr Ile Leu Gly Ser
    50                  55                  60

Val Asn Val Arg Cys Asn Thr Ile Val Arg Arg Ala Lys Gly Ser
 65                  70                  75                  80

Val Ser Leu Glu Gln Ile Leu Pro Ala Glu Glu Val Arg Ala Arg
                85                  90                  95

Leu Arg Ser Gly Leu Tyr Ser Ala Val Ile Val Tyr Asp Glu Arg Ser
            100                 105                 110

Pro Arg Ala Glu Ser Leu Arg Glu Asp Ser Thr Val Ser Leu Val Val
        115                 120                 125

Gln Ala Leu Arg Arg Asn Ala Glu Arg Thr Asp Ile Cys Leu Leu Lys
    130                 135                 140

Gly Gly Tyr Glu Arg Phe Ser Ser Glu Tyr Pro Glu Phe Cys Ser Lys
145                 150                 155                 160

Thr Lys Ala Leu Ala Ala Ile Pro Pro Val Pro Pro Ser Ala Thr
                165                 170                 175

Glu Pro Leu Asp Leu Gly Cys Ser Ser Cys Gly Thr Pro Leu His Asp
            180                 185                 190

Gln Gly Gly Pro Val Glu Ile Leu Pro Phe Leu Tyr Leu Gly Ser Ala
        195                 200                 205

Tyr His Ala Ala Arg Arg Asp Met Leu Asp Ala Leu Gly Ile Thr Ala
    210                 215                 220

Leu Leu Asn Val Ser Ser Asp Cys Pro Asn His Phe Glu Gly His Tyr
225                 230                 235                 240

Gln Tyr Lys Cys Ile Pro Val Glu Asp Asn His Lys Ala Asp Ile Ser
                245                 250                 255

Ser Trp Phe Met Glu Ala Ile Glu Tyr Ile Asp Ala Val Lys Asp Cys
            260                 265                 270

Arg Gly Arg Val Leu Val His Cys Gln Ala Gly Ile Ser Arg Ser Ala
        275                 280                 285

Thr Ile Cys Leu Ala Tyr Leu Met Met Lys Lys Arg Val Arg Leu Glu
    290                 295                 300

Glu Ala Phe Glu Phe Val Lys Gln Arg Arg Ser Ile Ile Ser Pro Asn
305                 310                 315                 320

Phe Ser Phe Met Gly Gln Leu Leu Gln Phe Glu Ser Gln Val Leu Ala
                325                 330                 335

Thr Ser Cys Ala Ala Glu Ala Ala Ser Pro Ser Gly Pro Leu Arg Glu
            340                 345                 350

Arg Gly Lys Thr Pro Ala Thr Pro Thr Ser Gln Phe Val Phe Ser Phe
```

```
                    355                 360                 365
Pro Val Ser Val Gly Val His Ser Ala Pro Ser Ser Leu Pro Tyr Leu
    370                 375                 380

His Ser Pro Ile Thr Thr Ser Pro Ser Cys
385                 390

<210> SEQ ID NO 18
<211> LENGTH: 2498
<212> TYPE: DNA
<213> ORGANISM: Homo sapiens

<400> SEQUENCE: 18
gctgagcgcc ggaggagcgt aggcagggca gcgctggcgc cagtggcgac aggagccgcg      60
cgaccggcaa aaatacacgg gaggccgtcg ccgaaaagag tccgcggtcc tctctcgtaa     120
acacactctc ctccaccggc gcctcccct  ccgctctgcg cgccgcccgg ctgggcgccc     180
gaggccgctc cgactgctat gtgaccgcga ggctgcggga ggaagggac  agggaagaag     240 aggctctccc gcgggagccc ttgaggacca agtttgcggc cacttctgca ggcgtccctt     300
cttagctctc gcccgcccct ttctgcagcc taggcggccc gggttctctt ctcttcctcg     360
cgcgcccagc cgcctcggtt cccggcgacc atggtgacga tggaggagct gcgggagatg     420
gactgcagtg tgctcaaaag gctgatgaac cggacgagaa atggcggcgg cgcgggcggc     480
agcggcagcc acggcaccct ggggctgccg agcggcggca agtgcctgct gctggactgc     540
agaccgttcc tggcgcacag cgcgggctac atcctaggtt cggtcaacgt gcgctgtaac     600
accatcgtgc ggcggcgggc taagggctcc gtgagcctgg agcagatcct gcccgccgag     660
gaggaggtac gcgcccgctt cgcgctccggc ctctactcgg cggtcatcgt ctacgacgag     720
cgcagcccgc gcgccgagag cctccgcgag gacagcaccg tgtcgctggt ggtgcaggcg     780
ctgcgccgca acgccgagcg caccgacatc tgcctgctca aaggcggcta tgagaggttt     840
tcctccgagt acccagaatt ctgttctaaa accaaggccc tggcagccat cccaccccg      900 gttccccca gtgccacaga gcccttggac ctgggctgca gctcctgtgg gaccccacta     960
cacgaccagg ggggtcctgt ggagatcctt cccttcctct acctcggcag tgcctaccat    1020
gctgcccgga gagacatgct ggacgccctg gcatcacgg  ctctgttgaa tgtctcctcg    1080
gactgcccaa accactttga aggacactat cagtacaagt gcatcccagt ggaagataac    1140
cacaaggccg acatcagctc ctggttcatg gaagccatag agtacatcga tgccgtgaag    1200
gactgccgtg ggcgcgtgct ggtgcactgc caggcgggca tctcgcggtc ggccaccatc    1260
tgcctggcct acctgatgat gaagaaacgg gtgaggctgg aggaggcctt cgagttcgtt    1320
aagcagcgcc gcagcatcat ctcgcccaac ttcagcttca tgggggcagct gctgcagttc    1380 gagtcccagg tgctggccac gtcctgtgct gcggaggctg ctagcccctc gggaccctg     1440 cgggagcggg gcaagacccc cgccacccc  acctcgcagt tcgtcttcag ctttccggtc    1500
tccgtgggcg tgcactcggc ccccagcagc ctgccctacc tgcacagccc catcaccacc    1560
tctcccagct gttagagccg ccctgggggc cccagaacca gagctggctc ccagcaaggg    1620
taggacgggc cgcatgcggg cagaaagttg ggactgagca gctgggagca ggcgaccgag    1680
ctccttcccc atcatttctc cttggccaac gacgaggcca gccagaatgg caataaggac    1740
tccgaataca taataaaagc aaacagaaca ctccaactta gagcaataac ggctgccgca    1800
gcagccaggg aagaccttgg tttggttat  gtgtcagttt cacttttccg atagaaattt    1860
cttacctcat ttttttaagc agtaaggctt gaagtgatga aacccacaga tcctagcaaa    1920
```

```
tgtgcccaac cagctttact aaaggggggag gaagggaggg caaagggatg agaagacaag    1980
tttcccagaa gtgcctggtt ctgtgtactt gtccctttgt tgtcgttgtt gtagttaaag    2040
gaatttcatt ttttaaaaga aatcttcgaa ggtgtggttt tcatttctca gtcaccaaca    2100
gatgaataat tatgcttaat aataaagtat ttattaagac tttcttcaga gtatgaaagt    2160
acaaaaagtc tagttacagt ggatttagaa tatatttatg ttgatgtcaa acagctgagc    2220
accgtagcat gcagatgtca aggcagttag gaagtaaatg gtgtcttgta gatatgtgca    2280
aggtagcatg atgagcaact tgagtttgtt gccactgaga agcaggcggg ttgggtggga    2340
ggaggaagaa agggaagaat taggtttgaa ttgcttttta aaaaaaaaag aaaagaaaaa    2400
gacagcatct cactatgttg ccaaggctca tcttgagaag caggcgggtt gggtgggagg    2460
aggaagaaag ggaagaatta ggtttgaatt gctttttt                            2498

<210> SEQ ID NO 19
<211> LENGTH: 271
<212> TYPE: PRT
<213> ORGANISM: Homo sapiens

<400> SEQUENCE: 19

Met Phe Arg Asp Phe Gly Glu Pro Gly Pro Ser Ser Gly Asn Gly Gly
 1               5                  10                  15

Gly Tyr Gly Gly Pro Ala Gln Pro Ala Ala Ala Gln Ala Ala Gln
                20                  25                  30

Gln Lys Phe His Leu Val Pro Ser Ile Asn Thr Met Ser Gly Ser Gln
            35                  40                  45

Glu Leu Gln Trp Met Val Gln Pro His Phe Leu Gly Pro Ser Ser Tyr
        50                  55                  60

Pro Arg Pro Leu Thr Tyr Pro Gln Tyr Ser Pro Pro Gln Pro Arg Pro
65                  70                  75                  80

Gly Val Ile Arg Ala Leu Gly Pro Pro Gly Val Arg Arg Pro
                    85                  90                  95

Cys Glu Gln Ile Ser Pro Glu Glu Glu Arg Arg Val Arg Arg
               100                 105                 110

Glu Arg Asn Lys Leu Ala Ala Ala Lys Cys Arg Asn Arg Arg Lys Glu
           115                 120                 125

Leu Thr Asp Phe Leu Gln Ala Glu Thr Asp Lys Leu Glu Asp Glu Lys
       130                 135                 140

Ser Gly Leu Gln Arg Glu Ile Glu Glu Leu Gln Lys Gln Lys Glu Arg
145                 150                 155                 160

Leu Glu Leu Val Leu Glu Ala His Arg Pro Ile Cys Lys Ile Pro Glu
                165                 170                 175

Gly Ala Lys Glu Gly Asp Thr Gly Ser Thr Ser Gly Thr Ser Ser Pro
            180                 185                 190

Pro Ala Pro Cys Arg Pro Val Pro Cys Ile Ser Leu Ser Pro Gly Pro
        195                 200                 205

Val Leu Glu Pro Glu Ala Leu His Thr Pro Thr Leu Met Thr Thr Pro
    210                 215                 220

Ser Leu Thr Pro Phe Thr Pro Ser Leu Val Phe Thr Tyr Pro Ser Thr
225                 230                 235                 240

Pro Glu Pro Cys Ala Ser Ala His Arg Lys Ser Ser Ser Ser Gly
                245                 250                 255

Asp Pro Ser Ser Asp Pro Leu Gly Ser Pro Thr Leu Leu Ala Leu
            260                 265                 270
```

<210> SEQ ID NO 20
<211> LENGTH: 1693
<212> TYPE: DNA
<213> ORGANISM: Homo sapiens

<400> SEQUENCE: 20

```
acgggccaag gcggcgcgtc tcggggtgg agcctggagg tgaccgcgcc gctgcaacgc        60
ccccacccc cgcggtcgca gtggttcagc ccgagaactt tcattcata aaagaaaag         120
actccgcacg gcgcgggtga gtcagaaccc agcagccgtg taccccgcag agccgccagc      180
cccgggcatg ttccgagact tcggggaacc cggcccgagc tccgggaacg gcggcgggta      240
cggcggcccc gcgcagcccc cggccgcagc gcaggcagcc cagcagaagt tccacctggt      300
gccaagcatc aacaccatga gtggcagtca ggagctgcag tggatggtac agcctcattt      360
cctggggccc agcagttacc ccaggcctct gacctaccct cagtacagcc cccacaacc      420
ccggccagga gtcatccggg ccctggggcc gcctccaggg gtacgtcgaa ggccttgtga      480
acagatcagc ccggaggaag aggagcgccg ccgagtaagg gcgagcgga acaagctggc       540
tgcggccaag tgcaggaacc ggaggaagga actgaccgac ttcctgcagg cggagactga      600
caaactggaa gatgagaaat ctgggctgca gcgagagatt gaggagctgc agaagcagaa      660
ggagcgccta gagctggtgc tggaagccca ccgacccatc tgcaaaatcc cggaaggagc      720
caaggagggg gacacaggca gtaccagtgg caccagcagc ccaccagccc cctgccgccc      780
tgtaccttgt atctcccttt ccccagggcc tgtgcttgaa cctgaggcac tgcacacccc      840
cacactcatg accacaccct ccctaactcc tttcaccccc agcctggtct tcacctaccc      900
cagcactcct gagccttgtg cctcagctca tcgcaagagt agcagcagca gcggagaccc      960
atcctctgac cccttggct ctccaaccct cctcgctttg tgaggcgcct gagccctact      1020
ccctgcagat gccaccctag ccaatgtctc ctccccttcc cccaccggtc agctggcct       1080
ggacagtatc ccacatccaa ctccagcaac ttcttctcca tccctctaat gagactgacc      1140
atattgtgct tcacagtaga gccagcttgg ggccaccaaa gctgcccact gtttctcttg      1200
agctggcctc tctagcacaa tttgcactaa atcagagaca aaatatttcc catttgtgcc      1260
agaggaatcc tggcagccca gagactttgt agatccttag aggtcctctg agccctaac       1320
cccttccaga tcactgccac actctccatc accctcttcc tgtgatccac ccaaccctat      1380
ctcctgacag aaggtgccac tttacccacc tagaacacta actcaccagc cccactgcca      1440
gcagcagcag gtgattggac caggccattc tgccgccccc tcctgaaccg cacagctcag      1500
gaggcgccct tggcttctgt gatgagctga tctgcggatc tcagctttga gaagccttca      1560
gctccaggga atccaagcct ccacagcgag ggcagctgct atttattttc ctaaagagag      1620
tatttttata caaacctacc aaaatggaat aaaaggcttg aagctgtgaa aaaaaaaaa       1680
aaaaaaaaa aaa                                                          1693
```

<210> SEQ ID NO 21
<211> LENGTH: 646
<212> TYPE: PRT
<213> ORGANISM: Homo sapiens

<400> SEQUENCE: 21

```
Met Glu Pro Ala Ala Gly Phe Leu Ser Pro Arg Pro Phe Gln Arg Ala
 1               5                  10                  15

Ala Ala Ala Pro Ala Pro Pro Ala Gly Pro Gly Pro Pro Pro Ser Ala
```

```
                    20                  25                  30
Leu Arg Gly Pro Glu Leu Glu Met Leu Ala Gly Leu Pro Thr Ser Asp
             35                  40                  45
Pro Gly Arg Leu Ile Thr Asp Pro Arg Ser Gly Arg Thr Tyr Leu Lys
 50                  55                  60
Gly Arg Leu Leu Gly Lys Gly Gly Phe Ala Arg Cys Tyr Glu Ala Thr
 65                  70                  75                  80
Asp Thr Glu Thr Gly Ser Ala Tyr Ala Val Lys Val Ile Pro Gln Ser
                 85                  90                  95
Arg Val Ala Lys Pro His Gln Arg Glu Lys Ile Leu Asn Glu Ile Glu
            100                 105                 110
Leu His Arg Asp Leu Gln His Arg His Ile Val Arg Phe Ser His His
        115                 120                 125
Phe Glu Asp Ala Asp Asn Ile Tyr Ile Phe Leu Glu Leu Cys Ser Arg
        130                 135                 140
Lys Ser Leu Ala His Ile Trp Lys Ala Arg His Thr Leu Leu Glu Pro
145                 150                 155                 160
Glu Val Arg Tyr Tyr Leu Arg Gln Ile Leu Ser Gly Leu Lys Tyr Leu
                165                 170                 175
His Gln Arg Gly Ile Leu His Arg Asp Leu Lys Leu Gly Asn Phe Phe
            180                 185                 190
Ile Thr Glu Asn Met Glu Leu Lys Val Gly Asp Phe Gly Leu Ala Ala
        195                 200                 205
Arg Leu Glu Pro Pro Glu Gln Arg Lys Lys Thr Ile Cys Gly Thr Pro
210                 215                 220
Asn Tyr Val Ala Pro Glu Val Leu Leu Arg Gln Gly His Gly Pro Glu
225                 230                 235                 240
Ala Asp Val Trp Ser Leu Gly Cys Val Met Tyr Thr Leu Leu Cys Gly
                245                 250                 255
Ser Pro Pro Phe Glu Thr Ala Asp Leu Lys Glu Thr Tyr Arg Cys Ile
            260                 265                 270
Lys Gln Val His Tyr Thr Leu Pro Ala Ser Leu Ser Leu Pro Ala Arg
        275                 280                 285
Gln Leu Leu Ala Ala Ile Leu Arg Ala Ser Pro Arg Asp Arg Pro Ser
        290                 295                 300
Ile Asp Gln Ile Leu Arg His Asp Phe Phe Thr Lys Gly Tyr Thr Pro
305                 310                 315                 320
Asp Arg Leu Pro Ile Ser Ser Cys Val Thr Val Pro Asp Leu Thr Pro
                325                 330                 335
Pro Asn Pro Ala Arg Ser Leu Phe Ala Lys Val Thr Lys Ser Leu Phe
            340                 345                 350
Gly Arg Lys Lys Lys Ser Lys Asn His Ala Gln Glu Arg Asp Glu Val
        355                 360                 365
Ser Gly Leu Val Ser Gly Leu Met Arg Thr Ser Val Gly His Gln Asp
        370                 375                 380
Ala Arg Pro Glu Ala Pro Ala Ser Gly Pro Ala Pro Val Ser Leu
385                 390                 395                 400
Val Glu Thr Ala Pro Glu Asp Ser Ser Pro Arg Gly Thr Leu Ala Ser
                405                 410                 415
Ser Gly Asp Gly Phe Glu Glu Gly Leu Thr Val Ala Thr Val Val Glu
            420                 425                 430
Ser Ala Leu Cys Ala Leu Arg Asn Cys Ile Ala Phe Met Pro Pro Ala
        435                 440                 445
```

Glu Gln Asn Pro Ala Pro Leu Ala Gln Pro Glu Pro Leu Val Trp Val
            450                 455                 460

Ser Lys Trp Val Asp Tyr Ser Asn Lys Phe Gly Phe Gly Tyr Gln Leu
465                 470                 475                 480

Ser Ser Arg Arg Val Ala Val Leu Phe Asn Asp Gly Thr His Met Ala
                485                 490                 495

Leu Ser Ala Asn Arg Lys Thr Val His Tyr Asn Pro Thr Ser Thr Lys
            500                 505                 510

His Phe Ser Phe Ser Val Gly Ala Val Pro Arg Ala Leu Gln Pro Gln
        515                 520                 525

Leu Gly Ile Leu Arg Tyr Phe Ala Ser Tyr Met Glu Gln His Leu Met
    530                 535                 540

Lys Gly Gly Asp Leu Pro Ser Val Glu Glu Val Pro Ala Pro
545                 550                 555                 560

Pro Leu Leu Leu Gln Trp Val Lys Thr Asp Gln Ala Leu Leu Met Leu
                565                 570                 575

Phe Ser Asp Gly Thr Val Gln Val Asn Phe Tyr Gly Asp His Thr Lys
            580                 585                 590

Leu Ile Leu Ser Gly Trp Glu Pro Leu Leu Val Thr Phe Val Ala Arg
        595                 600                 605

Asn Arg Ser Ala Cys Thr Tyr Leu Ala Ser His Leu Arg Gln Leu Gly
    610                 615                 620

Cys Ser Pro Asp Leu Arg Gln Arg Leu Arg Tyr Ala Leu Arg Leu Leu
625                 630                 635                 640

Arg Asp Arg Ser Pro Ala
                645

<210> SEQ ID NO 22
<211> LENGTH: 2369
<212> TYPE: DNA
<213> ORGANISM: Homo sapiens

<400> SEQUENCE: 22
cctgggcgcc agcgcagcgt agcaaatcca ggcagcgcca cgcgcggccg gggccgggcg      60
gaaccgagaa gccgggaccg cgctgcgacg cgccggccgc atggagcctg ccgccggttt     120
cctgtctccg cgccccttcc agcgtgcggc cgccgcgccc gctccccgg ccgggcccgg      180 gccgcctccg agtgccttgc gcggacctga gctggagatg ctggccgggc taccgacgtc     240
agaccccggg cgcctcatca cggacccgcg cagcggccgc acctacctca aggccgcttt     300
gttgggcaag gggggcttcg cccgctgcta cgaggccact gacacagaga ctggcagcgc     360
ctacgctgtc aaagtcatcc gcagagccg cgtcgccaag ccgcatcagc gcgagaagat     420
cctaaatgag attgagctgc accgagacct gcagcaccgc cacatcgtgc gttttttcgca    480 ccactttgag gacgctgaca acatctacat tttcttggag ctctgcagcc gaaagtccct     540
ggcccacatc tggaaggccc ggcacaccct gttggagcca gaagtgcgct actacctgcg     600
gcagatcctt tctggcctca gtacttgca ccagcgcggc atcttgcacc gggacctcaa      660
gttgggaaat tttttcatca ctgagaacat ggaactgaag gtgggggatt tgggctggc      720 agccggttg gagcctccgg agcagaggaa gaagaccatc tgtggcaccc caactatgt       780 ggctccagaa gtgctgctga cagggccaa cggccctgag gcggatgtat ggtcactggg     840
ctgtgtcatg tacacgctgc tctgcgggag ccctcccttt gagacggctg acctgaagga    900
gacgtaccgc tgcatcaagc aggttcacta cacgctgcct gccagcctct cactgcctgc     960

```
ccggcagctc ctggccgcca tccttcgggc ctcaccccga gaccgcccct ctattgacca      1020
gatcctgcgc catgacttct ttaccaaggg ctacaccccc gatcgactcc ctatcagcag      1080
ctgcgtgaca gtcccagacc tgacaccccc caacccagct aggagtctgt ttgccaaagt      1140
taccaagagc ctctttggca gaaagaagaa gagtaagaat catgcccagg agagggatga      1200
ggtctccggt ttggtgagcg gcctcatgcg cacatccgtt ggccatcagg atgccaggcc      1260
agaggctcca gcagcttctg gcccagcccc tgtcagcctg gtagagacag cacctgaaga      1320
cagctcaccc cgtgggacac tggcaagcag tggagatgga tttgaagaag gtctgactgt      1380
ggccacagta gtggagtcag cccttttgtgc tctgagaaat tgtatagcct tcatgccccc      1440
agcggaacag aacccggccc ccctggccca gccagagcct ctggtgtggg tcagcaagtg      1500
ggttgactac tccaataagt tcggctttgg gtatcaactg tccagccgcc gtgtggctgt      1560
gctcttcaac gatggcacac atatggccct gtcggccaac agaaagactg tgcactacaa      1620
tcccaccagc acaaagcact tctccttctc cgtgggtgct gtgccccggg ccctgcagcc      1680
tcagctgggt atcctgcggt acttcgcctc ctacatggag cagcacctca tgaagggtgg      1740
agatctgccc agtgtggaag aggtagaggt acctgctccg cccttgctgc tgcagtgggt      1800
caagacggat caggctctcc tcatgctgtt tagtgatggc actgtccagg tgaacttcta      1860
cggggaccac accaagctga ttctcagtgg ctggagcccc tccttgtga cttttgtggc      1920 ccgaaatcgt agtgcttgta cttacctcgc ttcccacctt cggcagctgg gctgctctcc      1980
agacctgcgg cagcgactcc gctatgctct gcgcctgctc cgggaccgca gcccagccta      2040
ggacccaagc cctgaggcct gaggcctgtg cctgtcaggc tctggccctt gcctttgtgg      2100
ccttccccct tcctttggtg cctcactggg gctttgggc cgaatccccc agggaatcag      2160
ggaccagctt tactggagtt gggggcggct tgtcttcgct ggctcctacc ccatctccaa      2220
gataagcctg agccttagct cccagctagg gggcgttatt tatggaccac ttttatttat      2280
tgtcagacac ttatttattg ggatgtgagc cccagggggg cctcctccta ggataataaa      2340
caattttgca gaattggaaa aaaaaaaaaa                                       2369
```

<210> SEQ ID NO 23
<211> LENGTH: 283
<212> TYPE: PRT
<213> ORGANISM: Homo sapiens

<400> SEQUENCE: 23

```
Met Asn Trp Thr Gly Leu Tyr Thr Leu Leu Ser Gly Val Asn Arg His
 1               5                  10                  15

Ser Thr Ala Ile Gly Arg Val Trp Leu Ser Val Ile Phe Ile Phe Arg
            20                  25                  30

Ile Met Val Leu Val Val Ala Ala Glu Ser Val Trp Gly Asp Glu Lys
        35                  40                  45

Ser Ser Phe Ile Cys Asn Thr Leu Gln Pro Gly Cys Asn Ser Val Cys
    50                  55                  60

Tyr Asp Gln Phe Phe Pro Ile Ser His Val Arg Leu Trp Ser Leu Gln
65                  70                  75                  80

Leu Ile Leu Val Ser Thr Pro Ala Leu Leu Val Ala Met His Val Ala
                85                  90                  95

His Gln Gln His Ile Glu Lys Lys Met Leu Arg Leu Glu Gly His Gly
            100                 105                 110

Asp Pro Leu His Leu Glu Glu Val Lys Arg His Lys Val His Ile Ser
```

```
                115                 120                 125
Gly Thr Leu Trp Trp Thr Tyr Val Ile Ser Val Phe Arg Leu Leu
        130                 135                 140

Phe Glu Ala Val Phe Met Tyr Val Phe Tyr Leu Leu Tyr Pro Gly Tyr
145                 150                 155                 160

Ala Met Val Arg Leu Val Lys Cys Asp Val Tyr Pro Cys Pro Asn Thr
                165                 170                 175

Val Asp Cys Phe Val Ser Arg Pro Thr Glu Lys Thr Val Phe Thr Val
                180                 185                 190

Phe Met Leu Ala Ala Ser Gly Ile Cys Ile Ile Leu Asn Val Ala Glu
                195                 200                 205

Val Val Tyr Leu Ile Ile Arg Ala Cys Ala Arg Arg Ala Gln Arg Arg
        210                 215                 220

Ser Asn Pro Pro Ser Arg Lys Gly Ser Gly Phe Gly His Arg Leu Ser
225                 230                 235                 240

Pro Glu Tyr Lys Gln Asn Glu Ile Asn Lys Leu Leu Ser Glu Gln Asp
                245                 250                 255

Gly Ser Leu Lys Asp Ile Leu Arg Arg Ser Pro Gly Thr Gly Ala Gly
                260                 265                 270

Leu Ala Glu Lys Ser Asp Arg Cys Ser Ala Cys
        275                 280

<210> SEQ ID NO 24
<211> LENGTH: 1638
<212> TYPE: DNA
<213> ORGANISM: Homo sapiens

<400> SEQUENCE: 24
gcggtgatga attgggacgc aggcgcggag cccagggacc actcccctg cacagacatg        60 agaccatagg ggacctgtct gggtggcctc agggataggc gctccccaag gtgtgaatga     120
ggcaggatga actggacagg tttgtacacc ttgctcagtg gcgtgaaccg gcattctact     180
gccattggcc gagtatggct ctcggtcatc ttcatcttca gaatcatggt gctggtggtg     240
gctgcagaga gtgtgtgggg tgatgagaaa tcttccttca tctgcaacac actccagcct     300
ggctgcaaca cgctttgcta tgaccaattc ttccccatct cccatgtgcg gctgtggtcc     360
ctgcagctca tcctagtttc caccccagct ctcctcgtgg ccatgcacgt ggctcaccag     420 caaacacatag agaagaaaat gctacggctt gagggccatg ggacccccct acacctggag     480
gaggtgaaga ggcacaaggt ccacatctca gggacactgt ggtggaccta tgtcatcagc     540
gtggtgttcc ggctgttgtt tgaggccgtc ttcatgtatg tcttttatct gctctaccct     600
ggctatgcca tggtgcggct ggtcaagtgc gacgtctacc cctgccccaa cacagtggac     660
tgcttcgtgt cccgccccac cgagaaaacc gtcttcaccg tcttcatgct agctgcctct     720
ggcatctgca tcatcctcaa tgtggccgag gtggtgtacc tcatcatccg ggcctgtgcc     780
cgccgagccc agcgccgctc caatccacct tcccgcaagg gctcgggctt cggccaccgc     840
ctctcacctg aatacaagca gaatgagatc aacaagctgc tgagtgagca ggatggctcc     900
ctgaaagaca tactgcgccg cagccctggc accggggctg gctggctga aagagcgac      960 cgctgctcgg cctgctgatg ccacatacca ggcaacctcc catcccaccc ccgaccctgc    1020
cctgggcgag cccctccttc tccctgccg gtgcacaggc ctctgcctgc tgggattac     1080 tcgatcaaaa ccttccttcc ctggctactt cccttcctcc cggggccttc cttttgagga    1140
gctggagggg tggggagcta gaggccacct atgccagtgc tcaaggttac tgggagtgtg    1200
```

```
ggctgccctt gttgcctgca cccttccctc ttccctctcc ctctctctgg gaccactggg    1260
tacaagagat gggatgctcc gacagcgtct ccaattatga aactaatctt aaccctgtgc    1320
tgtcagatac cctgtttctg gagtcacatc agtgaggagg gatgtgggta agaggagcag    1380
agggcagggg tgctgtggac atgtgggtgg agaagggagg gtggccagca ctagtaaagg    1440
aggaatagtg cttgctggcc acaaggaaaa ggaggaggtg tctggggtga gggagttagg    1500
gagagagaag caggcagata agttggagca ggggttggtc aaggccacct ctgcctctag    1560
tccccaaggc ctctctctgc ctgaaatgtt acacattaaa caggatttta cagccaaaaa    1620
aaaaaaaaaa aaaaaaaa                                                  1638
```

<210> SEQ ID NO 25
<211> LENGTH: 510
<212> TYPE: PRT
<213> ORGANISM: Homo sapiens

<400> SEQUENCE: 25

```
Met Glu Glu Pro Gln Ala Gly Asp Ala Ala Arg Phe Ser Cys Pro Pro
 1               5                  10                  15

Asn Phe Thr Ala Lys Pro Pro Ala Ser Glu Ser Pro Arg Phe Ser Leu
            20                  25                  30

Glu Ala Leu Thr Gly Pro Asp Thr Glu Leu Trp Leu Ile Gln Ala Pro
        35                  40                  45

Ala Asp Phe Ala Pro Glu Cys Phe Asn Gly Arg His Val Pro Leu Ser
    50                  55                  60

Gly Ser Gln Ile Val Lys Gly Leu Ala Gly Lys Arg His Arg Tyr
 65                 70                  75                  80

Arg Val Leu Ser Ser Cys Pro Gln Ala Gly Glu Ala Thr Leu Leu Ala
                85                  90                  95

Pro Ser Thr Glu Ala Gly Gly Gly Leu Thr Cys Ala Ser Ala Pro Gln
           100                 105                 110

Gly Thr Leu Arg Ile Leu Glu Gly Pro Gln Gln Ser Leu Ser Gly Ser
        115                 120                 125

Pro Leu Gln Pro Ile Pro Ala Ser Pro Pro Pro Gln Ile Pro Pro Gly
    130                 135                 140

Leu Arg Pro Arg Phe Cys Ala Phe Gly Gly Asn Pro Pro Val Thr Gly
145                 150                 155                 160

Pro Arg Ser Ala Leu Ala Pro Asn Leu Leu Thr Ser Gly Lys Lys Lys
                165                 170                 175

Lys Glu Met Gln Val Thr Glu Ala Pro Val Thr Gln Glu Ala Val Asn
            180                 185                 190

Gly His Gly Ala Leu Glu Val Asp Met Ala Leu Gly Ser Pro Glu Met
        195                 200                 205

Asp Val Arg Lys Lys Lys Lys Lys Asn Gln Gln Leu Lys Glu Pro
    210                 215                 220

Glu Ala Ala Gly Pro Val Gly Thr Glu Pro Thr Val Glu Thr Leu Glu
225                 230                 235                 240

Pro Leu Gly Val Leu Phe Pro Ser Thr Thr Lys Lys Arg Lys Lys Pro
                245                 250                 255

Lys Gly Lys Glu Thr Phe Glu Pro Glu Asp Lys Thr Val Lys Gln Glu
            260                 265                 270

Gln Ile Asn Thr Glu Pro Leu Glu Asp Thr Val Leu Ser Pro Thr Lys
        275                 280                 285
```

```
Lys Arg Lys Arg Gln Lys Gly Thr Glu Gly Met Glu Pro Glu Glu Gly
        290                 295                 300

Val Thr Val Glu Ser Gln Pro Gln Val Lys Val Glu Pro Leu Glu Glu
305                 310                 315                 320

Ala Ile Pro Leu Pro Pro Thr Lys Lys Arg Lys Lys Glu Lys Gly Gln
                325                 330                 335

Met Ala Met Met Glu Pro Gly Thr Glu Ala Met Glu Pro Val Glu Pro
            340                 345                 350

Glu Met Lys Pro Leu Glu Ser Pro Gly Gly Thr Met Ala Pro Gln Gln
                355                 360                 365

Pro Glu Gly Ala Lys Pro Gln Ala Gln Ala Ala Leu Ala Ala Pro Lys
    370                 375                 380

Lys Lys Thr Lys Lys Glu Lys Gln Gln Asp Ala Thr Val Glu Pro Glu
385                 390                 395                 400

Thr Glu Val Val Gly Pro Glu Leu Pro Asp Asp Leu Glu Pro Gln Ala
                405                 410                 415

Ala Pro Thr Ser Thr Lys Lys Lys Lys Lys Lys Glu Arg Gly His
                420                 425                 430

Thr Val Thr Glu Pro Ile Gln Pro Leu Glu Pro Glu Leu Pro Gly Glu
            435                 440                 445

Gly Gln Pro Glu Ala Arg Ala Thr Pro Gly Ser Thr Lys Lys Arg Lys
    450                 455                 460

Lys Gln Ser Gln Glu Ser Arg Met Pro Glu Thr Val Pro Gln Glu Glu
465                 470                 475                 480

Met Pro Gly Pro Pro Leu Asn Ser Glu Ser Gly Glu Glu Ala Pro Thr
                485                 490                 495

Gly Arg Asp Lys Lys Arg Lys Gln Gln Gln Gln Gln Pro Val
            500                 505                 510

<210> SEQ ID NO 26
<211> LENGTH: 3286
<212> TYPE: DNA
<213> ORGANISM: Homo sapiens

<400> SEQUENCE: 26
aagttctgaa cttgtgaggc atctgggcct ccccagaaga catttaacac agaaagcaca      60
gccctactaa ctagtattct tacctgtctc ttcaagaatt tcagaccaat cgaccgtcct     120
gtctctttaa ggcttaggaa gagcagtgtg gctgcccctt taaggaggcg ttgcaacaaa     180
ccatattgga cagacgatgg gggcgaccca tcgggacccg acgggcctct gactccagca     240
atacagcgaa tcagcggctt tcgggaatac attttccgga aaaagacttc ttcctcggtt     300
ttctgctctg cacacgttga aatttttccc cagtttttcct gcagatcggg agtcgagcaa     360
tgcctacccc cgcgctcccg caccagttgg gcgctcccgg atgatgccct accccttggg     420
atccacgtgg tctgcaacct ggtgcgagca gcccgggcta cagggttgcc tgaggtgtgg     480
gtcccaggat ggaggagccc caggccggcg atgctgctcg gttctcttgt cccccaact      540 ttaccgcgaa gccccagcc tcagagtccc ctcgtttctc cttggaggcg ctgacgggtc      600
cagatacgga gctgtggctt attcaggccc ctgcagactt tgccccagaa tgcttcaatg     660
ggcggcatgt gcctctctct ggctcccaga tcgtcaaggg caaattggca ggcaagcggc     720
accgctatcg agtcctcagc agctgtcccc aagctggaga agcgaccctg ctggcccct      780 caacggaggc aggaggtgga ctcacctgtg cctcagcccc ccagggcacc ctaaggatcc     840
ttgagggtcc ccagcaatcc ctgtcaggga gccctctgca gcccatccca gcaagtcccc     900
```

```
caccacagat ccctcctggc ctgaggcctc ggttctgtgc cttggggggc aacccaccag     960
tcacagggcc taggtcagcc ttggccccca acctgctcac ctcagggaag aagaaaaagg    1020
agatgcaggt gacagaggcc ccagtcactc aggaggcagt gaatgggcac ggggccctgg    1080
aggtggacat ggctttgggg tcgccagaaa tggatgtgcg gaagaagaag aagaaaaaaa    1140
atcagcagct gaaagaacca gaggcagcag ggcctgtggg gacagagccc acagtggaga    1200
cactggagcc tctgggagtg ctgttcccgt ccaccaccaa gagaggaag aagcccaaag     1260
ggaaagaaac cttcgagcca gaagacaaga cagtgaagca ggaacagatt aacactgagc    1320
ctctagaaga cacagtcctg tccccgacca aaaagagaaa gaggcaaaag gggacggaag    1380
ggatggagcc agaggagggg gtgacagttg agtctcagcc acaggtgaag gtggagccac    1440
tggaggaagc catccctctg cccctacga agaagaggaa aaaagaaaag ggacagatgg     1500
caatgatgga gccagggacg gaggcgatgg agccagtgga gccggagatg aagcctctgg    1560
agtccccagg ggggaccatg gcgcctcaac agccagaagg agcgaagcct caggcccagg    1620
cagctctggc agctcccaaa aagaagacga gaaagaaaa acagcaagat gccacagtgg    1680
agccagagac agaggtggtg gggcctgagc tgccggatga ccttgagcct caggcagctc    1740
ccacatccac caagaagaag aagaagaaga agagagagg tcacacagtg actgagccaa    1800
ttcagccact agagcctgaa ctgccagggg agggacagcc tgaagccagg gcaactccgg    1860
gatccaccaa gaagaggaag aagcagagtc aggaaagccg gatgccagag acagtgcccc    1920
aagaggagat gccagggccg ccactgaatt cagagtctgg ggaggaggct cccacaggcc    1980
gggacaagaa gcggaagcag cagcagcagc agcctgtgta gtctgccccc gggaaactga    2040
ggaactaaag aaagctgaag gtgcccacct gggccaccag aaggtgacac ccccagaatc    2100
cctccccaga gactgcacca gcgcagccag caggagcctg gcctgggagg acgatttatt    2160
attacactgg gggtttcctt ggcagctggg gtcatcaggg tactttcaag aagggctcgt    2220
gcaggacatc aaacagcctc cgggcctgga tgggagggag aaaaaaatga ggaaccagtc    2280
attaaaggag ctgtttcctg ggtaaatcta gagtgggggtt ttggttcttt attttcccct    2340
ataccctcaa gcatttatcc attgagttac aaacaatcca gttacaatct ttttaagtta    2400
ttattattat tattattttt tttttttttg agatggagtc tcgctctgtc gcccaggttg    2460
gagtgcagtg gcgcaatctc ggctcactgc aagctccgcc tcccgggttc acgccattct    2520
cctgcctcag cctcctgagt agctgggact acaggcccct gcccagctaa ttttttgtat    2580
ttttttttag tagagatggg gtttcaccac gttagccagg atggtctcga tctcctgacc    2640
tcctgatgcg cctgcctcag cctcccagtg ctgggattat aggtgtgagc cactgcgcct    2700
ggctaagtta ttattatttt tttgagacag tctcctggtg tcacccaggc tggagtgcag    2760
tggtgtgatc ttggctcact gcaacctccg cctcctgggt tccaacgatt ctcctgcctc    2820
agcctcccga gtagctgggc ctaaaggtgc ccaccactat acccggctaa ttttttgtatt    2880
tttagtagag acagggggttt caccatattg gccaggctgg tctcgaactc ctgacctcgt    2940
gatccacctg ccttgacctc ccaaagtgct aggataacag gtgtgagcca ccgcaccctg    3000
ccaagttatt ttaaaatgta ccattattat tgactatagt cacctggttg tgttatcaaa    3060
tagtatgtct tattcattct ttctttgtgt gtgtgtgtgt gtgtgtgtgt gtgtgtggta    3120
cccattaacc ttccccatct ccctgccagc cctaactac cctccccagc ctccaggaac     3180
tatccatcca ctcttatctc catgagttca attgttttga tttttagata cacaaataaa    3240
```

```
taagaacatg caatgtttgt ctttctgtgc ctggcttatt tcactt        3286
```

<210> SEQ ID NO 27
<211> LENGTH: 1214
<212> TYPE: PRT
<213> ORGANISM: Homo sapiens

<400> SEQUENCE: 27

```
Met Glu Arg Phe Arg Leu Glu Lys Lys Leu Pro Gly Pro Asp Glu Glu
 1               5                  10                  15

Ala Val Val Asp Leu Gly Lys Thr Ser Ser Thr Val Asn Thr Lys Phe
            20                  25                  30

Glu Lys Glu Glu Leu Glu Ser His Arg Ala Val Tyr Ile Gly Val His
        35                  40                  45

Val Pro Phe Ser Lys Glu Ser Arg Arg Arg His Arg His Arg Gly His
    50                  55                  60

Lys His His His Arg Arg Arg Lys Asp Lys Glu Ser Asp Lys Glu Asp
65                  70                  75                  80

Gly Arg Glu Ser Pro Ser Tyr Asp Thr Pro Ser Gln Arg Val Gln Phe
                85                  90                  95

Ile Leu Gly Thr Glu Asp Asp Glu Glu His Ile Pro His Asp Leu
           100                 105                 110

Phe Thr Glu Met Asp Glu Leu Cys Tyr Arg Asp Gly Glu Glu Tyr Glu
       115                 120                 125

Trp Lys Glu Thr Ala Arg Trp Leu Lys Phe Glu Glu Asp Val Glu Asp
   130                 135                 140

Gly Gly Asp Arg Trp Ser Lys Pro Tyr Val Ala Thr Leu Ser Leu His
145                 150                 155                 160

Ser Leu Phe Glu Leu Arg Ser Cys Ile Leu Asn Gly Thr Val Met Leu
               165                 170                 175

Asp Met Arg Ala Ser Thr Leu Asp Glu Ile Ala Asp Met Val Leu Asp
           180                 185                 190

Asn Met Ile Ala Ser Gly Gln Leu Asp Glu Ser Ile Arg Glu Asn Val
       195                 200                 205

Arg Glu Ala Leu Leu Lys Arg His His His Gln Asn Glu Lys Arg Phe
   210                 215                 220

Thr Ser Arg Ile Pro Leu Val Arg Ser Phe Ala Asp Ile Gly Lys Lys
225                 230                 235                 240

His Ser Asp Pro His Leu Leu Glu Arg Asn Gly Glu Gly Leu Ser Ala
               245                 250                 255

Ser Arg His Ser Leu Arg Thr Gly Leu Ser Ala Ser Asn Leu Ser Leu
           260                 265                 270

Arg Gly Glu Ser Pro Leu Ser Leu Leu Gly His Leu Leu Pro Ser
       275                 280                 285

Ser Arg Ala Gly Thr Pro Ala Gly Ser Arg Cys Thr Thr Pro Val Pro
   290                 295                 300

Thr Pro Gln Asn Ser Pro Pro Ser Ser Pro Ile Ser Arg Leu Thr
305                 310                 315                 320

Ser Arg Ser Ser Gln Glu Ser Gln Arg Gln Ala Pro Glu Leu Leu Val
               325                 330                 335

Ser Pro Ala Ser Asp Asp Ile Pro Thr Val Val Ile His Pro Pro Glu
           340                 345                 350

Glu Asp Leu Glu Ala Ala Leu Lys Gly Glu Glu Gln Lys Asn Glu Glu
       355                 360                 365
```

-continued

Asn Val Asp Leu Thr Pro Gly Ile Leu Ala Ser Pro Gln Ser Ala Pro
    370             375             380

Gly Asn Leu Asp Asn Ser Lys Ser Gly Glu Ile Lys Gly Asn Gly Ser
385             390             395             400

Gly Gly Ser Arg Glu Asn Ser Thr Val Asp Phe Ser Lys Val Asp Met
            405             410             415

Asn Phe Met Arg Lys Ile Pro Thr Gly Ala Glu Ala Ser Asn Val Leu
        420             425             430

Val Gly Glu Val Asp Phe Leu Glu Arg Pro Ile Ile Ala Phe Val Arg
        435             440             445

Leu Ala Pro Ala Val Leu Leu Thr Gly Leu Thr Glu Val Pro Val Pro
    450             455             460

Thr Arg Phe Leu Phe Leu Leu Gly Pro Ala Gly Lys Ala Pro Gln
465             470             475             480

Tyr His Glu Ile Gly Arg Ser Ile Ala Thr Leu Met Thr Asp Glu Ile
            485             490             495

Phe His Asp Val Ala Tyr Lys Ala Lys Asp Arg Asn Asp Leu Leu Ser
        500             505             510

Gly Ile Asp Glu Phe Leu Asp Gln Val Thr Val Leu Pro Pro Gly Glu
    515             520             525

Trp Asp Pro Ser Ile Arg Ile Glu Pro Pro Lys Ser Val Pro Ser Gln
530             535             540

Glu Lys Arg Lys Ile Pro Val Phe His Asn Gly Ser Thr Pro Thr Leu
545             550             555             560

Gly Glu Thr Pro Lys Glu Ala Ala His Ala Gly Pro Glu Leu Gln
            565             570             575

Arg Thr Gly Arg Leu Phe Gly Leu Ile Leu Asp Ile Lys Arg Lys
        580             585             590

Ala Pro Phe Phe Leu Ser Asp Phe Lys Asp Ala Leu Ser Leu Gln Cys
            595             600             605

Leu Ala Ser Ile Leu Phe Leu Tyr Cys Ala Cys Met Ser Pro Val Ile
    610             615             620

Thr Phe Gly Gly Leu Leu Gly Glu Ala Thr Glu Gly Arg Ile Ser Ala
625             630             635             640

Ile Glu Ser Leu Phe Gly Ala Ser Leu Thr Gly Ile Ala Tyr Ser Leu
            645             650             655

Phe Ala Gly Gln Pro Leu Thr Ile Leu Gly Ser Thr Gly Pro Val Leu
        660             665             670

Val Phe Glu Lys Ile Leu Tyr Lys Phe Cys Arg Asp Tyr Gln Leu Ser
        675             680             685

Tyr Leu Ser Leu Arg Thr Ser Ile Gly Leu Trp Thr Ser Phe Leu Cys
    690             695             700

Ile Val Leu Val Ala Thr Asp Ala Ser Ser Leu Val Cys Tyr Ile Thr
705             710             715             720

Arg Phe Thr Glu Glu Ala Phe Ala Ala Leu Ile Cys Ile Ile Phe Ile
            725             730             735

Tyr Glu Ala Leu Glu Lys Leu Phe Asp Leu Gly Glu Thr Tyr Ala Phe
        740             745             750

Asn Met His Asn Asn Leu Asp Lys Leu Thr Ser Tyr Ser Cys Val Cys
        755             760             765

Thr Glu Pro Pro Asn Pro Ser Asn Glu Thr Leu Ala Gln Trp Lys Lys
    770             775             780

Asp Asn Ile Thr Ala His Asn Ile Ser Trp Arg Asn Leu Thr Val Ser

-continued

```
            785                 790                 795                 800
Glu Cys Lys Lys Leu Arg Gly Val Phe Leu Gly Ser Ala Cys Gly His
                    805                 810                 815

His Gly Pro Tyr Ile Pro Asp Val Leu Phe Trp Cys Val Ile Leu Phe
                820                 825                 830

Phe Thr Thr Phe Phe Leu Ser Ser Phe Leu Lys Gln Phe Lys Thr Lys
            835                 840                 845

Arg Tyr Phe Pro Thr Lys Val Arg Ser Thr Ile Ser Asp Phe Ala Val
        850                 855                 860

Phe Leu Thr Ile Val Ile Met Val Thr Ile Asp Tyr Leu Val Gly Val
865                 870                 875                 880

Pro Ser Pro Lys Leu His Val Pro Glu Lys Phe Glu Pro Thr His Pro
                885                 890                 895

Glu Arg Gly Trp Ile Ile Ser Pro Leu Gly Asp Asn Pro Trp Trp Thr
                900                 905                 910

Leu Leu Ile Ala Ala Ile Pro Ala Leu Leu Cys Thr Ile Leu Ile Phe
                915                 920                 925

Met Asp Gln Gln Ile Thr Ala Val Ile Ile Asn Arg Lys Glu His Lys
        930                 935                 940

Leu Lys Lys Gly Ala Gly Tyr His Leu Asp Leu Leu Met Val Gly Val
945                 950                 955                 960

Met Leu Gly Val Cys Ser Val Met Gly Leu Pro Trp Phe Val Ala Ala
                965                 970                 975

Thr Val Leu Ser Ile Ser His Val Asn Ser Leu Lys Val Glu Ser Glu
                980                 985                 990

Cys Ser Ala Pro Gly Glu Gln Pro Lys Phe Leu Gly Ile Arg Glu Gln
                995                 1000                1005

Arg Val Thr Gly Leu Met Ile Phe Ile Leu Met Gly Leu Ser Val Phe
        1010                1015                1020

Met Thr Ser Val Leu Lys Phe Ile Pro Met Pro Val Leu Tyr Gly Val
1025                1030                1035                1040

Phe Leu Tyr Met Gly Val Ser Ser Leu Lys Gly Ile Gln Leu Phe Asp
                1045                1050                1055

Arg Ile Lys Leu Phe Gly Met Pro Ala Lys His Gln Pro Asp Leu Ile
            1060                1065                1070

Tyr Leu Arg Tyr Val Pro Leu Trp Lys Val His Ile Phe Thr Val Ile
        1075                1080                1085

Gln Leu Thr Cys Leu Val Leu Leu Trp Val Ile Lys Val Ser Ala Ala
    1090                1095                1100

Ala Val Val Phe Pro Met Met Val Leu Ala Leu Val Phe Val Arg Lys
1105                1110                1115                1120

Leu Met Asp Leu Cys Phe Thr Lys Arg Glu Leu Ser Trp Leu Asp Asp
                1125                1130                1135

Leu Met Pro Glu Ser Lys Lys Lys Lys Glu Asp Asp Lys Lys Lys Lys
                1140                1145                1150

Glu Lys Glu Glu Ala Glu Arg Met Leu Gln Asp Asp Asp Thr Val
        1155                1160                1165

His Leu Pro Phe Glu Gly Gly Ser Leu Leu Gln Ile Pro Val Lys Ala
    1170                1175                1180

Leu Lys Tyr Ser Pro Asp Lys Pro Val Ser Val Lys Ile Ser Phe Glu
1185                1190                1195                1200

Asp Glu Pro Arg Lys Lys Tyr Val Asp Ala Glu Thr Ser Leu
                1205                1210
```

<210> SEQ ID NO 28
<211> LENGTH: 7757
<212> TYPE: DNA
<213> ORGANISM: Homo sapiens

<400> SEQUENCE: 28

| | | | | | |
|---|---|---|---|---|---|
| ctcactgtcc | ctggaatctt | caagggagtt | actgcattac | atcatcagaa | acaaggcatt | 60 |
| tctatattac | tatggaaaga | tttcgtctgg | agaagaagtt | acctggtcct | gatgaagaag | 120 |
| ctgttgtgga | tcttggcaaa | actagctcaa | ctgtgaacac | caagtttgaa | aaagaagaac | 180 |
| tagaaagtca | tagagctgta | tatattggtg | ttcacgtccc | gtttagtaaa | gagagtcgtc | 240 |
| ggcgtcatag | gcatcgcgga | cacaaacatc | accaccggag | aagaaaagat | aaagaatcag | 300 |
| ataaagaaga | tggacgggaa | tctccttctt | atgatacacc | atcccagaga | gttcagttta | 360 |
| tccttggtac | tgaagatgat | gatgaagaac | atattcccca | tgatctcttc | acggaaatgg | 420 |
| atgaactgtg | ttacagagat | ggagaagaat | atgaatggaa | agaaactgct | agatggctga | 480 |
| aatttgaaga | ggatgttgaa | gatggcggtg | accgatggag | taaaccttat | gtggcaactc | 540 |
| tctctttgca | cagtcttttt | gaactaagga | gttgcatcct | caatggaaca | gtcatgctgg | 600 |
| atatgagagc | aagcactcta | gatgaaatag | cagatatggt | attagacaac | atgatagctt | 660 |
| ctggccaatt | agacgagtcc | atacgagaga | atgtcagaga | agctcttctg | aagagacatc | 720 |
| atcatcagaa | tgagaaaaga | ttccagtc | ggattcctct | tgttcgatct | tttgcagata | 780 |
| taggcaagaa | acattctgac | cctcacttgc | ttgaaaggaa | tggggaaggc | ctttcagcct | 840 |
| cccgccactc | tttgcgaaca | ggtctgtctg | cctcaaacct | ttccttgaga | ggagaatcac | 900 |
| ctttatctct | tcttcttggt | catcttcttc | cttcttcaag | agctgaaacc | cctgcaggct | 960 |
| caaggtgtac | aaccccagta | cccacccctc | aaaacagtcc | tccttctagc | cctagcatca | 1020 |
| gccgcctgac | ctccagaagt | tcccaagaga | gtcagcgtca | ggccccagaa | ctactggttt | 1080 |
| cacctgccag | tgatgatatt | cccacagtag | taattcatcc | gcctgaggaa | gacttagaag | 1140 |
| cagcgctgaa | aggcgaggag | cagaagaatg | aggaaaatgt | tgacttaact | ccaggtattt | 1200 |
| tggcctctcc | ccagtctgct | cctggaaact | tggacaatag | taaaagtgga | gaaattaaag | 1260 |
| gtaatggaag | tggtggaagc | agagaaaata | gtactgttga | cttcagcaag | gttgatatga | 1320 |
| atttcatgag | aaaaattcct | acgggtgctg | aggcatccaa | cgtcctggtg | ggcgaagtag | 1380 |
| acttttggga | aaggccaata | attgcatttg | tgagactggc | tcctgctgtc | ctccttacag | 1440 |
| ggttgactga | ggtccctgtt | ccaaccaggt | ttttgttttt | gttattgggt | ccagcgggca | 1500 |
| aggcaccaca | gtaccatgaa | attggacgat | caatagccac | tctcatgaca | gatgagattt | 1560 |
| tccatgatgt | agcttataaa | gcaaaagaca | gaaatgacct | cttatctgga | attgatgaat | 1620 |
| ttttagatca | agtaactgtc | ctacctccag | gagagtggga | tccttctata | cgcatagaac | 1680 |
| caccaaaaag | tgtcccttct | caggaaaaga | gaaagattcc | tgtgtttcac | aatggatcta | 1740 |
| cccccacact | gggtgagact | cctaaagagg | ccgctcatca | tgctgggcct | gagctacaga | 1800 |
| ggactggacg | gcttttttggt | ggtttgatac | ttgacatcaa | aaggaaagca | ccttttttct | 1860 |
| tgagtgactt | caaggatgca | ttaagcctgc | agtgcctggc | ctcgattctt | ttcctatact | 1920 |
| gtgcctgtat | gtctcctgta | atcacttttg | gagggctgct | tggagaagct | acagaaggca | 1980 |
| gaataagtgc | aatagagtct | cttttttggag | catcattaac | tgggattgcc | tattcattgt | 2040 |
| ttgctgggca | acctctaaca | atattgggga | gcacaggtcc | agttctagtg | tttgaaaaaa | 2100 |

-continued

```
ttttatataa attctgcaga gattatcaac tttcttatct gtctttaaga accagtattg    2160
gtctgtggac ttcttttttg tgcattgttt tggttgcaac agatgcaagc agccttgtgt    2220
gttatattac tcgatttaca gaagaggctt ttgcagccct tatttgcatc atattcatct    2280
acgaggcttt ggagaagctc tttgatttag gagaaacata tgcatttaat atgcacaaca    2340
acttagataa actgaccagc tactcatgtg tatgtactga acctccaaac cccagcaatg    2400
aaactctagc acaatggaag aaagataata taacagcaca caatatttcc tggagaaatc    2460
ttactgtttc tgaatgtaaa aaacttcgtg gtgtattctt ggggtcagct tgtggtcatc    2520
atggacctta tattccagat gtgctctttt ggtgtgtcat cttgttttc acaacatttt     2580 ttctgtcttc attcctcaag caatttaaga ccaagcgtta cttttcctacc aaggtgcgat   2640 cgacaatcag tgattttgct gtatttctca caatagtaat aatggttaca attgactacc    2700
ttgtaggagt tccatctcct aaacttcatg ttcctgaaaa atttgagcct actcatccag    2760
agagagggtg gatcataagc ccactgggag ataatccttg gtggacctta ttaatagctg    2820
ctattcctgc tttgctttgt accattctca tctttatgga tcaacaaatc acagctgtaa    2880
ttataaacag aaaggaacac aaattgaaga aaggagctgg ctatcacctt gatttgctca    2940
tggttggcgt tatgttggga gtttgctctg tcatgggact tccatggttt gtggctgcaa    3000
cagtgttgtc aataagtcat gtcaacagct taaaagttga atctgaatgt tctgctccag    3060
gggaacaacc caagtttttg ggaattcgtg aacagcgggt tacagggcta atgatttta    3120 ttctaatggg cctctctgtg ttcatgactt cagtcctaaa gtttattcca atgcctgttc    3180
tgtatggtgt tttcctttat atgggagttt cctcattaaa aggaatccag ttatttgacc    3240
gtataaaatt atttggaatg cctgctaagc atcagcctga tttgatatac ctccgttatg    3300
tgccgctctg gaaggtccat attttcacag tcattcagct tacttgtttg gtccttttat    3360
gggtgataaa agtttcagct gctgcagtgg ttttttcccat gatggttctt gcattagtgt   3420
ttgtgcgcaa actcatggac ctgtgtttca cgaagagaga acttagttgg cttgatgatc    3480
ttatgccaga aagtaagaaa aagaaagaag atgacaaaaa gaaaaagag aaagaggaag     3540 ctgaacggat gcttcaagat gatgatgata ctgtgcacct tccatttgaa gggggaagtc    3600
tcttgcaaat tccagtcaag gccctaaaat atagtcctga taaacctgtg agtgtgaaaa    3660
taagttttga agatgaacca agaaagaaat acgtggatgc tgaaacttca ttatagaatt    3720
gaaccaagag gcattataca tatagatata tacatatgta atgtgtgcgt atcatgtcac    3780
tatatataag aatattgtat gtcatgctgt ttatgtgtga ctaccgggtt tttaaaagta    3840
gtgtctggag tttgtaatga gcaccgtgga gactatgtat ttaatgaaat gctctctttg    3900
aagtgaggta catggttctt aactattcaa atatttattc tgttagaaaa aaaaattttc    3960
tgttttgcaa tagaaggatg tggagaaatg cttttcagtct acttttctta aatctctgtt    4020
catcagtggc aattcgtaaa aaccttaagt gatactttgt ttatatgttt ataatttta    4080 ggtgtttcct gaaattttca catattattt cacttttgtt agtgctttat gggaagaata    4140
gggagtctat accagtgctg tgggaaaaat ggtaacattt cagggcttct ctatttgtgt    4200
ttcatttctg tagatgtcca tcgtgtttca ctaactggcg ttttcttagc catagagatg    4260
actgtagaac aatagaaact ttaataatga tagttttttaa cttttatgtt taaattttt    4320 ttaaatctta aaaccttcat atctaggtat ccattgtgac agacaagtaa aattgcaggt    4380
gatttgataa ttaagcaccc ataccattta taacttctga atttaaaaag ttatacaatg    4440
ccagtttgca atagttgatt ttgatgcctt tgtagaatat ttttctgaa tccttatgct     4500
```

```
cttttaaagc caatgattcc cactctgttc tctgccttgt ctctctttgt cttaaaatgc   4560
tttagtttcc atcaggttca agttcttgac tattattctc ttataagtag taggcgtaaa   4620
taatcaggag ttagaattct ctcagaaggg tctatgatca gtattacttt attaagaatt   4680
acctttcatt ttctctttat gttattcttt cacttttgta gattacattt aatagcttgt   4740
tacctgtgat tttattttaa aatatttatt ttgatatgat gcttaaatat tatataaaca   4800
tttggaaaag taacaaatag agtaaattgt taatgtaaat agttggtgct tactttcatt   4860
tatgtttatt atcttaaagc aattgataga ttttacatct ttgatataaa gcactgccat   4920
atttatattt taaaaggaaa ttagacattt tatatgtagc tcagattaat gacattttta   4980
ttttgtgtat tagttttgc tttctgagc tttttaaagt ctaacaaatc tttttagtca   5040
tcttttatat acttttagtt ccacatgaaa taaatgttgt taagcctgta ggactggatg   5100 aatgggttg tgaaactgat ttgacaagag aataatttac aaaaatcaaa tgagtattga   5160
gaagccacag aaatatcaaa aatggtgaca tcactattag gatgaaaatt ttatgaaatt   5220
ccaatgctcc ctttaaccat ataattaaat tacaaaggta tacataatta atctaataaa   5280
ggatcatgag gaatgccaaa agctgaaatt ttagcaagtc tggtgtttta aattcattat   5340
aaactattta ttaactaatg taatgtcctc ctctaagacc atattgtaag agtcttgtta   5400
aaatgatgga ttcaacttct gcctcggatg agaggttgga aatgtagctg cttttcttta   5460
gaaaatatgt agctgtcatc atttggtact gcctaaaaag agttagactc tattggcaat   5520
tgatagagta ttacccacgg tgcttattat tgtttatgag cttccattgt aatgattcct   5580
ttttatttgt agcagcataa ttatttccaa agaccccagt atttgctgct attttttaaa   5640
ctcccctgat gtacctgaac aagaggattt cctcacatca tttccttgtg tctggacatc   5700
aggggtaaca actgtactta ctttacagga agaaatttta aaactgaaaa ctacctggga   5760
tcatagtgtt tctgtgattt tatttaattg tgtatagtaa ttatccagtg ccagaaaaac   5820
cgtcacttgc aaaatacttt gcactcaaaa tgttttttaca atgcttctaa atgttactgg   5880
tttctgcttt cttttgacta cttgactgac aaaatgatct gactactcca tttaagagca   5940
aaggtaactc atgtttaggt aattaactgc ttgttttaag tgattatatt tcttccactg   6000
tttttgaaaa ataatcaaag atagcattca ttgagagaca gtgacagata taatttacta   6060
catatattga ttttttaaata aagttgcctt aaataagtgt atgtaagcag tagtagttgc   6120
tatgtactga tttacctcaa ggtgcaaaat aattaaacct gtacatattc catttacaaa   6180
ataaattcag ccctgcactt tctttagatg ccttgatttc cagaatggag cttagtgcta   6240
ctgaataccc tggccacaga gccacctcag gatattcttt tctccaccct agtttattta   6300
tttatagata tctgtttaca aagtctgtag taaatcctga tgctgaccat ctgaaatgta   6360 cttttttttct gaatgctgtt tcaatctaaa atagcagctt ttgagaaaac aatgatgtaa   6420
attccttatg ataaaaggat gattctatat attctttaat gatattaaat atgccgaagc   6480
caagcacaca gtcttttctaa agtgtgtgta tgtttgtgtg aatgtgaatg atactgatct   6540
tatatctgtt aaaagttgtt ttaaaaagct gtggcatccc attgttcata tttgccaagt   6600
cttctgtaaa gatgtctagg acgaaatatt ttatgtgcta atgcatgtat ttgtaaacca   6660
gatttgttta ccactcaaaa ttaacttgtt ttcttcatcc aaaaaagttt atttcttcca   6720
cgtacttaaa ttttctgtgt gggtataata tagcttccta atttttttct ttcacaaagg   6780
caggttcaaa attctgttga aagaaaaatg ctttctgaaa ctgaggtata acaccagagc   6840
```

-continued

```
ttgctgttta aaggattata tgatgtacat cagttctata aatgtgctca gcagtttaac    6900
atgtgaatcc tgttttaaag tgctcagatt tcaactgtgt aagccattga tataacgctg    6960
taattaaaaa tgtttatatg aaataactta atgttttaaa tttatttatg tagatcacat    7020
cattttatc gtatgcagtg caaatatgtg aaatgtcttt tggtttattc caacaattat     7080
ttattttaga aagtaagttt aaagacttta aggacattca aagtttaaaa tagtgttcaa    7140
attgcaaaat ttggcaatct tcatataaat tggtttcttt tctaactttt caaaaactaa    7200
cattaaatgt caattatagg aaaacatagt tggaaatgta atcatccaaa gatcattttt    7260
aaaatgaaat ttaattagca catattgaac atttgactta attgttaaac cccagttttg    7320
ttttgttttt ttaatcagat ttttgcacac tgattagttt ttgtgttgtg gcttttgttg    7380
ctttattatt caaggttttt ttttttttc ttccccatgg gggagattgt cttccaatgt     7440
ttaactacgt ttaaataaat aaaaattgaa ttttattgtt catttatata aaatctgata    7500
ccttgatgta atttcacaat acagttccaa tttttatggc ttttataatt acaatgatat    7560
tttcttctat aataaaatcc aaagtaaaca tttaaattgt agaactgata tttttcattt    7620
atatgaagta taagcctcta ctgggtctat attgtgaatc atcctgcctt tcaaatttgt    7680
ttcataattg ttagatgaaa actatttttt tggagatgtt actgaagttg attgagcaat    7740
aaaagtctac ttaatta                                                   7757
```

<210> SEQ ID NO 29
<211> LENGTH: 295
<212> TYPE: PRT
<213> ORGANISM: Homo sapiens

<400> SEQUENCE: 29

```
Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205
```

```
Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Val Asp Leu Ala Cys Thr Pro Thr
        275                 280                 285

Asp Val Arg Asp Val Asp Ile
    290                 295

<210> SEQ ID NO 30
<211> LENGTH: 4221
<212> TYPE: DNA
<213> ORGANISM: Homo sapiens

<400> SEQUENCE: 30
```

| | | | | | |
|---|---|---|---|---|---|
| gtagcagcga | gcagcagagt | ccgcacgctc | cggcgagggg | cagaagagcg | cgagggagcg | 60 |
| cggggcagca | gaagcgagag | ccgagcgcgg | acccagccag | gacccacagc | cctccccagc | 120 |
| tgcccaggaa | gagccccagc | catggaacac | cagctcctgt | gctgcgaagt | ggaaaccatc | 180 |
| cgccgcgcgt | accccgatgc | caacctcctc | aacgaccggg | tgctgcgggc | catgctgaag | 240 |
| gcggaggaga | cctgcgcgcc | ctcggtgtcc | tacttcaaat | gtgtgcagaa | ggaggtcctg | 300 |
| ccgtccatgc | ggaagatcgt | cgccacctgg | atgctggagg | tctgcgagga | acagaagtgc | 360 |
| gaggaggagg | tcttcccgct | ggccatgaac | tacctggacc | gcttcctgtc | gctggagccc | 420 |
| gtgaaaaaga | gccgcctgca | gctgctgggg | gccacttgca | tgttcgtggc | ctctaagatg | 480 |
| aaggagacca | tcccccctgac | ggccgagaag | ctgtgcatct | acaccgacaa | ctccatccgg | 540 |
| cccgaggagc | tgctgcaaat | ggagctgctc | ctggtgaaca | agctcaagtg | gaacctggcc | 600 |
| gcaatgaccc | cgcacgattt | cattgaacac | ttcctctcca | aaatgccaga | ggcggaggag | 660 |
| aacaaacaga | tcatccgcaa | acacgcgcag | accttcgttg | ccctctgtgc | cacagatgtg | 720 |
| aagttcattt | ccaatccgcc | ctccatggtg | gcagcgggga | gcgtggtggc | cgcagtgcaa | 780 |
| ggcctgaacc | tgaggagccc | caacaacttc | ctgtcctact | accgcctcac | acgcttcctc | 840 |
| tccagagtga | tcaagtgtga | cccggactgc | ctccgggcct | gccaggagca | gatcgaagcc | 900 |
| ctgctggagt | caagcctgcg | ccaggcccag | cagaacatgg | accccaaggc | cgccgaggag | 960 |
| gaggaagagg | aggaggagga | ggtggacctg | gcttgcacac | ccaccgacgt | gcgggacgtg | 1020 |
| gacatctgag | ggcgccaggc | aggcgggcgc | caccgccacc | cgcagcgagg | gcggagccgg | 1080 |
| ccccaggtgc | tccactgaca | gtccctcctc | tccggagcat | tttgatacca | gaagggaaag | 1140 |
| cttcattctc | cttgttgttg | gttgtttttt | cctttgctct | ttccccttc | catctctgac | 1200 |
| ttaagcaaaa | gaaaagatt | acccaaaaac | tgtctttaaa | agagagagag | agaaaaaaaa | 1260 |
| aatagtattt | gcataaccct | gagcggtggg | ggaggagggt | tgtgctacag | atgatagagg | 1320 |
| attttatacc | ccaataatca | actcgttttt | atattaatgt | acttgtttct | ctgttgtaag | 1380 |
| aataggcatt | aacacaaagg | aggcgtctcg | ggagaggatt | aggttccatc | ctttacgtgt | 1440 |
| ttaaaaaaaa | gcataaaaac | attttaaaaa | catagaaaaa | ttcagcaaac | cattttttaaa | 1500 |
| gtagaagagg | gttttaggta | gaaaaacata | ttccttgtgct | tttcctgata | aagcacagct | 1560 |
| gtagtggggt | tctaggcatc | tctgtacttt | gcttgctcat | atgcatgtag | tcactttata | 1620 |

-continued

```
agtcattgta tgttattata ttccgtaggt agatgtgtaa cctcttcacc ttattcatgg   1680
ctgaagtcac ctcttggtta cagtagcgta gcgtggccgt gtgcatgtcc tttgcgcctg   1740
tgaccaccac cccaacaaac catccagtga caaaccatcc agtggaggtt tgtcgggcac   1800
cagccagcgt agcagggtcg ggaaaggcca cctgtcccac tcctacgata cgctactata   1860
aagagaagac gaaatagtga cataatatat tctatttta tactcttcct atttttgtag    1920
tgacctgttt atgagatgct ggttttctac ccaacggccc tgcagccagc tcacgtccag   1980
gttcaaccca cagctacttg gtttgtgttc ttcttcatat tctaaaacca ttccatttcc   2040
aagcactttc agtccaatag gtgtaggaaa tagcgctgtt tttgttgtgt gtgcagggag   2100
ggcagttttc taatggaatg gtttgggaat atccatgtac ttgtttgcaa gcaggacttt   2160
gaggcaagtg tgggccactg tggtggcagt ggaggtgggg tgtttgggag gctgcgtgcc   2220
agtcaagaag aaaaaggttt gcattctcac attgccagga tgataagttc ctttccttt    2280
ctttaaagaa gttgaagttt aggaatcctt tggtgccaac tggtgtttga aagtagggac   2340
ctcagaggtt tacctagaga acaggtggtt tttaagggtt atcttagatg tttcacaccg   2400
gaaggttttt aaacactaaa atatataatt tatagttaag gctaaaaagt atatttattg   2460
cagaggatgt tcataaggcc agtatgattt ataaatgcaa tctcccttg atttaaacac    2520
acagatacac acacacacac acacacacac acaaaccttc tgcctttgat gttacagatt   2580
taatacagtt tattttaaa gatagatcct tttataggtg agaaaaaaac aatctggaag    2640
aaaaaaacca cacaaagaca ttgattcagc ctgtttggcg tttcccagag tcatctgatt   2700
ggacaggcat gggtgcaagg aaaattaggg tactcaacct aagttcggtt ccgatgaatt   2760
cttatcccct gccccttcct ttaaaaaact tagtgacaaa atagacaatt tgcacatctt   2820
ggctatgtaa ttcttgtaat ttttattag gaagtgttga agggaggtgg caagagtgtg    2880
gaggctgacg tgtgagggag gacaggcggg aggaggtgtg aggaggaggc tcccgagggg   2940
aaggggcggt gcccacaccg gggacaggcc gcagctccat tttcttattg cgctgctacc   3000
gttgacttcc aggcacggtt tggaaatatt cacatcgctt ctgtgtatct ctttcacatt   3060
gtttgctgct attggaggat cagtttttg ttttacaatg tcatatactg ccatgtacta    3120
gttttagttt tctcttagaa cattgtatta cagatgcctt ttttgtagtt tttttttttt   3180
ttttatgtga tcaattttga cttaatgtga ttactgctct attccaaaaa ggttgctgtt   3240
tcacaatacc tcatgcttca cttagccatg gtggacccag cgggcaggtt ctgcctgctt   3300
tggcgggcag acacgcgggc gcgatcccac acaggctggc gggggccggc cccgaggccg   3360
cgtgcgtgag aaccgcgccg gtgtcccag agaccaggct gtgtccctct tctcttccct    3420
gcgcctgtga tgctgggcac ttcatctgat cgggggcgta gcatcatagt agtttttaca   3480
gctgtgttat tctttgcgtg tagctatgga agttgcataa ttattattat tattattata   3540
acaagtgtgt cttacgtgcc accacggcgt tgtacctgta ggactctcat tcgggatgat   3600
tggaatagct tctggaattt gttcaagttt tgggtatgtt taatctgtta tgtactagtg   3660
ttctgtttgt tattgtttg ttaattacac cataatgcta atttaaagag actccaaatc    3720
tcaatgaagc cagctcacag tgctgtgtgc cccggtcatc tagcaagctg ccgaaccaaa   3780
agaatttgca ccccgctgcg ggcccacgtg gttgggccc tgccctggca gggtcatcct    3840
gtgctcggag gccatctcgg gcacaggccc accccgcccc accctccag aacacggctc    3900
acgcttacct caaccatcct ggctgcggcg tctgtctgaa ccacgcgggg gccttgaggg   3960
```

-continued

```
acgctttgtc tgtcgtgatg gggcaagggc acaagtcctg gatgttgtgt gtatcgagag    4020
gccaaaggct ggtggcaagt gcacggggca cagcggagtc tgtcctgtga cgcgcaagtc    4080
tgagggtctg gcggcgggc ggctgggtct gtgcatttct ggttgcaccg cggcgcttcc    4140
cagcaccaac atgtaaccgg catgtttcca gcagaagaca aaaagacaaa catgaaagtc    4200
tagaaataaa actggtaaaa c                                              4221
```

<210> SEQ ID NO 31
<211> LENGTH: 381
<212> TYPE: PRT
<213> ORGANISM: Homo sapiens

<400> SEQUENCE: 31

```
Met Ile Asp Thr Leu Arg Pro Val Pro Phe Ala Ser Glu Met Ala Ile
  1               5                  10                  15

Ser Lys Thr Val Ala Trp Leu Asn Glu Gln Leu Glu Leu Gly Asn Glu
                 20                  25                  30

Arg Leu Leu Leu Met Asp Cys Arg Pro Gln Glu Leu Tyr Glu Ser Ser
             35                  40                  45

His Ile Glu Ser Ala Ile Asn Val Ala Ile Pro Gly Ile Met Leu Arg
         50                  55                  60

Arg Leu Gln Lys Gly Asn Leu Pro Val Arg Ala Leu Phe Thr Arg Gly
 65                  70                  75                  80

Glu Asp Arg Asp Arg Phe Thr Arg Arg Cys Gly Thr Asp Thr Val Val
                 85                  90                  95

Leu Tyr Asp Glu Ser Ser Ser Asp Trp Asn Glu Asn Thr Gly Gly Glu
            100                 105                 110

Ser Leu Leu Gly Leu Leu Leu Lys Lys Leu Lys Asp Glu Gly Cys Arg
        115                 120                 125

Ala Phe Tyr Leu Glu Gly Gly Phe Ser Lys Phe Gln Ala Glu Phe Ser
    130                 135                 140

Leu His Cys Glu Thr Asn Leu Asp Gly Ser Cys Ser Ser Ser Ser Pro
145                 150                 155                 160

Pro Leu Pro Val Leu Gly Leu Gly Gly Leu Arg Ile Ser Ser Asp Ser
                165                 170                 175

Ser Ser Asp Ile Glu Ser Asp Leu Asp Arg Asp Pro Asn Ser Ala Thr
            180                 185                 190

Asp Ser Asp Gly Ser Pro Leu Ser Asn Ser Gln Pro Ser Phe Pro Val
        195                 200                 205

Glu Ile Leu Pro Phe Leu Tyr Leu Gly Cys Ala Lys Asp Ser Thr Asn
    210                 215                 220

Leu Asp Val Leu Glu Glu Phe Gly Ile Lys Tyr Ile Leu Asn Val Thr
225                 230                 235                 240

Pro Asn Leu Pro Asn Leu Phe Glu Asn Ala Gly Glu Phe Lys Tyr Lys
                245                 250                 255

Gln Ile Pro Ile Ser Asp His Trp Ser Gln Asn Leu Ser Gln Phe Phe
            260                 265                 270

Pro Glu Ala Ile Ser Phe Ile Asp Glu Ala Arg Gly Lys Asn Cys Gly
        275                 280                 285

Val Leu Val His Cys Leu Ala Gly Ile Ser Arg Ser Val Thr Val Thr
    290                 295                 300

Val Ala Tyr Leu Met Gln Lys Leu Asn Leu Ser Met Asn Asp Ala Tyr
305                 310                 315                 320

Asp Ile Val Lys Met Lys Lys Ser Asn Ile Ser Pro Asn Phe Asn Phe
```

```
                    325                 330                 335
Met Gly Gln Leu Leu Asp Phe Glu Arg Thr Leu Gly Leu Ser Ser Pro
        340                 345                 350

Cys Asp Asn Arg Val Pro Ala Gln Gln Leu Tyr Phe Thr Thr Pro Ser
        355                 360                 365

Asn Gln Asn Val Tyr Gln Val Asp Ser Leu Gln Ser Thr
        370                 375                 380

<210> SEQ ID NO 32
<211> LENGTH: 2710
<212> TYPE: DNA
<213> ORGANISM: Homo sapiens

<400> SEQUENCE: 32
cttggaggga gggattagaa gccgctagac ttttttttcct cccctctcag tagcacggag      60
tccgaattaa ttggatttca ttcactgggg aggaacaaaa actatctggg cagcttcatt     120
gagagagatt cattgacact aagagccagc ggctgcagct gggtgcagag agaacctccg     180
gctttacttc tgtctcgtct gccccaaccg ctagcctcgg cttgggtaag gcgaggcgga     240
attaaacccc gctccgagag cggcagcttc gcgcgcggtg cgctcggcct atgcctgccc     300
cgaggggcgt ctggtaggca ccccgccctc tcccgcagct cgaccccat gatagatacg      360 ctcagacccg tgcccttcgc gtcggaaatg gcgatcagca agacggtggc gtggctcaac     420
gagcagctgg agctgggcaa cgagcggctg ctgctgatgg actgccggcc gcaggagcta     480
tacgagtcgt cgcacatcga gtcggccatc aacgtggcca tcccgggcat catgctgcgg     540
cgcctgcaga gggtaacct gccggtgcgc gcgctcttca cgcgcggcga ggaccgggac      600
cgcttcaccc ggcgctgtgg caccgacaca gtggtgctct acgacgagag cagcagcgac     660
tggaacgaga atacgggcgg cgagtcgttg ctcgggctgc tgctcaagaa gctcaaggac     720
gagggctgcc gggcgttcta cctggaaggt ggcttcagta agttccaagc cgagttctcc     780
ctgcattgcg agaccaatct agacggctcg tgtagcagca gctcgccgcc gttgccagtg     840
ctggggctcg ggggcctgcg gatcagctct gactcttcct cggacatcga gtctgaccct     900
gaccgagacc ccaatagtgc aacagactcg gatggtagtc cgctgtccaa cagccagcct     960
tccttcccag tggagatctt gcccttcctc tacttgggct gtgccaaaga ctccaccaac    1020
ttggacgtgt tggaggaatt cggcatcaag tacatcttga acgtcacccc caatttgccg    1080
aatctctttg agaacgcagg agagtttaaa tacaagcaaa tccccatctc ggatcactgg    1140
agccaaaacc tgtcccagtt ttttccctgag gccatttctt tcatagatga agcccggggc    1200
aagaactgtg tgtcttggt acattgcttg gctggcatta gccgctcagt cactgtgact    1260
gtggcttacc ttatgcagaa gctcaatctg tcgatgaacg atgccatga cattgtcaaa    1320 atgaaaaaat ccaacatatc ccctaacttc aacttcatgg gtcagctgct ggacttcgag    1380
aggacgctgg gactcagcag cccatgtgac aacagggttc cagcacagca gctgtatttt    1440 accaccccttt ccaaccagaa tgtataccag gtggactctc tgcaatctac gtgaaagacc    1500
ccacatccct ccttgctgga atgtgtctgg cccttcagca gtttctcttg gcagcatcag    1560
ctgggctgct ttctttgtgt gtggcccag gtgtcaaaat gacaccagct gtctgtacta    1620
gacaaggtta ccaagtgcgg aattggttaa tactaacaga gagatttgct ccattctctt    1680
tggaataaca ggcatgctg tatagataca ggcagtaggt ttgctctgta cccatgtgta    1740
cagcctaccc atgcagggac tgggattcga ggacttccag gcgcataggg tagaaccaaa    1800
```

```
tgatagggta ggagcatgtg ttctttaggg ccttgtaagg ctgtttcctt ttgcatctgg    1860
aactgactat ataattgtct tcaatgaaga ctaattcaat tttgcatata gaggagccaa    1920
agagagattt cagctctgta tttgtggtat cagtttggaa aaaaaaatct gatactccat    1980
ttgattattg taaatatttg atcttgaatc acttgacagt gtttgtttga attgtgtttg    2040
ttttttcctt tgatgggctt aaaagaaatt atccaaaggg agaaagagca gtatgccact    2100
tcttaaaaca gaacaaaaca aaaaagaaa attgtgctct tttctaatcc aaagggtata    2160
tttgcagcat gcttgacttt accaattctg atgacatctt tacggacact attatcacta    2220
agaccttgtt atggcgaagt cttagtctt tttcatgtat tttcctcatg attttttctc    2280
tttatgtagt ttgactatgc cttacctttg taaatatttt tgcttgtgtt gtcgcaaagg    2340
ggataatctg ggaagacac caaatcatgg gctcacttta aaaaagaaa gaataaaaaa    2400 accttcagct gtgctaaaca gtatattacc tctgtataaa attcttcagg gagtgtcacc    2460
tcaaatgcaa tactttgggt tggtttcttt cctttaaaaa aatttgtata aaactggaag    2520
tgtgtgtgtg tgagcatggg tacccatttg ataagagaaa tgcatttgat tgtgaagaag    2580
ggagagttaa attctccatt atgttcgtgg tgtaaagttt agagctggaa tttattataa    2640
gaatgtaaaa ccttaaatta ttaataaata actatttggg ctattgaaaa aaaaaaaaa    2700 aaaaaaaaa                                                           2710

<210> SEQ ID NO 33
<211> LENGTH: 346
<212> TYPE: PRT
<213> ORGANISM: Homo sapiens

<400> SEQUENCE: 33

Met Ala Ala Ser Gln Ala Val Glu Glu Met Arg Ser Arg Val Val Leu
 1               5                  10                  15

Gly Glu Phe Gly Val Arg Asn Val His Thr Thr Asp Phe Pro Gly Asn
             20                  25                  30

Tyr Ser Gly Tyr Asp Asp Ala Trp Asp Gln Asp Arg Phe Glu Lys Asn
         35                  40                  45

Phe Arg Val Asp Val Val His Met Asp Glu Asn Ser Leu Glu Phe Asp
     50                  55                  60

Met Val Gly Ile Asp Ala Ala Ile Ala Asn Ala Phe Arg Arg Ile Leu
 65                  70                  75                  80

Leu Ala Glu Val Pro Thr Met Ala Val Glu Lys Val Leu Val Tyr Asn
                 85                  90                  95

Asn Thr Ser Ile Val Gln Asp Glu Ile Leu Ala His Arg Leu Gly Leu
            100                 105                 110

Ile Pro Ile His Ala Asp Pro Arg Leu Phe Glu Tyr Arg Asn Gln Gly
        115                 120                 125

Asp Glu Glu Gly Thr Glu Ile Asp Thr Leu Gln Phe Arg Leu Gln Val
    130                 135                 140

Arg Cys Thr Arg Asn Pro His Ala Ala Lys Asp Ser Ser Asp Pro Asn
145                 150                 155                 160

Glu Leu Tyr Val Asn His Lys Val Tyr Thr Arg His Met Thr Trp Ile
                165                 170                 175

Pro Leu Gly Asn Gln Ala Asp Leu Phe Pro Glu Gly Thr Ile Arg Pro
            180                 185                 190

Val His Asp Asp Ile Leu Ile Ala Gln Leu Arg Pro Gly Gln Glu Ile
        195                 200                 205
```

```
Asp Leu Leu Met His Cys Val Lys Gly Ile Gly Lys Asp His Ala Lys
        210                 215                 220

Phe Ser Pro Val Ala Thr Ala Ser Tyr Arg Leu Leu Pro Asp Ile Thr
225                 230                 235                 240

Leu Leu Glu Pro Val Glu Gly Glu Ala Ala Glu Leu Ser Arg Cys
                245                 250                 255

Phe Ser Pro Gly Val Ile Glu Val Gln Glu Val Gln Gly Lys Lys Val
                260                 265                 270

Ala Arg Val Ala Asn Pro Arg Leu Asp Thr Phe Ser Arg Glu Ile Phe
            275                 280                 285

Arg Asn Glu Lys Leu Lys Lys Val Val Arg Leu Ala Arg Val Arg Asp
        290                 295                 300

His Tyr Ile Phe Ser Val Glu Ser Thr Gly Val Leu Pro Pro Asp Val
305                 310                 315                 320

Leu Val Ser Glu Ala Ile Lys Val Leu Met Gly Lys Cys Arg Arg Phe
                325                 330                 335

Leu Asp Glu Leu Asp Ala Val Gln Met Asp
            340                 345
```

<210> SEQ ID NO 34
<211> LENGTH: 1277
<212> TYPE: DNA
<213> ORGANISM: Homo sapiens

<400> SEQUENCE: 34

```
gagagagaga agatggcggc ttctcaggcg gtggaggaaa tgcggagccg cgtggttctg      60
ggggagtttg gggttcgcaa tgtccatact actgactttc ccggtaacta ttccggttat     120
gatgatgcct ggaccagga ccgcttcgag aagaatttcc gtgtggatgt agtacacatg      180
gatgaaaact cactggagtt tgacatggtg ggaattgacg cagccattgc caatgctttt     240
cgacgaattc tgctagctga ggtgccaact atggctgtgg agaaggtcct ggtgtacaat     300
aatacatcca ttgttcagga tgagattctt gctcaccgtc tggggctcat tcccattcat     360
gctgatcccc gtcttttga gtatcggaac caaggagatg aagaaggcac agagatagat     420
actctacagt ttcgtctcca ggtcagatgc actcggaacc ccatgctgc taaagattcc     480
tctgacccca cgaactgta cgtgaaccac aaagtgtata ccaggcatat gacatggatc     540
cccctgggga accaggctga tctctttcca gagggcacta tccgaccagt gcatgatgat     600
atcctcatcg ctcagctgcg gcctggccaa gaaattgacc tgctcatgca ctgtgtcaag     660
ggcattggca agatcatgc aagttttca ccagtggcaa cagccagtta caggctcctg     720
ccagacatca ccctgcttga gcccgtggaa ggggaggcag ctgaggagtt gagcaggtgc     780
ttctcacctg gtgttattga ggtgcaggaa gtccaaggta aaaaggtggc cagagttgcc     840
aaccccggc tggatacctt cagcagaaa atcttccgga atgagaagct aaagaaggtt     900
gtgaggcttg cccgggttcg agatcattat atcttctctg ttgagtcaac gggggtgttg     960
ccaccagatg tgctggtgag tgaagccatc aaagtactga tggggaagtg ccggcgcttc    1020
ttggatgaac tagatgcggt tcagatggac tgagcttgga tgcttctgag gcaagctgaa    1080
gctttgggtt ctgactgacc caccctacag gactgctgaa cagagagccc agtgtgacta    1140
gggatcctga gttttctggg acaattccag ctttaatcaa tacattttgt taaatgtgcc    1200
ataaaatgag acttttttacg cctttataag gccttagatg taaataaact cacccaaaca    1260
aaaaaaaaaa aaaaaaa                                                   1277
```

<210> SEQ ID NO 35
<211> LENGTH: 365
<212> TYPE: PRT
<213> ORGANISM: Homo sapiens

<400> SEQUENCE: 35

Met Glu Gly Gln Ser Val Glu Leu Leu Ala Lys Ala Glu Gln Asp
1               5                   10                  15

Glu Ala Glu Lys Leu Gln Arg Ile Thr Val His Lys Glu Leu Glu Leu
            20                  25                  30

Gln Phe Asp Leu Gly Asn Leu Leu Ala Ser Asp Arg Asn Pro Pro Thr
        35                  40                  45

Gly Leu Arg Cys Ala Gly Pro Thr Pro Glu Ala Glu Leu Gln Ala Leu
    50                  55                  60

Ala Arg Asp Asn Thr Gln Leu Leu Ile Asn Gln Leu Trp Gln Leu Pro
65                  70                  75                  80

Thr Glu Arg Val Glu Glu Ala Ile Val Ala Arg Leu Pro Glu Pro Thr
                85                  90                  95

Thr Arg Leu Pro Arg Glu Lys Pro Leu Pro Arg Pro Arg Pro Leu Thr
            100                 105                 110

Arg Trp Gln Gln Phe Ala Arg Leu Lys Gly Ile Arg Pro Lys Lys Lys
        115                 120                 125

Thr Asn Leu Val Trp Asp Glu Val Ser Gly Gln Trp Arg Arg Arg Trp
    130                 135                 140

Gly Tyr Gln Arg Ala Arg Asp Asp Thr Lys Glu Trp Leu Ile Glu Val
145                 150                 155                 160

Pro Gly Asn Ala Asp Pro Leu Glu Asp Gln Phe Ala Lys Arg Ile Gln
                165                 170                 175

Ala Lys Lys Glu Arg Val Ala Lys Asn Glu Leu Asn Arg Leu Arg Asn
            180                 185                 190

Leu Ala Arg Ala His Lys Met Gln Leu Pro Ser Ala Gly Leu His
        195                 200                 205

Pro Thr Gly His Gln Ser Lys Glu Glu Leu Gly Arg Ala Met Gln Val
    210                 215                 220

Ala Lys Val Ser Thr Ala Ser Val Gly Arg Phe Gln Glu Arg Leu Pro
225                 230                 235                 240

Lys Glu Lys Val Pro Arg Gly Ser Gly Lys Lys Arg Lys Phe Gln Pro
                245                 250                 255

Leu Phe Gly Asp Phe Ala Ala Glu Lys Lys Asn Gln Leu Glu Leu Leu
            260                 265                 270

Arg Val Met Asn Ser Lys Lys Pro Gln Leu Asp Val Thr Arg Ala Thr
        275                 280                 285

Asn Lys Gln Met Arg Glu Glu Asp Gln Glu Glu Ala Ala Lys Arg Arg
    290                 295                 300

Lys Met Ser Gln Lys Gly Lys Arg Lys Gly Arg Gln Gly Pro Gly
305                 310                 315                 320

Gly Lys Arg Lys Gly Gly Pro Pro Ser Gln Gly Gly Lys Arg Lys Gly
                325                 330                 335

Gly Leu Gly Gly Lys Met Asn Ser Gly Pro Pro Gly Leu Gly Gly Lys
            340                 345                 350

Arg Lys Gly Gly Gln Arg Pro Gly Gly Lys Arg Arg Lys
        355                 360                 365

<210> SEQ ID NO 36

<211> LENGTH: 1709
<212> TYPE: DNA
<213> ORGANISM: Homo sapiens

<400> SEQUENCE: 36

```
cacgtggtta tgctgccgga gtttgggccg ccactgtagg aaaagtaact tcagctgcag    60
ccccaaagcg agtgagccga gccggagcca tggagggcca gagcgtggag gagctgctcg   120
caaaggcaga gcaggacgag gcagagaagt tgcaacgcat cacggtgcac aaggagctgg   180
agctgcagtt tgacctgggc aacctgctgg cgtcggaccg gaaccccccg accgggctgc   240
ggtgcgccgg acccacgccg gaggccgagc tacaggccct ggcgcgggac aacacgcaac   300
tgctcatcaa ccagctgtgg cagctgccca cggagcgcgt ggaagaggcg atagtggcgc   360
ggctgccgga gcccaccaca cgcctgccgc gagagaagcc tctgccccga ccgcggccac   420
ttacacgctg gcagcagttc gcgcgcctca agggcatccg tcccaagaag aagaccaacc   480
tggtgtggga cgaggtgagt ggccagtggc ggcggcgctg gggctaccag cgcgcccggg   540
acgacaccaa agaatggctg attgaggtgc ccggcaatgc cgaccccttg gaggaccagt   600
cgccaagcg gattcaggcc aagaaggaaa gggtggccaa gaacgagctg aaccggctgc   660
gtaacctggc ccgcgcgcac aagatgcagc tgcccagcgc ggccggcttg caccctaccg   720
gacaccagag taaggaggag ctgggccgcg ccatgcaagt ggccaaggtc tccaccgcct   780
ctgtggggcg ctttcaggag cgcctcccca aggagaaggt gccccggggc tccggcaaga   840
aaaggaagtt tcaacccctt ttcgggagact ttgcagccga gaaaagaac cagttggagc   900
tgcttcgtgt catgaacagc aagaagcctc agctggatgt gactagggcc accaataagc   960
agatgaggga ggaggaccag gaggaggccg ccaagaggag gaaaatgagc cagaagggca  1020
agagaaaggg aggccggcag gggcctgggg gcaagaggaa aggggggcccg cccagccagg  1080
gagggaagag gaaagggggc ttgggaggca agatgaattc tgggccgcct ggcttgggtg  1140
gcaagagaaa aggaggacag cgcccaggag gaaagaggag gaagtaatag tttctaactg  1200
tcggacccgt ctgtaaacca aggactatga atactaaatg ttaagttcta ggcaattata  1260
cggggactca gaaggacctg gccgctgcct tcattgagtt taaagggaca ggattgccct  1320
tccgtcaaga aagtatgtaa gtgttggact gcacaaatta atgtttttcc cacaaccgag  1380
actttggaga ttaagaactt atttgaggat ttaagaatta gggaaataat ttggtggaaa  1440
ccggaatga gttctattct taaacagcct ttttttttct ttttaatgtt ggatatacgg  1500
cgaggtgagt ttggccatat ttcagagact tagattgacg tatatgtttc tgcattattt  1560
ttacaacaag tttgtgtatc agagcggag tgcggggag ggaaagaaaa caaacagttt  1620
cagaattgaa taggcaagtg actgttttaa agattaagta ataagatgt cttatctagt  1680
gtgacttta aaaaaaaaa aaaaaaaa                                       1709
```

<210> SEQ ID NO 37
<211> LENGTH: 152
<212> TYPE: PRT
<213> ORGANISM: Homo sapiens

<400> SEQUENCE: 37

```
Met Lys Ser Pro Asp Glu Val Leu Arg Glu Gly Glu Leu Glu Lys Arg
  1               5                  10                  15

Ser Asp Ser Leu Phe Gln Leu Trp Lys Lys Lys Arg Gly Val Leu Thr
             20                  25                  30

Ser Asp Arg Leu Ser Leu Phe Pro Ala Ser Pro Arg Ala Arg Pro Lys
```

```
                    35                  40                  45
Glu Leu Arg Phe His Ser Ile Leu Lys Val Asp Cys Val Glu Arg Thr
             50                  55                  60

Gly Lys Tyr Val Tyr Phe Thr Ile Val Thr Thr Asp His Lys Glu Ile
 65                  70                  75                  80

Asp Phe Arg Cys Ala Gly Glu Ser Cys Trp Asn Ala Ala Ile Ala Leu
                 85                  90                  95

Ala Leu Ile Asp Phe Gln Asn Arg Arg Ala Leu Gln Asp Phe Arg Ser
            100                 105                 110

Arg Gln Glu Arg Thr Ala Pro Ala Ala Pro Ala Glu Asp Ala Val Ala
        115                 120                 125

Ala Ala Ala Ala Ala Pro Ser Glu Pro Ser Glu Pro Ser Arg Pro Ser
130                 135                 140

Pro Gln Pro Lys Pro Arg Thr Pro
145                 150
```

<210> SEQ ID NO 38
<211> LENGTH: 760
<212> TYPE: DNA
<213> ORGANISM: Homo sapiens

<400> SEQUENCE: 38

```
agagccggcg ccgtcaccgc ccgcattgcc gctcccagtc ccgcgctcgg cacgacatga        60
aatccccga  cgaggtgcta cgcgagggcg agttggagaa gcgcagcgac agcctcttcc       120
agctatggaa gaagaagcgc ggggtgctca cctccgaccg cctgagcctg ttccccgcca       180
gcccccgcgc gcgcccccaag gagctgcgct tccactccat cctcaaggtg gactgcgtgg      240
agcgcacggg caagtacgtg tacttcacca tcgtcaccac cgaccacaag gagatcgact       300
tccgctgcgc gggcgagagc tgctggaacg cggccatcgc gctggcgctc atcgatttcc       360
agaaccgccg cgccctgcag gactttcgca gccgccagga acgcaccgca cccgccgcac       420
ccgccgagga cgccgtggct gccgcggccg ccgcaccctc cgagccctcg agccctcca       480
ggccatcccc gcagcccaaa ccccgcacgc catgagcccg ccgcgggcca tacgctggac       540
gagtcggacc gaggctagga cgtggccggc gctctccagc cctgcagcag aagaacttcc       600
cgtgcgcgcg gatcctcgct ccgttgcacg ggcgccttaa gttattggac tatctaatat       660
ctatgtattt atttcgctgg ttctttgtag tcacatattt tatagtctta atatcttgtt       720
tttgcatcac tgtgcccatt gcaaataaat cacttggcca                            760
```

<210> SEQ ID NO 39
<211> LENGTH: 341
<212> TYPE: PRT
<213> ORGANISM: Homo sapiens

<400> SEQUENCE: 39

```
Met Ala Val Leu Ala Trp Lys Phe Pro Arg Thr Arg Leu Pro Met Gly
 1               5                  10                  15

Ala Ser Ala Leu Cys Val Val Leu Cys Trp Leu Tyr Ile Phe Pro
             20                  25                  30

Val Tyr Arg Leu Pro Asn Glu Lys Glu Ile Val Gln Gly Val Leu Gln
             35                  40                  45

Gln Gly Thr Ala Trp Arg Arg Asn Gln Thr Ala Ala Arg Ala Phe Arg
         50                  55                  60

Lys Gln Met Glu Asp Cys Cys Asp Pro Ala His Leu Phe Ala Met Thr
 65                  70                  75                  80
```

Lys Met Asn Ser Pro Met Gly Lys Ser Met Trp Tyr Asp Glu Phe
                85                  90                  95
Leu Tyr Ser Phe Thr Ile Asp Asn Ser Thr Tyr Ser Leu Phe Pro Gln
            100                 105                 110
Ala Thr Pro Phe Gln Leu Pro Leu Lys Lys Cys Ala Val Val Gly Asn
        115                 120                 125
Gly Gly Ile Leu Lys Lys Ser Gly Cys Gly Arg Gln Ile Asp Glu Ala
    130                 135                 140
Asn Phe Val Met Arg Cys Asn Leu Pro Pro Leu Ser Ser Glu Tyr Thr
145                 150                 155                 160
Lys Asp Val Gly Ser Lys Ser Gln Leu Val Thr Ala Asn Pro Ser Ile
                165                 170                 175
Ile Arg Gln Arg Phe Gln Asn Leu Leu Trp Ser Arg Lys Thr Phe Val
            180                 185                 190
Asp Asn Met Lys Ile Tyr Asn His Ser Tyr Ile Tyr Met Pro Ala Phe
        195                 200                 205
Ser Met Lys Thr Gly Thr Glu Pro Ser Leu Arg Val Tyr Tyr Thr Leu
    210                 215                 220
Ser Asp Val Gly Ala Asn Gln Thr Val Leu Phe Ala Asn Pro Asn Phe
225                 230                 235                 240
Leu Arg Ser Ile Gly Lys Phe Trp Lys Ser Arg Gly Ile His Ala Lys
                245                 250                 255
Arg Leu Ser Thr Gly Leu Phe Leu Val Ser Ala Ala Leu Gly Leu Cys
            260                 265                 270
Glu Glu Val Ala Ile Tyr Gly Phe Trp Pro Phe Ser Val Asn Met His
        275                 280                 285
Glu Gln Pro Ile Ser His His Tyr Tyr Asp Asn Val Leu Pro Phe Ser
    290                 295                 300
Gly Phe His Ala Met Pro Glu Glu Phe Leu Gln Leu Trp Tyr Leu His
305                 310                 315                 320
Lys Ile Gly Ala Leu Arg Met Gln Leu Asp Pro Cys Glu Asp Thr Ser
                325                 330                 335
Leu Gln Pro Thr Ser
            340

<210> SEQ ID NO 40
<211> LENGTH: 1650
<212> TYPE: DNA
<213> ORGANISM: Homo sapiens

<400> SEQUENCE: 40
tccgctgcca cttcgcctag ctttgtgctg aggccccggc ccccgcccct gggacgccgg    60
ggctgcgatg agcccctgcg gcgggcccg gcgacaaacg tccagagggg ccatggctgt   120
actggcgtgg aagttcccgc ggacccggct gccatggga gccagtgccc tctgtgtcgt   180
ggtcctctgt tggctctaca tcttccccgt ctaccggctg cccaacgaga agagatcgt   240 gcagggggtg ctgcaacagg gcacggcgtg gaggaggaac cagaccgcgg ccagagcgtt   300
caggaaacaa atggaagact gctgcgaccc tgccatctc tttgctatga ctaaaatgaa   360
ttcccctatg gggaagagca tgtggtatga cggggagttt ttatactcat tcaccattga   420
caattcaact tactctctct cccacaggc aaccccattc cagctgccat gaagaaatg   480 cgcggtggtg ggaaatggtg ggattctgaa gaagagtggc tgtggccgtc aaatagatga   540
agcaaatttt gtcatgcgat gcaatctccc tcctttgtca agtgaataca ctaaggatgt   600

```
tggatccaaa agtcagttag tgacagctaa tcccagcata attcggcaaa ggtttcagaa        660
ccttctgtgg tccagaaaga catttgtgga acatgaaa atttataacc acagttacat         720
ctacatgcct gccttttcta tgaagacagg aacagagcca tctttgaggg tttattatac       780
actgtcagat gttggtgcca atcaaacagt gctgtttgcc aaccccaact ttctgcgtag       840
cattggaaag ttctggaaaa gtagaggaat ccatgccaag cgcctgtcca caggactttt       900
tctggtgagc gcagctctgg gtctctgtga agaggtggcc atctatggct tctggccctt       960
ctctgtgaat atgcatgagc agcccatcag ccaccactac tatgacaacg tcttacccc      1020 ttctggcttc catgccatgc ccgaggaatt tctccaactc tggtatcttc ataaaatcgg      1080
tgcactgaga atgcagctgg acccatgtga agatacctca ctccagccca cttcctagga     1140
acaatggaag aagaaaggac tgaaccaggg tattttgtt aggttttcta tgtgactcca      1200
agagggaatg gtcaagttgt ttcatgagtt tgcatgggcc cttggaaaaa caggaaagga     1260
gcaatgaaga tccaagcaaa actttacttt cagcgttggc ttggaggaca aataagaaat     1320
gaaacatcct atgaaatact ttatagcaca tggcagattt gcaactagta aaatgctggt     1380
gaaatgctgt tggtaaagca catggtccaa atctagaaga tgcagttcaa aaacaagaca     1440
gactcgagtt gttagggctg aggaaccaat caaggtagaa caaagaaaat gttgggggtaa    1500 aagtgttgct gattgtcaac acaaactggc ttaataatat taataagaac ctgtcttatt     1560
aagactggct ttagaaccgt aggtttttt aaaaaattat tattttattttt tgccctcttt    1620 ggggaagtgg gtgggtagat ttaaaaaatc                                       1650

<210> SEQ ID NO 41
<211> LENGTH: 885
<212> TYPE: PRT
<213> ORGANISM: Homo sapiens

<400> SEQUENCE: 41

Met Ser Thr Met Arg Leu Leu Thr Leu Ala Leu Leu Phe Ser Cys Ser
 1               5                   10                  15

Val Ala Arg Ala Ala Cys Asp Pro Lys Ile Val Asn Ile Gly Ala Val
                20                  25                  30

Leu Ser Thr Arg Lys His Glu Gln Met Phe Arg Glu Ala Val Asn Gln
            35                  40                  45

Ala Asn Lys Arg His Gly Ser Trp Lys Ile Gln Leu Asn Ala Thr Ser
        50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
```

-continued

```
                180                 185                 190
Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
            275                 280                 285

Ala Gln Ala Val His Glu Leu Leu Glu Lys Glu Asn Ile Thr Asp Pro
            290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
            355                 360                 365

Gly Thr His Val Ile Pro Asn Asp Arg Lys Ile Ile Trp Pro Gly Gly
            370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
            435                 440                 445

His Thr Val Pro Gln Cys Cys Tyr Gly Phe Cys Ile Asp Leu Leu Ile
            450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
            515                 520                 525

Phe Ser Lys Pro Phe Lys Tyr Gln Gly Leu Thr Ile Leu Val Lys Lys
            530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
            595                 600                 605
```

```
Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Gln
    850                 855                 860

Tyr His Pro Thr Asp Ile Thr Gly Pro Leu Asn Leu Ser Asp Pro Ser
865                 870                 875                 880

Val Ser Thr Val Val
                885

<210> SEQ ID NO 42
<211> LENGTH: 3245
<212> TYPE: DNA
<213> ORGANISM: Homo sapiens

<400> SEQUENCE: 42
gcccgcggcc cgagcccatg agcaccatgc gcctgctgac gctcgccctg ctgttctcct      60
gctccgtcgc ccgtgccgcg tgcgacccca agatcgtcaa cattggcgcg gtgctgagca     120
cgcggaagca cgagcagatg ttccgcgagg ccgtgaacca ggccaacaag cggcacggct     180
cctggaagat tcagctcaat gccacctccg tcacgcacaa gcccaacgcc atccagatgg     240
ctctgtcggt gtgcgaggac ctcatctcca gccaggtcta cgccatccta gttagccatc     300
cacctacccc caacgaccac ttcactccca cccctgtctc ctacacagcc ggcttctacc     360 gcataccccgt gctggggctg accacccgca tgtccatcta ctcggacaag agcatccacc     420
tgagcttcct gcgcaccgtg ccgccctact cccaccagtc cagcgtgtgg tttgagatga      480
```

| | |
|---|---|
| tgcgtgtcta cagctggaac cacatcatcc tgctggtcag cgacgaccac gagggccggg | 540 |
| cggctcagaa acgcctggag acgctgctgg aggagcgtga gtccaaggca gagaaggtgc | 600 |
| tgcagtttga cccagggacc aagaacgtga cggccctgct gatggaggcg aaagagctgg | 660 |
| aggcccgggt catcatcctt tctgccagcg aggacgatgc tgccactgta taccgcgcag | 720 |
| ccgcgatgct gaacatgacg ggctccgggt acgtgtggct ggtcggcgag cgcgagatct | 780 |
| cggggaacgc cctgcgctac gccccggacg gcatcctcgg gctgcagctc atcaacggca | 840 |
| agaacgagtc ggcccacatc agcgacgccg taggcgtggt ggcccaggcc gtgcacgagc | 900 |
| tcctcgagaa ggagaacatc accgacccgc gcggggctg cgtgggcaac accaacatct | 960 |
| ggaagaccgg gccgctcttc aagagagtgc tgatgtcttc caagtatgcg gatggggtga | 1020 |
| ctggtcgcgt ggagttcaat gaggatgggg accggaagtt cgccaactac agcatcatga | 1080 |
| acctgcagaa ccgcaagctg gtgcaagtgg gcatctacaa tggcacccac gtcatcccta | 1140 |
| atgacaggaa gatcatctgg ccaggcggag agacagagaa gcctcgaggg taccagatgt | 1200 |
| ccaccagact gaagattgtg acgatccacc aggagcccct cgtgtacgtc aagcccacgc | 1260 |
| tgagtgatgg gacatgcaag gaggagttca cagtcaacgg cgacccagtc aagaaggtga | 1320 |
| tctgcaccgg gcccaacgac acgtcgccgg gcagcccccg ccacacggtg cctcagtgtt | 1380 |
| gctacggctt ttgcatcgac ctgctcatca agctggcacg gaccatgaac ttcacctacg | 1440 |
| aggtgcacct ggtggcagat ggcaagttcg gcacacagga gcgggtgaac aacagcaaca | 1500 |
| agaaggagtg gaatgggatg atgggcgagc tgctcagcgg gcaggcagac atgatcgtgg | 1560 |
| cgccgctaac cataaacaac gagcgcgcgc agtacatcga gttttccaag cccttcaagt | 1620 |
| accagggcct gactattctg gtcaagaagg agattccccg gagcacgctg gactcgttca | 1680 |
| tgcagccgtt ccagagcaca ctgtggctgc tggtggggct gtcggtgcac gtggtggccg | 1740 |
| tgatgctgta cctgctggac cgcttcagcc ccttcggccg gttcaaggtg aacagcgagg | 1800 |
| aggaggagga ggacgcactg accctgtcct cggccatgtg gttctcctgg ggcgtcctgc | 1860 |
| tcaactccgg catcggggaa ggcgcccca gaagcttctc agcgcgcatc ctgggcatgg | 1920 |
| tgtgggccgg cttttgccatg atcatcgtgg cctcctacac cgccaacctg gcggccttcc | 1980 |
| tggtgctgga ccggcggag gagcgcatca cgggcatcaa cgaccctcgg ctgaggaacc | 2040 |
| cctcggacaa gtttatctac gccacggtga agcagagctc cgtggatatc tacttccggc | 2100 |
| gccaggtgga gctgagcacc atgtaccggc atatggagaa gcacaactac gagagtgcgg | 2160 |
| cggaggccat ccaggccgtg agagacaaca agctgcatgc cttcatctgg gactcggcg | 2220 |
| tgctggagtt cgaggcctcg cagaagtgcg acctggtgac gactggagag ctgtttttcc | 2280 |
| gctcgggctt cggcataggc atgcgcaaag acagccctg gaagcagaac gtctccctgt | 2340 |
| ccatcctcaa gtcccacgag aatggcttca tggaagacct ggacaagacg tgggttcggt | 2400 |
| atcaggaatg tgactcgcgc agcaacgccc tgcgaccct tacttttgag aacatggccg | 2460 |
| gggtcttcat gctggtagct gggggcatcg tggccgggat cttcctgatt ttcatcgaga | 2520 |
| ttgcctacaa gcgcacaag gatgctcgcc ggaagcagat gcagctggcc tttgccgccg | 2580 |
| ttaacgtgtg gcggaagaac ctgcagcagt accatcccac tgatatcacg ggcccgctca | 2640 |
| acctctcaga tccctcggtc agcaccgtgg tgtgaggccc ccggaggcgc ccacctgccc | 2700 |
| agttagcccg gccaaggaca ctgatgggtc ctgctgctcg ggaaggcctg agggaagccc | 2760 |
| acccgcccca gagactgccc accctgggcc tccgtccgt ccgccgccc accccgctgc | 2820 |
| ctggcgggca gccctgctg gaccaaggtg cggaccggag cggctgagga cggggcagag | 2880 |

-continued

```
ctgagtcggc tgggcagggc cgcagggcgc tccggcagag gcagggccct ggggtctctg    2940
agcagtgggg agcgggggct aactggcccc aggcggaggg gcttggagca gagacggcag    3000
ccccatcctt cccgcagcac cagcctgagc cacagtgggg cccatggccc cagctggctg    3060
ggtcgcccct cctcgggcgc ctgcgctcct ctgcagcctg agctccaccc tcccctcttc    3120
ttgcggcacc gcccacccac accccgtctg cccttgacc ccacacgccg gggctggccc    3180
tgccctcccc cacggccgtc cctgacttcc cagctgcagc gcctcccgcc gcctcgggcc    3240
gcctc                                                                3245
```

<210> SEQ ID NO 43
<211> LENGTH: 669
<212> TYPE: PRT
<213> ORGANISM: Homo sapiens

<400> SEQUENCE: 43

```
Met Glu Ser Cys Tyr Asn Pro Gly Leu Asp Gly Ile Ile Glu Tyr Asp
  1               5                  10                  15

Asp Phe Lys Leu Asn Ser Ser Ile Val Glu Pro Lys Glu Pro Ala Pro
                 20                  25                  30

Glu Thr Ala Asp Gly Pro Tyr Leu Val Ile Val Glu Gln Pro Lys Gln
             35                  40                  45

Arg Gly Phe Arg Phe Arg Tyr Gly Cys Glu Gly Pro Ser His Gly Gly
         50                  55                  60

Leu Pro Gly Ala Ser Ser Glu Lys Gly Arg Lys Thr Tyr Pro Thr Val
 65                  70                  75                  80

Lys Ile Cys Asn Tyr Glu Gly Pro Ala Lys Ile Glu Val Asp Leu Val
                 85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125

Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300
```

```
Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
            325                 330                 335

Arg Lys Arg Arg Lys Ala Leu Pro Thr Phe Ser Gln Pro Phe Gly Gly
                340                 345                 350

Gly Ser His Met Gly Gly Ser Gly Gly Ala Ala Gly Gly Tyr Gly
            355                 360                 365

Gly Ala Gly Gly Gly Ser Leu Gly Phe Phe Pro Ser Ser Leu Ala
370                 375                 380

Tyr Ser Pro Tyr Gln Ser Gly Ala Gly Pro Met Gly Cys Tyr Pro Gly
385                 390                 395                 400

Gly Gly Gly Gly Ala Gln Met Ala Ala Thr Val Pro Ser Arg Asp Ser
                405                 410                 415

Gly Glu Glu Ala Ala Glu Pro Ser Ala Pro Ser Arg Thr Pro Gln Cys
                420                 425                 430

Glu Pro Gln Ala Pro Glu Met Leu Gln Arg Ala Arg Glu Tyr Asn Ala
                435                 440                 445

Arg Leu Phe Gly Leu Ala Gln Arg Ser Ala Arg Ala Leu Leu Asp Tyr
        450                 455                 460

Gly Val Thr Ala Asp Ala Arg Ala Leu Leu Ala Gly Gln Arg His Leu
465                 470                 475                 480

Leu Thr Ala Gln Asp Glu Asn Gly Asp Thr Pro Leu His Leu Ala Ile
                485                 490                 495

Ile His Gly Gln Thr Ser Val Ile Glu Gln Ile Val Tyr Val Ile His
            500                 505                 510

His Ala Gln Asp Leu Gly Val Val Asn Leu Thr Asn His Leu His Gln
        515                 520                 525

Thr Pro Leu His Leu Ala Val Ile Thr Gly Gln Thr Ser Val Val Ser
    530                 535                 540

Phe Leu Leu Arg Val Gly Ala Asp Pro Ala Leu Leu Asp Arg His Gly
545                 550                 555                 560

Asp Ser Ala Met His Leu Ala Leu Arg Ala Gly Ala Gly Ala Pro Glu
                565                 570                 575

Leu Leu Arg Ala Leu Leu Gln Ser Gly Ala Pro Ala Val Pro Gln Leu
                580                 585                 590

Leu His Met Pro Asp Phe Glu Gly Leu Tyr Pro Val His Leu Ala Val
        595                 600                 605

Arg Ala Arg Ser Pro Glu Cys Leu Asp Leu Leu Val Asp Ser Gly Ala
610                 615                 620

Glu Val Glu Ala Thr Glu Arg Gln Gly Gly Arg Thr Ala Leu His Leu
625                 630                 635                 640

Ala Thr Glu Met Glu Glu Leu Gly Leu Val Thr His Leu Val Thr Lys
                645                 650                 655

Leu Arg Ala Asn Val Asn Ala Arg Thr Phe Ser Ala Ser
                660                 665

<210> SEQ ID NO 44
<211> LENGTH: 2010
<212> TYPE: DNA
<213> ORGANISM: Homo sapiens

<400> SEQUENCE: 44
atggagagtt gctacaaccc aggtctggat ggtattattg aatatgatga tttcaaattg      60
```

```
aactcctcca ttgtggaacc caaggagcca gccccagaaa cagctgatgg cccctacctg      120
gtgatcgtgg aacagcctaa gcagagaggc ttccgatttc gatatggctg tgaaggcccc      180
tcccatggag gactgcccgg tgcctccagt gagaagggcc gaaagaccta tcccactgtc      240
aagatctgta actacgaggg accagccaag atcgaggtgg acctggtaac acacagtgac      300
ccacctcgtg ctcatgccca cagtctggtg ggcaagcaat gctcggagct ggggatctgc      360
gccgtttctg tggggcccaa ggacatgact gcccaattta caacctgggt gtcctgcat       420 gtgactaaga gaacatgat ggggactatg atacaaaaac ttcagaggca gcggctccgc       480
tctaggcccc agggccttac ggaggccgag cagcgggagc tggagcaaga ggccaaagaa      540
ctgaagaagg tgatggatct gagtatagtg cggctgcgct ctctgccttc cttagagcc       600 agtgatggct ccttctccct gccctgaag ccagtcatct cccagcccat ccatgacagc       660
aaatctccgg gggcatcaaa cctgaagatt tctcgaatgg acaagacagc aggctctgtg      720
cggggtggag atgaagttta tctgctttgt gacaaggtgc agaaagatga cattgaggtt      780
cggttctatg aggatgatga gaatggatgg caggcctttg ggacttctc tcccacagat       840 gtgcataaac agtatgccat tgtgttccgg acaccccct atcacaagat gaagattgag       900
cggcctgtaa cagtgtttct gcaactgaaa cgcaagcgag gaggggacgt gtctgattcc      960
aaacagttca cctattaccc tctggtggaa gacaaggaag aggtgcagcg aagcggagg      1020 aaggcctttgc ccaccttctc ccagcccttc ggggtggct cccacatggg tggaggctct     1080
gggggtgcag ccggggcta cggaggagct ggaggaggtg gcagcctcgg tttcttcccc      1140
tcctccctgg cctacagccc ctaccagtcc ggcgcgggcc ccatgggctg ctacccggga     1200 ggcggggggcg gggcgcagat ggccgccacg gtgcccagca gggactccgg ggaggaagcc    1260
gcggagccga gcgcccccctc caggaccccc cagtgcgagc cgcaggcccc ggagatgctg   1320
cagcgagctc gagagtacaa cgcgcgcctg ttcggcctgg cgcagcgcag cgcccgagcc    1380
ctactcgact acggcgtcac cgcggacgcg cgcgcgctgc tggcgggaca cgccaccctg    1440
ctgacggcgc aggacgagaa cggagacaca ccactgcacc tagccatcat ccacgggcag    1500
accagtgtca ttgagcagat agtctatgtc atccaccacg cccaggacct cggcgttgtc    1560
aacctcacca accacctgca ccagacgccc ctgcacctgg cggtgatcac ggggcagacg    1620
agtgtggtga gctttctgct gcgggtaggt gcagacccag ctctgctgga tcggcatgga    1680
gactcagcca tgcatctggc gctgcgggca ggcgctggtg ctcctgagct gctgcgtgca    1740
ctgcttcaga gtggagctcc tgctgtgccc cagctgttgc atatgcctga ctttgaggga    1800
ctgtatccag tacacctggc ggtccgagcc cgaagccctg agtgcctgga tctgctggtg    1860
gacagtgggg ctgaagtgga ggccacagag cggcaggggg gacgaacagc cttgcatcta    1920
gccacagaga tggaggagct ggggttggtc acccatctgg tcaccaagct ccgggccaac    1980
gtgaacgctc gcacctttc agcctcctga                                     2010

<210> SEQ ID NO 45
<211> LENGTH: 478
<212> TYPE: PRT
<213> ORGANISM: Homo sapiens

<400> SEQUENCE: 45

Met Ala Ser Thr Asp Tyr Ser Thr Tyr Ser Gln Ala Ala Ala Gln Gln
 1               5                  10                  15

Gly Tyr Ser Ala Tyr Thr Ala Gln Pro Thr Gln Gly Tyr Ala Gln Thr
```

-continued

```
                20                  25                  30
Thr Gln Ala Tyr Gly Gln Gln Ser Tyr Gly Thr Tyr Gly Gln Pro Thr
                35                  40                  45
Asp Val Ser Tyr Thr Gln Ala Gln Thr Thr Ala Thr Tyr Gly Gln Thr
                50                  55                  60
Ala Tyr Ala Thr Ser Tyr Gly Gln Pro Pro Thr Gly Tyr Thr Thr Pro
65                  70                  75                  80
Thr Ala Pro Gln Ala Tyr Ser Gln Pro Val Gln Gly Tyr Gly Thr Gly
                    85                  90                  95
Ala Tyr Asp Thr Thr Thr Ala Thr Val Thr Thr Thr Gln Ala Ser Tyr
                100                 105                 110
Ala Ala Gln Ser Ala Tyr Gly Thr Gln Pro Ala Tyr Pro Ala Tyr Gly
                115                 120                 125
Gln Gln Pro Ala Ala Thr Ala Pro Thr Arg Pro Gln Asp Gly Asn Lys
                130                 135                 140
Pro Thr Glu Thr Ser Gln Pro Gln Ser Ser Thr Gly Gly Tyr Asn Gln
145                 150                 155                 160
Pro Ser Leu Gly Tyr Gly Gln Ser Asn Tyr Ser Tyr Pro Gln Val Pro
                    165                 170                 175
Gly Ser Tyr Pro Met Gln Pro Val Thr Ala Pro Pro Ser Tyr Pro Pro
                180                 185                 190
Thr Ser Tyr Ser Ser Thr Gln Pro Thr Ser Tyr Asp Gln Ser Ser Tyr
                195                 200                 205
Ser Gln Gln Asn Thr Tyr Gly Gln Pro Ser Ser Tyr Gly Gln Gln Ser
                210                 215                 220
Ser Tyr Gly Gln Gln Ser Ser Tyr Gly Gln Gln Pro Pro Thr Ser Tyr
225                 230                 235                 240
Pro Pro Gln Thr Gly Ser Tyr Ser Gln Ala Pro Ser Gln Tyr Ser Gln
                    245                 250                 255
Gln Ser Ser Ser Tyr Gly Gln Gln Asn Val Thr Gly Cys Ala Ser Met
                260                 265                 270
Tyr Leu His Thr Glu Gly Phe Ser Gly Pro Ser Pro Gly Asp Gly Ala
                275                 280                 285
Met Gly Tyr Gly Tyr Glu Lys Pro Leu Arg Pro Phe Pro Asp Asp Val
                290                 295                 300
Cys Val Val Pro Glu Lys Phe Glu Gly Asp Ile Lys Gln Glu Gly Val
305                 310                 315                 320
Gly Ala Phe Arg Glu Gly Pro Pro Tyr Gln Arg Arg Gly Ala Leu Gln
                    325                 330                 335
Leu Trp Gln Phe Leu Val Ala Leu Leu Asp Asp Pro Thr Asn Ala His
                340                 345                 350
Phe Ile Ala Trp Thr Gly Arg Gly Met Glu Phe Lys Leu Ile Glu Pro
                355                 360                 365
Glu Glu Val Ala Arg Leu Trp Gly Ile Gln Lys Asn Arg Pro Ala Met
                370                 375                 380
Asn Tyr Asp Lys Leu Ser Arg Ser Leu Arg Tyr Tyr Tyr Glu Lys Gly
385                 390                 395                 400
Ile Met Gln Lys Val Ala Gly Glu Arg Tyr Val Tyr Lys Phe Val Cys
                    405                 410                 415
Glu Pro Glu Ala Leu Phe Ser Leu Ala Phe Pro Asp Asn Gln Arg Pro
                420                 425                 430
Ala Leu Lys Ala Glu Phe Asp Arg Pro Val Ser Glu Glu Asp Thr Val
                435                 440                 445
```

```
Pro Leu Ser His Leu Asp Glu Ser Pro Ala Tyr Leu Pro Glu Leu Ala
    450                 455                 460
Gly Pro Ala Gln Pro Phe Gly Pro Lys Gly Gly Tyr Ser Tyr
465                 470                 475

<210> SEQ ID NO 46
<211> LENGTH: 2107
<212> TYPE: DNA
<213> ORGANISM: Homo sapiens

<400> SEQUENCE: 46
agagggagac ggacgttgag agaacgagga ggaaggagag aaaatggcgt ccacggatta      60
cagtacctat agccaagctg cagcgcagca gggctacagt gcttacaccg cccagcccac     120
tcaaggatat gcacagacca cccaggcata tgggcaacaa agctatggaa cctatggaca     180
gcccactgat gtcagctata cccaggctca gaccactgca acctatgggc agaccgccta     240
tgcaacttct tatggacagc ctcccactgg ttatactact ccaactgccc cccaggcata     300
cagccagcct gtccaggggt atggcactgg tgcttatgat accaccactg ctacagtcac     360
caccacccag gcctcctatg cagctcagtc tgcatatggc actcagcctg cttatccagc     420
ctatgggcag cagccagcag ccactgcacc tacaagaccg caggatggaa acaagcccac     480
tgagactagt caacctcaat ctagcacagg gggttacaac cagcccagcc taggatatgg     540
acagagtaac tacagttatc cccaggtacc tgggagctac cccatgcagc cagtcactgc     600
acctccatcc taccctccta ccagctattc ctctacacag ccgactagtt atgatcagag     660
cagttactct cagcagaaca cctatgggca accgagcagc tatggacagc agagtagcta     720
tggtcaacaa agcagctatg ggcagcagcc tcccactagt tacccacccc aaactggatc     780
ctacagccaa gctccaagtc aatatagcca acagagcagc agctacgggc agcagaatgt     840
cacccgggtg cgcatcaatg tacctccaca gagggcttc tctgggccct ctccaggtga     900
cggggccatg ggctatggct atgagaaacc tctgcgacca ttcccagatg atgtctgcgt     960
tgtccctgag aaatttgaag gagacatcaa gcaggaaggg gtcggtgcat ttcgagaggg    1020
gccgccctac cagcgccggg gtgccctgca gctgtggcaa tttctggtgg ccttgctgga    1080
tgacccaaca aatgcccatt tcattgcctg gacgggccgg ggaatggagt tcaagctcat    1140
tgagcctgag gaggtcgcca ggctctgggg catccagaag aaccggccag ccatgaatta    1200
cgacaagctg agccgctcgc tccgatacta ttatgagaaa ggcatcatgc agaaggtggc    1260
tggtgagcgt tacgtgtaca gtttgtgtg tgagcccgag gccctcttct ctttggcctt    1320
cccggacaat cagcgtccag ctctcaaggc tgagtttgac cggcctgtca gtgaggagga    1380
cacagtccct ttgtcccact ggatgagag ccccgcctac ctcccagagc tggctggccc    1440
cgcccagcca tttggcccca agggtggcta ctcttactag ccccagcgg ctgttccccc    1500 tgccgcaggt gggtgctgcc ctgtgtacat ataaatgaat ctggtgttgg ggaaaccttc    1560
atctgaaacc cacagatgtc tctggggcag atccccactg tcctaccagt tgccctagcc    1620
cagactctga gctgctcacc ggagtcattg ggaaggaaaa gtggagaaat ggcaagtcta    1680
gagtctcaga aactccctg ggggtttcac ctgggccctg gaggaattca gctcagcttc    1740
ttcctaggtc caagccccc acaccttttc cccaaccaca gagaacaaga gtttgttctg    1800
ttctggggga cagagaaggc gcttcccaac ttcatactgg caggagggtg aggaggttca    1860
ctgagctccc cagatctccc actgcgggga gacagaagcc tggactctgc cccacgctgt    1920
```

```
ggccctggag ggtcccggtt tgtcagttct tggtgctctg tgttcccaga ggcaggcgga    1980
ggttgaagaa aggaacctgg gatgagggt gctgggtata agcagagagg gatgggttcc    2040
tgctccaagg gacccttgc ctttcttctg cccttcccta ggcccaggcc tgggtttgta    2100
tcccatt                                                               2107

<210> SEQ ID NO 47
<211> LENGTH: 418
<212> TYPE: PRT
<213> ORGANISM: Homo sapiens

<400> SEQUENCE: 47

Met Thr Glu Glu Thr His Pro Asp Asp Ser Tyr Ile Val Arg Val
 1               5                  10                  15

Lys Ala Val Val Met Thr Arg Asp Asp Ser Ser Gly Gly Trp Phe Pro
            20                  25                  30

Gln Glu Gly Gly Gly Ile Ser Arg Val Gly Val Cys Lys Val Met His
         35                  40                  45

Pro Glu Gly Asn Gly Arg Ser Gly Phe Leu Ile His Gly Glu Arg Gln
     50                  55                  60

Lys Asp Lys Leu Val Val Leu Glu Cys Tyr Val Arg Lys Asp Leu Val
 65                  70                  75                  80

Tyr Thr Lys Ala Asn Pro Thr Phe His His Trp Lys Val Asp Asn Arg
                 85                  90                  95

Lys Phe Gly Leu Thr Phe Gln Ser Pro Ala Asp Ala Arg Ala Phe Asp
            100                 105                 110

Arg Gly Val Arg Lys Ala Ile Glu Asp Leu Ile Glu Gly Ser Thr Thr
        115                 120                 125

Ser Ser Ser Thr Ile His Asn Glu Ala Glu Leu Gly Asp Asp Val
    130                 135                 140

Phe Thr Thr Ala Thr Asp Ser Ser Ser Asn Ser Ser Gln Lys Arg Glu
145                 150                 155                 160

Gln Pro Thr Arg Thr Ile Ser Ser Pro Thr Ser Cys Glu His Arg Arg
                165                 170                 175

Ile Tyr Thr Leu Gly His Leu His Asp Ser Tyr Pro Thr Asp His Tyr
            180                 185                 190

His Leu Asp Gln Pro Met Pro Arg Pro Cys Arg Gln Val Ser Phe Pro
        195                 200                 205

Asp Asp Asp Glu Glu Ile Val Arg Ile Asn Pro Arg Glu Lys Ile Trp
    210                 215                 220

Met Thr Gly Tyr Glu Asp Tyr Arg His Ala Pro Val Arg Gly Lys Tyr
225                 230                 235                 240

Pro Asp Pro Ser Glu Asp Ala Asp Ser Ser Tyr Val Arg Phe Ala Lys
                245                 250                 255

Gly Glu Val Pro Lys His Asp Tyr Asn Tyr Pro Tyr Val Asp Ser Ser
            260                 265                 270

Asp Phe Gly Leu Gly Glu Asp Pro Lys Gly Arg Gly Gly Ser Val Ile
        275                 280                 285

Lys Thr Gln Pro Ser Arg Gly Lys Ser Arg Arg Lys Glu Asp Gly
    290                 295                 300

Glu Arg Ser Arg Cys Val Tyr Cys Arg Asp Met Phe Asn His Glu Glu
305                 310                 315                 320

Asn Arg Arg Gly His Cys Gln Asp Ala Pro Asp Ser Val Arg Thr Cys
                325                 330                 335
```

```
Ile Arg Arg Val Ser Cys Met Trp Cys Ala Asp Ser Met Leu Tyr His
            340                 345                 350

Cys Met Ser Asp Pro Glu Gly Asp Tyr Thr Asp Pro Cys Ser Cys Asp
            355                 360                 365

Thr Ser Asp Glu Lys Phe Cys Leu Arg Trp Met Ala Leu Ile Ala Leu
        370                 375                 380

Ser Phe Leu Ala Pro Cys Met Cys Cys Tyr Leu Pro Leu Arg Ala Cys
385                 390                 395                 400

Tyr His Cys Gly Val Met Cys Arg Cys Cys Gly Gly Lys His Lys Ala
                405                 410                 415

Ala Ala

<210> SEQ ID NO 48
<211> LENGTH: 4119
<212> TYPE: DNA
<213> ORGANISM: Homo sapiens

<400> SEQUENCE: 48
```

| | | | | | |
|---|---|---|---|---|---|
| cacgaggtgc | accccttccc | ccaaacccta | tcccgcgccc | tgcttcccct | tctgctgcgg | 60 |
| cgccctcttc | atctctagcc | gccccccctc | cccaaatcag | gcgatctccg | gagatgtgaa | 120 |
| gaagggggc | gagcggacag | gaagatgaag | ggagcaaagc | tgcccgccgc | gggacaggcg | 180 |
| tctaggtaac | aagaaaatga | ccgaagaaac | acacccagac | gatgacagct | atattgtgcg | 240 |
| tgtcaaggct | gtggttatga | ccagagatga | ctccagcggg | ggatggttcc | cacaggaagg | 300 |
| aggcgggatc | agtcgcgtcg | gggtctgtaa | ggtcatgcac | cccgaaggca | atggacgaag | 360 |
| cggcttctc | atccatggtg | aacgacagaa | agacaaactg | gtggtattgg | aatgctatgt | 420 |
| aagaaaggac | ttggtctaca | ccaaagccaa | tccaacgttt | catcactgga | aggtcgataa | 480 |
| taggaagttt | ggacttactt | tccaaagccc | tgctgatgcc | cgagcctttg | acaggggagt | 540 |
| aaggaaagca | atcgaagacc | ttatagaagg | ttcaacaacg | tcatcttcca | ccatccataa | 600 |
| tgaagctgag | cttggcgatg | atgacgtttt | tacaacagct | acagacagtt | cttctaattc | 660 |
| ctctcagaag | agagagcaac | ctactcggac | aatctcctct | cccacatcct | gtgagcaccg | 720 |
| gaggatttat | accctgggcc | acctccacga | ctcatacccc | acagaccact | atcacctcga | 780 |
| tcagccgatg | ccaaggccct | gccgccaggt | gagcttcccg | gacgacgacg | aggagatcgt | 840 |
| gcgcatcaac | ccccgggaga | gatctggat | gacggggtac | gaggattacc | ggcacgcacc | 900 |
| cgtcagggc | aagtacccgg | acccctcgga | ggacgcggac | tcctcctacg | tgcgcttcgc | 960 |
| caagggcgag | gtccccaagc | atgactacaa | ctaccccta | gtggactcct | cagactttgg | 1020 |
| cctaggcgag | gaccccaaag | gccgcggggg | cagcgtgatc | aagacgcagc | cctcccgggg | 1080 |
| caagtcgcgg | cggcggaagg | aggacggaga | gcgctcgcgg | tgcgtgtact | gcagggacat | 1140 |
| gttcaaccac | gaggagaacc | gccggggcca | ctgccaggac | gccccgact | ccgtgagaac | 1200 |
| ttgcatccgc | cgggtgagct | gcatgtggtg | cgcggacagc | atgctctatc | actgtatgtc | 1260 |
| ggaccccgag | ggagactata | cagacccttg | ctcgtgcgat | actagcgacg | agaagttttg | 1320 |
| cctccggtgg | atggctctta | ttgccttgtc | tttcctggcc | ccctgtatgt | gctgttacct | 1380 |
| gccccttcgg | gcctgctacc | actgcggagt | gatgtgcagg | tgctgtggcg | ggaagcacaa | 1440 |
| agcggccgcg | tgactcagtt | tccctccctt | ctccctccat | ccgcagccac | agggggaactc | 1500 |
| gtctcttaca | tactctcatc | ttctcccccg | ctccctttcca | ctccaaggag | cgaggagggc | 1560 |
| aagcggcctc | ccagctcccct | ggtacctcga | ggcaccattc | cagccaggga | cgctgccggg | 1620 |

```
tagactctcc actcccsctg ccgcccacac tgcagcagcc acatccatac acacacgctc    1680
gcacagtgtt ctgaggaagg aaccttcgcc acagactcct gtactattaa caatctgtaa    1740
ccaagctaac tgtctcatcc atgtgttgat ttcctgtttc ctcctccccc gcctcttcca    1800
gttcaaagga gtctgcaatt ggaactgctg attttcggtg ggttttgtag ttgattttc     1860 caagagcgtc gaagactctc tttctcttgg ttccttgc ctgtcgctag caagcatctg     1920
gttcagcgga atgggatgt gagaatgatg aaacccgaca gaagtatctc agcctgcagt    1980
cagttattat gtataggagg tgagctagtt aacaaacttg taccacaaaa caatatcgct    2040
ttaacttttc taaagccaaa tttcccatgt aagctgcagt ttctatcttt agcccatcat    2100
cattttctgc cccccaaaa tctgttgaaa tgattcactg atgcaaaaca ttcacccgta     2160
atagactgag aattgagcct taacttcaga ttaacttgtg agaatcagga aaattccttc    2220
aactgcattg catcctcttg gaccagggct agaatgggga tttcaggttt ctatgagcct    2280
ccccattacc cctaaagtag aacatttttt aaattgtgtt gccaccactt ctaaaaattt    2340
agcaatatta gataggata ctagtgaagt aagaaatttt gcttgttgtt ttgcaaacca     2400
aatagttttc tcaaacacaa atcagtgttc ccacgaacaa gttccagttg agaaacacta    2460
aggttatggt gaataaaacc atagggagct tcttccccc aaccctggc tatttatat       2520 taatggggag aggggatttt taaatgtcat aaatttgaag agtggtgggt tgcattttct    2580
tcatgggttt atgttttcgt ttcattttgg actcaatttc acatcaccaa attcctcatt    2640
tatacttggg gaaaaaacaa ggccatatgt aaaaacccct tccaatgccta agtgtctttc   2700 tcctgcaact ccaaacccag actcgccact ttgggtgcac aggtggttag gtcagccaac    2760
tggttctgcc tgtcgccttg ccacggagga ggcttctaat tagctggaaa agagtatttt    2820
tctaatacgt tgcaaggatt agccaaatct tcttattgaa gaaagaagaa aagtgaagag    2880
tggttaccta tacctagcat agtacaatca gaacctcgtg gagaccaccg gggacaggct    2940
tgcggacgcc ggctgttctt cccgccacga tctttctgtg gtagcggcca gcagaagaca    3000
tggcctgctc cccactccct ttccccactc cttctttatt gcacacagga caccagtctt    3060
caaggaaagg gactttttttc cagtctgcca atcatattgg gaaagtgcta gctgtgctca    3120
ccttcatggg gctgtttcca gctcgtccac aagctcatcg attttcttta gtagattacc    3180
ggtgtaaata cccagtgtgc ttatgagtca gttagtagac gtcttcattc attggagtaa    3240
ctggtttagg ctttccagtt tggaaaagga gcagagagct gtccatctgg attgatggaa    3300
gaaaagagaa cctcatccat gcctggagaa catctagaaa accttcagcc agcctccagt    3360
gctgtcgaga gaccaccttc ccccgacccg gaggcacttc cttggggtct ttctctaggg    3420
tctcctctct acaaagcaca acactaatgt tcgtttcctt agacctcagt tcaagtgccc    3480
ctatttattt caataagaac gcacatatcc cagctgtttt ttgtttgtca cctctattta    3540
gttgttacct gtttctctct tctttcaccc cctgtccttt tccacccttt taagagttac    3600
gctagcagat cttactccac gtatactttt tggtttgtga aggcatcggt taagggcaca    3660
aagacagcca tggggacatt tatgtaaata cgtctctaat tgccacactg cagctgaaca    3720
gtgtgtagta ttttcccagt cagctttgcc atactgacgt caatcatttg agagaaatta    3780
ttcagatttt attttttgtat ctgtggtaac aaaacattaa ccaaaagatt ttctgtccag   3840
aagcctcccc gacccccaa gctatttgct cacattaaca aattaaagtg cctgaagcat     3900
aattcattct ttacctgtat actaaaaacc ctgttgtatt gattttttta taataagcct    3960
ttttacctct gtgtaaaaaa tatatataca agtgtatgat gtacatttta gttcttaact    4020
```

```
tttttttttat ggtttctaat atgtatgacc aatgtagcca ttgctttaaa atgtaccgtg    4080
taaatataaa cacatcctat cagaaaaaaa aaaaaaaaa                           4119
```

<210> SEQ ID NO 49
<211> LENGTH: 614
<212> TYPE: PRT
<213> ORGANISM: Homo sapiens

<400> SEQUENCE: 49

```
Arg Ser Gly Gln Pro Arg Ala Glu Gly Leu Gly Ala Gly Ala Ala Gly
  1               5                  10                  15

Pro Leu Arg Ala Met Ala Ala Pro Val Lys Gly Asn Arg Lys Gln Ser
                 20                  25                  30

Thr Glu Gly Asp Ala Leu Asp Pro Ala Ser Pro Lys Pro Ala Gly
             35                  40                  45

Lys Gln Asn Gly Ile Gln Asn Pro Ile Ser Leu Glu Asp Ser Pro Glu
     50                  55                  60

Ala Gly Gly Glu Arg Glu Glu Gln Glu Arg Glu Glu Gln Ala
 65                  70                  75                  80

Phe Leu Val Ser Leu Tyr Lys Phe Met Lys Glu Arg His Thr Pro Ile
                 85                  90                  95

Glu Arg Val Pro His Leu Gly Phe Lys Gln Ile Asn Leu Trp Lys Ile
                100                 105                 110

Tyr Lys Ala Val Glu Lys Leu Gly Ala Tyr Glu Leu Val Thr Gly Arg
            115                 120                 125

Arg Leu Trp Lys Asn Val Tyr Asp Glu Leu Gly Gly Ser Pro Gly Ser
        130                 135                 140

Thr Ser Ala Ala Thr Cys Thr Arg Arg His Tyr Glu Arg Leu Val Leu
145                 150                 155                 160

Pro Tyr Val Arg His Leu Lys Gly Glu Asp Asp Lys Pro Leu Pro Thr
                165                 170                 175

Ser Lys Pro Arg Lys Gln Tyr Lys Met Ala Lys Glu Asn Arg Gly Asp
            180                 185                 190

Asp Gly Ala Thr Glu Arg Pro Lys Lys Ala Lys Glu Glu Arg Arg Met
        195                 200                 205

Asp Gln Met Met Pro Gly Lys Thr Lys Ala Asp Ala Ala Asp Pro Ala
    210                 215                 220

Pro Leu Pro Ser Gln Glu Pro Pro Arg Asn Ser Thr Glu Gln Gln Gly
225                 230                 235                 240

Leu Ala Ser Gly Ser Ser Val Ser Phe Val Gly Ala Ser Gly Cys Pro
                245                 250                 255

Glu Ala Tyr Lys Arg Leu Leu Ser Ser Phe Tyr Cys Lys Gly Thr His
            260                 265                 270

Gly Ile Met Ser Pro Leu Ala Lys Lys Leu Leu Ala Gln Val Ser
        275                 280                 285

Lys Val Glu Ala Leu Gln Cys Gln Glu Glu Gly Cys Arg His Gly Ala
    290                 295                 300

Glu Pro Gln Ala Ser Pro Ala Val His Leu Pro Glu Ser Pro Gln Ser
305                 310                 315                 320

Pro Lys Gly Leu Thr Glu Asn Ser Arg His Arg Leu Thr Pro Gln Glu
                325                 330                 335

Gly Leu Gln Ala Pro Gly Gly Ser Leu Arg Glu Glu Ala Gln Ala Gly
            340                 345                 350
```

```
Pro Cys Pro Ala Ala Pro Ile Phe Lys Gly Cys Phe Tyr Thr His Pro
        355                 360                 365
Thr Glu Val Leu Lys Pro Val Ser Gln His Pro Arg Asp Phe Phe Ser
    370                 375                 380
Arg Leu Lys Asp Gly Val Leu Leu Gly Pro Pro Gly Lys Glu Gly Leu
385                 390                 395                 400
Ser Val Lys Glu Pro Gln Leu Val Trp Gly Gly Asp Ala Asn Arg Pro
            405                 410                 415
Ser Ala Phe His Lys Gly Ser Arg Lys Gly Ile Leu Tyr Pro Lys
        420                 425                 430
Pro Lys Ala Cys Trp Val Ser Pro Met Ala Lys Val Pro Ala Glu Ser
        435                 440                 445
Pro Thr Leu Pro Pro Thr Phe Pro Ser Ser Pro Gly Leu Gly Ser Lys
    450                 455                 460
Arg Ser Leu Glu Glu Glu Gly Ala Ala His Ser Gly Lys Arg Leu Arg
465                 470                 475                 480
Ala Val Ser Pro Phe Leu Lys Glu Ala Asp Ala Lys Lys Cys Gly Ala
                485                 490                 495
Lys Pro Ala Gly Ser Gly Leu Val Ser Cys Leu Leu Gly Pro Ala Leu
        500                 505                 510
Gly Pro Val Pro Pro Glu Ala Tyr Arg Gly Thr Met Leu His Cys Pro
    515                 520                 525
Leu Asn Phe Thr Gly Thr Pro Gly Pro Leu Lys Gly Gln Ala Ala Leu
    530                 535                 540
Pro Phe Ser Pro Leu Val Ile Pro Ala Phe Pro Ala His Phe Leu Ala
545                 550                 555                 560
Thr Ala Gly Pro Ser Pro Met Ala Ala Gly Leu Met His Phe Pro Pro
            565                 570                 575
Thr Ser Phe Asp Ser Ala Leu Arg His Arg Leu Cys Pro Ala Ser Ser
                580                 585                 590
Ala Trp His Ala Pro Pro Val Thr Thr Tyr Ala Ala Pro His Phe Phe
        595                 600                 605
His Leu Asn Thr Lys Leu
        610

<210> SEQ ID NO 50
<211> LENGTH: 2173
<212> TYPE: DNA
<213> ORGANISM: Homo sapiens

<400> SEQUENCE: 50
cggtccggac agccgcgcgc tgagggtctc ggggcgggcg ccgcgggacc tctccgggcc    60
atggcagccc ctgtcaaagg aacaggaag cagtccacgg agggtgacgc cctagaccca   120
cctgcatccc ccaaacctgc tggcaagcag aacggaatcc agaacccat ctcgctggag   180
gactccccg aggcaggcgg ggagcgggag gaggagcagg agcgggagga ggagcaggcc   240
ttcctggtca gcctctacaa gttcatgaag gagcgcacaca cgcccatcga gggtgcccc   300
catctcggct tcaagcagat taacctgtgg aagatctaca aagcagtgga gaagctgggg   360
gcctatgagc tggtgaccgg cgcgccgcctc tggaagaacg tgtacgacga gctgggggc   420
agcccaggca gcaccagcgc ggccacgtgc acgccgcc actacgagag gctggtcctg   480
ccatacgtgc ggcacctgaa gggggaggat gacaagccgc tgcccacctc caagcccagg   540
aaacagtaca gatggctaa ggagaacagg ggggatgatg gggccaccga gaggccgaag   600
```

-continued

```
aaggccaagg aggagcggcg catggaccag atgatgccag gaaagaccaa agcagatgct    660
gctgacccag caccacttcc cagccaggag ccccccagga acagcacaga acagcagggc    720
ctggcctctg ggtcttctgt gtcctttgtg ggtgccagcg gctgtcctga ggcctacaag    780
cggctcctat ccagcttcta ctgcaagggg acacacggca tcatgtcacc actggccaaa    840
aagaagctcc tggcccaggt gagcaaggtg gaggccttgc agtgccagga ggagggctgc    900
cgccatgggg cagagcccca ggcgtcccca gctgttcacc tcccagagag tccccagagc    960
cccaaagggc tgactgagaa ctccaggcac cggctgaccc ctcaggaggg attgcaggcc   1020
ccaggtggca gcctcagaga ggaggcgcag gcaggcccct gcccggcagc cccatcttc    1080
aagggctgct tctacaccca ccccaccgag gtgctgaagc ctgtcagcca gcacccagg    1140
gacttcttct ctagacttaa agatggggtg ctattgggc ctcctggcaa agaggggctg    1200
tcagtgaaag agccccagct ggtgtggggc ggagacgcta accgcccttc tgcgttccat    1260
aaaggtggct ccagaaaggg catcctctac cccaagccca aagcctgctg ggtgtccccc    1320
atggccaagg tcccagccga gagccccacg ctcccgccca ccttcccag tagcccaggc    1380
ctgggcagca agcgcagcct ggaggaagag ggtgctgccc acagtgggaa gagactgcgg    1440
gccgtgtctc cctttcttaa ggaggcggat gccaagaagt gtggggccaa acctgcaggg    1500
tccggcctgg tctcctgcct tctgggccca gccctgggc ctgtgccccc agaggcctac    1560
aggggcacca tgctgcactg cccgctgaac ttcactggca ccccgggccc cttgaagggc    1620
caggctgcac tcccccttcag ccccctggtc atcccggcct tccgccca cttcctggcc    1680
accgcaggcc cctcgcccat ggccgctggc ctgatgcact tcccccaac gtccttcgac    1740
agtgccctcc gccacagact ttgcccggcc tcatctgcct ggcacgcacc accagtcaca    1800
acctatgcag cgccccactt cttccacctc aacaccaagc tgtaggccag cccatggtgt    1860
tgtgtacact gtggagtcga caggggccta caacaggcag gtactgctgc caggggctc    1920
tgaactagtg cctgctaccc aggacacccg ggccatgccc ctggctgggc agcctggcac    1980
aagtgaagaa gaaggcagtg ggaaaactgg gtttatctca aggcagcagc ctgagcccag    2040
gagcagagga cccagttgtt ataaggcgct gggagaggat gggcagctcc cactgcccca    2100
gagcggasst cgaagcaccc aggttgccca cggaaaatcc aataaaaaga caccagtgtg    2160
aatccaaaaa aaa                                                      2173
```

<210> SEQ ID NO 51
<211> LENGTH: 701
<212> TYPE: PRT
<213> ORGANISM: Homo sapiens

<400> SEQUENCE: 51

```
Met Met Lys Arg Gln Leu His Arg Met Arg Gln Leu Ala Gln Thr Gly
1               5                  10                  15

Ser Leu Gly Arg Thr Pro Glu Thr Ala Glu Phe Leu Gly Glu Asp Leu
            20                  25                  30

Leu Gln Val Glu Gln Arg Leu Glu Pro Ala Lys Arg Ala Ala His Asn
        35                  40                  45

Ile His Lys Arg Leu Gln Ala Cys Leu Gln Gly Gln Ser Gly Ala Asp
    50                  55                  60

Met Asp Lys Arg Val Lys Lys Leu Pro Leu Met Ala Leu Ser Thr Thr
65                  70                  75                  80

Met Ala Glu Ser Phe Lys Glu Leu Asp Pro Asp Ser Ser Met Gly Lys
                85                  90                  95
```

```
Ala Leu Glu Met Ser Cys Ala Ile Gln Asn Gln Leu Ala Arg Ile Leu
            100                 105                 110

Ala Glu Phe Glu Met Thr Leu Glu Arg Asp Val Leu Gln Pro Leu Ser
        115                 120                 125

Arg Leu Ser Glu Glu Glu Leu Pro Ala Ile Leu Lys His Lys Lys Ser
    130                 135                 140

Leu Gln Lys Leu Val Ser Asp Trp Asn Thr Leu Lys Ser Arg Leu Ser
145                 150                 155                 160

Gln Ala Thr Lys Asn Ser Gly Ser Ser Gln Gly Leu Gly Gly Ser Pro
                165                 170                 175

Gly Ser His Ser His Thr Thr Met Ala Asn Lys Val Glu Thr Leu Lys
            180                 185                 190

Glu Glu Glu Glu Glu Leu Lys Arg Lys Val Glu Gln Cys Arg Asp Glu
        195                 200                 205

Tyr Leu Ala Asp Leu Tyr His Phe Val Thr Lys Glu Asp Ser Tyr Ala
    210                 215                 220

Asn Tyr Phe Ile Arg Leu Leu Glu Ile Gln Ala Asp Tyr His Arg Arg
225                 230                 235                 240

Ser Leu Ser Ser Leu Asp Thr Ala Leu Ala Glu Leu Arg Glu Asn His
                245                 250                 255

Gly Gln Ala Asp His Ser Pro Ser Met Thr Ala Thr His Phe Pro Arg
            260                 265                 270

Val Tyr Gly Val Ser Leu Ala Thr His Leu Gln Glu Leu Gly Arg Glu
        275                 280                 285

Ile Ala Leu Pro Ile Glu Ala Cys Val Met Met Leu Leu Ser Glu Gly
    290                 295                 300

Met Lys Glu Glu Gly Leu Phe Arg Leu Ala Ala Gly Ala Ser Val Leu
305                 310                 315                 320

Lys Arg Leu Lys Gln Thr Met Ala Ser Asp Pro His Ser Leu Glu Glu
                325                 330                 335

Phe Cys Ser Asp Pro His Ala Val Ala Gly Ala Leu Lys Ser Tyr Leu
            340                 345                 350

Arg Glu Leu Pro Glu Pro Leu Met Thr Phe Asp Leu Tyr Asp Asp Trp
        355                 360                 365

Met Arg Ala Ala Ser Leu Lys Glu Pro Gly Ala Arg Leu Gln Ala Leu
    370                 375                 380

Gln Glu Val Cys Ser Arg Leu Pro Pro Glu Asn Leu Ser Asn Leu Arg
385                 390                 395                 400

Tyr Leu Met Lys Phe Leu Ala Arg Leu Ala Glu Glu Gln Glu Val Asn
                405                 410                 415

Lys Met Thr Pro Ser Asn Ile Ala Ile Val Leu Gly Pro Asn Leu Leu
            420                 425                 430

Trp Pro Pro Glu Lys Glu Gly Asp Gln Ala Gln Leu Asp Ala Ala Ser
        435                 440                 445

Val Ser Ser Ile Gln Val Val Gly Val Val Glu Ala Leu Ile Gln Ser
    450                 455                 460

Ala Asp Thr Leu Phe Pro Gly Asp Ile Asn Phe Asn Val Ser Gly Leu
465                 470                 475                 480

Phe Ser Ala Val Thr Leu Gln Asp Thr Val Ser Asp Arg Leu Ala Ser
                485                 490                 495

Glu Glu Leu Pro Ser Thr Ala Val Pro Thr Pro Ala Thr Thr Pro Ala
            500                 505                 510
```

```
Pro Ala Pro Ala Pro Ala Pro Ala Pro Ala Leu Ala Ser Ala
        515                 520                 525
Ala Thr Lys Glu Arg Thr Glu Ser Glu Val Pro Arg Pro Ala Ser
    530                 535                 540
Pro Lys Val Thr Arg Ser Pro Glu Thr Ala Ala Pro Val Glu Asp
545                 550                 555                 560
Met Ala Arg Arg Thr Lys Arg Pro Ala Pro Arg Pro Thr Met Pro
                565                 570                 575
Pro Pro Gln Val Ser Gly Ser Arg Ser Ser Pro Ala Pro Pro Leu
            580                 585                 590
Pro Pro Gly Ser Gly Ser Pro Gly Thr Pro Gln Ala Leu Pro Arg Arg
        595                 600                 605
Leu Val Gly Ser Ser Leu Arg Ala Pro Thr Val Pro Pro Leu Pro
    610                 615                 620
Pro Thr Pro Pro Gln Pro Ala Arg Arg Gln Ser Arg Ser Pro Ala
625                 630                 635                 640
Ser Pro Ser Pro Ala Ser Pro Gly Pro Ala Ser Pro Ser Pro Val Ser
                645                 650                 655
Leu Ser Asn Pro Ala Gln Val Asp Leu Gly Ala Ala Thr Ala Glu Gly
            660                 665                 670
Gly Ala Pro Glu Ala Ile Ser Gly Val Pro Thr Pro Ala Ile Pro
        675                 680                 685
Pro Gln Pro Arg Pro Arg Ser Leu Ala Ser Glu Thr Asn
    690                 695                 700

<210> SEQ ID NO 52
<211> LENGTH: 2592
<212> TYPE: DNA
<213> ORGANISM: Homo sapiens

<400> SEQUENCE: 52
cgcccaccca tccggggcaa gagccgcgcc gcaggagagg caggctggac cggggggctcc     60 ccgggcccgc gacccccgcc gtgaccccgc agccccagc tcgccccaa gatgatgaag     120 aggcagctgc accgcatgcg gcagctggcc cagacgggca gcttgggacg caccccggag     180
accgctgagt tcctgggtga ggacctgctg caggtagaac agcggctgga gccgccaag     240 cgggcagccc acaacatcca aagcggctg caggcctgtc tgcagggcca gagcggggca     300
gacatggaca gcgggtgaa gaagcttccc ctcatggctc tgtccaccac gatggctgag     360
agcttcaagg agctggaccc tgattccagc atggggaagg ccttggagat gagctgtgcc     420
atccagaatc agctggcccg catcctggcc gagtttgaga tgaccctgga gagggacgtc     480
ctgcagccac tcagcaggct gagtgaggag gagctgccag ccatcctcaa acacaagaaa     540
agcctccaga gctcgtgtc cgactggaac acactcaaga gcaggctcag tcaggcaacc     600
aagaattcag gcagcagtca aggcctagga ggcagcccgg gtagtcacag ccatacgacc     660
atggccaaca aggtggagac gctgaaggag gaggaggagg agctgaagag gaaagtggag     720
caatgcaggg acgagtactt ggctgacctg taccactttg ttaccaagga ggactccatat     780 gccaactact tcattcgtct cctggagatt caggccgatt accatcgcag gtcactgagc     840
tcgctggaca cagccctggc tgagctgagg gagaaccacg ccaagcaga ccactccccct     900 tcgatgacag ccacccactt ccccagggtg tatgggggtgt cgctggcaac ccacctgcaa     960
gagctgggcc gggagattgc cctgccccatc gaggcctgcg tcatgatgct gctttctgag    1020
ggcatgaagg aagagggtct cttccgtctg gctgctgggg cctcggtgct gaagcgtctc    1080
```

```
aagcagacaa tggcctcgga cccccacagc ctggaggagt tctgctccga cccgcacgct  1140
gtggcaggtg ccctcaagtc ctatctgcgg gagctgccag agcctctgat gaccttcgac  1200
ctctatgatg actggatgag ggcagccagc ctgaaggagc aggggcccg gctgcaggcc  1260 ctccaagagg tgtgcagccg cctaccccc gagaacctca gcaacctcag gtacctgatg  1320
aagttcctgg cacggctggc cgaggagcag gaggtgaaca agatgacacc cagcaacatc  1380
gccatagtcc tgggacccaa cttgctgtgg ccacctgaga agaagggga ccaggcccag  1440 ctggatgcag cctccgtgtc ttccatccag gtggtgggcg tcgtcgaggc gctgatccag  1500
agcgcagaca ccctcttccc tggagacatc aacttcaacg tgtcaggcct cttctcagct  1560
gttaccctcc aggacacagt cagtgacagg ctggcctctg aggaacttcc gtccactgcc  1620
gtgcccaccc cagccaccac cccggctccg gctccggctc cagctccagc tccggcccca  1680
gccttggctt cagcagctac caaggaaagg acagagtctg aggtgcctcc cagaccagcc  1740
tcccccaagg tcaccaggag tccccggag acagctgccc cagtggagga catggctcgg  1800
aggaccaagc gccggcgcc agccggccc accatgccgc cccccaggt ctccggctcc  1860 cgctcctccc ctccagcccc gcccttgccc cctggctctg gcagccctgg gacccccaa  1920 gccctgcccc gacgtctggt tggcagcagc ctccgagccc cacagtgcc accccgtta  1980 cccccacac cccctcagcc tgccggcgc caaagccggc gttcaccagc ctcccccagc  2040
ccggcctccc caggtccagc ctcccccagc ccagtctctt tgagtaaccc tgcacaggtg  2100
gacctggggg ctgccacagc agagggagga gcccctgagg ctatcagtgg ggtccccact  2160
cccccagcta tcccccctca gccccgcccc aggagccttg cctcagagac caactgagtg  2220
gctggtttct ccctaagcag ccctcagcac cccctccctc cccacctggc cctcccagga  2280
cagctctcgc ccccacaaa ggggcatggg cctccagcct ttgcccacaa gtgcctcagt  2340
gcccactggg tcgccccca tggccaggag ggctcaggac aatcctctat ttcctgacct  2400
tttcctcgtc caccctgggc ttggggaccc ccaccggga ctctccactc tccggcaggt  2460
cctaggggag ccaccggaag gaaggagagg tttgcctgct cctacgggac tgattcttct  2520
cttgccgaca tgttttttgt aaggctggta aataaattat tttggacaaa actggaaaaa  2580 aaaaaaaaa aa                                                       2592
```

<210> SEQ ID NO 53
<211> LENGTH: 347
<212> TYPE: PRT
<213> ORGANISM: Homo sapiens

<400> SEQUENCE: 53

```
Met Glu Ser Pro Ala Ser Ser Gln Pro Ala Ser Met Pro Gln Ser Lys
  1               5                  10                  15

Gly Lys Ser Lys Arg Lys Lys Asp Leu Arg Ile Ser Cys Met Ser Lys
             20                  25                  30

Pro Pro Ala Pro Asn Pro Thr Pro Pro Arg Asn Leu Asp Ser Arg Thr
         35                  40                  45

Phe Ile Thr Ile Gly Asp Arg Asn Phe Glu Val Glu Ala Asp Asp Leu
     50                  55                  60

Val Thr Ile Ser Glu Leu Gly Arg Gly Ala Tyr Gly Val Val Glu Lys
 65                  70                  75                  80

Val Arg His Ala Gln Ser Gly Thr Ile Met Ala Val Lys Arg Ile Arg
                 85                  90                  95
```

```
Ala Thr Val Asn Ser Gln Glu Gln Lys Arg Leu Leu Met Asp Leu Asp
            100                 105                 110

Ile Asn Met Arg Thr Val Asp Cys Phe Tyr Val Thr Phe Tyr Gly
        115                 120                 125

Ala Leu Phe Arg Glu Gly Asp Val Trp Ile Cys Met Glu Leu Met Asp
        130                 135                 140

Thr Ser Leu Asp Lys Phe Tyr Arg Lys Val Leu Asp Lys Asn Met Thr
145                 150                 155                 160

Ile Pro Glu Asp Ile Leu Gly Glu Ile Ala Val Ser Ile Val Arg Ala
                165                 170                 175

Leu Glu His Leu His Ser Lys Leu Ser Val Ile His Arg Asp Val Lys
                180                 185                 190

Pro Ser Asn Val Leu Ile Asn Lys Glu Gly His Val Lys Met Cys Asp
            195                 200                 205

Phe Gly Ile Ser Gly Tyr Leu Val Asp Ser Val Ala Lys Thr Met Asp
    210                 215                 220

Ala Gly Cys Lys Pro Tyr Met Ala Pro Glu Arg Ile Asn Pro Glu Leu
225                 230                 235                 240

Asn Gln Lys Gly Tyr Asn Val Lys Ser Asp Val Trp Ser Leu Gly Ile
                245                 250                 255

Thr Met Ile Glu Met Ala Ile Leu Arg Phe Pro Tyr Glu Ser Trp Gly
            260                 265                 270

Thr Pro Phe Gln Gln Leu Lys Gln Val Val Glu Glu Pro Ser Pro Gln
        275                 280                 285

Leu Pro Ala Asp Arg Phe Ser Pro Glu Phe Val Asp Phe Thr Ala Gln
        290                 295                 300

Cys Leu Arg Lys Asn Pro Ala Glu Arg Met Ser Tyr Leu Glu Leu Met
305                 310                 315                 320

Glu His Pro Phe Phe Thr Leu His Lys Thr Lys Lys Thr Asp Ile Ala
                325                 330                 335

Ala Phe Val Lys Glu Ile Leu Gly Glu Asp Ser
            340                 345

<210> SEQ ID NO 54
<211> LENGTH: 2252
<212> TYPE: DNA
<213> ORGANISM: Homo sapiens

<400> SEQUENCE: 54
cggcgccgcc cgtcgcggac tcgtccttgc tgcagtcgcc gccgcagtcc tcgccgcagt    60
cgccgccgcc gccgccgccg ccgccgctgc tcctccgcct ggcctgggcc gtctgcccgc   120
agccatgagc gtgctcggcc ccggtggagc ccgcagtcct ctagattagt ctccaccgcc   180
gtccaggacc cacttgcagc atggagtcgc ccgcctcgag ccagcccgcc agcatgcccc   240
agtccaaagg aaaatccaag aggaagaagg atctacggat atcctgcatg tccaagccac   300
ccgcacccaa cccccacccc ccccggaacc tggactcccg gaccttcatc accattggag   360
acagaaactt tgaggtggag gctgatgact tggtgaccat ctcagaactg ggccgtggag   420 cctatgggt ggtagagaag gtgcggcacg cccagagcgg caccatcatg gccgtgaagc   480
ggatccgggc caccgtgaac tcacaggagc agaagcggct gctcatggac ctggacatca   540
acatgcgcac ggtcgactgc ttctacactg tcaccttcta cggggcacta ttcagagagg   600
gagacgtgtg gatctgcatg gagctcatgg acacatcctt ggacaagttc taccggaagg   660
tgctggataa aaacatgaca attccagagg acatccttgg ggagattgct gtgtctatcg   720
```

```
tgcgggccct ggagcatctg cacagcaagc tgtcggtgat ccacagagat gtgaagccct    780
ccaatgtcct tatcaacaag gagggccatg tgaagatgtg tgactttggc atcagtggct    840
acttggtgga ctctgtggcc aagacgatgg atgccggctg caagccctac atggcccctg    900
agaggatcaa cccagagctg aaccagaagg ctacaatgt caagtccgac gtctggagcc    960
tgggcatcac catgattgag atggccatcc tgcggttccc ttacgagtcc tggggaccc   1020 cgttccagca gctgaagcag gtggtggagg agccgtcccc ccagctccca gccgaccgtt   1080
tctcccccga gtttgtggac ttcactgctc agtgcctgag gaagaacccc gcagagcgta   1140
tgagctacct ggagctgatg gagcaccct tcttcacct gcacaaaacc aagaagacgg    1200
acattgctgc cttcgtgaag gagatcctgg gagaagactc ataggggctg ggcctcggac   1260
cccactccgg ccctccagag ccccacagcc ccatctgcgg gggcagtgct cacccacacc   1320
ataagctact gccatcctgg cccagggcat ctgggaggaa ccgaggggc tgctcccacc    1380 tggctctgtg gcgagccatt tgtcccaagt gccaaagaag cagaccattg gggctcccag   1440
ccaggccctt gtcggcccca ccagtgcctc tccctgctgc tcctaggacc cgtctccagc   1500
tgctgagatc ctggactgag ggggcctgga tgcccctgt ggatgctgct gcccctgcac    1560
agcaggctgc cagtgcctgg gtggatgggc caccgccttg cccagcctgg atgccatcca   1620
agttgtatat ttttttaatc tctcgactga atggactttg cacactttgg cccagggtgg   1680
ccacacctct atcccggctt tggtgcgggg tacacaagag gggatgagtt gtgtgaatac   1740
cccaagactc ccatgaggga gatgccatga ccgcccaag gccttcccct ggcactggca    1800
aacagggcct ctgcggagca cactggctca cccagtcctg cccgccaccg ttatcggtgt   1860
cattcacctt tcgtgttttt tttaatttat cctctgttga ttttttcttt tgctttatgg   1920
gtttggcttg tttttcttgc atggtttgga gctgatcgct tctcccccac ccctagggt    1980 accagcaggc agagccttgc cctctgctca ggctggggtc cagtgggagg gcccaagat    2040 ctctgctcag agaagtgcag ggggagcctt ccagctcact ctccctgagg actggcttga   2100
caggggctat gggtttgctt tggtgttgtt tttaaaaaaa gaaatatat tttttttgaaa   2160 aaacgactgc ccatcccggg tcctttccct gatgggttgg ggcagttacc tggttgctgt   2220
tttaattaaa aaaaaaaaa aaaaaaaaa aa                                   2252
```

<210> SEQ ID NO 55
<211> LENGTH: 2201
<212> TYPE: PRT
<213> ORGANISM: Homo sapiens

<400> SEQUENCE: 55

```
Met Gly Ala Met Thr Gln Leu Leu Ala Gly Val Phe Leu Ala Phe Leu
 1               5                  10                  15

Ala Leu Ala Thr Glu Gly Gly Val Leu Lys Lys Val Ile Arg His Lys
             20                  25                  30

Arg Gln Ser Gly Val Asn Ala Thr Leu Pro Glu Glu Asn Gln Pro Val
         35                  40                  45

Val Phe Asn His Val Tyr Asn Ile Lys Leu Pro Val Gly Ser Gln Cys
     50                  55                  60

Ser Val Asp Leu Glu Ser Ala Ser Gly Glu Lys Asp Leu Ala Pro Pro
 65                  70                  75                  80

Ser Glu Pro Ser Glu Ser Phe Gln Glu His Thr Val Asp Gly Glu Asn
                 85                  90                  95
```

-continued

```
Gln Ile Val Phe Thr His Arg Ile Asn Ile Pro Arg Arg Ala Cys Gly
            100                 105                 110
Cys Ala Ala Ala Pro Asp Val Lys Glu Leu Leu Ser Arg Leu Glu Glu
        115                 120                 125
Leu Glu Asn Leu Val Ser Ser Leu Arg Glu Gln Cys Thr Ala Gly Ala
    130                 135                 140
Gly Cys Cys Leu Gln Pro Ala Thr Gly Arg Leu Asp Thr Arg Pro Phe
145                 150                 155                 160
Cys Ser Gly Arg Gly Asn Phe Ser Thr Glu Gly Cys Gly Cys Val Cys
                165                 170                 175
Glu Pro Gly Trp Lys Gly Pro Asn Cys Ser Glu Pro Glu Cys Pro Gly
            180                 185                 190
Asn Cys His Leu Arg Gly Arg Cys Ile Asp Gly Gln Cys Ile Cys Asp
        195                 200                 205
Asp Gly Phe Thr Gly Glu Asp Cys Ser Gln Leu Ala Cys Pro Ser Asp
    210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
            260                 265                 270
Gly Phe Ala Gly Asp Asp Cys Asn Lys Pro Leu Cys Leu Asn Asn Cys
        275                 280                 285
Tyr Asn Arg Gly Arg Cys Val Glu Asn Glu Cys Val Cys Asp Glu Gly
    290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
            340                 345                 350
Gln Gly Arg Cys Glu Glu Gly Gln Cys Val Cys Asp Glu Gly Phe Ala
        355                 360                 365
Gly Leu Asp Cys Ser Glu Lys Arg Cys Pro Ala Asp Cys His Asn Arg
    370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
        435                 440                 445
Cys Val Glu Gly Lys Cys Val Cys Glu Gln Gly Phe Lys Gly Tyr Asp
    450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
            500                 505                 510
Asp Gly Gln Cys Val Cys Glu Asp Gly Phe Thr Gly Pro Asp Cys Ala
```

```
                515                 520                 525
Glu Leu Ser Cys Pro Asn Asp Cys His Gly Gln Gly Arg Cys Val Asn
            530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
            580                 585                 590
Ser Cys Pro Ser Asp Cys Asn Asn Leu Gly Gln Cys Val Ser Gly Arg
            595                 600                 605
Cys Ile Cys Asn Glu Gly Tyr Ser Gly Glu Asp Cys Ser Glu Val Ser
    610                 615                 620
Pro Pro Lys Asp Leu Val Val Thr Glu Val Thr Glu Glu Thr Val Asn
625                 630                 635                 640
Leu Ala Trp Asp Asn Glu Met Arg Val Thr Glu Tyr Leu Val Val Tyr
                645                 650                 655
Thr Pro Thr His Glu Gly Gly Leu Glu Met Gln Phe Arg Val Pro Gly
            660                 665                 670
Asp Gln Thr Ser Thr Ile Ile Gln Glu Leu Glu Pro Gly Val Glu Tyr
        675                 680                 685
Phe Ile Arg Val Phe Ala Ile Leu Glu Asn Lys Lys Ser Ile Pro Val
        690                 695                 700
Ser Ala Arg Val Ala Thr Tyr Leu Pro Ala Pro Glu Gly Leu Lys Phe
705                 710                 715                 720
Lys Ser Ile Lys Glu Thr Ser Val Glu Val Glu Trp Asp Pro Leu Asp
                725                 730                 735
Ile Ala Phe Glu Thr Trp Glu Ile Ile Phe Arg Asn Met Asn Lys Glu
            740                 745                 750
Asp Glu Gly Glu Ile Thr Lys Ser Leu Arg Arg Pro Glu Thr Ser Tyr
            755                 760                 765
Arg Gln Thr Gly Leu Ala Pro Gly Gln Glu Tyr Glu Ile Ser Leu His
770                 775                 780
Ile Val Lys Asn Asn Thr Arg Gly Pro Gly Leu Lys Arg Val Thr Thr
785                 790                 795                 800
Thr Arg Leu Asp Ala Pro Ser Gln Ile Glu Val Lys Asp Val Thr Asp
                805                 810                 815
Thr Thr Ala Leu Ile Thr Trp Phe Lys Pro Leu Ala Glu Ile Asp Gly
            820                 825                 830
Ile Glu Leu Thr Tyr Gly Ile Lys Asp Val Pro Gly Asp Arg Thr Thr
            835                 840                 845
Ile Asp Leu Thr Glu Asp Glu Asn Gln Tyr Ser Ile Gly Asn Leu Lys
        850                 855                 860
Pro Asp Thr Glu Tyr Glu Val Ser Leu Ile Ser Arg Arg Gly Asp Met
865                 870                 875                 880
Ser Ser Asn Pro Ala Lys Glu Thr Phe Thr Thr Gly Leu Asp Ala Pro
                885                 890                 895
Arg Asn Leu Arg Arg Val Ser Gln Thr Asp Asn Ser Ile Thr Leu Glu
            900                 905                 910
Trp Arg Asn Gly Lys Ala Ala Ile Asp Ser Tyr Arg Ile Lys Tyr Ala
            915                 920                 925
Pro Ile Ser Gly Gly Asp His Ala Glu Val Asp Val Pro Lys Ser Gln
930                 935                 940
```

```
Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
            965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
            995                 1000                1005

Leu Ala Lys Phe Asp Arg Tyr Arg Leu Asn Tyr Ser Leu Pro Thr Gly
    1010                1015                1020

Gln Trp Val Gly Val Gln Leu Pro Arg Asn Thr Thr Ser Tyr Val Leu
1025                1030                1035                1040

Arg Gly Leu Glu Pro Gly Gln Glu Tyr Asn Val Leu Leu Thr Ala Glu
                1045                1050                1055

Lys Gly Arg His Lys Ser Lys Pro Ala Arg Val Lys Ala Ser Thr Glu
                1060                1065                1070

Gln Ala Pro Glu Leu Glu Asn Leu Thr Val Thr Glu Val Gly Trp Asp
                1075                1080                1085

Gly Leu Arg Leu Asn Trp Thr Ala Ala Asp Gln Ala Tyr Glu His Phe
    1090                1095                1100

Ile Ile Gln Val Gln Glu Ala Asn Lys Val Glu Ala Ala Arg Asn Leu
1105                1110                1115                1120

Thr Val Pro Gly Ser Leu Arg Ala Val Asp Ile Pro Gly Leu Lys Ala
                1125                1130                1135

Ala Thr Pro Tyr Thr Val Ser Ile Tyr Gly Val Ile Gln Gly Tyr Arg
                1140                1145                1150

Thr Pro Val Leu Ser Ala Glu Ala Ser Thr Gly Glu Thr Pro Asn Leu
    1155                1160                1165

Gly Glu Val Val Ala Glu Val Gly Trp Asp Ala Leu Lys Leu Asn
    1170                1175                1180

Trp Thr Ala Pro Glu Gly Ala Tyr Glu Tyr Phe Phe Ile Gln Val Gln
1185                1190                1195                1200

Glu Ala Asp Thr Val Glu Ala Ala Gln Asn Leu Thr Val Pro Gly Gly
                1205                1210                1215

Leu Arg Ser Thr Asp Leu Pro Gly Leu Lys Ala Ala Thr His Tyr Thr
                1220                1225                1230

Ile Thr Ile Arg Gly Val Thr Gln Asp Phe Ser Thr Thr Pro Leu Ser
    1235                1240                1245

Val Glu Val Leu Thr Glu Glu Val Pro Asp Met Gly Asn Leu Thr Val
    1250                1255                1260

Thr Glu Val Ser Trp Asp Ala Leu Arg Leu Asn Trp Thr Thr Pro Asp
1265                1270                1275                1280

Gly Thr Tyr Asp Gln Phe Thr Ile Gln Val Gln Glu Ala Asp Gln Val
                1285                1290                1295

Glu Glu Ala His Asn Leu Thr Val Pro Gly Ser Leu Arg Ser Met Glu
                1300                1305                1310

Ile Pro Gly Leu Arg Ala Gly Thr Pro Tyr Thr Val Thr Leu His Gly
    1315                1320                1325

Glu Val Arg Gly His Ser Thr Arg Pro Leu Ala Val Glu Val Val Thr
    1330                1335                1340

Glu Asp Leu Pro Gln Leu Gly Asp Leu Ala Val Ser Glu Val Gly Trp
1345                1350                1355                1360
```

-continued

Asp Gly Leu Arg Leu Asn Trp Thr Ala Ala Asp Asn Ala Tyr Glu His
            1365                1370                1375

Phe Val Ile Gln Val Gln Glu Val Asn Lys Val Glu Ala Ala Gln Asn
        1380                1385                1390

Leu Thr Leu Pro Gly Ser Leu Arg Ala Val Asp Ile Pro Gly Leu Glu
    1395                1400                1405

Ala Ala Thr Pro Tyr Arg Val Ser Ile Tyr Gly Val Ile Arg Gly Tyr
1410                1415                1420

Arg Thr Pro Val Leu Ser Ala Glu Ala Ser Thr Ala Lys Glu Pro Glu
1425                1430                1435                1440

Ile Gly Asn Leu Asn Val Ser Asp Ile Thr Pro Glu Ser Phe Asn Leu
            1445                1450                1455

Ser Trp Met Ala Thr Asp Gly Ile Phe Glu Thr Phe Thr Ile Glu Ile
        1460                1465                1470

Ile Asp Ser Asn Arg Leu Leu Glu Thr Val Glu Tyr Asn Ile Ser Gly
    1475                1480                1485

Ala Glu Arg Thr Ala His Ile Ser Gly Leu Pro Pro Ser Thr Asp Phe
1490                1495                1500

Ile Val Tyr Leu Ser Gly Leu Ala Pro Ser Ile Arg Thr Lys Thr Ile
1505                1510                1515                1520

Ser Ala Thr Ala Thr Thr Glu Ala Leu Pro Leu Leu Glu Asn Leu Thr
            1525                1530                1535

Ile Ser Asp Ile Asn Pro Tyr Gly Phe Thr Val Ser Trp Met Ala Ser
        1540                1545                1550

Glu Asn Ala Phe Asp Ser Phe Leu Val Thr Val Val Asp Ser Gly Lys
    1555                1560                1565

Leu Leu Asp Pro Gln Glu Phe Thr Leu Ser Gly Thr Gln Arg Lys Leu
1570                1575                1580

Glu Leu Arg Gly Leu Ile Thr Gly Ile Gly Tyr Glu Val Met Val Ser
1585                1590                1595                1600

Gly Phe Thr Gln Gly His Gln Thr Lys Pro Leu Arg Ala Glu Ile Val
            1605                1610                1615

Thr Glu Ala Glu Pro Glu Val Asp Asn Leu Leu Val Ser Asp Ala Thr
        1620                1625                1630

Pro Asp Gly Phe Arg Leu Ser Trp Thr Ala Asp Glu Gly Val Phe Asp
    1635                1640                1645

Asn Phe Val Leu Lys Ile Arg Asp Thr Lys Lys Gln Ser Glu Pro Leu
1650                1655                1660

Glu Ile Thr Leu Leu Ala Pro Glu Arg Thr Arg Asp Leu Thr Gly Leu
1665                1670                1675                1680

Arg Glu Ala Thr Glu Tyr Glu Ile Glu Leu Tyr Gly Ile Ser Lys Gly
            1685                1690                1695

Arg Arg Ser Gln Thr Val Ser Ala Ile Ala Thr Thr Ala Met Gly Ser
        1700                1705                1710

Pro Lys Glu Val Ile Phe Ser Asp Ile Thr Glu Asn Ser Ala Thr Val
    1715                1720                1725

Ser Trp Arg Ala Pro Thr Ala Gln Val Glu Ser Phe Arg Ile Thr Tyr
1730                1735                1740

Val Pro Ile Thr Gly Gly Thr Pro Ser Met Val Thr Val Asp Gly Thr
1745                1750                1755                1760

Lys Thr Gln Thr Arg Leu Val Lys Leu Ile Pro Gly Val Glu Tyr Leu
            1765                1770                1775

Val Ser Ile Ile Ala Met Lys Gly Phe Glu Glu Ser Glu Pro Val Ser

-continued

```
                   1780                1785                1790
     Gly Ser Phe Thr Thr Ala Leu Asp Gly Pro Ser Gly Leu Val Thr Ala
         1795                1800                1805

Asn Ile Thr Asp Ser Glu Ala Leu Ala Arg Trp Gln Pro Ala Ile Ala
         1810                1815                1820

Thr Val Asp Ser Tyr Val Ile Ser Tyr Thr Gly Glu Lys Val Pro Glu
     1825                1830                1835                1840

Ile Thr Arg Thr Val Ser Gly Asn Thr Val Glu Tyr Ala Leu Thr Asp
             1845                1850                1855

Leu Glu Pro Ala Thr Glu Tyr Thr Leu Arg Ile Phe Ala Glu Lys Gly
                 1860                1865                1870

Pro Gln Lys Ser Ser Thr Ile Thr Ala Lys Phe Thr Thr Asp Leu Asp
             1875                1880                1885

Ser Pro Arg Asp Leu Thr Ala Thr Glu Val Gln Ser Glu Thr Ala Leu
         1890                1895                1900

Leu Thr Trp Arg Pro Pro Arg Ala Ser Val Thr Gly Tyr Leu Leu Val
     1905                1910                1915                1920

Tyr Glu Ser Val Asp Gly Thr Val Lys Glu Val Ile Val Gly Pro Asp
                 1925                1930                1935

Thr Thr Ser Tyr Ser Leu Ala Asp Leu Ser Pro Ser Thr His Tyr Thr
             1940                1945                1950

Ala Lys Ile Gln Ala Leu Asn Gly Pro Leu Arg Ser Asn Met Ile Gln
         1955                1960                1965

Thr Ile Phe Thr Thr Ile Gly Leu Leu Tyr Pro Phe Pro Lys Asp Cys
         1970                1975                1980

Ser Gln Ala Met Leu Asn Gly Asp Thr Thr Ser Gly Leu Tyr Thr Ile
     1985                1990                1995                2000

Tyr Leu Asn Gly Asp Lys Ala Gln Ala Leu Glu Val Phe Cys Asp Met
                 2005                2010                2015

Thr Ser Asp Gly Gly Gly Trp Ile Val Phe Leu Arg Arg Lys Asn Gly
             2020                2025                2030

Arg Glu Asn Phe Tyr Gln Asn Trp Lys Ala Tyr Ala Ala Gly Phe Gly
         2035                2040                2045

Asp Arg Arg Glu Glu Phe Trp Leu Gly Leu Asp Asn Leu Asn Lys Ile
         2050                2055                2060

Thr Ala Gln Gly Gln Tyr Glu Leu Arg Val Asp Leu Arg Asp His Gly
     2065                2070                2075                2080

Glu Thr Ala Phe Ala Val Tyr Asp Lys Phe Ser Val Gly Asp Ala Lys
                 2085                2090                2095

Thr Arg Tyr Lys Leu Lys Val Glu Gly Tyr Ser Gly Thr Ala Gly Asp
             2100                2105                2110

Ser Met Ala Tyr His Asn Gly Arg Ser Phe Ser Thr Phe Asp Lys Asp
         2115                2120                2125

Thr Asp Ser Ala Ile Thr Asn Cys Ala Leu Ser Tyr Lys Gly Ala Phe
         2130                2135                2140

Trp Tyr Arg Asn Cys His Arg Val Asn Leu Met Gly Arg Tyr Gly Asp
     2145                2150                2155                2160

Asn Asn His Ser Gln Gly Val Asn Trp Phe His Trp Lys Gly His Glu
                 2165                2170                2175

His Ser Ile Gln Phe Ala Glu Met Lys Leu Arg Pro Ser Asn Phe Arg
             2180                2185                2190

Asn Leu Glu Gly Arg Arg Lys Arg Ala
         2195                2200
```

<210> SEQ ID NO 56
<211> LENGTH: 7560
<212> TYPE: DNA
<213> ORGANISM: Homo sapiens

<400> SEQUENCE: 56

| | | | | | |
|---|---|---|---|---|---|
| accggccaca | gcctgcctac | tgtcacccgc | ctctcccgcg | cgcagataca | cgccccgcc | 60 |
| tccgtgggca | caaaggcagc | gctgctgggg | aactcggggg | aacgcgcacg | tgggaaccgc | 120 |
| cgcagctcca | cactccaggt | acttcttcca | aggacctagg | tctctcgccc | atcggaaaga | 180 |
| aaataattct | ttcaagaaga | tcagggacaa | ctgatttgaa | gtctactctg | tgcttctaaa | 240 |
| tccccaattc | tgctgaaagt | gaatccctag | agccctagag | ccccagcagc | acccagccaa | 300 |
| acccacctcc | accatggggg | ccatgactca | gctgttggca | ggtgtctttc | ttgctttcct | 360 |
| tgccctcgct | accgaaggtg | gggtcctcaa | gaaagtcatc | cggcacaagc | gacagagtgg | 420 |
| ggtgaacgcc | accctgccag | aagagaacca | gccagtggtg | tttaaccacg | tttacaacat | 480 |
| caagctgcca | gtgggatccc | agtgttcggt | ggatctggag | tcagccagtg | gggagaaaga | 540 |
| cctggcaccg | ccttcagagc | ccagcgaaag | cttttcagga | cacacagtag | atggggaaaa | 600 |
| ccagattgtc | ttcacacatc | gcatcaacat | ccccgccgg | gcctgtggct | gtgccgcagc | 660 |
| ccctgatgtt | aaggagctgc | tgagcagact | ggaggagctg | gagaacctgg | tgtcttccct | 720 |
| gagggagcaa | tgtactgcag | gagcaggctg | ctgtctccag | cctgccacag | gccgcttgga | 780 |
| caccaggccc | ttctgtagcg | gtcggggcaa | cttcagcact | gaaggatgtg | gctgtgtctg | 840 |
| cgaacctggc | tggaaaggcc | ccaactgctc | tgagcccgaa | tgtccaggca | actgtcacct | 900 |
| tcgaggccgt | gcattgatg | ggcagtgcat | ctgtgacgac | ggcttcacgg | gcgaggactg | 960 |
| cagccagctg | gcttgcccca | gcgactgcaa | tgaccagggc | aagtgcgtga | atggagtctg | 1020 |
| catctgtttc | gaaggctacg | ccggggctga | ctgcagccgt | gaaatctgcc | cagtgccctg | 1080 |
| cagtgaggag | cacggcacat | gtgtagatgg | cttgtgtgtg | tgccacgatg | gctttgcagg | 1140 |
| cgatgactgc | aacaagcctc | tgtgtctcaa | caattgctac | aaccgtggac | gatgcgtgga | 1200 |
| gaatgagtgc | gtgtgtgatg | agggtttcac | gggcgaagac | tgcagtgagc | tcatctgccc | 1260 |
| caatgactgc | ttcgaccggg | gccgctgcat | caatggcacc | tgctactgcg | aagaaggctt | 1320 |
| cacaggtgaa | gactgcggga | acccacctg | cccacatgcc | tgccacaccc | agggccggtg | 1380 |
| tgaggagggg | cagtgtgtat | gtgatgaggg | ctttgccggt | ttggactgca | gcagaagag | 1440 |
| gtgtcctgct | gactgtcaca | atcgtggccg | ctgtgtagac | gggcggtgtg | agtgtgatga | 1500 |
| tggtttcact | ggagctgact | gtggggagct | caagtgtccc | aatggctgca | gtggccatgg | 1560 |
| ccgctgtgtc | aatgggcagt | gtgtgtgtga | tgagggctat | actggggagg | actgcagcca | 1620 |
| gctacggtgc | cccaatgact | gtcacagtcg | gggccgctgt | gtcgagggca | atgtgtatg | 1680 |
| tgagcaaggc | ttcaagggct | atgactgcag | tgacatgagc | tgccctaatg | actgtcacca | 1740 |
| gcacggccgc | tgtgtgaatg | gcatgtgtgt | ttgtgatgac | ggctacacag | gggagactg | 1800 |
| ccgggatcgc | caatgcccca | gggactgcag | caacagggc | ctctgtgtgg | acggacagtg | 1860 |
| cgtctgtgag | gacggcttca | ccggccctga | ctgtgcagaa | ctctcctgtc | caaatgactg | 1920 |
| ccatggccag | ggtcgctgtg | tgaatgggca | gtgcgtgtgc | catgaaggat | ttatgggcaa | 1980 |
| agactgcaag | gagcaaagat | gtcccagtga | ctgtcatggc | cagggccgct | gcgtggacgg | 2040 |
| ccagtgcatc | tgccacgagg | gcttcacagg | cctggactgt | ggccagcact | cctgccccag | 2100 |

```
tgactgcaac aacttaggac aatgcgtctc gggccgctgc atctgcaacg agggctacag    2160
cggagaagac tgctcagagg tgtctcctcc caaagacctc gttgtgacag aagtgacgga    2220
agagacggtc aacctggcct gggacaatga gatgcgggtc acagagtacc ttgtcgtgta    2280
cacgcccacc cacgagggtg gtctggaaat gcagttccgt gtgcctgggg accagacgtc    2340
caccatcatc caggagctgg agcctggtgt ggagtacttt atccgtgtat ttgccatcct    2400
ggagaacaag aagagcattc ctgtcagcgc cagggtggcc acgtacttac ctgcacctga    2460
aggcctgaaa ttcaagtcca tcaaggagac atctgtggaa gtggagtggg atcctctaga    2520
cattgctttt gaaacctggg agatcatctt ccggaatatg aataaagaag atgagggaga    2580
gatcaccaaa agcctgagga ggccagagac ctcttaccgg caaactggtc tagctcctgg    2640
gcaagagtat gagatatctc tgcacatagt gaaaaacaat acccggggcc ctggcctgaa    2700
gagggtgacc accacacgct tggatgcccc cagccagatc gaggtgaaag atgtcacaga    2760
caccactgcc ttgatcacct ggttcaagcc cctggctgag atcgatggca ttgagctgac    2820
ctacggcatc aaagacgtgc aggagaccg taccaccatc gatctcacag aggacgagaa    2880
ccagtactcc atcgggaacc tgaagcctga cactgagtac gaggtgtccc tcatctcccg    2940
cagaggtgac atgtcaagca acccagccaa agagaccttc acaacaggcc tcgatgctcc    3000
caggaatctt cgacgtgttt cccagacaga taacagcatc accctggaat ggaggaatgg    3060
caaggcagct attgacagtt acagaattaa gtatgccccc atctctggag gggaccacgc    3120
tgaggttgat gttccaaaga gccaacaagc cacaaccaaa accacactca caggtctgag    3180
gccgggaact gaatatggga ttggagtttc tgctgtgaag gaagacaagg agagcaatcc    3240
agcgaccatc aacgcagcca cagagttgga cacgcccaag gaccttcagg tttctgaaac    3300
tgcagagacc agcctgaccc tgctctggaa cacaccgttg ccaaatttg accgctaccg    3360 cctcaattac agtctcccca caggccagtg ggtgggagtg cagcttccaa gaaacaccac    3420
ttcctatgtc ctgagaggcc tggaaccagg acaggagtac aatgtcctcc tgacagccga    3480
gaaaggcaga cacaagagca agcccgcacg tgtgaaggca tccactgaac aagcccctga    3540
gctggaaaac ctcaccgtga ctgaggttgg ctgggatggc ctcagactca actgaccgc    3600 ggctgaccag gcctatgagc actttatcat tcaggtgcag gaggccaaca aggtggaggc    3660
agctcggaac ctcaccgtgc ctggcagcct tcgggctgtg acataccgg gcctcaaggc    3720 tgctacgcct tatacagtct ccatctatgg ggtgatccag ggctatagaa caccagtgct    3780
ctctgctgag gcctccacag gggaaactcc caatttggga gaggtcgtgg tggccgaggt    3840
gggctgggat gccctcaaac tcaactggac tgctccagaa ggggcctatg agtacttttt    3900
cattcaggtg caggaggctg acacagtaga ggcagcccag aacctcaccg tcccaggagg    3960
actgaggtcc acagacctgc ctgggctcaa agcagccact cattatacca tcaccatccg    4020
cggggtcact caggacttca gcacaacccc tctctctgtt gaagtcttga cagaggaggt    4080
tccagatatg ggaaacctca cagtgaccga ggttagctgg gatgctctca gactgaactg    4140
gaccacgcca gatggaacct atgaccagtt tactattcag gtccaggagg ctgaccaggt    4200
ggaagaggct cacaatctca cggttcctgg cagcctgcgt tccatggaaa tcccaggcct    4260
cagggctggc actccttaca cagtcaccct gcacggcgag tcaggggcc acagcactcg    4320 acccccttgct gtagaggtcg tcacagagga tctcccacag ctgggagatt agccgtgtc    4380 tgaggttggc tgggatggcc tcagactcaa ctggaccgca gctgacaatg cctatgagca    4440
ctttgtcatt caggtgcagg aggtcaacaa agtggaggca gcccagaacc tcacgttgcc    4500
```

```
tggcagcctc agggctgtgg acatcccggg cctcgaggct gccacgcctt atagagtctc    4560
catctatggg gtgatccggg gctatagaac accagtactc tctgctgagg cctccacagc    4620
caaagaacct gaaattggaa acttaaatgt ttctgacata actcccgaga gcttcaatct    4680
ctcctggatg gctaccgatg ggatcttcga gacctttacc attgaaatta ttgattccaa    4740
taggttgctg gagactgtgg aatataatat ctctggtgct gaacgaactg cccatatctc    4800
agggctaccc cctagtactg attttattgt ctacctctct ggacttgctc ccagcatccg    4860
gaccaaaacc atcagtgcca cagccacgac agaggccctg ccccttctgg aaaacctaac    4920
catttccgac attaatccct acgggttcac agtttcctgg atggcatcgg agaatgcctt    4980
tgacagcttt ctagtaacgg tggtggattc tgggaagctg ctggacccce aggaattcac    5040 actttcagga acccagagga agctggagct tagaggcctc ataactggca ttggctatga    5100
ggttatggtc tctggcttca cccaagggca tcaaaccaag cccttgaggg ctgagattgt    5160
tacagaagcc gaaccggaag ttgacaacct tctggtttca gatgccaccc cagacggttt    5220
ccgtctgtcc tggacagctg atgaaggggg cttcgacaat tttgttctca aaatcagaga    5280
taccaaaaag cagtctgagc cactggaaat aaccctactt gccccgaac gtaccaggga    5340 cttaacaggt ctcagagagg ctactgaata cgaaattgaa ctctatggaa taagcaaagg    5400
aaggcgatcc cagacagtca gtgctatagc aacaacagcc atgggctccc caaggaagt    5460 cattttctca gacatcactg aaaattcggc tactgtcagc tggagggcac ccacggccca    5520
agtggagagc ttccggatta cctatgtgcc cattacagga ggtacaccct ccatggtaac    5580
tgtggacgga accaagactc agaccaggct ggtgaaactc ataccctggcg tggagtacct    5640 tgtcagcatc atcgccatga agggcttttga ggaaagtgaa cctgtctcag ggtcattcac    5700
cacagctctg gatggcccat ctggcctggt gacagccaac atcactgact cagaagcctt    5760
ggccaggtgg cagccagcca ttgccactgt ggacagttat gtcatctcct acacaggcga    5820
gaaagtgcca gaaattacac gcacggtgtc cgggaacaca gtggagtatg ctctgaccga    5880
cctcgagcct gccacggaat acacactgag aatctttgca gagaaagggc cccagaagag    5940
ctcaaccatc actgccaagt tcacaacaga cctcgattct ccaagagact tgactgctac    6000
tgaggttcag tcggaaactg ccctccttac ctggcgaccc cccgggcat cagtcaccgg    6060 ttacctgctg gtctatgaat cagtggatgg cacagtcaag gaagtcattg tgggtccaga    6120
taccacctcc tacagcctgg cagacctgag cccatccacc cactacacag caagatcca    6180 ggcactcaat gggcccctga ggagcaatat gatccagacc atcttcacca caattggact    6240
cctgtacccc ttccccaagg actgctccca agcaatgctg aatggagaca cgacctctgg    6300
cctctacacc atttatctga atggtgataa ggctcaggcg ctggaagtct tctgtgacat    6360
gacctctgat gggggtggat ggattgtgtt cctgagacgc aaaaacggac gcagaaactt    6420
ctaccaaaac tggaaggcat atgctgctgg atttgggga cgcagagaag aattctggct    6480
tgggctggac aacctgaaca aaatcacagc ccagggcag tacgagctcc gggtggacct    6540
gcgggaccat ggggagacag cctttgctgt ctatgacaag ttcagcgtgg agatgccaa    6600 gactcgctac aagctgaagg tggaggggta cagtgggaca gcaggtgact ccatggccta    6660
ccacaatggc agatccttct ccacctttga caaggacaca gattcagcca tcaccaactg    6720
tgctctgtcc tacaaagggg cttttctggta caggaactgt caccgtgtca acctgatggg    6780
gagatatggg gacaataacc acagtcaggg cgttaactgg ttccactgga agggccacga    6840
```

```
acactcaatc cagtttgctg agatgaagct gagaccaagc aacttcgaaa atcttgaagg      6900
caggcgcaaa cgggcataaa ttggagggac cactgggtga gagaggaata aggcggccca      6960
gagcgaggaa aggattttac caaagcatca atacaaccag cccaaccatc ggtccacacc      7020
tgggcatttg gtgagaatca aagctgacca tggatccctg ggccaacgg caacagcatg       7080 ggcctcacct cctctgtgat ttctttcttt gcaccaaaga catcagtctc caacatgttt      7140
ctgttttgtt gtttgattca gcaaaaatct cccagtgaca acatcgcaat agttttttac      7200
ttctcttagg tggctctggg atgggagagg ggtaggatgt acaggggtag tttgttttag      7260
aaccagccgt attttacatg aagctgtata attaattgtc attattttg ttagcaaaga       7320 ttaaatgtgt cattggaagc catcccttt tttacatttc atacaacaga aaccagaaaa       7380
gcaatactgt ttccatttta aggatatgat taatattatt aatataataa tgatgatgat      7440
gatgatgaaa actaaggatt tttcaagaga tctttctttc caaaacattt ctggacagta      7500
cctgattgta ttttttttt aaataaaagc acaagtactt ttgaaaaaaa accggaattc       7560
```

<210> SEQ ID NO 57
<211> LENGTH: 464
<212> TYPE: PRT
<213> ORGANISM: Homo sapiens

<400> SEQUENCE: 57

```
Met Met Ala Ala Met Leu Ser His Ala Tyr Gly Pro Gly Gly Cys Gly
  1               5                  10                  15

Ala Ala Ala Ala Leu Asn Gly Glu Gln Ala Leu Leu Arg Arg
             20                  25                  30

Lys Ser Val Asn Thr Thr Glu Cys Val Pro Val Pro Ser Ser Glu His
         35                  40                  45

Val Ala Glu Ile Val Gly Arg Gln Gly Cys Lys Ile Lys Ala Leu Arg
     50                  55                  60

Ala Lys Thr Asn Thr Tyr Ile Lys Thr Pro Val Arg Gly Glu Glu Pro
 65                  70                  75                  80

Ile Phe Val Val Thr Gly Arg Lys Glu Asp Val Ala Met Ala Lys Arg
                 85                  90                  95

Glu Ile Leu Ser Ala Ala Glu His Phe Ser Met Ile Arg Ala Ser Arg
            100                 105                 110

Asn Lys Asn Gly Pro Ala Leu Gly Gly Leu Ser Cys Ser Pro Asn Leu
        115                 120                 125

Pro Gly Gln Thr Thr Val Gln Val Arg Val Pro Tyr Arg Val Val Gly
    130                 135                 140

Leu Val Val Gly Pro Lys Gly Ala Thr Ile Lys Arg Ile Gln Gln Gln
145                 150                 155                 160

Thr His Thr Tyr Ile Val Thr Pro Ser Arg Asp Lys Glu Pro Val Phe
                165                 170                 175

Glu Val Thr Gly Met Pro Glu Asn Val Asp Arg Ala Arg Glu Glu Ile
            180                 185                 190

Glu Met His Ile Ala Met Arg Thr Gly Asn Tyr Ile Glu Leu Asn Glu
        195                 200                 205

Glu Asn Asp Phe His Tyr Asn Gly Thr Asp Val Ser Phe Glu Gly Gly
    210                 215                 220

Thr Leu Gly Ser Ala Trp Leu Ser Ser Asn Pro Val Pro Pro Ser Arg
225                 230                 235                 240

Ala Arg Met Ile Ser Asn Tyr Arg Asn Asp Ser Ser Ser Ser Leu Gly
                245                 250                 255
```

Ser Gly Ser Thr Asp Ser Tyr Phe Gly Ser Asn Arg Leu Ala Asp Phe
        260                 265                 270

Ser Pro Thr Ser Pro Phe Ser Thr Gly Asn Phe Trp Phe Gly Asp Thr
        275                 280                 285

Leu Pro Ser Val Gly Ser Glu Asp Leu Ala Val Asp Ser Pro Ala Phe
        290                 295                 300

Asp Ser Leu Pro Thr Ser Ala Gln Thr Ile Trp Thr Pro Phe Glu Pro
305                 310                 315                 320

Val Asn Pro Leu Ser Gly Phe Gly Ser Asp Pro Ser Gly Asn Met Lys
                325                 330                 335

Thr Gln Arg Arg Gly Ser Gln Pro Ser Thr Pro Arg Leu Ser Pro Thr
                340                 345                 350

Phe Pro Glu Ser Ile Glu His Pro Leu Ala Arg Arg Val Arg Ser Asp
        355                 360                 365

Pro Pro Ser Thr Gly Asn His Val Gly Leu Pro Ile Tyr Ile Pro Ala
        370                 375                 380

Phe Ser Asn Gly Thr Asn Ser Tyr Ser Ser Asn Gly Gly Ser Thr
385                 390                 395                 400

Ser Ser Ser Pro Pro Glu Ser Arg Arg Lys His Asp Cys Val Ile Cys
                405                 410                 415

Phe Glu Asn Glu Val Ile Ala Ala Leu Val Pro Cys Gly His Asn Leu
                420                 425                 430

Phe Cys Met Glu Cys Ala Asn Lys Ile Cys Glu Lys Arg Thr Pro Ser
        435                 440                 445

Cys Pro Val Cys Gln Thr Ala Val Thr Gln Ala Ile Gln Ile His Ser
        450                 455                 460

<210> SEQ ID NO 58
<211> LENGTH: 3493
<212> TYPE: DNA
<213> ORGANISM: Homo sapiens

<400> SEQUENCE: 58
ggccgagctg gagctggaag aggacgagga ggaggggag gaagcggagc tggacggaga      60
cctgctggag gaggaggagc tggaggaagc agaggaggag gaccggtcgt cgctgctgct     120
gctgtcgccg cccgcggcca ccgcctctca gacccagcag atcccaggcg ggtccctggg     180
gtctgtgctg ctgccagccg ccaggttcga tgcccgggag gcggcggccg cggcggcggc     240
ggcgggggtg ctgtacggag gggacgatgc ccagggcatg atggcggcga tgctgtccca     300
cgcctacggc cccggcggtt gtggggcggc ggcggccgcc ctgaacgggg agcaggcggc     360
cctgctccgg agaaagagcg tcaacaccac cgagtgcgtc ccggtgccca gctccgagca     420
cgtcgccgag atcgtcggcc gccagggttg taaaattaaa gcactgagag ccaagacaaa     480
cacgtatatc aagactcctg ttcgtggtga agagcccatt tttgttgtca ctggaaggaa     540
agaagatgtt gccatggcca aagagagat cctctcagct gcagagcact tctccatgat     600
tcgtgcatct cgaaacaaaa atgggcctgc cctggaggg ttatcatgta gtcctaatct     660
gcccggtcaa accaccgtcc aagtcagggt cccttatcgt gtggtaggat agtggttgg     720 acccaaagga gcaactatta aagaattca gcagcagacc cacacctaca tagtaactcc     780
gagcagagat aaggaacctg tctttgaagt gacagggatg cctgaaaatg ttgaccgagc     840 acggaagaa atagaaatgc atattgccat gcgtacagga aactatatag agctcaatga     900
agagaatgat ttccattaca atggtaccga tgtaagcttt gaaggtggca ctcttggctc     960

```
tgcgtggctc tcctccaatc ctgttcctcc tagccgcgca agaatgatat ccaattatcg   1020
aaatgatagt tccagttctc taggaagtgg ctctacagat tcctactttg gaagcaatag   1080
gctggctgac tttagtccaa caagcccatt tagcacagga aacttctggt ttggagatac   1140
actaccatct gtaggctcag aagacctagc agttgactct cctgcctttg actctttacc   1200
aacatctgct caaactatct ggactccatt tgaaccagtt aacccactct ctggctttgg   1260
gagtgatcct tctggtaaca tgaagactca gcgcagagga agtcagccat ctactcctcg   1320
tctgtctcct acatttcctg agagcataga acatccactt gctcggaggg ttaggagcga   1380
cccacctagt acaggcaacc atgttggcct tccaatatat atccctgctt tttctaatgg   1440
taccaatagt tactcctctt ccaatggtgg ttccacctct agctcacctc cagaatcaag   1500
acgaaagcac gactgtgtga tttgcttttga gaatgaggtt attgctgccc tagttccatg   1560
tggccacaac ctcttctgca tggaatgtgc caacaagatc tgtgaaaaga gaacgccatc   1620
atgtccagtt tgccagacag ctgttactca ggcaatccaa attcactctt aactatatat   1680
atatacataa atactatatc tctatatgga ctcgtaaagg catgggtata atggtacccc   1740 ccagtaaaact tcctaatgat ttcttatgac tgttatcagg ctttattggg attaggctaa   1800
agttgttagt aaacttataa aaggctgcta tggtaacact aaacctaagt ggtctcttgt   1860
ctattagttt ggtttgaatt attagtacta tcctgtagac ccagagacat agtttatata   1920
agaattgcta aagctgaagt tcaacttggc tgagtgaaga taatcatagg ttgtgtgagc   1980
ctatgaaaaa gtgtatacgt ctaagatttc aaaacaatgg gtcccaaagc ctaaccactt   2040
taagagttta tggagggtac ttggcattac agacgattca tacacttcca gtgctgcctt   2100
ctttacactg ccagttttga caaaacaggt ttgttttta ttttacaaca acatatgcct   2160
aattctgcag gattgcaagt aactttttaa tgcattgtga ttacttattg gtaatgatag   2220
ggctgatggc agtttactag atcactggtt ataatttggg acaaaaactg ctacatcaac   2280
tttcatctcg cccagagtgc tcaaggctgg tatgatcagt ggatcaggaa tgcaattgtg   2340
aattcctgcc cattgcctct cttggtgaat gtggaaatgg ccacctgggt tttcccatat   2400
caggaagggc tttgggatgg cacctatatt ggctgataat tgaggatgca acattccat    2460 tcattagtgt gatcgagctg ttaattttta gactatagat caaaatgtga acatttttat   2520
gttcaatcca tatttgtctt gcacattata aatatatttt tattttttag taatttaggg   2580
gagggaggag ggagaaaggg ataatgatgc ccttggcata attcacaaaa gcagctgtga   2640
caacctccaa tcagtttact tcatttcaaa actatttcca atcacaagga aagatttatt   2700
taaaatatac tcgtacattt cacctgtgga tgtctataac ttcatcctca gtatgttccc   2760
aaatctgtgc tggcattgaa aggacaaaac attatactag tgggttttc tactaattat   2820 tttttgaagc attattttcc caacacaaaa gagcttttt ctcggtataa tgaaaattga   2880
aatcctatgt gtattcaata gtaaatagac aaatttttatt ttttatttcc acttgaagag   2940
ttacatttcg tataaaagtt tacaaataac ggttttttatt ttgatttttt cagtataaaa   3000
aaagttgcct tgatggcata ttatgatgta atgctaattg cttgtaggat agtaaatggt   3060
cagtattgaa acctaatctc tagctgccgt cttgtagata tgaacgaatg ttcaccaagc   3120
atgtattttg tattttgttg cattgtacac tgcaactaat aagccaagga atcgacatat   3180
attaggtgcg tgtactgttt ctaaaaacca caaactaaga atgataaatt atcaatatag   3240
tttagtattt gctaattttta ctacactctt ttgttatgta tatgtaggga agtcataggg   3300
```

```
attataaatt caatttgagt aaaatttaaa accatatatt ttatgataaa gggcctttaa    3360
cttaagatgg ccaaagcact gatattatat atttgctgta aagagaatta taagagtttt    3420
atttttctga tattaaaagt tacttgataa agacttgttt ccattaactt gaaaaaaaaa    3480
aaaaaaaaaa aaa                                                       3493
```

<210> SEQ ID NO 59
<211> LENGTH: 304
<212> TYPE: PRT
<213> ORGANISM: Homo sapiens

<400> SEQUENCE: 59

```
Met Lys Arg Ala His Pro Glu Tyr Ser Ser Asp Ser Glu Leu Asp
 1               5                  10                  15

Glu Thr Ile Glu Val Glu Lys Glu Ser Ala Asp Glu Asn Gly Asn Leu
            20                  25                  30

Ser Ser Ala Leu Gly Ser Met Ser Pro Thr Thr Ser Ser Gln Ile Leu
        35                  40                  45

Ala Arg Lys Arg Arg Arg Gly Ile Ile Glu Lys Arg Arg Arg Asp Arg
    50                  55                  60

Ile Asn Asn Ser Leu Ser Glu Leu Arg Arg Leu Val Pro Ser Ala Phe
65                  70                  75                  80

Glu Lys Gln Gly Ser Ala Lys Leu Glu Lys Ala Glu Ile Leu Gln Met
                85                  90                  95

Thr Val Asp His Leu Lys Met Leu His Thr Ala Gly Gly Lys Gly Tyr
            100                 105                 110

Phe Asp Ala His Ala Leu Ala Met Asp Tyr Arg Ser Leu Gly Phe Arg
        115                 120                 125

Glu Cys Leu Ala Glu Val Ala Arg Tyr Leu Ser Ile Ile Glu Gly Leu
    130                 135                 140

Asp Ala Ser Asp Pro Leu Arg Val Arg Leu Val Ser His Leu Asn Asn
145                 150                 155                 160

Tyr Ala Ser Gln Arg Glu Ala Ala Ser Gly Ala His Ala Gly Leu Gly
                165                 170                 175

His Ile Pro Trp Gly Thr Val Phe Gly His His Pro His Ile Ala His
            180                 185                 190

Pro Leu Leu Leu Pro Gln Asn Gly His Gly Asn Ala Gly Thr Thr Ala
        195                 200                 205

Ser Pro Thr Glu Pro His His Gln Gly Arg Leu Gly Ser Ala His Pro
    210                 215                 220

Glu Ala Pro Ala Leu Arg Ala Pro Ser Gly Ser Leu Gly Pro Val
225                 230                 235                 240

Leu Pro Val Val Thr Ser Ala Ser Lys Leu Ser Pro Leu Leu Ser
                245                 250                 255

Ser Val Ala Ser Leu Ser Ala Phe Pro Phe Ser Phe Gly Ser Phe His
            260                 265                 270

Leu Leu Ser Pro Asn Ala Leu Ser Pro Ser Ala Pro Thr Gln Ala Ala
        275                 280                 285

Asn Leu Gly Lys Pro Tyr Arg Pro Trp Gly Thr Glu Ile Gly Ala Phe
    290                 295                 300
```

<210> SEQ ID NO 60
<211> LENGTH: 2319
<212> TYPE: DNA
<213> ORGANISM: Homo sapiens

<400> SEQUENCE: 60

```
ttccccactc ccccgccctc cccagggccc tgggaagggg ctcagcgtgg gaaaggatgg      60
ttgagtttta accagaggca aagcgtgagc gggatcagtg tgtgcggaac gcaagcagcc     120
gagagcggag aggcgccgct gtagttaact cctccctgcc cgccgcgccg accctcccca     180
ggaaccccca gggagccagc atgaagcgag ctcaccccga gtacagctcc tcggacagcg     240
agctggacga gaccatcgag gtggagaagg agagtgcgga cgagaatgga aacttgagtt     300
cggctctagg ttccatgtcc ccaactacat cttcccagat tttggccaga aaagacgga     360
gaggaataat tgagaagcgc cgacgagacc ggatcaataa cagtttgtct gagctgagaa     420
ggctggtacc cagtgctttt gagaagcagg atctgctaa gctagaaaaa gccgagatcc     480
tgcagatgac cgtggatcac ctgaaaatgc tgcatacggc aggagggaaa ggttactttg     540
acgcgcacgc ccttgctatg gactatcgga gtttgggatt tcgggaatgc ctggcagaag     600
ttgcgcgtta tctgagcatc attgaaggac tagatgcctc tgacccgctt cgagttcgac     660
tggtttcgca tctcaacaac tacgcttccc agcgggaagc cgcgagcggc gcccacgcgg     720
gcctcggaca cattccctgg gggaccgtct tcggacatca cccgcacatc gcgcacccgc     780
tgttgctgcc ccagaacggc cacgggaacg cgggcaccac ggcctcaccc acggaaccgc     840
accaccaggg caggctgggc tcggcacatc cggaggcgcc tgctttgcga gcgccccta     900
gcggcagcct cggaccggtg ctccctgtgg tcacctccgc ctccaaactg tcgccgcctc     960
tgctctcctc agtggcctcc ctgtcggcct tccccttctc tttcggctcc ttccacttac    1020
tgtctcccaa tgcactgagc ccttcagcac ccacgcaggc tgcaaacctt ggcaagccct    1080
atagaccttg ggggacggag atcggagctt tttaaagaac tgatgtagaa tgagggaggg    1140
gaaagtttaa atcccagct gggctggact gttgccaaca tcaccttaaa gtcgtcagta    1200
aaagtaaaaa ggaaaaaggt cacttcag ataattttt ttttaaagac taaaggtttg    1260
ttggtttact tttatctttt ttaatgtttt tttcatcatg tcatgtatta gcagttttta    1320
aaaactagtt gttaaatttt gttcaagaca ttaaattgaa atagtgagta taagccaaca    1380
ctttgtgata ggtttgtact gtgcctaatt tactttgtaa accagaatga ttccgttttt    1440
gcctcaaaat ttggggaatc ttaacattta gtattttgg tctgtttttc tccttgtata    1500
gttatggtct gtttttagaa ttaattttcc aaaccactat gcttaatgtt aacatgattc    1560
tgtttgttaa tattttgaca gattaaggtg ttgtataaat aatattcttt tgggggagg    1620
ggaactatat tgaattttat atttctgagc aaagcgttga caaatcagat gatcagcttt    1680
atccaagaaa gaagactagt aaattgtctg cctcctatag cagaaaggtg aatgtacaaa    1740
ctgttggtgg ccctgaatcc atctgaccag ctgctgtat ctgccaggac tggcagttct    1800
gatttagtta ggagagagcc gctgataggt taggtctcat ttggagtgtt ggtggaaagg    1860
aaactgaagg taattgaata gaatacgcct gcatttacca gccccagcaa cacaaagaat    1920
ttttaatcac acggatctca aattcacaaa tgttaacatg gataagtgat catggtgtgc    1980
gagtggtcaa ttgagtagta cagtggaaac tgttaaatgc ataacctaat ttcctggga    2040
ctgccatatt ttcttttaac tggaaatttt tatgtgagtt ttccttttgg tgcatggaac    2100
tgtggttgcc aaggtattta aagggctttt cctgcctcct tctctttgat ttatttaatt    2160
tgatttgggc tataaaatat catttttcag gtttattctt ttagcaggtg tagttaaacg    2220
acctccactg aactgggttt gacctctgtt gtactgatgt gttgtgacta aataaaaaag    2280
aaagaacaaa gtaaaaaaaa aaaaaaaaa aaaaaaaa                              2319
```

<210> SEQ ID NO 61
<211> LENGTH: 274
<212> TYPE: PRT
<213> ORGANISM: Homo sapiens

<400> SEQUENCE: 61

Met Ala Ala Ala Glu Pro Ser Pro Arg Arg Val Gly Phe Val Gly Ala
1               5                   10                  15

Gly Arg Met Ala Gly Ala Ile Ala Gln Gly Leu Ile Arg Ala Gly Lys
            20                  25                  30

Val Glu Ala Gln His Ile Leu Ala Ser Ala Pro Thr Asp Arg Asn Leu
        35                  40                  45

Cys His Phe Gln Ala Leu Gly Cys Arg Thr Thr His Ser Asn Gln Glu
    50                  55                  60

Val Leu Gln Ser Cys Leu Leu Val Ile Phe Ala Thr Lys Pro His Val
65                  70                  75                  80

Leu Pro Ala Val Leu Ala Glu Val Ala Pro Val Val Thr Thr Glu His
                85                  90                  95

Ile Leu Val Ser Val Ala Ala Gly Val Ser Leu Ser Thr Leu Glu Glu
            100                 105                 110

Leu Leu Pro Pro Asn Thr Arg Val Leu Arg Val Leu Pro Asn Leu Pro
        115                 120                 125

Cys Val Val Gln Glu Gly Ala Ile Val Met Ala Arg Gly Arg His Val
    130                 135                 140

Gly Ser Ser Glu Thr Lys Leu Leu Gln His Leu Leu Glu Ala Cys Gly
145                 150                 155                 160

Arg Cys Glu Glu Val Pro Glu Ala Tyr Val Asp Ile His Thr Gly Leu
                165                 170                 175

Ser Gly Ser Gly Val Ala Phe Val Cys Ala Phe Ser Glu Ala Leu Ala
            180                 185                 190

Glu Gly Ala Val Lys Met Gly Met Pro Ser Ser Leu Ala His Arg Ile
        195                 200                 205

Ala Ala Gln Thr Leu Leu Gly Thr Ala Lys Met Leu Leu His Glu Gly
    210                 215                 220

Gln His Pro Ala Gln Leu Arg Ser Asp Val Cys Thr Pro Gly Gly Thr
225                 230                 235                 240

Thr Ile Tyr Gly Leu His Ala Leu Glu Gln Gly Gly Leu Arg Ala Ala
                245                 250                 255

Thr Met Ser Ala Val Glu Ala Ala Thr Cys Arg Ala Lys Glu Leu Ser
            260                 265                 270

Arg Lys

<210> SEQ ID NO 62
<211> LENGTH: 2331
<212> TYPE: DNA
<213> ORGANISM: Homo sapiens

<400> SEQUENCE: 62
agcgcagcgg cgtccgaggc aacaagatgg cagctgcgga gccgtctccg cggcgcgtgg     60
gcttcgtggg cgcgggccgc atggcggggg ccatcgcgca gggcctcatc agagcaggaa    120
aagtggaagc tcagcacata ctggccagtg caccaacaga caggaaccta tgtcactttc    180
aagctctggg ttgccggacc acgcactcca accaggaggt gctacagagc tgcctgctcg    240
tcatctttgc caccaagcct catgtgctgc cagctgtcct ggcagaggtg gctcctgtgg    300

```
tcaccactga acacatcttg gtgtccgtgg ctgctggggt gtctctgagc accctggagg      360
agctgctgcc cccaaacaca cgggtgctgc gggtcttgcc caacctgccc tgtgtggtcc      420
aggaaggggc catagtgatg cgcgggggcc gccacgtggg gagcagcgag accaagctcc      480
tgcagcatct gctggaggcc tgtgggcggt gtgaggaggt gcctgaagcc tacgtcgaca      540
tccacactgg cctcagtggc agtggcgtgg ccttcgtgtg tgcattctcc gaggccctgg      600
ctgaaggagc cgtcaagatg ggcatgccca gcagcctggc ccaccgcatc gctgcccaga      660
ccctgctggg gacggccaag atgctgctgc acgagggcca acacccagcc cagctgcgct      720
cagacgtgtg cacccccggg tggcaccacca tctatggact ccacgccctg gagcagggcg      780
ggctgcgagc agccaccatg agcgccgtgg aggctgccac ctgccgggcc aaggagctca      840
gcagaaagta ggctgggctc tggccatcct ttcctgcctc tgtgccctg cctctccctg       900 tgtcccttcc cctgaggact gcggctccct ccctcctgca tgagggtctc ctactgctcc      960
ttctcccctt gcacagggaa atgcagggg caggacttgg gaggttccag caggcggggg      1020
agccccgacc agtggggaca ctcctccctc cccagtgagc agaaggcacc gtggtggtgg      1080
ctctgcccct tgctgcagtg agcccacctt gctgcaacat tggttctgag gggcccaaga      1140
gatggcgtct tggtcatttg cccgcatggt tgggcagttg gttgaggcca tgaacagaac      1200
ttacggtaac aggcacggct ggcccaatgc ctggtctgga gctggagctt gcctttggct      1260
ttccaggtgg ctccgtgcag ctacagccag gccggctgcc tcatctcagc tctaggggc      1320 acgagccata tgggtctgc acaagagacc ctctcccctg cagtaaagcc aggggccctg      1380
gcctgatggg gcccccatgg ggagctggag cctgccctgc agcctggaga agagggtggc      1440
tgtggtgggc gtgctcatcc cctgctaagg agcaggagct gctgggccag gtctgcggca      1500
gtgctggggt ggcaccaggt gggcagtggt aggtgggtg gcttgaggtc tgggagggtg      1560
gccctggcca gccaggacac atgcagaccc ctggcttagt ctggatacag gctccctctt      1620
tcctcccaat cctaagctcc tgacaagtgg ccaggtggct ctgggccctc ctgccccgtg      1680
cctaggtcag gggtcctgga ataccccgta gctctggcac caccacactg gcctctgatg      1740
gcaagacttg gcccctccac ctgtccctaa cggacggcag gtcaggaaag ccaggactca      1800
ggggagaagc aaaccccag gattgaaggc tagggttcta gggcctttgg gtggggaggg       1860
cccgggccgg acagcctcag ctccgtcccc tgccccacaa gattcacctg gcctccagt       1920 cccacgctgg cccaactgc tgcagctctc ggcttccgcc caacagcctc tggaggtgag       1980
gcgggagcat gccctcagcg aggctgggcg gcgggtcctg ctgtgccatc tccctgtgcg      2040
cctgagcaga tcaatccacc agtgcaaaac agggctaacg gcacctgcag gacagcagca      2100
cgctccatcc ctcatgctca gctgcctctg cggccacgga cttctgccct tcatctgctc      2160
tctcttactc tcctgagcct agcccgtccg taagctccct cccctgcctg gttcccaggg      2220
caggctgact cagttgactg cttggtccaa gcctggccct ggcacttgtc agggtcagcc      2280
taaggagatg ggaataaaga ggccagagag caccaagtga gctcatgttt c              2331
```

<210> SEQ ID NO 63
<211> LENGTH: 1017
<212> TYPE: PRT
<213> ORGANISM: Homo sapiens

<400> SEQUENCE: 63

Met Thr Ser Arg Arg Leu Glu Glu Ser Met Gly Ala Val Gln Met Gly
1               5                   10                  15

-continued

Leu Val Asn Met Phe Lys Gly Phe Gln Ser Lys Val Leu Pro Pro Leu
            20                  25                  30

Ser Pro Lys Val Val Thr Glu Glu Val Asn Arg Met Leu Thr Pro
        35                  40                  45

Ser Glu Phe Leu Lys Glu Met Ser Leu Thr Thr Glu Gln Arg Leu Ala
    50                  55                  60

Lys Thr Arg Leu Met Cys Arg Pro Gln Ile Ile Glu Leu Leu Asp Met
65                  70                  75                  80

Gly Glu Thr Thr His Gln Lys Phe Ser Gly Ile Asp Leu Asp Gln Ala
                85                  90                  95

Leu Phe Gln Pro Phe Pro Ser Glu Ile Ile Phe Gln Asn Tyr Thr Pro
                100                 105                 110

Cys Glu Val Tyr Glu Val Pro Leu Ile Leu Arg Asn Asn Asp Lys Ile
                115                 120                 125

Pro Arg Leu Val Lys Val Val Glu Glu Ser Ser Pro Tyr Phe Lys Val
            130                 135                 140

Ile Ser Pro Lys Asp Ile Gly His Lys Val Ala Pro Gly Val Pro Ser
145                 150                 155                 160

Ile Phe Arg Ile Leu Phe Thr Pro Glu Glu Asn Lys Asp Tyr Ala His
                165                 170                 175

Thr Leu Thr Cys Val Thr Glu Arg Glu Lys Phe Ile Val Pro Ile Lys
                180                 185                 190

Ala Arg Gly Ala Arg Ala Ile Leu Asp Phe Pro Asp Lys Leu Asn Phe
            195                 200                 205

Ser Thr Cys Pro Val Lys Tyr Ser Thr Gln Lys Ile Leu Leu Val Arg
    210                 215                 220

Asn Ile Gly Asn Lys Asn Ala Val Phe His Ile Lys Thr Cys Arg Pro
225                 230                 235                 240

Phe Ser Ile Glu Pro Ala Ile Gly Thr Leu Asn Val Gly Glu Ser Met
                245                 250                 255

Gln Leu Glu Val Glu Phe Glu Pro Gln Ser Val Gly Asp His Ser Gly
            260                 265                 270

Arg Leu Ile Val Cys Tyr Asp Thr Gly Glu Lys Val Phe Val Ser Leu
        275                 280                 285

Tyr Gly Ala Ala Ile Asp Met Asn Ile Arg Leu Asp Lys Asn Ser Leu
    290                 295                 300

Thr Ile Glu Lys Thr Tyr Ile Ser Leu Ala Asn Gln Arg Thr Ile Thr
305                 310                 315                 320

Ile His Asn Arg Ser Asn Ile Ile Ala His Phe Leu Trp Lys Val Phe
                325                 330                 335

Ala Thr Gln Gln Glu Glu Asp Arg Glu Lys Tyr Arg Ala Cys Asp Asp
            340                 345                 350

Leu Ile Lys Glu Glu Lys Asp Glu Thr Asp Glu Phe Phe Glu Glu Cys
        355                 360                 365

Ile Thr Asp Pro Leu Leu Arg Glu His Leu Ser Val Leu Ser Arg Thr
    370                 375                 380

Phe Ala Asn Gln Arg Arg Leu Val Gln Gly Asp Ser Lys Leu Phe Phe
385                 390                 395                 400

Asn Asn Val Phe Thr Val Glu Pro Leu Glu Gly Asp Val Trp Pro Asn
                405                 410                 415

Ser Ser Ala Glu Ile Thr Val Tyr Phe Asn Pro Leu Glu Ala Lys Leu
            420                 425                 430

-continued

```
Tyr Gln Gln Thr Ile Tyr Cys Asp Ile Leu Gly Arg Glu Ile Arg Leu
        435                 440                 445

Pro Leu Arg Ile Lys Gly Glu Gly Met Gly Pro Lys Ile His Phe Asn
450                 455                 460

Phe Glu Leu Leu Asp Ile Gly Lys Val Phe Thr Gly Ser Ala His Cys
465                 470                 475                 480

Tyr Glu Ala Ile Leu Tyr Asn Lys Gly Ser Ile Asp Ala Leu Phe Asn
                485                 490                 495

Met Thr Pro Pro Thr Ser Ala Leu Gly Ala Cys Phe Val Phe Ser Pro
            500                 505                 510

Lys Glu Gly Ile Ile Glu Pro Ser Gly Val Gln Ala Ile Gln Ile Ser
        515                 520                 525

Phe Ser Ser Thr Ile Leu Gly Asn Phe Glu Glu Phe Leu Val Asn
530                 535                 540

Val Asn Gly Ser Pro Glu Pro Val Lys Leu Thr Ile Arg Gly Cys Val
545                 550                 555                 560

Ile Gly Pro Thr Phe His Phe Asn Val Pro Ala Leu His Phe Gly Asp
                565                 570                 575

Val Ser Phe Gly Phe Pro His Thr Leu Ile Cys Ser Leu Asn Asn Thr
            580                 585                 590

Ser Leu Ile Pro Met Thr Tyr Lys Leu Arg Ile Pro Gly Asp Gly Leu
        595                 600                 605

Gly His Lys Ser Ile Ser Tyr Cys Glu Gln His Val Asp Tyr Lys Arg
610                 615                 620

Pro Ser Trp Thr Lys Glu Glu Ile Ser Ser Met Lys Pro Lys Glu Phe
625                 630                 635                 640

Thr Ile Ser Pro Asp Cys Gly Thr Ile Arg Pro Gln Gly Phe Ala Ala
                645                 650                 655

Ile Arg Val Thr Leu Cys Ser Asn Thr Val Gln Lys Tyr Glu Leu Ala
            660                 665                 670

Leu Val Val Asp Val Glu Gly Ile Gly Glu Glu Val Leu Ala Leu Leu
        675                 680                 685

Ile Thr Ala Arg Cys Val Pro Ala Leu His Leu Val Asn Thr Glu
690                 695                 700

Val Asp Phe Gly His Cys Phe Leu Lys Tyr Pro Tyr Glu Lys Thr Leu
705                 710                 715                 720

Gln Leu Ala Asn Gln Asp Asp Leu Pro Gly Phe Tyr Glu Val Gln Pro
                725                 730                 735

Gln Val Cys Glu Glu Val Pro Thr Val Leu Phe Ser Ser Pro Thr Pro
            740                 745                 750

Ser Gly Val Ile Ser Pro Ser Thr Ile His Ile Pro Leu Val Leu
        755                 760                 765

Glu Thr Gln Val Thr Gly Glu His Arg Ser Thr Val Tyr Ile Ser Ile
770                 775                 780

Phe Gly Ser Gln Asp Pro Leu Val Cys His Leu Lys Ser Ala Gly
785                 790                 795                 800

Glu Gly Pro Val Ile Tyr Val His Pro Asn Gln Val Asp Phe Gly Asn
                805                 810                 815

Ile Tyr Val Leu Lys Asp Ser Ser Arg Ile Leu Asn Leu Cys Asn Gln
            820                 825                 830

Ser Phe Ile Pro Ala Phe Phe Gln Ala His Met Ala His Lys Lys Ser
        835                 840                 845

Leu Trp Thr Ile Glu Pro Asn Glu Gly Met Val Pro Pro Glu Thr Asp
```

```
                850                 855                 860
Val Gln Leu Ala Leu Thr Ala Asn Leu Asn Asp Thr Leu Thr Phe Lys
865                 870                 875                 880

Asp Cys Val Ile Leu Asp Ile Glu Asn Ser Ser Thr Tyr Arg Ile Pro
                885                 890                 895

Val Gln Ala Ser Gly Thr Gly Ser Thr Ile Val Ser Asp Lys Pro Phe
                900                 905                 910

Ala Pro Glu Leu Asn Leu Gly Ala His Phe Ser Leu Asp Thr His Tyr
                915                 920                 925

Tyr His Phe Lys Leu Ile Asn Lys Gly Arg Arg Ile Gln Gln Leu Phe
        930                 935                 940

Trp Met Asn Asp Ser Phe Arg Pro Gln Ala Lys Leu Ser Lys Lys Gly
945                 950                 955                 960

Arg Val Lys Lys Gly His Ala His Val Gln Pro Gln Pro Ser Gly Ser
                965                 970                 975

Gln Glu Pro Arg Asp Pro Gln Ser Pro Val Phe His Leu His Pro Ala
                980                 985                 990

Ser Met Glu Leu Tyr Pro Gly Gln Ala Ile Asp Val Ile Leu Glu Gly
                995                1000                1005

Tyr Ser Ala Thr Pro Arg Val Arg Gly
    1010                1015

<210> SEQ ID NO 64
<211> LENGTH: 3659
<212> TYPE: DNA
<213> ORGANISM: Homo sapiens

<400> SEQUENCE: 64
aagctgggta tggagcccct cagcggcggc ggggtctgtg agttggacgc ggggtcttgg    60
cggggaatgg aggtagaata aacgtgggac ccggagtgca ccagaaaaaa aaaattacta   120
aaaatgacaa gtagaagact tgaggagtcc atggggctg ttcagatggg attggtcaat   180
atgttcaaag gatttcaaag caaggttttg ccaccctga gtccaaaggt ggttacagaa    240
gaagaagtaa accgaatgct tacaccctca gagttcctga aggaaatgtc cctgaccacc    300
gagcagagac tggcaaaaac acgtttgatg tgccgaccac agatcatcga actcttagat    360
atgggggaaa caacacatca gaagttttca ggaattgacc tggatcaggc attattccag    420
cccttttccat cagaaattat atttcagaac tacactccct gtgaagtcta tgaagttcca    480
ctgatttttga ggaacaatga caaaattcca aggttggtga agttgtgga agaaagttcg    540
ccttacttta agtaatcag ccccaaagat attggccaca agtggctcc tggagtgcct    600
tccatattcc gaatcctctt tactccagag gagaacaagg attacgccca tcgttgacc    660
tgtgttactg aaagagaaaa gtttattgta cccatcaaag ctagggggc acgagccatt    720
ctcgattttc ctgacaagct gaatttttcc acttgtcctg tcaaatacag cacccagaag    780
attctgctgg tacgaaacat tggcaacaaa aatgctgtat ttcacatcaa acttgtagg    840
cctttctcta tagaaccagc tattggaact cttaatgtgg gagagtccat gcaactggaa    900
gtggagtttg agccacagag tgtgggcgat cacagtggaa gacttatcgt gtgttatgac    960
acaggtgaaa agtgtttgt atctctctat ggagctgcca tagacatgaa ataaggctg    1020
gataagaatt ccttgaccat cgagaaaacc tacatatctc tggccaatca gcgaactata    1080
accattcaca atcgcagtaa tatcattgcc catttcctgt ggaaggtatt tgctacccag    1140
caagaagagg acagagaaaa atatagggcc tgtgatgatc tgatcaaaga ggagaaggat    1200
```

-continued

```
gagactgatg agtttttga agagtgcatt actgatcctt tactccgaga acatctttct    1260
gttctgtccc gaacctttgc gaatcagagg aggctggtgc agggagacag caagctgttc   1320
ttcaataacg ttttcactgt ggagcccctg gaaggtgatg tctggcccaa ctcatcagct   1380
gaaatcaccg tgtactttaa cccactagaa gccaagctct atcaacagac catttactgc   1440
gacattttag gccgagaaat ccgtctgccc ctccgaatca aggggaagg catgggacct    1500
aagattcact tcaactttga attgctggat attgggaaag ttttcactgg atctgcacat   1560
tgttatgagg cgatactgta caacaaaggc agcatcgatg ctctcttcaa catgacccct   1620
ccaacttcag ctttgggggc ctgctttgtt ttcagtccca aggaaggcat cattgaacca   1680
agtggagtcc aagctatcca gatctccttc agctctacca tcctgggaaa ctttgaagaa   1740
gagttcctgg tcaatgtcaa tgggtcacct gagcctgtga aactgaccat tagaggctgt   1800
gtcattggac ctaccttcca ttttaatgtt ccagctctgc actttggtga tgtttccttt   1860
gggtttcctc ataccttgat atgttccctc aataatacct ctttgatccc catgacttac   1920
aaactgcgta tccctgggga tggccttggc cataaaagca tttcatattg tgagcagcat   1980
gtggactaca aaagaccatc ttggaccaag gaagaaatat cctcaatgaa accaaaagaa   2040
ttcaccatct ctcctgactg tggcaccatt cgcccccagg gatttgctgc tatcagggtg   2100
acattatgct ccaacactgt gcagaaatac gagctggcac tcgtggtgga cgtggagggc   2160
atcggagaag aggtgctggc gctcttaatt acagcaaggt gtgttgtacc tgccctccac   2220
ctggtcaata cagaggtgga cttgggcac tgcttcctga agtacccgta tgagaaaaca   2280
ctccagcttg ccaatcaaga tgacctccca ggattctatg aggtccagcc tcaggtgtgt   2340
gaggaggtgc ctactgtgct gttttccagc cccaccccca gcggggtcat ctccccaagc   2400
agcaccatcc acataccact ggtcctggag acccaggtca ctggagaaca cagatccacg   2460
gtttacatct caatctttgg gagccaggac ccccctttgg tatgtcactt aaagagcgct   2520
ggagaaggcc cagttatcta cgtccatccc aatcaagtgg acttcgggaa tatctacgtc   2580
ctaaaagact cttccaggat tctcaaccta tgcaaccagt ccttcattcc cgcatttttc   2640
caggcacaca tggcacacaa aaaatccctt tggacgattg aacccaatga aggcatggtt   2700
cctccagaaa ctgatgttca actggcactg accgccaacc tgaatgacac actgacattc   2760
aaggactgtg ttattttgga cattgaaaat agcagtacct atcggattcc tgttcaggct   2820
tccggaactg gttccactat tgtttcagat aagccctttg ctccagaact caatttgggg   2880
gcacatttta gcctggatac ccactattac cactttaagt tgatcaacaa gggacgtcgg   2940
atccaacagt tgttctggat gaatgatagc ttccgacccc aggccaagct gagtaagaag   3000
ggccgggtta agaagggaca tgctcatgtc caaccccagc ccagtggctc tcaggagccc   3060
agggatccac agagcccgt gtttcatctc caccccgcca gcatggagct gtacccaggc   3120
caggcaattg atgtgatact cgaaggctat tctgctactc ccagggtaag gggatagcac   3180
atttggaagc tattgttttt tcctaaataa atctctactg tatctatttc ttaggaaagt   3240
cccttgacat ttatctgagg aaggatatgg tttctcaagg attgtgtaca atcctgagtt   3300
accatagtag catccgttgc tttcggggtg cagctctgct cagtcttcaa tttgtttctg   3360
tagctactgt gaacccaatc ttaaaggagg ttctcatgcc cagggtccac agtgaccagc   3420
cagcaagtct ctggtagaaa aacacccagt ttttagccaa agcaaattct cctattaaca   3480
cttagcagga tgaatttaat attcattcaa aaagggtgtt tatatcgaca ctctgggctg   3540
```

-continued

```
cctctcctat tcaggtattg ggacatccct gttcctttct ttccagcctg actgcaactc    3600
acatttcaaa acatcttctt tttatgcatt aataaaagag ccacatttat cttcagcaa     3659
```

<210> SEQ ID NO 65
<211> LENGTH: 880
<212> TYPE: PRT
<213> ORGANISM: Homo sapiens

<400> SEQUENCE: 65

```
Met Asn Thr Gly Arg Asp Ser Gln Ser Pro Asp Ser Ala Lys Gly Phe
 1               5                  10                  15

Arg Ser Val Arg Pro Asn Leu Gln Asp Lys Arg Ser Pro Thr Gln Ala
            20                  25                  30

Pro Pro Pro Pro Glu Arg Lys Glu Ser Phe His Ser Ser Leu Ile Thr
        35                  40                  45

Ser His Thr Lys Gly Val Ile Leu Asp Gln Leu Val Thr Asn Thr Gln
    50                  55                  60

Ile Pro Ser Ser Thr Glu Tyr Phe Ala Asn Lys Lys Pro Leu Gln Gly
 65                  70                  75                  80

Thr Met Tyr Ser Asn Glu Asp Ser Arg Gln Thr Ile Val Tyr Ser Glu
                85                  90                  95

Glu Ser Asn Thr Thr Met Ser Tyr Thr Gln Lys Ile Thr Asn Pro Leu
            100                 105                 110

Pro Ala Ala Ser Ser Thr Asp Pro Ala Pro Phe Ala Asn Ile Asn Thr
        115                 120                 125

Pro Val Leu Gln Glu Asp Tyr Arg Gln Asp Ser Gln Thr Arg Arg Ile
    130                 135                 140

Ser Thr Leu Lys Leu Thr His Asn Gln Asp Leu Gly Ser Ser Ser Pro
145                 150                 155                 160

Ile Ser Thr Pro Gln Val Leu Gln Ile Cys Arg Ser Thr Val Ile Ser
                165                 170                 175

Gln Lys Ala Arg Ser Leu Thr Pro Asn Pro Val Pro Glu Thr His Thr
            180                 185                 190

Ala Ser Leu Ser Ile Gln Ile Ala Pro Leu Ser Gly Gln Asp Leu Glu
        195                 200                 205

Ser His Lys Gln Leu Pro Glu Leu Ser Pro Glu Thr Ala Lys Ile Pro
    210                 215                 220

Leu Gln Gln Glu Arg Gln Lys Ser Ala Val Ala Ala Ser Gln Ser
225                 230                 235                 240

Ser Asp Cys Arg Val Ser Gln Ile Thr Val Asn Gly Asn Ser Gly Gly
                245                 250                 255

Ala Val Ser Pro Met Ser Tyr Tyr Gln Arg Pro Phe Ser Pro Ser Ala
            260                 265                 270

Tyr Ser Leu Pro Ala Ser Leu Asn Ser Ser Ile Val Met Gln His Gly
        275                 280                 285

Thr Ser Leu Asp Ser Thr Asp Thr Tyr Pro Gln His Ala Gln Ser Leu
    290                 295                 300

Asp Gly Thr Thr Ser Ser Ser Ile Pro Leu Tyr Arg Ser Ser Glu Glu
305                 310                 315                 320

Glu Lys Arg Val Thr Val Ile Lys Ala Pro His Tyr Pro Gly Ile Gly
                325                 330                 335

Pro Val Asp Glu Ser Gly Ile Pro Thr Ala Ile Arg Thr Thr Val Asp
            340                 345                 350

Arg Pro Lys Asp Trp Tyr Lys Thr Met Phe Lys Gln Ile His Met Val
```

-continued

```
            355                 360                 365
His Lys Pro Asp Asp Thr Asp Met Tyr Asn Thr Pro Tyr Thr Tyr
    370                 375                 380
Asn Ala Gly Leu Tyr Asn Pro Tyr Ser Ala Gln Ser His Pro Ala
385                 390                 395                 400
Ala Lys Thr Arg Thr Tyr Arg Pro Leu Ser Lys Ser His Ser Asp Asn
            405                 410                 415
Ser Pro Asn Ala Phe Lys Asp Ala Ser Ser Pro Val Pro Pro His
            420                 425                 430
Val Pro Pro Val Pro Pro Leu Arg Pro Arg Asp Arg Ser Ser Thr
        435                 440                 445
Glu Lys His Asp Trp Asp Pro Asp Arg Lys Val Asp Thr Arg Lys
    450                 455                 460
Phe Arg Ser Glu Pro Arg Ser Ile Phe Glu Tyr Glu Pro Gly Lys Ser
465                 470                 475                 480
Ser Ile Leu Gln His Glu Arg Pro Thr Asp Arg Ile Asn Pro Asp Asp
            485                 490                 495
Ile Asp Leu Glu Asn Glu Pro Trp Tyr Lys Phe Phe Ser Glu Leu Glu
        500                 505                 510
Phe Gly Arg Pro Pro Lys Lys Pro Leu Asp Tyr Val Gln Asp His
    515                 520                 525
Ser Ser Gly Val Phe Asn Glu Ala Ser Leu His Gln Ser Ser Ile Asp
        530                 535                 540
Arg Ser Leu Glu Arg Pro Met Ser Ser Ala Ser Met Ala Ser Asp Phe
545                 550                 555                 560
Arg Lys Arg Arg Lys Ser Glu Pro Ala Val Gly Pro Pro Arg Gly Leu
            565                 570                 575
Gly Asp Gln Ser Ala Ser Arg Thr Ser Pro Gly Arg Val Asp Leu Pro
            580                 585                 590
Gly Ser Ser Thr Thr Leu Thr Lys Ser Phe Thr Ser Ser Pro Ser
        595                 600                 605
Ser Pro Ser Arg Ala Lys Asp Arg Glu Ser Pro Arg Ser Tyr Ser Ser
    610                 615                 620
Thr Leu Thr Asp Met Gly Arg Ser Ala Pro Arg Glu Arg Arg Gly Thr
625                 630                 635                 640
Pro Glu Lys Glu Lys Leu Pro Ala Lys Ala Val Tyr Asp Phe Lys Ala
            645                 650                 655
Gln Thr Ser Glu Glu Leu Ser Phe Lys Lys Gly Asp Thr Val Tyr Ile
            660                 665                 670
Leu Arg Lys Ile Asp Gln Asn Trp Tyr Glu Gly Glu His His Gly Arg
        675                 680                 685
Val Gly Ile Phe Pro Ile Ser Tyr Val Glu Lys Leu Thr Pro Pro Glu
    690                 695                 700
Lys Ala Gln Pro Ala Arg Pro Pro Pro Ala Gln Pro Gly Glu Ile
705                 710                 715                 720
Gly Glu Ala Ile Ala Lys Tyr Asn Phe Asn Ala Asp Thr Asn Val Glu
            725                 730                 735
Leu Ser Leu Arg Lys Gly Asp Arg Val Ile Leu Leu Lys Arg Val Asp
            740                 745                 750
Gln Asn Trp Tyr Glu Gly Lys Ile Pro Gly Thr Asn Arg Gln Gly Ile
        755                 760                 765
Phe Pro Val Ser Tyr Val Glu Val Lys Lys Asn Thr Lys Gly Ala
    770                 775                 780
```

```
Glu Asp Tyr Pro Asp Pro Pro Ile Pro His Ser Tyr Ser Ser Asp Arg
785                 790                 795                 800

Ile His Ser Leu Ser Ser Asn Lys Pro Gln Arg Pro Val Phe Thr His
            805                 810                 815

Glu Asn Ile Gln Gly Gly Gly Glu Pro Phe Gln Ala Leu Tyr Asn Tyr
        820                 825                 830

Thr Pro Arg Asn Glu Asp Glu Leu Glu Leu Arg Glu Ser Asp Val Ile
    835                 840                 845

Asp Val Val Glu Lys Cys Asp Asp Gly Trp Phe Val Gly Thr Ser Arg
850                 855                 860

Arg Ala Lys Phe Phe Gly Thr Phe Pro Gly Asn Tyr Val Lys Arg Leu
865                 870                 875                 880

<210> SEQ ID NO 66
<211> LENGTH: 2688
<212> TYPE: DNA
<213> ORGANISM: Homo sapiens

<400> SEQUENCE: 66
tgtacaaaaa agcaggctcc accatgaaca cagggcgtga ttctcagtca ccagactcag     60
caaaaggttt tagaagcgtt cgaccaaacc tacaagataa agatcacca actcaggcac     120 cccctccacc agaaagaaaa gagagctttc atagctcttt gataaccagt cacacaaagg    180
gtgtcatttt agaccagtta gtaactaaca cacaaattcc ctccagtaca gagtactttg    240
ctaacaaaaa acctcttcag ggaactatgt attccaatga agattcgaga cagacaattg    300
tatattctga agaatctaac acaaccatgt catatacaca aaaaatcact aatcctctac    360
cagcagcttc cagcacggat cctgcaccat tcgctaacat caacacccca gttctacaag    420
aggactacag gcaagattct caaactcgga ggatttctac cttgaaacta acccataacc    480
aggatctagg aagtagcagc cccattagta ctccacaggt tctccaaatc tgtcgaagta    540
ccgtcatttc tcaaaaggcc cgctcactga ccctaatcc agtgcctgag acacacacag     600
catctctttc cattcagata gctccccttt caggacagga tcttgaaagc cacaaacagc    660
tacctgagct ttctccagag actgcaaaga tacctcttca gcaagagaga caaaaatctg    720
cagttgcagc ggcctctcag tcctcagact gcagagtgag ccagataaca gtgaatggaa    780
actcaggagg tgccgtgagt cccatgagtt actatcagag gccgttttcc ccctcggcat    840
attctctccc agcctcactc aactccagca ttgtcatgca gcacggcaca tccctcgatt    900
ccacagacac atatccccag catgcgcagt ctctggatgg caccaccagc agctctatcc    960
ccctgtaccg atcctcagag gaagagaaga gagtgacagt catcaaagcc ccgcattacc    1020
cagggatcgg gcccgtggat gaatccggaa tccccacagc aattagaacg acagtcgacc    1080
ggcccaagga ctggtacaag acgatgttta gcagattca catggtgcac aagccggatg    1140
atgacacaga catgtataat actccttata catacaatgc aggtctgtac aacccaccct    1200
acagtgctca gtcacccct gctgcaaaga cccgaaccta cagacctctt tccaaaagcc    1260
actccgacaa cagccccaat gcctttaagg atgcgtcctc cccagtgcct ccccacatg    1320 ttccacctcc agtcccgccg cttcgaccaa gagatcggtc ttcaacagaa aagcatgact    1380
gggatcctcc agacagaaaa gtggacacaa gaaaatttcg gtctgagcca aggagtattt    1440
ttgaatatga acctgcaag tcatcaattc ttcagcatga aagaccaact gatcgcataa    1500
atccagatga catagattta gaaaatgagc cctggtataa attcttttca gaactggagt    1560
```

-continued

```
ttggacgccc gcctcctaaa aagcctctgg actatgttca agatcattct tctggtgttt   1620
tcaatgaggc ctccttgcat cagtcctcta tagacagaag cctggaaaga cccatgagtt   1680
ctgcaagcat ggccagtgac ttcaggaagc ggaggaagag cgagcctgca gtgggtccac   1740
cacggggctt gggagatcaa agtgcgagca ggactagccc aggccgagtg gacctcccag   1800
gatcaagcac cactcttaca aagtctttca ctagctcttc tccttcttcc ccatcaagag   1860
caaaagaccg tgagtcccct agaagttact catccacttt gactgacatg gggagaagtg   1920
caccaaggga agaagagga actccagaaa aagagaaatt gcctgcaaaa gctgtttatg   1980
attttaaggc tcagacatct gaggagttgt catttaagaa aggagatact gtctacatcc   2040
tcaggaaaat tgatcaaaat tggtatgagg gagaacacca cgggagagtg ggcatcttcc   2100
cgatctcata cgtagagaaa ctcacacctc ctgagaaagc acagcctgca agaccacctc   2160
cgccagccca gcccggagaa atcggagaag ctatagccaa atacaacttc aacgcagaca   2220
caaatgtgga gctgtcactg agaaagggag atagagttat tcttcttaaa agagttgatc   2280
aaaactggta tgaaggtaaa atcccaggaa ccaacagaca aggcatcttc cctgtttcct   2340
atgtggaggt cgtcaagaag aacacaaaag gtgctgagga ctaccctgac cctccaatac   2400
cccacagcta ttctagtgat aggattcaca gcttgagctc aaataagcca cagcgtcctg   2460
tgtttactca tgaaaatatt caaggtgggg gggaaccgtt tcaggctctg tataactata   2520
ctcccaggaa tgaagatgag ctggagctca gagaaagtga tgtcattgat gtcgtggaaa   2580
agtgtgatga cggctggttt gtggggacct caagaagagc caaattcttt ggtactttcc   2640
ccggaaacta cgtcaagagg ctgtagcttg acccagcttt cttgtaca                2688
```

<210> SEQ ID NO 67
<211> LENGTH: 299
<212> TYPE: PRT
<213> ORGANISM: Homo sapiens

<400> SEQUENCE: 67

```
Met Glu Pro Pro Ile Pro Gln Ser Ala Pro Leu Thr Pro Asn Ser Val
1               5                   10                  15

Met Val Gln Pro Leu Leu Asp Ser Arg Met Ser His Ser Arg Leu Gln
                20                  25                  30

His Pro Leu Thr Ile Leu Pro Ile Asp Gln Val Lys Thr Ser His Val
            35                  40                  45

Glu Asn Asp Tyr Ile Asp Asn Pro Ser Leu Ala Leu Thr Thr Gly Pro
        50                  55                  60

Lys Arg Thr Arg Gly Gly Ala Pro Glu Leu Ala Pro Thr Pro Ala Arg
65                  70                  75                  80

Cys Asp Gln Asp Val Thr His His Trp Ile Ser Phe Ser Gly Arg Pro
                85                  90                  95

Ser Ser Val Ser Ser Asn Ser Ser Thr Ser Ser Asp Gln Arg Leu Leu
                100                 105                 110

Asp His Met Ala Pro Pro Val Ala Asp Gln Ala Ser Pro Arg Ala
            115                 120                 125

Val Arg Ile Gln Pro Lys Val Val His Cys Gln Pro Leu Asp Leu Lys
        130                 135                 140

Gly Pro Ala Val Pro Pro Glu Leu Asp Lys His Phe Leu Leu Cys Glu
145                 150                 155                 160

Ala Cys Gly Lys Cys Lys Cys Lys Glu Cys Ala Ser Pro Arg Thr Leu
                165                 170                 175
```

```
Pro Ser Cys Trp Val Cys Asn Gln Glu Cys Leu Cys Ser Ala Gln Thr
            180                 185                 190
Leu Val Asn Tyr Gly Thr Cys Met Cys Leu Val Gln Gly Ile Phe Tyr
        195                 200                 205
His Cys Thr Asn Glu Asp Glu Gly Ser Cys Ala Asp His Pro Cys
    210                 215                 220
Ser Cys Ser Arg Ser Asn Cys Cys Ala Arg Trp Ser Phe Met Gly Ala
225                 230                 235                 240
Leu Ser Val Val Leu Pro Cys Leu Leu Cys Tyr Leu Pro Ala Thr Gly
                245                 250                 255
Cys Val Lys Leu Ala Gln Arg Gly Tyr Asp Arg Leu Arg Arg Pro Gly
            260                 265                 270
Cys Arg Cys Lys His Thr Asn Ser Val Ile Cys Lys Ala Ala Ser Gly
            275                 280                 285
Asp Ala Lys Thr Ser Arg Pro Asp Lys Pro Phe
            290                 295
```

```
<210> SEQ ID NO 68
<211> LENGTH: 2400
<212> TYPE: DNA
<213> ORGANISM: Homo sapiens

<400> SEQUENCE: 68
gccccggctt caggatttac acagacgtgg ggcgatgctt gtgaccctgc agctcctcaa      60
aggcccctag aagcctgttt ctccgtacag tccaggacct ccagcccat ggagcccccg     120
atcccacaga gcgccccctt gactcccaac tcagtcatgg tccagcccct tcttgacagc     180
cggatgtccc acagccggct ccagcaccca ctcaccatcc tacccattga ccaggtgaag     240
accagccatg tggagaatga ctacatagac aaccctagcc tggccctgac caccggccca     300
aagcggaccc ggggcggggc cccagagctg gccccgacgc ccgccccgctg tgaccaggat     360
gtcacccacc attggatctc cttcagcggg cgccccagct ctgtgagcag caacagcagc     420
acatcctctg accaacggct cttagaccac atggcaccac acccgtggc tgaccaggcc     480
tcaccaaggg ctgtgcgcat ccagcccaag gtggtccact gccagccgct ggacctcaag     540
ggcccggcgg tcccacccga gctggacaag cacttcttgc tgtgcgaggc ctgtgggaag     600
tgtaaatgca aggagtgtgc atcccccgg acgttgcctt cctgctgggt ctgcaaccag     660
gagtgcctgt gctcagccca gactctggtc aactatggca cgtgcatgtg tttggtgcag     720
ggcatcttct accactgcac gaatgaggac gatgagggcc cctgcgctga ccaccctgc    780
tcctgctccc gctccaactg ctgcgcccgc tggtccttca tgggtgctct ctccgtggtg     840
ctgcctgcc tgctctgcta cctgcctgcc accggctgcg tgaagctggc ccagcgtggc     900
tacgaccgtc tgcgccgccc tggttgccgc tgcaagcaca cgaacagcgt catctgcaaa     960
gcagccagcg gggatgccaa gaccagcagg cccgacaagc ctttctgaca gtttgtgtcg    1020
aagcccagt gctctgcctg gaaacctggt tctcttctga catctaagaa gactgcagca    1080
aggtcagagg ttttagcctc ctgaggctga ccttgctagt ctgcccactc cctaccccca    1140
gcttcggaaa atacagagac caccaccacg taccctgtat tccccaagat gatgaagaag    1200
cactttgggg cttttttttca gggtcctgaa actttgtgtc aaacagacaa tgcaggggca    1260
gggtgtggtt tggggggaaa ttttcttttt tcagaagaca gaacacagat gtggacacat    1320
atccggaaac tgcagctgct tgaatgcctt cccagcccct ccttctccct ccctccctcc    1380
gcaccccct tcctcttttc cattgtcttt ggctctcaca ggagctagct gcctgggagg    1440
```

```
aattgttaac tgagtaccag ggtaccttta aagaagaccc ttggagtctt ctataccttc    1500
ttctccttcc ccatctcact ccaccccact ttgtccctga tgtcttgggg aaggtgtaga    1560
acaccctagc agttcctatt gtatatactt gggagccact gagaacagag gacggccagt    1620
gagtccaagc ctcgttcctc cttctgcctc cccggagcca caggatggat ttaggagcca    1680
ctgctcagtg cacttctccc ttccaactgc atcaactaac tctcggggt gttctgctca    1740 ccacaccgtc cttcggttct tactgagtca cagactcgcc tgcccactac gtgtcctggg    1800
ttctctctac tcagatccct tccagaaact ttatatgggt agaggaagcc agggcggcaa    1860
atgcgagacc aaatatcatt tgccaatga gtctgaggct gtggtctctg gatccagtca     1920
ttatgttttt atagaataat taaaccggat gctaacggtg ttttaaaaaa taataataaa    1980
acaacttgtt tccttttggc cacccccagg aagggctgat ttcaaaatct gggggcgagc    2040
aacctcaagg aacacaattt ccctccctat caacaagagg attttaacag caaagaagag    2100
aggcagcacc tcccattggc agaatgaccg ctgagccagg ctgggtttgg gtttcttctc    2160
ttctgattct gctgctcact gtcatagcct tttgtgtata gtgatgtgtc tgtatcttta    2220
atgtaaatag agagatgatg aaaaaagagt ctattttagt gttaggaagc cccagcaggg    2280
gagtcggaag agcttggaag agctggggag agggtagggg aaaggttttt ccagggccca    2340
ctgggtttga gccctgcttc tgtgcacagc cacaccaccc tctcccgaca gccctcaaag    2400
```

<210> SEQ ID NO 69
<211> LENGTH: 477
<212> TYPE: PRT
<213> ORGANISM: Homo sapiens

<400> SEQUENCE: 69

```
Met Asp Gly Phe Tyr Asp Gln Gln Val Pro Tyr Met Val Thr Asn Ser
 1               5                  10                  15

Gln Arg Gly Arg Asn Cys Asn Glu Lys Pro Thr Asn Val Arg Lys Arg
                20                  25                  30

Lys Phe Ile Asn Arg Asp Leu Ala His Asp Ser Glu Glu Leu Phe Gln
            35                  40                  45

Asp Leu Ser Gln Leu Gln Glu Thr Trp Leu Ala Glu Ala Gln Val Pro
        50                  55                  60

Asp Asn Asp Glu Gln Phe Val Pro Asp Tyr Gln Ala Glu Ser Leu Ala
    65                  70                  75                  80

Phe His Gly Leu Pro Leu Lys Ile Lys Lys Glu Pro His Ser Pro Cys
                85                  90                  95

Ser Glu Ile Ser Ser Ala Cys Ser Gln Glu Gln Pro Phe Lys Phe Ser
                100                 105                 110

Tyr Gly Glu Lys Cys Leu Tyr Asn Val Ser Ala Tyr Asp Gln Lys Pro
            115                 120                 125

Gln Val Gly Met Arg Pro Ser Asn Pro Pro Thr Pro Ser Ser Thr Pro
        130                 135                 140

Val Ser Pro Leu His His Ala Ser Pro Asn Ser Thr His Thr Pro Lys
145                 150                 155                 160

Pro Asp Arg Ala Phe Pro Ala His Leu Pro Pro Ser Gln Ser Ile Pro
                165                 170                 175

Asp Ser Ser Tyr Pro Met Asp His Arg Phe Arg Arg Gln Leu Ser Glu
            180                 185                 190

Pro Cys Asn Ser Phe Pro Pro Leu Pro Thr Met Pro Arg Glu Gly Arg
        195                 200                 205
```

```
Pro Met Tyr Gln Arg Gln Met Ser Glu Pro Asn Ile Pro Phe Pro Pro
    210                 215                 220
Gln Gly Phe Lys Gln Glu Tyr His Asp Pro Val Tyr Glu His Asn Thr
225                 230                 235                 240
Met Val Gly Ser Ala Ala Ser Gln Ser Phe Pro Pro Leu Met Ile
                245                 250                 255
Lys Gln Glu Pro Arg Asp Phe Ala Tyr Asp Ser Glu Val Pro Ser Cys
            260                 265                 270
His Ser Ile Tyr Met Arg Gln Glu Gly Phe Leu Ala His Pro Ser Arg
        275                 280                 285
Thr Glu Gly Cys Met Phe Glu Lys Gly Pro Arg Gln Phe Tyr Asp Asp
    290                 295                 300
Thr Cys Val Val Pro Glu Lys Phe Asp Gly Asp Ile Lys Gln Glu Pro
305                 310                 315                 320
Gly Met Tyr Arg Glu Gly Pro Thr Tyr Gln Arg Arg Gly Ser Leu Gln
                325                 330                 335
Leu Trp Gln Phe Leu Val Ala Leu Leu Asp Asp Pro Ser Asn Ser His
            340                 345                 350
Phe Ile Ala Trp Thr Gly Arg Gly Met Glu Phe Lys Leu Ile Glu Pro
        355                 360                 365
Glu Glu Val Ala Arg Arg Trp Gly Ile Gln Lys Asn Arg Pro Ala Met
    370                 375                 380
Asn Tyr Asp Lys Leu Ser Arg Ser Leu Arg Tyr Tyr Tyr Glu Lys Gly
385                 390                 395                 400
Ile Met Gln Lys Val Ala Gly Glu Arg Tyr Val Tyr Lys Phe Val Cys
                405                 410                 415
Asp Pro Glu Ala Leu Phe Ser Met Ala Phe Pro Asp Asn Gln Arg Pro
            420                 425                 430
Leu Leu Lys Thr Asp Met Glu Arg His Ile Asn Glu Glu Asp Thr Val
        435                 440                 445
Pro Leu Ser His Phe Asp Glu Ser Met Ala Tyr Met Pro Glu Gly Gly
    450                 455                 460
Cys Cys Asn Pro His Pro Tyr Asn Glu Gly Tyr Val Tyr
465                 470                 475
```

<210> SEQ ID NO 70
<211> LENGTH: 6158
<212> TYPE: DNA
<213> ORGANISM: Homo sapiens

<400> SEQUENCE: 70

| | | |
|---|---|---|
| gttgatagaa gtccagatcc tgaggaaatc tccagctaaa tgctcaaaat ataaatact | 60 |
| gagctgagat ttgcgaagag cagcagcatg gatggatttt atgaccagca agtgccttac | 120 |
| atggtcacca atagtcagcg tgggagaaat tgtaacgaga accaacaaa tgtcaggaaa | 180 |
| agaaaattca ttaacagaga tctggctcat gattcagaag aactctttca agatctaagt | 240 |
| caattcagg aaacatggct tgcagaagct caggtacctg acaatgatga gcagtttgta | 300 |
| ccagactatc aggctgaaag tttggctttt catggcctgc cactgaaaat caagaaagaa | 360 |
| ccccacagtc catgttcaga aatcagctct gcctgcagtc aagaacagcc ctttaaattc | 420 |
| agctatggag aaaagtgcct gtacaatgtc agtgcctatg atcagaagcc acaagtggga | 480 |
| atgaggccct ccaaccccc cacaccatcc agcacgccag tgtccccact gcatcatgca | 540 |
| tctccaaaact caactcatac accgaaacct gaccgggcct tcccagctca cctccctcca | 600 |

-continued

```
tcgcagtcca taccagatag cagctacccc atggaccaca gatttcgccg ccagctttct    660
gaaccctgta actcctttcc tcctttgccg acgatgccaa gggaaggacg tcctatgtac    720
caacgccaga tgtctgagcc aaacatcccc ttcccaccac aaggctttaa gcaggagtac    780
cacgacccag tgtatgaaca acaccatg gttggcagtg cggccagcca aagctttccc     840
cctcctctga tgattaaaca ggaacccaga gattttgcat atgactcaga gtgcctagc    900
tgccactcca tttatatgag gcaagaaggc ttcctggctc atcccagcag aacagaaggc    960
tgtatgtttg aaaagggccc caggcagttt tatgatgaca cctgtgttgt cccagaaaaa   1020
ttcgatggag acatcaaaca agagccagga atgtatcggg aaggacccac ataccaacgg   1080
cgaggatcac ttcagctctg gcagttttg gtagctcttc tggatgaccc ttcaaattct    1140
cattttattg cctggactgg tcgaggcatg gaatttaaac tgattgagcc tgaagaggtg   1200
gcccgacgtt gggcattca gaaaaacagg ccagctatga actatgataa acttagccgt    1260
tcactccgct attactatga gaaggaatt atgcaaaagg tggctggaga gagatatgtc    1320
tacaagtttg tgtgtgatcc agaagccctt ttctccatgg cctttccaga taatcagcgt   1380
ccactgctga agacagacat ggaacgtcac atcaacgagg aggacacagt gcctctttct   1440
cactttgatg agagcatggc ctacatgccg aaggggggct gctgcaaccc ccacccctac   1500
aacgaaggct acgtgtatta acacaagtga cagtcaagca gggcgttttt gcgcttttcc   1560
ttttttctgc aagatacaga gaattgctga atctttgttt tatttctgtt gtttgtattt   1620
tattttaaa taataataca caaaaggggg cttttcctgt tgcattattc tatggtctgc    1680
catggactgt gcactttatt tgagggtggg tgggagtaat ctaaacattt attctgtgta   1740
acaggaagct aatgggtgaa tgggcagagg gatttgggga ttacttttta cttaggcttg   1800
ggatggggtc ctacaagttt tgagtatgat gaaactatat catgtctgtt tgatttcata   1860
acaacataag ataatgttta ttttatcggg gtatctatgg tacagttaat ttcacgttgt   1920
gtaaatatcc acttggagac tatttgcctt gggcattttc ccctgtcatt tatgagtctc   1980
tgcaggtgta caaaaaaacc ccaatctact gtaaatggca gtttaattgt tagaaatgac   2040
tgttttgca ccacttgtaa aaaggtattt agcgattgca tttgctgttt gttgttttat    2100
tttgctttat atatgacttg cagaggataa ccataaaatg ggtaattctc tctgaagttg   2160
aataatcacc atgactgtaa atgaggggca caattttgga ctctggcgcc aaactgagtc   2220
ataggccagt agcattacgt gtatctggtg ccaccttgct gtttagatac aaatcatacc   2280
gtcttttaaa tattttgaag cccatttcag ttaaataatg acatgtcatg gtcctttgga   2340
atcttcattt aaatgttaaa tctggaatca aaatgaagca aaaatatct gtctcctttt    2400
cactttcttc agtacataaa tacattattt aatcaataag aattaactgt actaaatcat   2460
gtattatgct gttctagtta cagcaaacac tctttaagaa aaatatccaa tacactaaat   2520
aggtactata gtaatttta gacatggtac ccattgatat gcatttaaac cttttactgc    2580
tgtgttatgt tgataacata tataaatatt agataatgct aatgcttctg ctgctgtctt   2640
ttctgtaata ttctctttca tgctgaattt actatgacca tttataagca gtgcagttaa   2700
ctacagatag catttcagga caaaatagat gactcaaacc attttattgct taaaaaatag   2760
cttacgccat gctatgctat aagcagcttt tatgcacatt gacaaatgaa gagtaagctt   2820
cagcttgcta aaggaaactg tggaaccttt tgtaacttt ggtgatatgg aaaattattt    2880
acaaaccgtc aaagaatatg aggaagttgc tgtatgacat agtgctggca ctgatattat   2940
```

```
ccatcatctc tttttggaca cttctgtaaa tgtgattgga ttgtttgaaa gaagatttaa    3000
agtttcaaag ttttttgttc tgtttttgct ttgcatttgg agaaaatatt gaaagcaggg    3060
tatgttgttt cattcacctt gaaaaaacca tgagtaaatg gggatataga atctctgaat    3120
agctcgctaa aagattcaag caagggacat gaattttgtt ccatctatca ataatatcca    3180
gaagaacaac tttttaaag agtctatagc aaaaagcaaa aaaaaaaaaa aattctaaac     3240
acaaagtcaa aataaaccta ttgtaaaagc atttcgtgat gagcatgaaa aagattgttt    3300
aaagatgatc cccccagcta cccattttcc aaaactacac agatcacagc tcatttctct    3360
aagtggagca gttatcaaga aacccaaaca ccaaaattgc tactcttcac atttaatcct    3420
acaaaaagta ctccaatttc aaaatatgta tgtaacctgc gatttcaatg attgttgttc    3480
atatacatca tgtattattt tggcccattt tgggcctaaa aaagaaaact atgccttaaa    3540
aatcagaacc ttttctcccc actatgctta tgtggccatc tacagcactt agaataaaaa    3600
cagatgttaa aatattcagt gaaagtttta ttggaaaaag gaattgagat atataattga    3660
gatttggtga aattgaagga gaaaatttaa gtgagtcttt aaaatatatt ctgaatgaaa    3720
actgtattga ggattcattt ttgttccttt tttttctttt tctcttttct ccttttcttt   3780 cttttaata gtctagtttt agtcagtcag tgaggaagaa ttgggccatg ctaacgttat     3840
cacaagagaa caatggcaga aatggtatta gttatataat atttaaggac aaactatatg    3900
ttttgctgtt ttaacgtagt gactcactga actaaataca taattgacca acattaagtg    3960
tatttccaat acagaagggt tgaaaatatt acattataaa ctcttttgaa aaatgtatct    4020
aaaatttttt aagttctgtt ttgattccac tttttggttg agttttatg ttttttgtttt    4080 caggtagatt aataaatctg gcagctgatt tctgcaagat tcttgtgttt tgaatttctc    4140
attgaattgg ctactcaaac atagaaatca tttgttaatg atgtaatgtc ttctctcagc    4200
ttttatcttc actgctgttt gctgtctctt gatgatgaca tgttaatacc caatagatta    4260
attgcaacaa acacttatac tcaaataact aagtaaaaat aattttttctt gttatgtcca   4320 tgaaaagtgc ttcagaataa aaatccacaa gactgacagt gcagaacatt tttctcaaat    4380
catgggcgga tcttggaggt ctagtttccc gtagatgctg taaccaatta ccacaacttc    4440
agtaatttac acaaatttat cttatagttc tggaggcaga agttcaaaag aagccttaag    4500
agactaaaac caagatgtcc ttaggtctgg ttccttctgg aggctccagg ggagattctt    4560
ccagctttca cttctagagt ctgctgacat tccttggctc ctggctacat cacttcaatc    4620
tctgcttcca tggtcacata ctcttctact atagtcaaat ttccttcctg cctcttataa    4680
ggatgcttgt gattacattt aggggatgct cagataatcc aggacaatct ctccatctca    4740
agatccttaa cttaatgacg tgtgccaagt cccttttggct agataattat tcataggtcc   4800
cagggattag gacatggatg taaggggtga gggcagggct gttattcaga acaccgcacg    4860
gaggaggaag actgtgtagc aaagactcta attgatttac tcaggaacag tggagttctg    4920
ctgagggatc taggatttga aagtactaga gtttgctttt atttaccact gagatatttt    4980 cccttattc tgcataaata attttgaaaa ctttctctat aaatttcaa ctattccact      5040 aaaatgtctg gtaatcacat caagcctttta gattattcaa atccttcccc agccccagg    5100 aaaacactaa gtcatgaaac agaaaaacag aaggtatgat aataatagta ataacagtta    5160
aatcagtggt ctaatccaga ttttattttt taatacatttt cttttggtgt taatatgggt   5220
tactatgtga tcttatcatt tgctagtgat tattacttat taggtaagaa caatgtgtaa    5280
aatatgtcta ttactcaaaa gaacaattgc aaaatgagtc aacttatctt tatataacca    5340
```

```
ggaaagaaat atattgccag aagctacaga attttgccag atgataggga tttctaaaat    5400
gagccacttt gtctatcatg cagccttttc agagcttgta atgagaaaac attacagagg    5460
agaaggtcat ttggatgttt gttacttgga atcctagaaa acaaaaacta aaatttaaaa    5520
ataagaagtg agtaagctat tttccatttg cgatttggta tggagaagag aggaaataga    5580
attattaaaa aaatacaaat tgggtaaaag tgatggtgga aaaaatataa agaaggcaaa    5640
tgtacatatt aagcaattct actaagaatt ggaaaaatca agtttcaaaa agatggtaat    5700
agttgggcat gatactagaa aatttcaccc agtttattca gagctcaact agtactttta    5760
ggacttcttt tttatatac atgagactca ctttgacata cttaaaaaaa aaacagttta    5820
tggaaagtac agtttaagag gagaatttga ttagactaag tggatatctt tatagaaata    5880
ttaatgattt cagaattttc agttacaagt gtatataccg tggctattgt ttatggattc    5940
atatgtaagg tagggtcttt tttgcatata gactccagta ttagttactt tcattctaaa    6000
attatattta tgcttctatg gggaagaaaa tttttaattc acttggttgt attaaaatta    6060
tacttacggt ttgagaaaac atgctatgaa aatcatgatt atagcaaatt aaatatgctc    6120
aaaatttaaa tctaaaataa aagcccagaa actgaaaa                            6158
```